(12) United States Patent
Falck et al.

(10) Patent No.: US 11,690,825 B2
(45) Date of Patent: Jul. 4, 2023

(54) 20-HETE RECEPTOR (GPR75) ANTAGONISTS AND METHODS OF USE

(71) Applicants: BOARD OF REGENTS, THE UNIVERSITY OF TEXAS SYSTEM, Austin, TX (US); New York Medical College, Valhalla, NY (US)

(72) Inventors: John R. Falck, Austin, TX (US); Michal L. Schwartzman, Valhalla, NY (US); Victor Garcia, Valhalla, NY (US)

(73) Assignees: Board of Regents, The University of Texas System, Austin, TX (US); New York Medical College, Valhalla, NY (US)

( * ) Notice: Subject to any disclaimer, the term of this patent is extended or adjusted under 35 U.S.C. 154(b) by 1063 days.

(21) Appl. No.: 16/083,404

(22) PCT Filed: Mar. 8, 2017

(86) PCT No.: PCT/US2017/021419
§ 371 (c)(1),
(2) Date: Dec. 23, 2019

(87) PCT Pub. No.: WO2017/156164
PCT Pub. Date: Sep. 14, 2017

(65) Prior Publication Data
US 2020/0030291 A1 Jan. 30, 2020

Related U.S. Application Data

(60) Provisional application No. 62/305,947, filed on Mar. 9, 2016.

(51) Int. Cl.
| | |
|---|---|
| *A61K 31/201* | (2006.01) |
| *C07C 59/42* | (2006.01) |
| *A61K 31/41* | (2006.01) |
| *A61K 47/54* | (2017.01) |
| *A61P 13/12* | (2006.01) |
| *A61K 31/197* | (2006.01) |
| *C07C 233/49* | (2006.01) |
| *C07C 247/12* | (2006.01) |
| *C07D 257/06* | (2006.01) |
| *C40B 40/04* | (2006.01) |
| *C07K 14/72* | (2006.01) |
| *C40B 30/04* | (2006.01) |
| *G01N 33/92* | (2006.01) |
| *C07D 257/04* | (2006.01) |

(52) U.S. Cl.
CPC .......... *A61K 31/41* (2013.01); *A61K 31/197* (2013.01); *A61K 31/201* (2013.01); *A61K 47/542* (2017.08); *A61P 13/12* (2018.01); *C07C 59/42* (2013.01); *C07C 233/49* (2013.01); *C07C 247/12* (2013.01); *C07D 257/04* (2013.01); *C07D 257/06* (2013.01); *C07K 14/723* (2013.01); *C40B 30/04* (2013.01); *C40B 40/04* (2013.01); *G01N 33/92* (2013.01); *G01N 2333/705* (2013.01); *G01N 2500/00* (2013.01)

(58) Field of Classification Search
CPC ...... A61K 31/201; C07C 57/00; C07C 59/00; C07C 59/42
See application file for complete search history.

(56) References Cited

U.S. PATENT DOCUMENTS

| | | | |
|---|---|---|---|
| 4,035,405 A | 7/1977 | Bodor et al. | |
| 4,055,634 A | 10/1977 | Brenner et al. | |
| 4,094,983 A | 6/1978 | Bodor | |
| 4,138,581 A | 2/1979 | Minatoya et al. | |
| 4,145,441 A | 3/1979 | Bodor | |
| 4,275,219 A | 6/1981 | Zupan | |
| 4,289,547 A | 9/1981 | King et al. | |
| 4,775,662 A | 10/1988 | Gleason et al. | |
| 5,190,782 A | 3/1993 | Yarger et al. | |
| 5,652,247 A | 7/1997 | Ogawa et al. | |
| 6,136,778 A | 10/2000 | Kamiya | |
| 6,323,166 B1 | 11/2001 | Kamiya | |
| 6,395,781 B1 | 5/2002 | Roman et al. | |
| 6,462,054 B1 | 10/2002 | Boger | |
| 7,018,965 B2 | 3/2006 | Yan et al. | |
| 7,732,470 B2 | 6/2010 | Imig et al. | |
| 8,889,716 B2 | 11/2014 | Prime et al. | |
| 2004/0029207 A1 | 2/2004 | Marnett et al. | |
| 2004/0132820 A1 | 7/2004 | Gosselin et al. | |
| 2008/0287548 A1 | 11/2008 | Anziano | |

(Continued)

FOREIGN PATENT DOCUMENTS

| | | | |
|---|---|---|---|
| EP | 0 032 725 B1 | 5/1985 | |
| EP | 0 099 572 B1 | 9/1989 | |

(Continued)

OTHER PUBLICATIONS

PubChem compound CID 59672023; Aug. 20, 2012; p. 4, p. 6; https://pubchem.ncbi.nim.nih.gov/compound/59672023#section=Top.
PubChem compound CID 58805823; Aug. 19, 2012; p. 3, p. 5; https://pubchem.ncbi.nim.nih.gov/compound/58805823#section=Names-and-Identifiers.

(Continued)

*Primary Examiner* — Theodore R. Howell
(74) *Attorney, Agent, or Firm* — Dentons US LLP

(57) ABSTRACT

The present invention concerns compounds and their use to treat cardiovascular disease, renal disease, thrombic disease, stroke, metabolic syndrome, cell proliferation, and ischemic cardiovascular disorders. Compounds of the present invention display significant potency as antagonists of 20-hydroxyeicosatetraenoic acid (20-HETE), and function as antihypertensive, anti-inflammatory, or anti-growth agents.

28 Claims, 19 Drawing Sheets

Specification includes a Sequence Listing.

(56) References Cited

U.S. PATENT DOCUMENTS

| | | | |
|---|---|---|---|
| 2008/0306155 | A1 | 12/2008 | Roman et al. |
| 2009/0215895 | A1 | 8/2009 | Ferrante et al. |
| 2010/0184033 | A1 | 7/2010 | West et al. |
| 2011/0277043 | A1 | 11/2011 | Senger et al. |
| 2012/0021519 | A1 | 1/2012 | Ichida et al. |
| 2012/0122972 | A1 | 5/2012 | Schunck et al. |
| 2013/0302247 | A1 | 11/2013 | Pichika et al. |
| 2014/0113884 | A1 | 4/2014 | Imig et al. |
| 2014/0200191 | A1 | 7/2014 | Henry |
| 2015/0086694 | A1 | 3/2015 | Shi et al. |
| 2015/0250882 | A1 | 9/2015 | Reslow et al. |
| 2015/0252290 | A1 | 9/2015 | Snead et al. |

FOREIGN PATENT DOCUMENTS

| | | | |
|---|---|---|---|
| WO | 1994/001113 | A1 | 1/1994 |
| WO | 1996/13507 | A1 | 5/1996 |
| WO | 1997/38688 | A1 | 10/1997 |
| WO | 1999/059964 | A1 | 11/1999 |
| WO | 2001/021172 | A1 | 3/2001 |
| WO | 2002/059072 | A2 | 8/2002 |
| WO | 2003/024390 | A2 | 3/2003 |
| WO | 2004/080389 | A2 | 9/2004 |
| WO | 2004/108941 | A1 | 12/2004 |
| WO | 2005/073164 | A1 | 8/2005 |
| WO | 2006/044381 | A2 | 4/2006 |
| WO | 2007/054429 | A1 | 5/2007 |
| WO | 2011/073294 | A1 | 6/2011 |
| WO | 2012/058298 | A1 | 5/2012 |
| WO | 2012/065745 | A1 | 5/2012 |
| WO | 2012/138706 | A1 | 10/2012 |
| WO | 2012/153254 | A1 | 11/2012 |
| WO | 2012/156920 | A1 | 11/2012 |
| WO | 2014/060512 | A1 | 4/2014 |
| WO | 2014/143620 | A1 | 9/2014 |
| WO | 2014/152809 | A2 | 9/2014 |

OTHER PUBLICATIONS

International Search Report and Written Opinion for PCT/US2017/021419, dated Jul. 7, 2017.

Boger, et al., "Exceptionally Potent Inhibitors of Fatty Acid Amide Hydrolase: The Enzyme Responsible for Degradation of Endogenous Oleamide and Anandamide," Proceedings of the National Academy of Sciences of the United States of America 97(10):5044-5049 (2000).

Easton, et al., "Oxidation of Oxa and Thia Fatty Acids and Related Compounds Catalyzed by 5- and 15-Tipoxygenase," Bioorganic & Medicinal Chemistry 9(2):317-322 (2001).

Falck, et al., "Arachidonate Epoxygenase: Inhibitors and Metabolite Analogues," Tetrahedron Letters 26(19):2287-2290 (1985).

Grapov, et al., "Type 2 Diabetes Associated Changes in the Plasma Non-Esterified Fatty Acids, Oxylipins and Endocannabinoids," PLoS One 7(11):e48852 (2012).

Grazia Cascio, et al., "A Structure-Activity Relationship Study on N-Arachidonoyl-amino Acids as Possible Endogenous Inhibitors of Fatty Acid Amide Hydrolase," Biochemical and Biophysical Research Communications 314(1):192-196 (2004).

Hamilton, et al., "Fluorofatty Acids in Seed Oil of Dichapetalum toxicarium," Phytochemistry 44(6):1129-1132 (1997).

Ivanov, et al., "Enantioselective Substrate Specificity of 15-Lipoxygenase 1," Biochemistry 43(50):15720-15728 (2004).

Jacobs, et al., "Tissue Protection and Endothelial Cell Signaling by 20-HETE Analogs in Intact Ex Vivo Lung Slices," Experimental Cell Research 318(16):2143-2152 (2012).

Kwok, et al., "Enzymatic Conversions of 10,10-difluoroarachidonic Acid with PGH Synthase and Soybean Lipoxygenase," Journal of the American Chemical Society 109(12):3692-3698 (1987).

Kowk, et al., "Total Synthesis of 7,7-, 10,10-, and 13,13-difluoroarachidonic Acids," Journal of the American Chemical Society 109(12):3684-3692 (1987).

Nagatsugi, et al., "20-[18F]Fluoroarachidonic Acid: Tissue Biodistribution and Incorporation Into Phospholipids," Biological & Pharmaceutical Bulletin 19(10):1316-1321 (1996).

Regner, et al., "Protective Effect of 20-HETE Analogues in Experimental Renal Ischemia Reperfusion Injury," Kidney International 75(5):511-517 (2009).

Snider, et al., "Anandamide Metabolism by Human Liver and Kidney Microsomal Cytochrome p450 Enzymes to Form Hydroxyeicosatetraenoic and Epoxyeicosatrienoic Acid Ethanolamides," Journal of Pharmacology and Experimental Therapeutics 321(2):590-597 (2007).

Taguchi, et al., "Synthesis of 5-fluoroarachidonic Acid and Its Biotransformation to 5-fluoro-12-hydroxyeicosatetraenoic Acid," Chemical & Pharmaceutical Bulletin, 35(4):1666-9 (1987).

Tunctan, et al., "A 20-hydroxyeicosatetraenoic Acid Agonist, N-[20-hydroxyeicosa-5(Z),14(Z)-dienoyl]glycine, Opposes the Fall in Blood Pressure and Vascular Reactivity in Endotoxin-treated Rats," Shock 30(3):329-335 (2008).

Watanabe, et al., "The Synthesis of Paleic Acid, an Antimicrobial Agent Effective Against Mannheimia and Pasteurella, and its Structurally Related Derivatives," Bioorganic & Medicinal Chemistry Letters 20(19):5843-5846 (2010).

* p< 0.05 against Cyp4a14-/- ; # p< 0.05 against Cyp4a14-/- + HFD

20-HETE RECEPTOR (GPR75) ANTAGONISTS AND METHODS OF USE

REFERENCE TO RELATED APPLICATION

This application is a 371 National Stage application of International Application No. PCT/US2017/021419, filed Mar. 8, 2017, which claims the benefit of U.S. provisional application No. 62/305,947, filed Mar. 9, 2016, the entire contents of each which are herein incorporated by reference in their entirety.

STATEMENT OF GOVERNMENT RIGHTS

This invention was, made with Government support under Grant No. HL034300 awarded by the National Institutes of Health. The Government has certain rights in the invention.

INCORPORATION OF SEQUENCE LISTING

A sequence listing containing the file named "UTSW011WO_ST25.txt" which is 13.9 KB (measured in MS-Windows®) and created on Mar. 8, 2017, and comprises 2 sequences, is filed herewith by electronic submission and is incorporated herein by reference in its entirety.

FIELD OF THE INVENTION

The present invention relates generally to the identification of a 20-hydroxyeicosa-5(Z),8(Z),11(Z),14(Z)-tetraenoic acid (20-HETE) receptor as well as molecules with 20-HETE antagonist activity. More particularly, the invention relates to 20-HETE, 19-hydroxyeicosa-5(Z),8(Z),11(Z), 14(Z)-tetraenoic acid (19-HETE), 18-hydroxyeicosa-5(Z),8 (Z),11(Z),14(Z)-tetraenoic acid (18-HETE), and related analogs useful in the treatment of cardiovascular disease, renal disease, thrombotic disease, stroke, obesity, metabolic syndrome, cancer, or tumor growth, methods of synthesis of these compounds, and methods of treatment employing these compounds.

BACKGROUND OF THE INVENTION

20-HETE is a potent vascular constrictor, and functions to increase inflammation, oxidation, growth and angiogenesis in many tissue types. It is also produced in the airways where it serves as an endogenous bronchodilator. Synthesis of 20-HETE is increased in tissues and biological fluids in cardiovascular, cerebral, and renal diseases, including hypertension, stroke, coronary artery disease, myocardial infarction, acute kidney failure, chronic kidney disease, polycystic kidney disease, as well as conditions that are associated with hypertrophy and hyperplasia including tumor growth and metastasis, end-organ damage, and fibrosis.

Molecules which interfere with the biological actions of 20-HETE function as anti-hypertensive, anti-inflammatory, or anti-growth agents in cardiovascular pathologies including vascular stiffening, atherosclerosis, and in disorders of abnormal blood vessels growth including diabetic retinopathy and tumor growth.

Although 20-HETE signaling pathways participate in the progression of a variety of malignancies, the receptor activated by 20-HETE has not previously been identified. Moreover, previously identified antagonists of 20-HETE have exhibited undesirable pharmacological profiles. For example, some extant 20-HETE antagonists are poorly soluble in aqueous and biological milieu, rapidly metabolized, chemically labile, and/or have low efficacy. The present invention therefore provides novel compounds having 20-HETE antagonist activity, an identification of the receptor through which 20-METE signaling occurs, and methods for identifying 20-HETE antagonists useful in the treatment of disease.

SUMMARY OF THE INVENTION

In one aspect, the invention provides a compound of formula I or II:

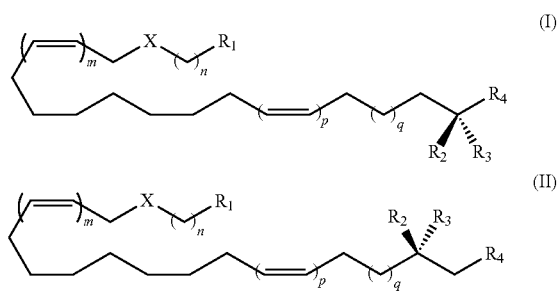

wherein:
$R_2$ is OH when $R_3$ is $C_1$-$C_3$ or H; $R_3$ is OH when $R_2$ is $C_1$-$C_3$ or H; $R_4$ is $C_1$-$C_3$, H, or —$CH_2N_3$ (azide); n is 1 when m is 1; n is 3 when m is 0; q is 1 when p is 1; q is 3 when p is 0; m and p may be 0 and 1, 1 and 0, or 1 and 1, respectively; X is O or C when n is 1; X is C when n is 3.

$R_1$ is $CO_2R_5$, wherein $R_5$ is H or a pharmaceutically acceptable salt, or $C(O)R_6$ where $R_6$=$OR_7$, or $NR_8R_9$, or D-/L-/D,L-α-amino acid (MW<250), or —NHS(O)$_2R_{10}$, or polyethylene glycol (MW<350), or glycerol, or glyceride mono- or diester (MW<800), or carboxylate isosteres or mimetics selected from the group consisting of:
—P(O)(OH)$_2$ or salts thereof
—(O)$_2$OH or salts thereof

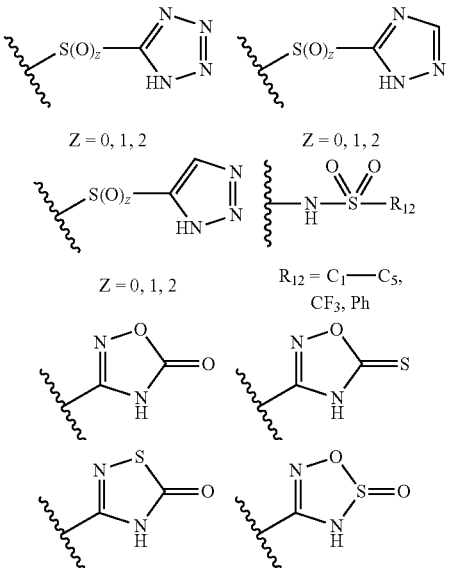

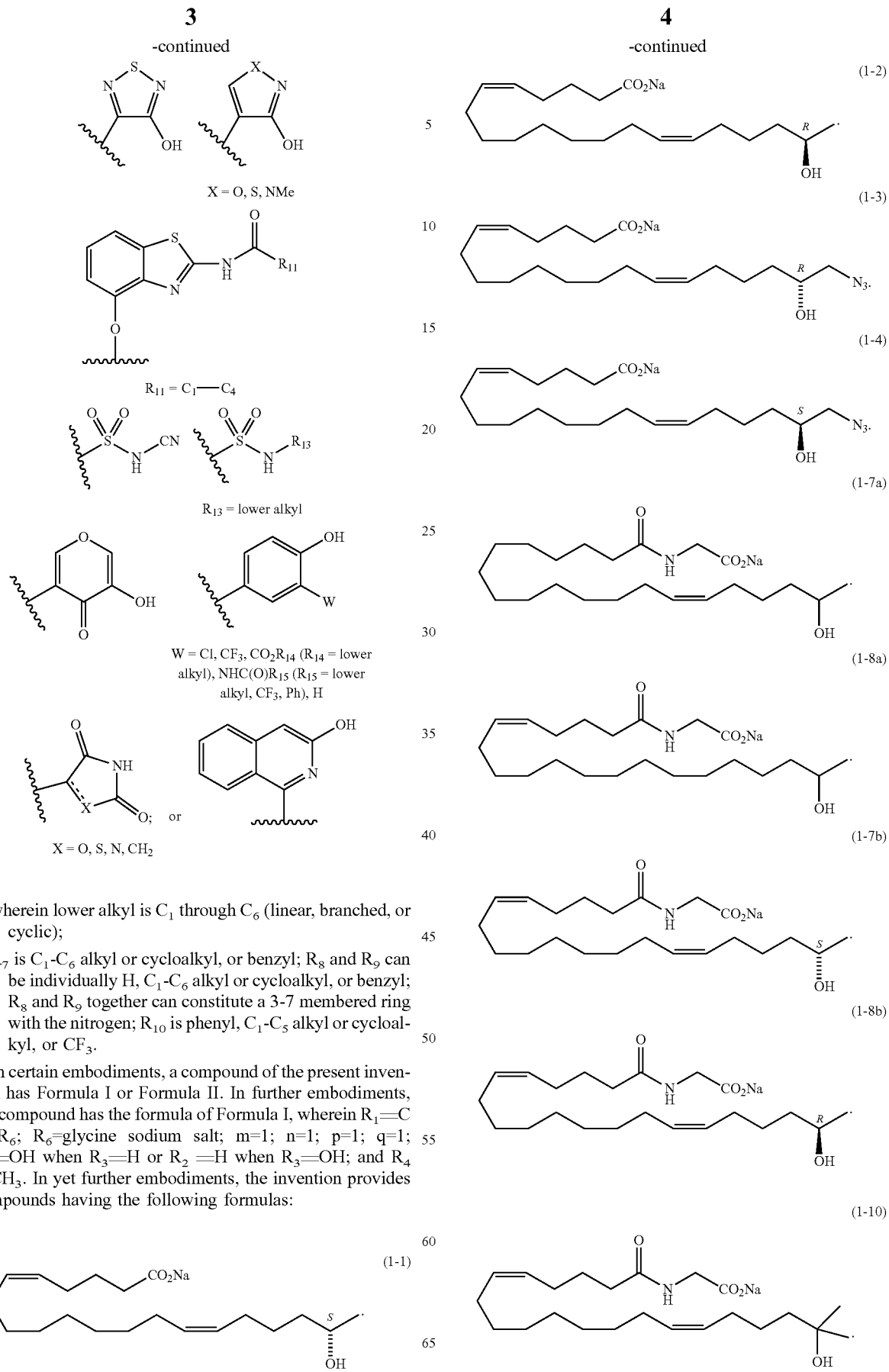

wherein lower alkyl is $C_1$ through $C_6$ (linear, branched, or cyclic);

$R_7$ is $C_1$-$C_6$ alkyl or cycloalkyl, or benzyl; $R_8$ and $R_9$ can be individually H, $C_1$-$C_6$ alkyl or cycloalkyl, or benzyl; $R_8$ and $R_9$ together can constitute a 3-7 membered ring with the nitrogen; $R_{10}$ is phenyl, $C_1$-$C_5$ alkyl or cycloalkyl, or $CF_3$.

In certain embodiments, a compound of the present invention has Formula I or Formula II. In further embodiments, the compound has the formula of Formula I, wherein $R_1$=C(O)$R_6$; $R_6$=glycine sodium salt; m=1; n=1; p=1; q=1; $R_2$=OH when $R_3$=H or $R_2$=H when $R_3$=OH; and $R_4$=$CH_3$. In yet further embodiments, the invention provides compounds having the following formulas:

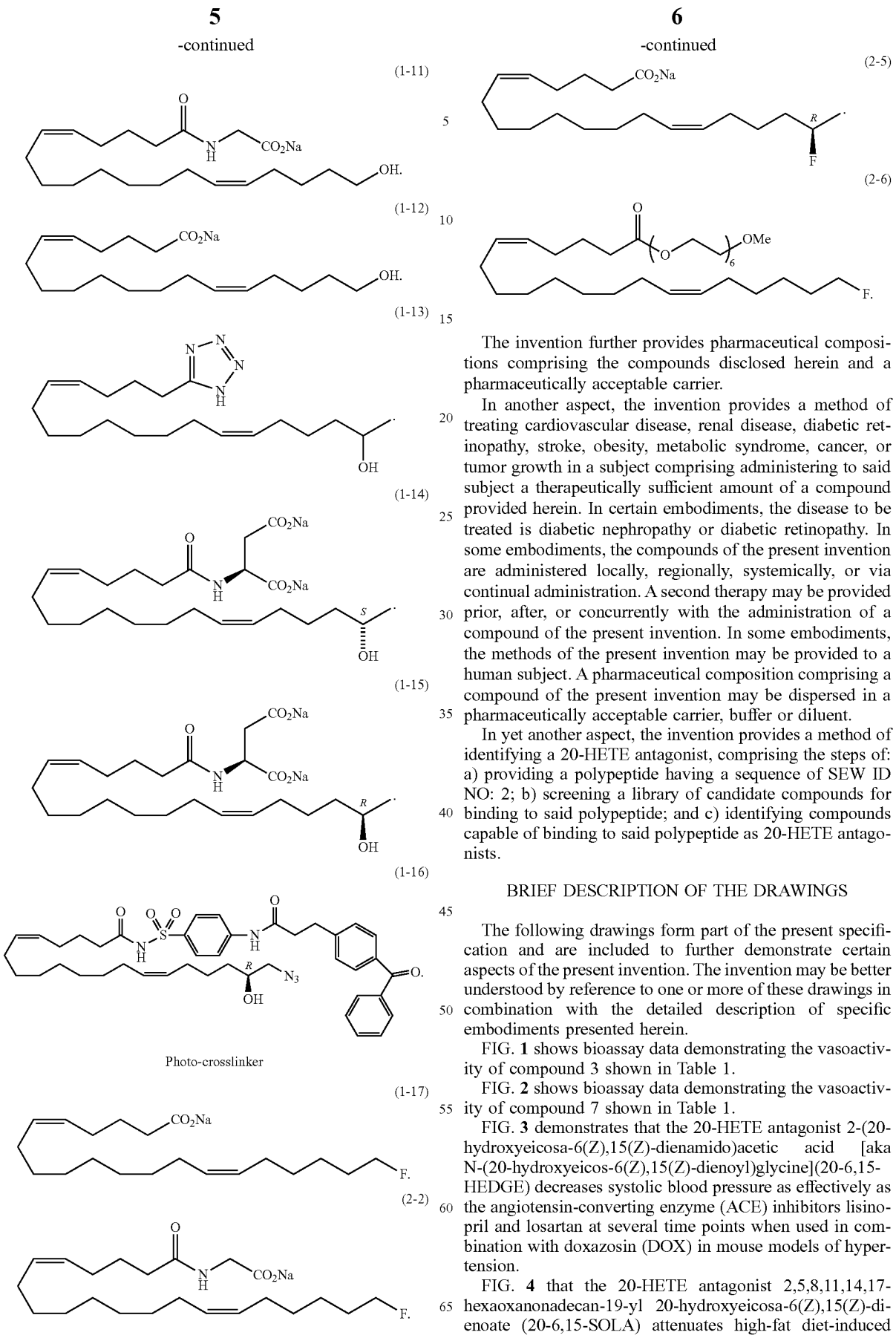

The invention further provides pharmaceutical compositions comprising the compounds disclosed herein and a pharmaceutically acceptable carrier.

In another aspect, the invention provides a method of treating cardiovascular disease, renal disease, diabetic retinopathy, stroke, obesity, metabolic syndrome, cancer, or tumor growth in a subject comprising administering to said subject a therapeutically sufficient amount of a compound provided herein. In certain embodiments, the disease to be treated is diabetic nephropathy or diabetic retinopathy. In some embodiments, the compounds of the present invention are administered locally, regionally, systemically, or via continual administration. A second therapy may be provided prior, after, or concurrently with the administration of a compound of the present invention. In some embodiments, the methods of the present invention may be provided to a human subject. A pharmaceutical composition comprising a compound of the present invention may be dispersed in a pharmaceutically acceptable carrier, buffer or diluent.

In yet another aspect, the invention provides a method of identifying a 20-HETE antagonist, comprising the steps of: a) providing a polypeptide having a sequence of SEW ID NO: 2; b) screening a library of candidate compounds for binding to said polypeptide; and c) identifying compounds capable of binding to said polypeptide as 20-HETE antagonists.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 13 shows that increased production of 20-HETE in the proximal tubules leads to hypertension, a major risk factor for chronic kidney disease.

DETAILED DESCRIPTION

I. Compounds with 20-HETE Antagonist Activity

Figure 1:
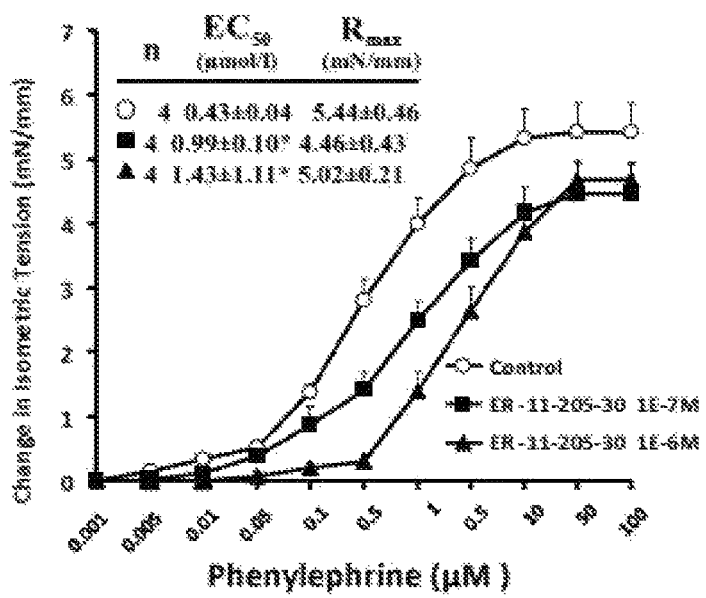
FIG. 1 shows bioassay data demonstrating the vasoactivity of compound 3 shown in Table 1.
Figure 1:
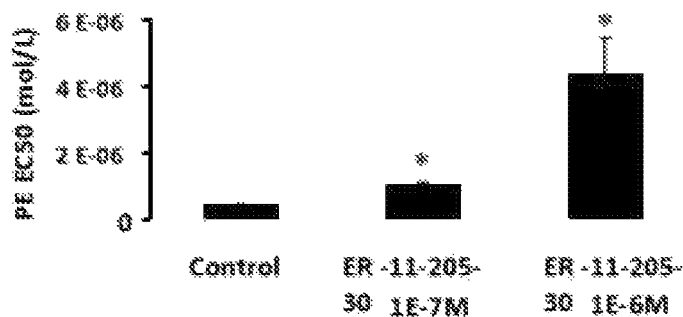

The present invention overcomes limitations in the art by providing compounds that display improved pharmacological profiles (e.g., biostability, bioavailability, enhanced tissue penetration, improved pharmacokinetics, increased potency) when compared with previously-known HETE-20 analogs. Compounds of the invention act as 20-HETE antagonists through a previously unknown receptor, GPR75, to function as anti-hypertensive, anti-inflammatory, anti-thrombotic and/or anti-growth agents. The present invention involves compounds that have utility in the treatment of hypertension and cardiovascular complications including vascular stiffening, atherosclerosis, and in disorders of abnormal blood vessels growth including diabetic retinopathy and tumor growth.

Previous studies have demonstrated that 20-HETE synthesis is increased in tissues and biological fluids in cardiovascular, cerebral, and renal diseases including hypertension, stroke, coronary artery disease, myocardial infarction, acute kidney failure, chronic kidney disease, polycystic kidney disease as well as conditions that are associated with hypertrophy and hyperplasia including tumor growth and metastasis, end-organ damage, and fibrosis. 20-HETE is a potent vascular constrictor, pro-inflammatory, pro-oxidative, pro-growth mediator and pro-angiogenic factor, except in the lung. In certain aspects of the invention, new compounds were synthesized, and in vitro screening revealed that these compounds have 20-HETE antagonist activity. The invention therefore provides molecular antagonistic compounds which interfere with the biological actions of 20-HETE and function as anti-hypertensive, anti-inflammatory, or anti-growth agents in hypertension and cardiovascular complications including vascular stiffening, atherosclerosis, and in disorders of abnormal blood vessels growth including diabetic retinopathy and tumor growth. The invention further comprises the characterization of the previously unknown 20-HETE receptor as GPR75, which mediates the activity of 20-HETE and the novel 20-HETE antagonists disclosed herein.

The present invention provides compounds with 20-HETE antagonist activity for the treatment of cardiovascular, cerebral, and renal diseases. Compounds according to the present invention are shown above, in the summary of the invention, the claims, as well as the examples. Exemplary molecules according to the present invention which exhibit 20-HETE antagonist activity are shown below.

One aspect of the invention comprises compounds of Formula I:

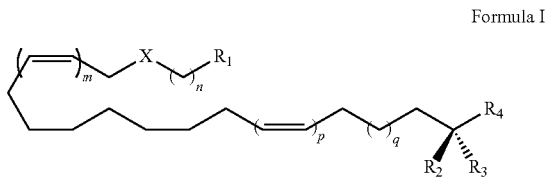

Formula I

In certain aspects of the invention, the chemical structures shown in Formula I may be defined as follows: $R_2$ is OH when $R_3$ is $C_1$-$C_3$, $^1H$ or $^2H$; $R_3$ is OH when $R_2$ is $C_1$-$C_3$, $^1H$, or $^2H$; $R_4$ is $C_1$-$C_3$, $^1H$, $^2H$, or —$CH_2N_3$ (azide); n is 1 when m is 1; n is 3 when m is 0; q is 1 when p is 1; q is 3 when p is 0; m and p may be 0 and 1, 1 and 0, or 1 and 1, respectively; X is O or C when n is 1; X is C when n is 3.

$R_1$ is $CO_2R_5$, wherein $R_5$ is H or a pharmaceutically acceptable salt, or $C(O)R_6$ where $R_6$=$OR_7$, or $NR_8R_9$, or D-/L-/D,L-α-amino acid (MW<250), or —NHS(O)$_2R_{10}$, or polyethylene glycol (MW<350), or glycerol, or glyceride mono- or diester (MW<800), or carboxylate isosteres or mimetics selected from, but not restricted to, the group consisting of.

—P(O)(OH)$_2$ or salts thereof

S(O)$_2$OH or salts thereof

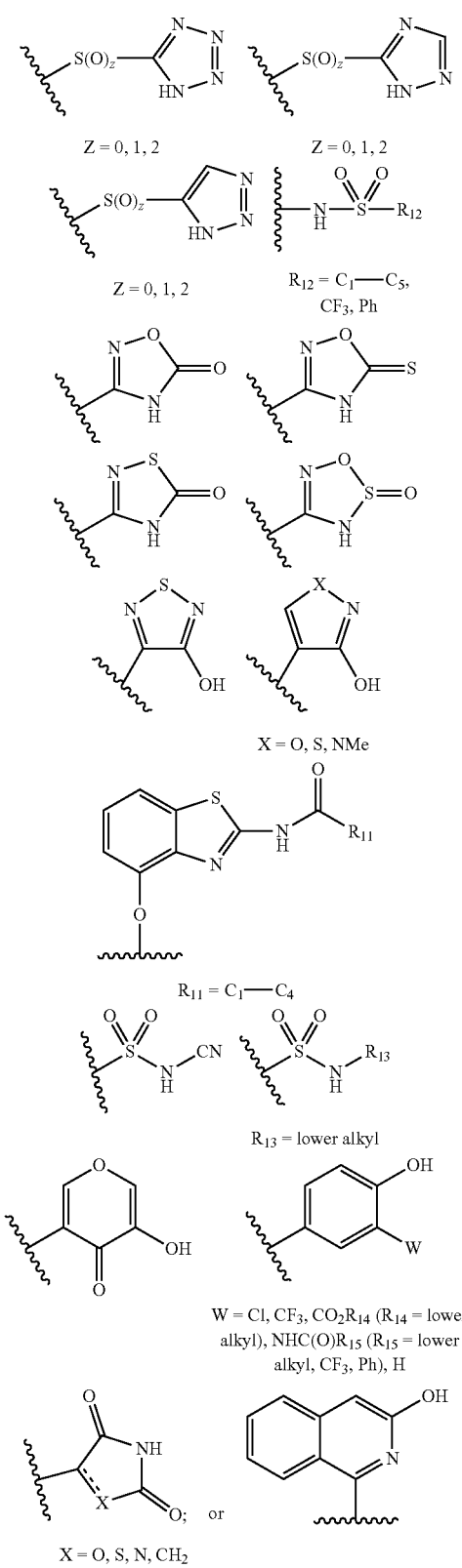

wherein lower alkyl is $C_1$ through $C_6$ (linear, branched, or cyclic).

$R_7$ is $C_1$-$C_6$ alkyl or cycloalkyl, or benzyl; $R_8$ and $R_9$ can be individually H, $C_1$—C alkyl or cycloalkyl, or benzyl; $R_8$ and $R_9$ together can constitute a 3-7 membered ring incorporating the nitrogen; $R_{10}$ is phenyl, $C_1$-$C_5$ alkyl or cycloalkyl, or $CF_3$.

Another aspect of the invention comprises compounds of Formula II:

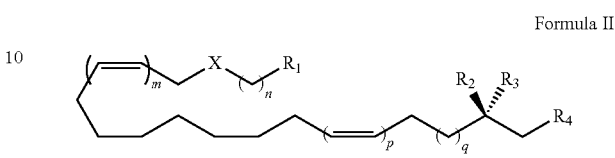

Formula II

In certain aspects of the invention, the chemical structures shown in Formula II may be defined as follows: $R_2$ is OH when $R_3$ is $C_1$-$C_3$ or H; $R_3$ is OH when $R_2$ is $C_1$-$C_3$ or H; $R_4$ is $C_1$-$C_3$, H, or —$CH_2N_3$ (azide); n is 1 when m is 1; n is 3 when m is 0; q is 1 when p is 1; q is 3 when p is 0; m and p may be 0 and 1, 1 and 0, or 1 and 1, respectively; X is O or C when n is 1; X is C when n is 3.

$R_1$ is $CO_2R_5$, wherein $R_5$ is H or a pharmaceutically acceptable salt, or $C(O)R_6$ where $R_6$ =$OR_7$, or $NR_8R_9$, or D-/L-/D,L-α-amino acid (MW<250), or —$NHS(O)_2R_{10}$, or polyethylene glycol (MW<350), or glycerol, or glyceride mono- or diester (MW<800), or carboxylate isosteres or mimetics selected from, but not restricted to, the group consisting of:

—$P(O)(OH)_2$ or salts thereof

—$(O)_2OH$ or salts thereof

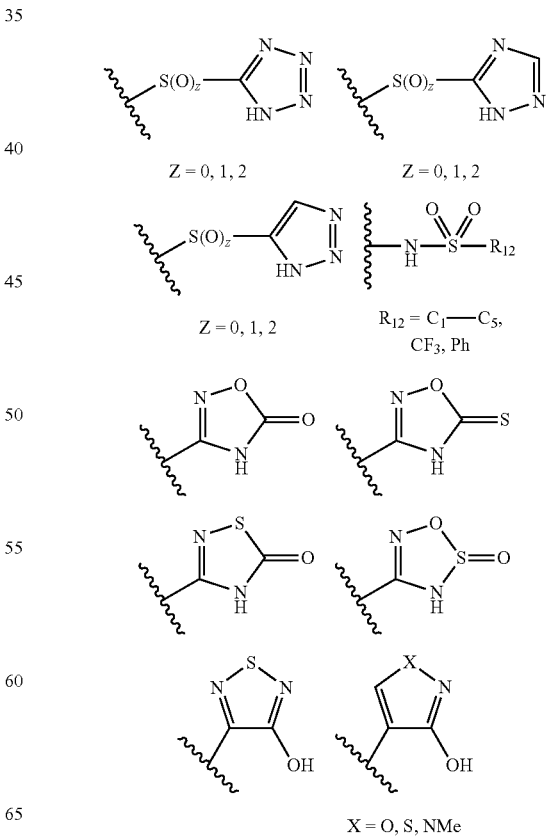

-continued

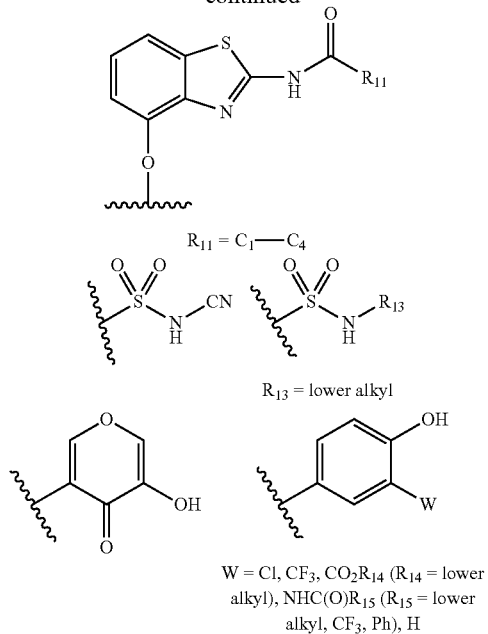

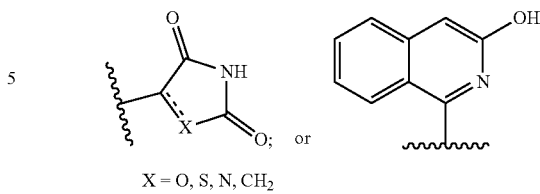

X = O, S, N, CH$_2$ wherein lower alkyl is C$_1$ through C$_6$ (linear, branched, or cyclic).

R$_7$ is C$_1$-C$_6$ alkyl or cycloalkyl, or benzyl; R$_8$ and R$_9$ can be individually H, C$_1$-C$_6$ alkyl or cycloalkyl, or benzyl; R$_8$ and R$_9$ together can constitute a 3-7 membered ring incorporating the nitrogen; R$_{10}$ is phenyl, C$_1$-C$_5$ alkyl or cycloalkyl, or CF$_3$.

Other aspects of the invention include pharmaceutically acceptable salts, hydrates, tautomers, and optical isomers of the compounds described above and throughout this application.

Table 1 shows specific examples of compounds provided by the invention.

TABLE 1

| Entry | Analog | Fold Change from 20-HETE |
|---|---|---|
| 1 | | −0.68 |
| 2 | | −0.85 |
| 3 | | −5.69 |
| 4 | | −5.45 |
| 5 | | 0.16 |
| 6 | | 0.50 |

TABLE 1-continued

| Entry | Analog | Fold Change from 20-HETE |
|---|---|---|
| 7 | (structure: fatty acid amide with glycine-CO$_2$Na, diene, S-OH) | −3.46 |
| 8 | (structure: fatty acid amide with glycine-CO$_2$Na, diene, R-OH) | −4.67 |
| 9 | (structure: fatty acid amide with aspartate di-CO$_2$Na, diene, S-OH) | −0.59 |
| 10 | (structure: fatty acid amide with aspartate di-CO$_2$Na, diene, R-OH) | −2.03 |
| 11 | (structure: CO$_2$Na fatty acid with single alkene and OH) | −1.66 |
| 12 | (structure: CO$_2$Na fatty acid with distal alkene and OH) | 0.79 |
| 13 | (structure: amide-glycine-CO$_2$Na with single alkene and OH) | −2.19 |
| 14 | (structure: amide-glycine-CO$_2$Na with distal alkene and OH) | −2.56 |
| 15 | (structure: CO$_2$Na diene with OH at position 19) | −2.17 |

TABLE 1-continued

| Entry | Analog | Fold Change from 20-HETE |
|---|---|---|
| 16 | | −1.13 |
| 17 | | 0.58 |
| 18 | | −1.16 |
| 19 | | −0.68 |
| 20 | | −0.74 |
| 21 | | −0.78 |
| PCL | | −3.28 |

In Table 1, analogs with negative values are 20-HETE antagonists. Analogs with positive values are 20-HETE agonists and are provided for comparative purposes. Table 2 shows further specific examples of compounds provided by the invention.

TABLE 2

| Entry | Analog | Fold increase/ decrese from 20-HETE |
| --- | --- | --- |
| 1 | [structure: fatty acid with CO₂H and terminal F] | −2.41 |
| 2 | [structure: amide with NH-CH₂-CO₂Na and terminal F] | 1.23 |
| 3 | [structure: ester with -O-CH₂-(CH₂)₆-OMe and terminal F] | −6.78 |
| 4 | [structure: CO₂Na with R-configured terminal CHF] | −6.38 |

Some of the compounds in Tables 1 and 2 are shown as single enantiomers or diastereomers. The invention provides for all possible stereoisomers of any of the compounds shown in Formula I and Formula II, and Tables 1 and 2, as well as those described throughout the application. In some embodiments, the compound provided will be a single enantiomer substantially free from other stereoisomers. In other embodiments, the compound will be a mixture of different stereoisomers, wherein each stereoisomer has the same molecular formula. In certain of these embodiments, the invention provides for a racemic mixture of a given molecular formula. Isotopic substitution such as $^2$H for $^1$H is contemplated.

A further aspect of the invention provides a method of treating a disease, including cardiovascular disease, renal disease, thrombic disease, stroke, obesity, metabolic syndrome, cancer, or tumor growth, comprising administering to a subject an amount of a first compound effective to treat the disease, wherein the first compound is one of the compounds the present invention, such as a compound according to Formula I or Formula II as shown in Tables 1 and 2.

Another aspect of the present invention concerns a method of treating a disease, including cardiovascular disease, renal disease, stroke, obesity, metabolic syndrome, cancer, or tumor growth, comprising administering a therapeutically relevant amount of a first compound of the present invention to a subject. In some embodiments, the first compound is of Formula I or Formula II, or the compounds listed in Table 1 or 2. The subject may be a mammal, and the mammal may be a human. The first compound may be comprised in a pharmaceutically acceptable excipient, diluent, or vehicle.

In certain embodiments, 20-HETE activation is reduced in a cell of the subject treated according to the methods of the present invention. The activation of EGFR may be increased in a cell of the subject, and the levels of ACE expression may be increased in a cell of the subject. Administration of a first compound of the present invention to a subject may result in vascular remodeling in the subject. The first compound may be administered in combination with a therapeutically relevant amount of a second compound. The first compound may be administered in combination with a surgery, a radiation therapy, or a gene therapy.

Any embodiment discussed herein with respect to one aspect of the invention applies to other aspects of the invention as well, unless specifically noted.

II. Chemical Definitions

As used herein, the term "amino" means —NH$_2$; the term "nitro" means —NO$_2$; the term "halo" designates —F, —Cl, —Br or —I; the term "mercapto" means —SH; the term "cyano" means —CN; the term "silyl" means —SiH$_3$, and the term "hydroxy" means —OH.

An "alkane" refers to an acyclic branched or unbranched hydrocarbon, in many cases having the general formula C$_n$H$_{2n+2}$. An "alkyl" refers to a univalent group derived from an alkane by removal of a hydrogen atom from any carbon atom thus having the formula —C$_n$H$_{2n+1}$ in many cases. Alkyl groups, either straight-chained or branched chained, may be substituted with additional acyclic alkyl, cycloalkyl, or cyclic alkyl groups. The alkyl group may be heteroatom-substituted or heteroatom-unsubstituted. Preferably, the alkyl group has 1 to 12 carbons. More preferably, it is a lower alkyl having 1 to 7 carbons, more preferably 1 to 4 carbons. An upper alkyl has 8 or more carbon atoms. A "divalent alkyl" refers to a divalent group derived from an alkane by removal of two hydrogen atoms from either the same carbon atom (e.g. methylene, ethylidene, propylidene) or from different carbon atoms (e.g. —C$_2$H$_4$—).

A "cycloalkane" refers to a saturated monocyclic hydrocarbon with or without side chains.

A "cycloalkyl" refers to a univalent group derived from cycloalkane by removal of a hydrogen atom from a ring carbon atom.

The term "heteroatom-substituted," when used to modify a class of organic radicals (e.g. alkyl, aryl, acyl, etc.), means that one, or more than one, hydrogen atom of that radical has been replaced by a heteroatom, or a heteroatom containing group. Examples of heteroatoms and heteroatom containing groups include: hydroxy, cyano, alkoxy, =O, =S, —NO$_2$, —N(CH$_3$)$_2$, amino, or —SH.

The term "heteroatom-unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group heteroatom-substituted. For example, the group —C$_6$H$_4$C≡CH is an example of a heteroatom-unsubstituted aryl group, while —C$_6$H$_4$F is an example of a heteroatom-substituted aryl group.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use-A Handbook (2002), which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse or rat exhibiting hypertension or metabolic syndrome. A patient can be a human suffering from a disease, for example a cardiovascular, renal, or metabolic disease, or cancer.

As used herein, the term "IC$_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastermomer, more preferably 2% of another enantiomer or diastereomer, and most preferably 1% of another enantiomer or diastereomer.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

III. 20-HETE, Vascular Function, and Cardiovascular Disease

In certain embodiments, compounds and methods of the present invention may be used to treat a wide variety of cardiovascular, cerebral, and renal diseases including pathologies such as hypertension, stroke, coronary artery disease, myocardial infarction, acute kidney failure, chronic kidney disease, polycystic kidney disease, and conditions that are associated with hypertrophy and hyperplasia including tumor growth and metastasis, end-organ damage, and fibrosis. The invention includes the characterization of the previously unknown 20-HETE receptor as GPR75, and molecular antagonistic compounds which interfere with the biological actions of 20-HETE and function as anti-hypertensive and/or anti-inflammatory and/or anti-growth agents in hypertension, thrombotic disease and cardiovascular complications including vascular stiffening, atherosclerosis, and in disorders of abnormal blood vessels growth including diabetic retinopathy and tumor growth.

20-HETE participates in the regulation of vascular tone by sensitizing the smooth muscle cells to constrictor stimuli such as angiotensin II, phenylephrine, and endothelin, and contributes to myogenic, mitogenic and angiogenic responses. 20-HETE release is stimulated by angiotensin II, endothelin, and serotonin and is also increased following treatment with NOS inhibitors. The vasoconstrictor action of 20-HETE was first documented in 1988 by Escalante et al., and was determined to be cyclooxygenase-dependent in rat aortic rings. Further studies demonstrated that in the microcirculation including the renal, cerebral, mesenteric and skeletal muscle arterioles, the constrictor activity of 20-HETE is largely cyclooxygenase-independent. 20-HETE can activate protein kinase C (PKC), mitogen activated protein kinase (MAPK), EGFR, and src-type tyrosine kinase, all of which phosphorylate and inhibit the conductance $Ca^{2+}$-activated $K^+$ channels, leading to depolarization and elevation in the cytosolic concentration of $Ca^{2+}$, as well as opening and increasing $Ca^{2+}$ entry through L-type $Ca^{2+}$ channels. 20-HEE alone also increases the conductance of L-type $Ca^{2+}$ channels through activation of PKC. In some blood vessels, 20-HETE acts through Rho-kinase to preserve phosphorylated myosin light chain 20 (MLC20) and to sensitize the contractile apparatus to $Ca^{2+}$. Previous studies have shown that suppression and overexpression of CYP4A proteins in small arteries and arterioles decreases and increases vascular reactivity and myogenic tone, respectively. These effects may contribute to the increase in blood pressure and the development of hypertension seen in experimental models where vascular 20-HETE synthesis is increased.

In addition to acting on the smooth muscle cells, 20-HETE can also act on the endothelium causing endothelial dysfunction which is a feature of hypertension and an early risk factor for cardiovascular disease. A link between 20-HETE levels and endothelial dysfunction has been shown in hypertensive individuals. The present inventors have demonstrated a causative link between the CYP4A-20-HETE pathway and endothelial dysfunction in vitro and in vivo. Additional studies have shown that 20-HETE causes endothelial nitric oxide synthase (eNOS) uncoupling by inhibiting the association of HSP90 with eNOS, leading to reduced NO production and bioavailability and that 20-HETE-mediated eNOS uncoupling and endothelial dysfunction is EGFR-, MAPK- and IkB Kinase (IKK)-dependent. The work of the present inventors implicates 20-HETE as an important determinant of endothelial dysfunction in the microcirculation, adding to the mechanisms underlying the pro-hypertensive effect of 20-HETE.

Vascular wall inflammation plays a key role in the pathogenesis of various diseases including atherosclerosis, cardiovascular disease, and hypertension. Hypertension is known to be associated with an increase in the wall/lumen ratio (W/L) of resistance arteries, and the greatest vascular resistance occurs in the small arteries and arterioles; hence, decrease in the lumen of the small arteries significantly increases resistance. 20-HETE has been identified as a potent pro-inflammatory, pro-oxidative, and angiogenic factor. Work from our laboratory demonstrated that 20-HETE increases oxidative stress and NF-kB activity in vitro and in vivo resulting in vascular inflammation and remodeling.

Recent studies by the present inventors have identified 20-HETE as a potent inducer of angiotensin converting enzyme (ACE) and led to a series of studies showing interactions between the renin-angiotensin system (RAS) and the CYP4A/F-20-HETE. These studies suggested the presence of a feed forward amplification of 20-HETE-induced vascular dysfunction by the RAS and the application of therapeutic strategies for cardiovascular/renal disease that target both systems. The induction of ACE by 20-HETE relies on the activation EGFR, MAPK, IKK and NF-kB signaling. Furthermore, therapies targeted at inhibition of the RAS alone are not adequate for the prevention of several of biological actions of 20-HETE and thus do not prevent 20-HETE-mediated microvascular remodeling. Additional studies by the present inventors suggest that a combination therapy ACE inhibitors I or angiotesin receptor blockers (ARBs) with 20-HETE antagonists may be beneficial to prevent hypertension-related cardiovascular complications.

IV. 20-HETE and Adipogenesis

A recent study by the present inventors has identified 20-METE as an adipogenic factor in vitro. In clinical studies, serum levels of 20-HETE have been found to directly correlate with body mass index (BMI) and the metabolic syndrome. These findings indicate that 20-HETE functions as a lipid mediator that regulates adipogenesis and thereby adiposity.

V. 20-HETE and Androgen-Related Disorders

Androgen has been implicated as a contributing factor to gender-specific differences in blood pressure and cardiovascular morbidity, postmenopausal hypertension, and to the pathogenesis of polycystic ovary diseases. Studies by the present inventors have identified 20-METE as the mediator of androgen-dependent hypertension and cardiovascular complications. It was also found that 20-HETE levels are highly elevated in human prostate cancer cell lines and these levels are subjected to regulation by androgen; moreover, inhibition of 20-HETE biosynthesis or blockade of its actions inhibited cancer cell and tumor growth. Studies by the present inventors therefore suggest that targeting 20-HETE may spare the beneficial effects of androgen while abrogating androgen-related hypertension, cardiovascular/renal complications and tumor growth.

VI. The 20-HETE Receptor: GPR75

Despite its role in many significant physiological processes, the receptor through which 20-HETE and its agonists and antagonists signal has not previously been identified.

The present invention demonstrates for the first time that 20-HETE activates a G protein-coupled receptor, GPR75, previously classified as an orphan receptor. The present invention demonstrates the pairing of 20-HETE-GPR75 and indicates that 20-HETE signals through GPR75 in the vasculature. Activation of GPR75 by 20-HETE promotes a G protein-independent GIT1-c-Src-dependent trans activation of EGFR resulting in a signaling cascade which promotes increases in vascular endothelial ACE expression. Furthermore GPR75-mediated signaling promotes vascular remodeling therefore molecular compounds such as the compounds of the present invention, which target the 20-HETE receptor, are anticipated to be active in the treatment of several cardiovascular pathologies. The nucleotide sequence of GPR75 is provided herein as SEQ ID NO: 1, and the amino acid sequence of GPR75 is provided herein as SEQ ID NO: 2.

The pairing of 20-HETE with its GPCR elicits a cell-specific signaling pathway leading to specific functional responses. The analogs of the present invention either mimic or block 20-HETE activation of its receptor. In animal models, 20-HETE antagonists interfere with the biological actions of 20-HETE acting as anti-hypertensive, anti-inflammatory, or anti-growth agents in cardiovascular pathologies including vascular remodeling and stiffening, atherosclerosis, and in disorders of abnormal blood vessels growth including diabetic retinopathy and tumor growth. The discovery of 20-HETE receptor provides the molecular basis for the signaling and pathophysiological functions mediated by 20-HETE in cardiovascular diseases and other pathologies.

VII. Therapeutic Use of 20-HETE Antagonists

Based on 20-HETE bioactivities in vitro and in vivo, it is anticipated that compounds of the present invention may be used alone or in combination with other therapeutic agents in the treatment of the following conditions:

Cardiovascular Disease

As described above, 20-HETE has several detrimental effects on the vasculature including increases in vascular tone, endothelial dysfunction, vascular inflammation and vascular wall remodeling; all of which underlie the pathogenesis and/or complications of cardiovascular diseases including hypertension, atherosclerosis, myocardial infarction, stroke, coronary artery diseases. The compounds of the present invention may be used alone or in combination with other agents to treat or prevent cardiovascular disease.

Renal Disease

20-HETE has been implicated as a causative factor in renal tissue injury in acute and chronic diseases. Inhibition of 20-HETE synthesis alleviates tissue fibrosis. The compounds of the present invention may be used alone or in combination with other agents to treat or prevent renal disease, including diabetic nephropathy.

Diabetic Retinopathy

Diabetic retinopathy is classified as a microvascular disease, and is characterized by microaneurysms, hemorrhages, pericyte loss, increased microvascular permeability, exudates, capillary basement membrane thickening, capillary occlusion, shunts, venous beading, edema, and neovascularization. 20-HETE is a lipid mediator of the microcirculation including the cerebral microcirculation. A recent study showed that inhibition of 20-HETE synthesis attenuated retinal hemodynamic changes induced by diabetes. The present inventors have shown that 20-HETE is angiogenic and as such can contribute to neovascularization of the retina. In addition, GPR75, the 20-HETE receptor, is highly expressed in retinal microvessels. Thus, the 20-HETE antagonists of the present invention are beneficial in treating diabetic retinopathy based on blockage of 20-HETE-mediated endothelial activation (inflammation, proliferation, angiogenesis) as well as thrombosis Stroke 20-HETE has been shown to constrict cerebral microvessels and inhibition of its synthesis prevents brain damage in a rat model of stroke. The compounds of the present invention may be used alone or in combination with other agents to treat or prevent stroke.

Obesity/Metabolic Syndrome

Studies by the present inventors have demonstrated that 20-HETE is adipogenic in vitro and that its serum levels correlate with obesity in human. Moreover, in obese metabolic syndrome mice demonstrated that blocking 20-HETE actions reduces adiposity, body weight, blood glucose and insulin resistance. The compounds of the present invention may be used alone or in combination with other agents to treat or prevent obesity or metabolic syndrome.

Cancer/Tumor Growth

Studies by the present inventors and others have shown that 20-HETE is produced by various cancer cells and serves to promote growth of cancer cells as well as growth of tumors. The compounds of the present invention may be used alone or in combination with other agents to treat or prevent cancers and tumor growths.

Ischemic Cardiovascular Disorders

Tissue ischemia is a common feature of many of the conditions in which neovascular growth is observed. Chronic exercise, coronary artery disease and myocardial infarction are all conditions that initiate with ischemia. The growth of blood vessels (collateralization) is a well-documented physiological response to myocardial infarction. Several Investigations have demonstrated the presence and release of angiogenic factors such as 20-HETE, by ischemic cardiac tissues and suggested that it may function in the initiation and/or potentiation of coronary collateral formation. 20-HETE is such a factor. Not only does it have the biological activities of a potent tissue-derived angiogenic factor but also there is evidence to suggest its formation in the skeletal muscle following ischemic/hypoxic injury and its ability to stimulate VEGF formation. It is therefore anticipated that the compounds of the present invention may be used alone or in combination with other agents to treat or prevent ischemic cardiovascular disease based on the angiogenic properties of 20-HETE. Stimulation of collateral formation could result in the protection and improvement of function of critically ischemic areas surrounding the infracted area. In addition, acceleration of angiogenesis within the infarct will facilitate fibrous healing which may be impaired due to inadequate blood supply (lack of oxygenation and nutrition of fibroblasts). Thus, therapeutic interventions such as local delivery of the 20-HETE antagonists of the present invention alone or in combination with other angiogenic factors, may be beneficial for such conditions.

Thrombotic Events

Recent studies indicated that in endothelial cells 20-HETE induces the expression TAFI, thrombin-activated fibrinolysis inhibitor, by 2-3 fold. This finding suggests that 20-HETE antagonists will be beneficial in promoting fibrinolysis of clots and preventing thrombotic incidences.

VIII. Pharmaceutical Compositions

The compounds of the present invention can be administered to interfere with the biological actions of 20-HETE and function as anti-hypertensive, anti-inflammatory, or anti-growth agents, by any method that allows contact of the active ingredient with the agent's site of action in a cell. They can be administered by any conventional methods available for use in conjunction with pharmaceuticals, either as individual therapeutically active ingredients or in a combination of therapeutically active ingredients. They can be administered alone but are generally administered with a pharmaceutically acceptable carrier selected on the basis of the selected route of administration and standard pharmaceutical practice.

Aqueous compositions of the present invention will have an effective amount of the compounds to function as anti-hypertensive, anti-inflammatory, or anti-growth agents. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-hypertensive, anti-inflammatory, or anti-growth agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including creams, lotions, mouthwashes, inhalants, lipid carriers, liposomes and the like.

Parenteral Administration

The active compounds will often be formulated for parenteral administration, e.g., formulated for injection via the intravenous, intramuscular, subcutaneous, or even intraperitoneal routes. The preparation of an aqueous composition that contains a 20-HETE antagonist of the present invention as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some forms, it will be desirable to formulate the compounds in salt form, generally to improve the solubility and bioavailability and to provide an active drug form more readily assimilated. As used herein, the term "pharmaceutically acceptable salt" refers to compounds which are formed from acidifying a 20-HETE antagonist solution of the invention with suitable physiologically tolerated acids. Suitable physiologically tolerated acids are organic and inorganic acids, such as hydrochloric acid, sulfuric acid, phosphoric acid, acetic acid, citric acid, oxalic acid, malonic acid, salicylic acid, maleic acid, methane sulfonic acid, isothionic acid lactic acid, gluconic acid, glucuronic acid, amidosulfuric acid, benzoic acid, tartaric acid and pamoaic acid. Typically, such salt forms of the active compound will be provided or mixed prior to use.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts and which are formed with inorganic acids such as, for example, hydrochloric or phosphoric acids, or such organic acids as acetic, oxalic, tartaric, mandelic, and the like.

The compounds of the present invention may also be formulated into a composition comprising liposomes or any other lipid carrier. Liposomes include: multivesicular liposomes, multilamellar liposomes, and unilamellar liposomes.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In certain cases, the therapeutic formulations of the invention could also be prepared in forms suitable for topical administration, such as in creams and lotions. These forms may be used for treating skin-associated diseases.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this regard, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

IX. Therapies

One way of achieving this is by combining new drugs with the traditional therapies.

In the context of the present invention, it is contemplated that the novel 20-HETE antagonist compounds provided by the invention could be used in combination with new or existing pharmaceutical agents, surgery, chemotherapy, radiotherapy, and/or gene therapy.

An "effective amount" or a "therapeutically relevant amount" are those amounts of a compound sufficient to produce a therapeutic benefit (e.g., effective to function as anti-hypertensive and/or anti-inflammatory and/or anti-growth agent). An effective amount, in the context of treating a subject, is sufficient to produce a therapeutic benefit. The term "therapeutic benefit" as used herein refers to anything that promotes or enhances the well-being of the subject with respect to the medical treatment of the subject's disease. A nonexhaustive list of examples of therapeutic benefits includes extension of the patients life by any period of time; decrease or delay in development of disease; decrease in hypertension; decrease in inflammation; decrease in cell growth or proliferation; and/or a decrease in pain to the subject that can be attributed to the patient's condition.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

As used herein, predominantly one enantiomer or substantially free from other optical isomers means that the compound contains at least 95% of one enantiomer, or more preferably at least 98% of one enantiomer, or most preferably at least 99% of one enantiomer.

Other objects, features and advantages of the present invention will become apparent from this detailed description and examples provided below. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Methods for Synthesis of 20-HETE Analogs

Molecules with 20-HETE antagonist or agonist activity were synthesized using the following methods. A person of skill in the art would understand that 20-HETE analogs according to the present invention could be produced according to various methods known in the art given the disclosure of the present application.

General Methods and Materials

Nuclear magnetic resonance (NMR) spectra were recorded $CDCl_3$ with TMS as internal standard, unless otherwise stated. $^1H$ NMR data are reported as follows: chemical shift (ppm), multiplicity (s=singlet, br s=broad singlet, d=doublet, t=triplet, q=quartet, app q=apparent quartet, qn=quintet, app qn=apparent quintet, m=multiplet) and coupling constant (Hz). Analytical thin layer chromatography (TLC) used EMD Chemicals TLC silica gel 60 F254 plates (0.040-0.063 mm) with visualization by UV light and/or $KMnO_4$ or phosphomolybdic acid (PMA) solution followed by heating. All oxygen and/or moisture sensitive reactions were performed under an argon atmosphere using oven-dried glassware and anhydrous solvents. Extracts were dried over anhydrous $Na_2SO_4$ and filtered prior to removal of all volatiles under reduced pressure. Chromatographic purifications utilized preparative TLC or flash chromatography using pre-packed $SiO_2$ columns on a CombiFlash® $R_f$200 chromatograph (Teledyne Isco). Unless otherwise noted, yields refer to isolated, purified material with spectral data consistent with assigned structures or, if known, were in agreement with published data. Reagents were purchased at the highest commercial quality available and used without further purification, unless otherwise noted. Anhydrous solvents were dried using a Glass Contours Solvent System by passage through columns of activated packing material under argon immediately prior to use.

Analog 1:
19(S)-Hydroxyeicosa-5(Z),14(Z)-dienoate

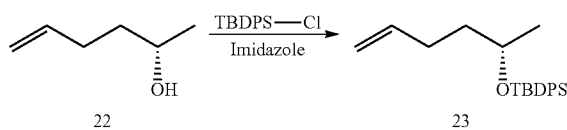

Imidazole (750 mg, 11 mmol) and TBDPS-Cl (2.74 g, 10 mmol) were added to a solution of commercial (S)-hex-5-en-2-ol (22) (500 mg, 5 mmol; Aldrich, 99.3% ee) in dry $CH_2Cl_2$ (15 mL). After stirring at room temperature for 16 h, the solution was washed with water (2×15 mL), brine (15 mL), and the organic layer was dried with $Na_2SO_4$, then concentrated in vacuo. The residue was purified by $SiO_2$ column chromatography using hexanes/EtOAc (10:1) to give (S)-tert-butyl(hex-5-en-2-yloxy)diphenylsilane (23) (1.4 g, 82%) as a colorless oil whose spectral data were in agreement with literature values (Gajul, et al., *Org. Biomol. Chem.* 2013, 11, 257-260). TLC: $SiO_2$, EtOAc/hexane (1:4), $R_f$=0.65.

$^1H$ NMR ($CDCl_3$, 500 MHz) δ 7.69 (dd, J=1.6, 7.6 Hz, 4H), 7.44-7.38 (m, 6H), 5.75-5.73 (m, 1H), 4.98-4.90 (m, 2H), 3.91-3.88 (m, 1H), 2.11-2.07 (m, 2H), 1.61-1.52 (m, 2H), 1.10-1.07 (m, 12H).

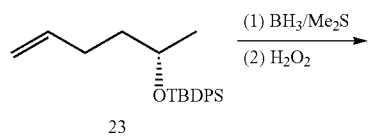

Neat $BH_3·Me_2S$ (225 mg, 3 mmol) was added dropwise to a 0° C. solution of (S)-tert-butyl(hex-5-en-2-yloxy)diphenylsilane (23) (500 mg, 1.5 mmol) in dry THF (15 mL). After stirring at rt for 6 h, the reaction mixture was re-cooled to 0° C., then 30% $H_2O_2$ (4 mL) and aq. NaOH (1.2 mL of 3 M soln) were added slowly. After 1 h at rt, the peroxide was quenched with excess saturated aq. $NaHSO_3$ and the THF was removed under reduced pressure. The remaining aqueous layer was extracted with EtOAc (2×15 mL). The combined extracts were washed with $H_2O$ (2×10 mL), dried, concentrated in vacuo, and the residue was purified via $SiO_2$ chromatography using hexane/EtOAc (10:1) to give (S)-5-(tert-butyldiphenylsilyloxy)hexan-1-ol (24) (358 mg, 68%) as an oil whose spectral data were consistent with literature values (Gajul, et al.). TLC: $SiO_2$, EtOAc/hexane (1:4), $R_f$=0.33.

$^1H$ NMR ($CDCl_3$, 500 MHz) δ 7.69 (dd, J=1.6, 7.6 Hz, 4H), 7.44-7.38 (m, 6H), 3.89-3.83 (m, 1H), 3.58 (t, J=6.5 Hz, 2H), 1.48-1.33 (m, 6H), 1.09-1.07 (m, 12H).

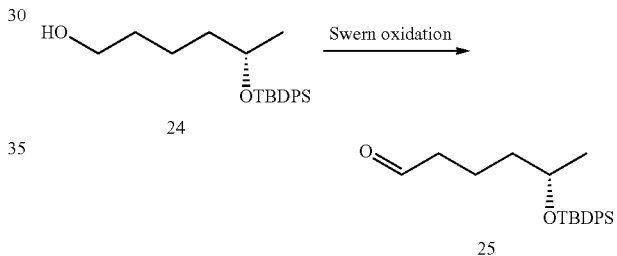

Freshly distilled oxalyl chloride (178 mg, 1.4 mmol) was added to a −78° C. solution of dimethyl sulfoxide (DMSO) (274 mg, 3.51 mmol) in anhydrous $CH_2Cl_2$ (5 mL). After 10 min, (S)-5-(tert-butyldiphenylsilyloxy)hexan-1-ol (24) (250 mg, 0.7 mmol) in $CH_2Cl_2$ (3 mL) was added dropwise. After 1.5 h, triethylamine (355 mg, 3.51 mmol) was added and the mixture was warmed over 30 min to −20° C., then poured into saturated aq. $NaHCO_3$ with vigorous stirring. The organic layer was separated and the aqueous layer was extracted with $CH_2Cl_2$ (2×10 mL). The combined organic phases were washed with brine (15 mL), dried, evaporated, and the residue was purified by $SiO_2$ column chromatography using $CH_2Cl_2$ to give crude (S)-5-(tert-butyldiphenylsilyloxy)hexanal (25) (228 mg, 92%) as an oil whose spectral data were consistent with literature values (Gonzalez, et al., *Tetrahedron Lett.* 1996, 37, 8949-8952; Yu, et al., *Bioorg. Med Chem.* 2003, 11, 2803-2821).

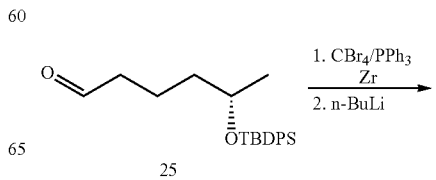

-continued

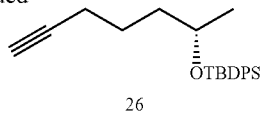

26

CBr₄ (471 mg, 1.41 mmol) was added slowly to a stirring, 0° C. suspension of triphenylphosphine (371 mg, 1.41 mmol) and zinc (92 mg, 1.41 mmol) in CH₂Cl₂ (20 mL). After 16 h at ambient, dry pyridine (10 drops) and the above (S)-5-(tert-butyldiphenylsilyloxy)hexanal (25) (250 mg, 0.71 mmol) in CH₂Cl₂ (10 mL) were added. After 12 h, hexane (20 mL) was added and the mixture was filtered and concentrated under reduced pressure. The crude mass was triturated with hexane (3×30 mL). The combined triturates were filtered and evaporated under reduced pressure to yield (S)-tert-butyl((7,7-dibromohept-6-en-2-yl)oxy)diphenylsilane (254 mg 71%) as an oil which was used immediately in the next step.

¹H NMR (500 MHz, CDCl₃) δ 7.79-7.67 (m, 4H), 7.52-7.44 (m, 6H), 6.37 (t, J=7.2 Hz, 1H), 3.97-3.93 (m, 11H), 2.07 (q, J=7.1 Hz, 2H), 1.64-1.46 (m, 4H), 1.17-1.04 (m, 12H);

¹³C NMR (126 MHz, CDCl₃) δ 138.73, 138.71, 135.97, 135.94, 134.77, 134.46, 129.68, 129.58, 127.67, 127.56, 88.83, 69.17, 38.66, 33.02, 27.19, 23.48, 23.34 19.38.

A solution of n-butyllithium (2.1 mmol, 0.81 mL of a 2.5 M solution in hexanes) was added dropwise to a −50° C. solution of (S)-tert-butyl((7,7-dibromohept-6-en-2-yl)oxy) diphenylsilane (500 mg, 0.98 mmol) in THF (15 mL). After stirring for 1 h at −40° C. and for 30 min at rt, the reaction was quenched with sat. aq. NH₄Cl (5 mL) and extracted with Et₂O (2×25 mL). The combined organic extracts were dried, and concentrated in vacuo. The crude mass was purified by SiO₂ column chromatography using 1% EtOAc/hexanes to afford (S)-tert-butyl(hept-6-yn-2-yloxy)diphenylsilane (26) (228 mg, 66%) as an oil whose spectral data were consistent with literature values (Moune, et al., *J. Org. Chen.* 1997, 62, 3332-3339). TLC: SiO₂, EtOAc/hexane (1:99), R_f=0.7.

¹H NMR (CDCl₃, 500 MHz) δ 7.69 (dd, J=1.6, 7.6 Hz, 4H), 7.39-7.41 (m, 6H), 3.88-3.83 (m, 1H), 2.10-2.08 (m, 2H), 1.92-1.91 (m, 1H), 1.57-1.53 (m, 4H), 1.08-1.04 (m, 12H). HRMS calcd for C₂₃H₃₀NaOSi [M+Na]⁺ 373.1964, found 373.1960.

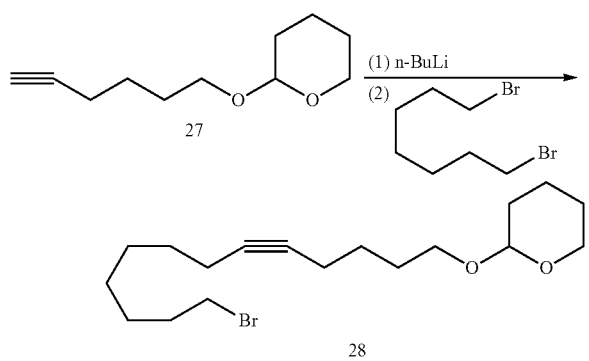

A solution of n-butyllithium (384 mg, 6.0 mmol, 2.4 mL of a 2.5 M solution in hexane) was added dropwise into a −78° C. solution of 2-(hex-5-yn-1-yloxy)tetrahydro-2H-pyran (27)* (1 g, 5.5 mmol) in anhydrous THF/HMPA (4:1, 16 mL) under an argon atmosphere. After 30 min, the reaction mixture was warmed over 1 h to 0° C. and held there for another 2 h. The mixture was re-cooled to −78° C. and a solution of 1,7-dibromoheptane (1.3 g, 5 mmol) in THF (5 mL) was added slowly. The reaction temperature was raised over 3 h to rt. After stirring another 12 h, the reaction mixture was quenched with sat. aq. NH₄Cl (5 mL) and extracted with EtOAc (2×250 mL). The combined organic extracts were washed with water (2×100 mL), brine (100 mL), dried, and then concentrated in vacuo. The crude residue was purified by SiO₂ column chromatography using 10% EtOAc/hexanes to afford 2-((13-bromotridec-5-yn-1-yl)oxy)tetrahydro-2H-pyran (28) (1.2 g, 62%) as an oil whose spectral data were in agreement with literature values (Falck, et al., *J. Med Chen.* 2014, 57, 6965-6972). TLC: SiO₂, EtOAc/hexane (1:9), R_f=0.4.

¹H NMR (400 MHz) δ 4.59-4.58 (m, 1H), 3.87-3.84 (m, 1H), 3.83-3.76 (m, 1H), 3.52-3.49 (m, 1H), 3.42-3.40 (m, 3H), 2.20-2.13 (m, 4H), 1.88-1.85 (m, 4H), 1.72-1.67 (m, 4H), 1.59-1.32 (m, 12H).

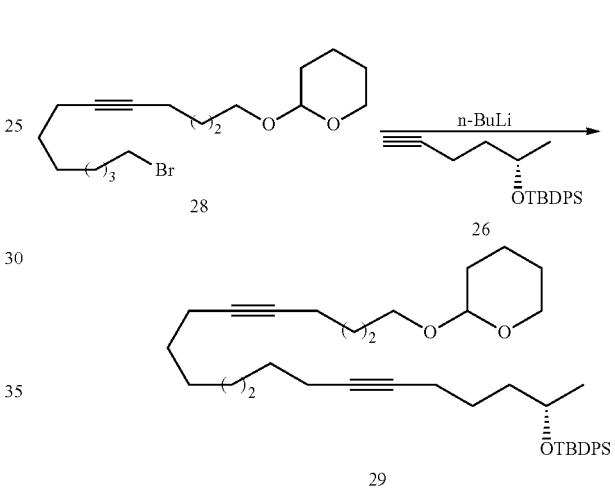

A solution of n-butyllithium (0.34 mL of a 2.5 M solution in hexane, 0.858 mmol) was added dropwise to a stirring, −78° C. solution of (S)-tert-butyl(hept-6-yn-2-yloxy)diphenylsilane (26) (250 mg, 0.71 mmol) in anhydrous THF/HMPA (4:1, 16 mL) under an argon atmosphere. After 30 min, the reaction mixture was warmed over 1 h to 0° C., held there for 2 h, then re-cooled to −78° C. To this was added a solution of 2-((13-bromotridec-5-yn-1-yl)oxy)tetrahydro-2H-pyran (28) (307 mg, 0.857 mmol) in dry THF (5 mL). The reaction temperature was then increased over 3 h to rt. After another 12 h, the reaction was quenched with sat. aq. NH₄Cl (5 mL) and extracted with EtOAc (2×250 mL). The combined organic extracts were washed with water (2×100 mL), brine (100 mL), dried, and concentrated in vacuo. The residue was purified by SiO₂ column chromatography using 10% EtOAc/hexanes to afford tert-butyldiphenyl(((2S)-20-(tetrahydro-2H-pyran-2-yloxy)eicosa-6,15-diyn-2-yl)oxy) silane (29) (323 mg, 72%) as a colorless oil. TLC: SiO₂, EtOAc/hexane (1:10), R_f=0.33. HRMS calcd for C₄₁H₆₀NaO₃Si [M+Na]⁺ 651.4209, found 651.4199.

¹H NMR (CDCl₃, 500 MHz) δ 7.69 (dd, J=1.6, 7.6 Hz, 4H), 7.39-7.41 (m, 6H), 4.61-4.59 (m, 1H), 3.88-3.83 (m, 2H), 3.73-3.70 (m, 1H), 3.50-3.47 (m, 1H), 3.39-3.35 (m, 1H), 2.21-2.07 (m, 8H), 1.73-1.70 (m, 2H), 1.62-1.35 (m, 22H), 1.07-1.06 (m, 12H); ¹³C NMR (101 MHz, CDCl₃) δ 135.14, 135.82, 134.82, 134.41, 129.45, 129.37, 127.46, 127.37, 98.74, 98.71, 80.39, 80.26, 80.00, 79.82, 69.17, 67.02, 62.22, 62.19, 38.59, 33.81, 32.74, 30.75, 29.09, 28.94, 28.75, 28.68, 27.03, 25.94, 25.52, 24.86, 23.22, 19.64, 19.25, 18.80, 18.74, 18.73, 18.69, 18.62.

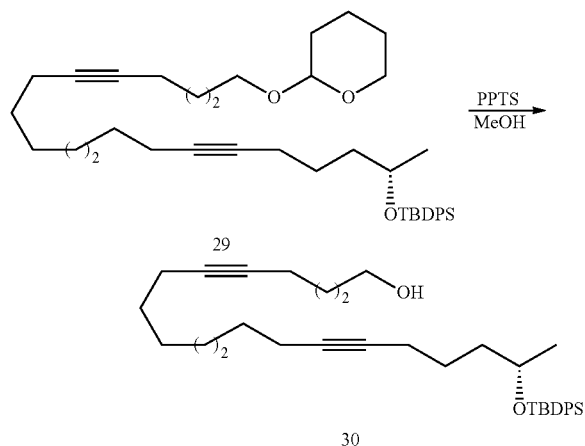

To a stirring, 0° C. solution of tert-butyldiphenyl(((2S)-20-((tetrahydro-2H-pyran-2-yl)oxy)eicosa-6,15-diyn-2-yl)oxy)silane (29) (250 mg, 0.38 mmol) in MeOH (10 mL) was added PPTS (5 mg). After 14 h, the reaction was quenched with sat. aq. NaHCO$_3$ (15 mL) and the methanol was removed under reduced pressure. Water (15 mL) was added and the reaction mixture was extracted with EtOAc (3×20 mL). The combined organic extracts were concentrated under reduced pressure and the residue was purified by SiO$_2$ column chromatography to afford 19(S)-tert-butyldiphenylsilyloxy)eicosa-5,14-diyn-1-ol (30) (142 mg, 68%) as an oil. TLC: 20% EtOAc/hexanes, R$_f$=0.44.

$^1$H NMR (400 MHz, CDCl$_3$) δ 7.70 (dd, J=1.6, 7.6 Hz, 4H), 7.39-7.36 (m, 6H), 3.86-3.85 (m, 1H), 3.67-3.63 (m, 2H), 2.18-2.05 (m, 8H), 1.57-1.36 (m, 18H), 1.09-1.06 (m, 12H); $^{13}$C NMR (126 MHz, CDCl$_3$) δ 136.13, 136.04, 135.82, 135.12, 134.70, 129.79, 129.73, 129.70, 129.66, 127.86, 127.79, 127.75, 127.68, 127.66, 80.93, 80.61, 80.34, 80.04, 69.46, 62.72, 38.87, 32.11, 29.36, 29.35, 29.03, 28.98, 28.95, 27.31, 27.13, 25.63, 25.13, 23.50, 19.55, 19.08, 19.05, 19.01, 19.00, 18.81. HRMS calcd for C$_{36}$H$_{52}$NaO$_2$Si [M+Na]$^+$ 567.3634, found 567.3629.

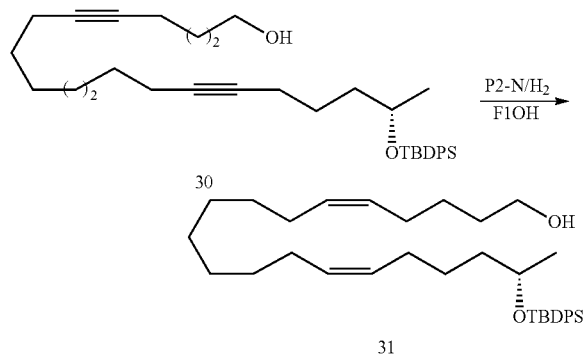

NaBH$_4$ (11 mg, 0.311 mmol) was added in portions with vigorous stirring to a room temperature solution of Ni(OAc)$_2$·4H$_2$O (77 mg, 0.311 mmol) in absolute ethanol (10 mL) under a hydrogen atmosphere (1 atm). After 15 min, freshly distilled ethylenediamine (33 μL, 0.415 mmol) was added to the black suspension, followed after a further 15 min by a solution of 19(S)-(tert-butyldiphenylsilyloxy)eicosa-5,14-diyn-1-ol (30) (225 mg, 0.415 mmol) in absolute EtOH (5 mL). After 1 h, the reaction mixture was diluted with Et$_2$O (10 mL) and passed through a small bed of silica gel. The bed was rinsed with another portion of Et$_2$O (5 mL). The combined ethereal filtrates were concentrated under reduced pressure to afford 19(S)-(tert-butyldiphenylsilyloxy)eicosa-5(Z),14(Z)-dien-1-ol (31) (195 mg, 86%) as a colorless oil. TLC: EtOAc/hexanes (3:7), R$_f$=0.46.

$^1$H NMR (400 MHz, CDCl$_3$) δ 7.76 (dd, J=1.6, 7.6 Hz, 4H), 7.47-7.41 (m, 6H), 5.44-5.35 (m, 4H), 3.94-3.89 (m, 1H), 3.69-3.67 (m, 2H), 2.14-2.00 (m, 8H), 1.48-1.35 (m, 18H), 1.13-1.12 (m, 12H); $^{13}$C NMR (126 MHz, CDCl$_3$) δ 136.17, 135.19, 134.84, 130.64, 130.34, 129.95, 129.74, 129.67, 129.65, 127.76, 127.74, 127.68, 69.80, 63.07, 39.31, 32.64, 30.07, 29.79, 29.62, 27.57, 27.53, 27.47, 27.37, 27.24, 26.19, 25.63, 23.55, 19.57. HRMS calcd for C$_{36}$H$_{56}$NaO$_2$Si [M+Na]$^+$ 571.3947, found 571.3942.

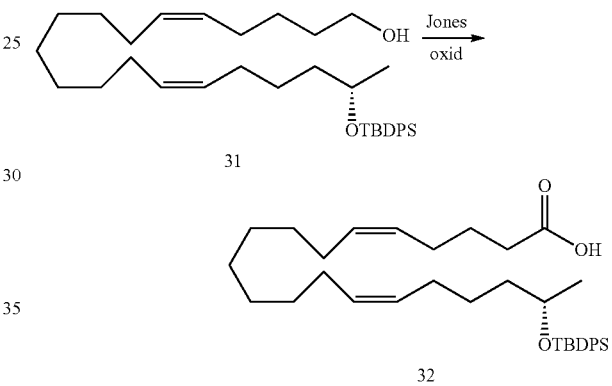

Jones reagent (0.25 mL of a 10 N solution in water) in acetone (8.25 mL) was added to a stirring, −78° C. solution of 19(S)-(tert-butyldiphenylsilyloxy)eicosa-5(Z),14(Z)-dien-1-ol (31) (100 mg, 0.18 mmol) in acetone (5 mL). After 1 h, the reaction mixture was warmed to −20° C. and maintained for another 2 h, then quenched with an excess (5 equiv) of isopropanol. The precipitated green chromium salts were moved by filtration and the filter cake was washed with acetone. The combined filtrates were concentrated in vacuo and the resultant residue was dissolved in EtOAc (40 mL), washed with water (20 mL), dried over anhydrous sodium sulphate, and concentrated in vacuo. The residue was purified by SiO$_2$ column chromatography using 35% EtOAc/hexanes as eluent to give 19(S)-(tert-butyldiphenylsilyloxy)eicosa-5(Z),14(Z)-dienoic acid (32) (70 mg, 69%) as an oil. TLC: 50% EtOAc/hexanes, R$_f$=0.2.

$^1$H NMR (400 MHz, CDCl$_3$) δ 7.75 (dd, J=1.6, 7.6 Hz, 4H), 7.46-7.39 (m, 6H), 5.48-5.31 (m, 4H), 3.90-3.87 (m, 1H), 2.40 (t, J=7.5 Hz, 2H), 2.15-1.97 (m, 8H), 1.76-1.73 (m, 2H), 1.39-1.30 (m, 14H), 1.12-1.09 (m, 12H); $^{13}$C NMR (126 MHz, CDCl$_3$) δ 180.49, 136.16, 135.19, 134.83, 131.61, 130.32, 129.93, 129.71, 129.64, 128.42, 127.73, 127.65, 69.78, 39.29, 33.73, 30.04, 29.98, 29.76, 29.58, 27.53, 27.51, 27.44, 27.33, 26.72, 25.60, 24.88, 23.51, 19.56. HRMS calcd for C$_{36}$H$_{54}$NaO$_3$Si [M+Na]$^+$ 585.3740, found 585.3734.

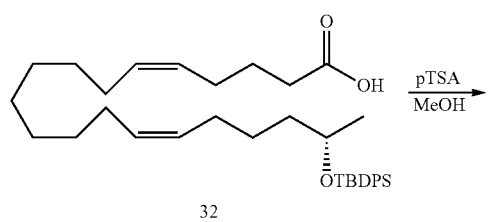

32

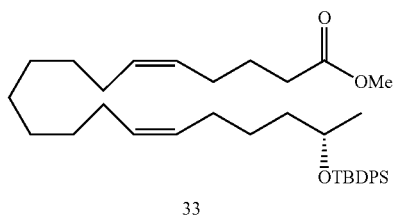

33

To a 0° C. solution of 19(S)-(tert-butyldiphenylsilyloxy) eicosa-5(Z),14(Z)-dienoic acid (32) (98 mg, 0.174 mmol) in MeOH (10 mL) was added a catalytic amount of pTSA (5 mg). After 1 h, the reaction was quenched with sat. aq. NaHCO$_3$ and the methanol was removed under reduced pressure. Water (20 mL) was added and then the reaction mixture was extracted with EtOAc (2×15 mL). The organic extracts were concentrated in vacuo and the residue was purified by SiO$_2$ column chromatography using 20% EtOAc/hexanes as eluent to afford methyl 19(S)-(tert-butyldiphenylsilyloxy)eicosa-5(Z),14(Z)-dienoate (33) (82 mg, 82%) as a colorless oil that was utilized directly in the next step.

$^1$H NMR (400 MHz, CDCl$_3$) δ 7.71-7.63 (m, 4H), 7.45-7.32 (m, 6H), 5.46-5.21 (m, 4H), 3.84-3.82 (m, 1H), 3.66 (s, 3H), 2.31-2.29 (m, 2H), 2.15-1.86 (m, 8H), 1.68-1.66 (m, 2H), 1.36-1.27 (m, 14H), 1.05-1.04 (m, 12H).

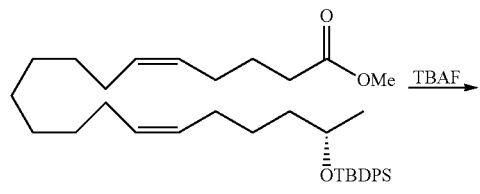

33

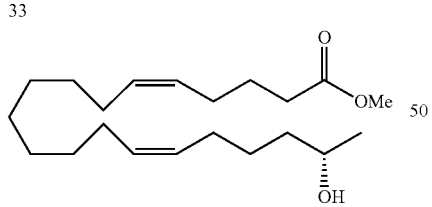

34

A mixture of methyl 19(S)-(tert-butyldiphenylsilyloxy) eicosa-5(Z),14(Z)-dienoate (33) (200 mg, 0.34 mmol) and n-tetrabutylammonium fluoride (0.412 mL of 1M soln, 0.412 mmol) in anhydrous THF (5 mL) was stirred at room temperature under an argon atmosphere for 12 h, and then evaporated to dryness in vacuo. The residue was dissolved in EtOAc (50 mL) and washed with water (30 mL), brine (30 mL), dried, and evaporated in vacuo. Purification of the residue via SiO$_2$ column chromatography gave methyl 19(S)-hydroxyeicosa-5(Z),14(Z)-dienoate (34) (72 mg, 62%) as a colorless oil. TLC: 30% EtOAc/hexanes, R$_f$=0.40.

$^1$H NMR (400 MHz, CDCl$_3$) δ 5.43-5.22 (m, 4H), 3.83-3.70 (m, 1H), 3.63 (s, 3H), 2.28 (t, J=7.5 Hz, 2H), 2.09-1.90 (m, 8H), 1.71-1.61 (m, 2H), 1.59-1.52 (m, 11H), 1.51-1.20 (m, 13H), 1.15 (d, J=6.2 Hz, 3H); 13C NMR (101 MHz, CDCl$_3$) δ 174.15, 131.09, 130.28, 129.34, 128.28, 67.27, 38.63, 37.78, 29.75, 29.70, 29.41, 29.23, 29.19, 27.16, 27.01, 26.80, 25.89, 22.40. HRMS calcd for C$_{21}$H$_{38}$O$_3$ [M+1]$^+$ 339.2821, found 339.2820.

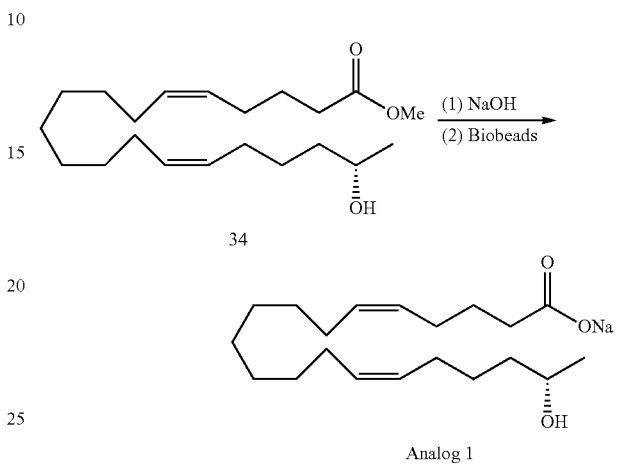

Analog 1

A solution of NaOH (2 mL of 2 M aq. soln) and methyl 19(S)-hydroxyeicosa-5(Z),14(Z)-dienoate (34) (70 mg, 0.2 mmol) in THF (25 mL) and deionized H$_2$O (4 mL) was stirred at it for 12 h, then the organic solvent was evaporated under reduced pressure. The resultant aqueous solution was diluted with additional water (5 mL) and BioRad SM-2 Bio-beads (5 g; pre-washed with 0.1 N NH$_4$OH and H$_2$O) were added. After gently stirring for 1 h, the beads were collected on a sintered glass funnel and washed with deionized water (2×10 mL) and then EtOH (3×10 mL). Concentration of the ethanolic washes afforded sodium 19(S)-hydroxyeicosa-5(Z),14(Z)-dienoate (Analog 1) (43 mg, 60%) as a colorless oil. TLC: 50% EtOAc/hexanes, R$_f$=0.2.

$^1$H NMR (500 MHz, CD$_3$OD) δ 5.38-5.30 (m, 4H), 3.75-3.71 (m, 1H), 2.19 (t, J=7.8 Hz, 2H), 2.20-2.07 (m, 8H), 1.71-1.59 (m, 2H), 1.54-1.29 (m, 14H), 1.16 (d, J=6.2 Hz, 3H); $^{13}$C NMR (125 MHz, CD$_3$OD) δ 181.72, 129.93, 129.90, 129.48, 129.39, 67.27, 77.01, 76.69, 67.98, 51.44, 38.86, 33.42, 29.67, 29.63, 29.39, 29.23, 27.19, 27.17, 27.06, 26.48, 25.83, 24.84, 23.46.

Analog 2:
19(R)-Hydroxyeicosa-5(Z),14(Z)-dienoate

Analog 2

Following the procedures utilized to prepare Analog 1, commercial (R)-hex-5-en-2-ol (Aldrich Chem. Co., 99.3% ee) was transformed into Analog 2. All yields and spectral data were comparable to their enantiomers.

Analog 3: Sodium 20-azido-19(R)-hydroxyeicosa-5(Z),14(Z)-dienoate

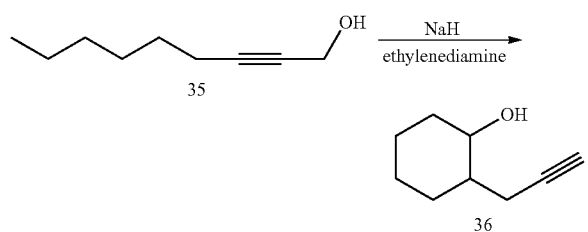

NaH (60% suspension in mineral oil, 17.1 g, 42.8 mmol, 4 equiv) was carefully added in portions to a flask containing neat anhydrous ethylenediamine (70 mL) at 0° C. The mixture was slowly warmed to room temperature and stirred at rt for 1 h, then warmed to 70° C. After 2 h, the reaction mixture was cooled to 45° C. and commercial 2-nonyl-1-ol (35) (15 g, 10.71 mmol) was added slowly. After stirring at 70° C. for 5 h, the reaction mixture was cooled to 0° C., slowly quenched with 1 M HCl (30 mL), and the organic and aqueous layers were separated. The aqueous layer was extracted with Et$_2$O (2×120 mL). The ethereal extracts were combined with the organic layer, dried (Na$_2$SO$_4$), and all volatiles removed under reduced pressure. Purification of the residue by SiO$_2$ column chromatography using 20% EtOAc/hexane afforded non-8-yn-1-ol (36) (4.1 g, 82%) as a colorless oil whose spectral data were consistent with literature values (Denmark, et al., *J. Org. Chem.* 1982, 47, 4595-4597).

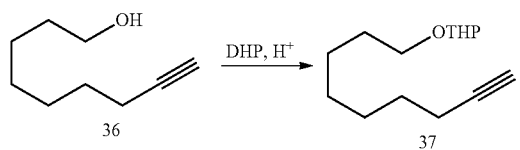

A mixture of 3,4-dihydro-2H-pyran (DHP)(10.4 mL, 114.2 mmol), non-8-yn-1-ol (36) (8 g, 57.14 mmol), and p-toluenesulfonic acid (pTSA) (10 mg) in CH$_2$Cl$_2$ (150 mL) was stirred at ambient temperature for 12 h, then diluted with Et$_2$O (250 mL) and filtered. The filtrate was evaporated in vacuo and the residue was chromatographed on SiO$_2$ using EtOAc/hexanes (5/95) to afford 2-(non-8-yn-1-yloxy)tetrahydro-2H-pyran (37) (11.0 g, 86%) as a colorless oil whose spectral data were consistent with literature values (Akakabe, et al., *Bioscience, Biotechnology, and Biochemistry*, 2005, 69, 1349-1352.

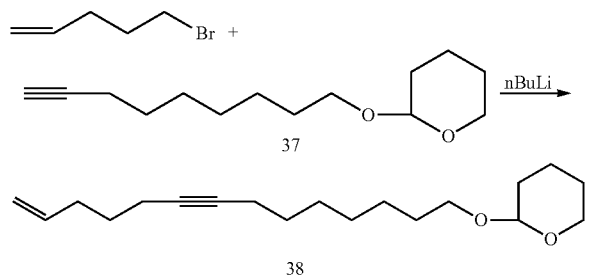

Alkylation of 2-(non-8-yn-1-yloxy)tetrahydro-2H-pyran (37) (5 g, 22.3 mmol) with 5-bromopent-1-ene (3.4 g, 22.3 mmol) following the procedure described in the preparation of Analog 1 provided 2-(tetradec-13-en-8-yn-1-yloxy)tetrahydro-2H-pyran (38) (5.8 g, 89%) as a colorless oil that was utilized directly in the next step. TLC: 10% EtOAc/hexane, R$_f$=0.55.

$^1$H NMR (CDCl$_3$, 500 MHz) δ 5.80-5.75 (m, 1H), 5.08-4.94 (m, 2H), 4.58-4.54 (m, 1H), 3.87-3.85 (m, 1H), 3.75-3.72 (m, 1H), 3.51 (dd, J=10.7, 5.3 Hz, 1H), 3.40-3.38 (m, 1H), 2.15-2.13 (m, 4H), 1.84-1.83 (m, 1H), 1.77-1.67 (m, 1H), 1.60-1.30 (m, 12H).

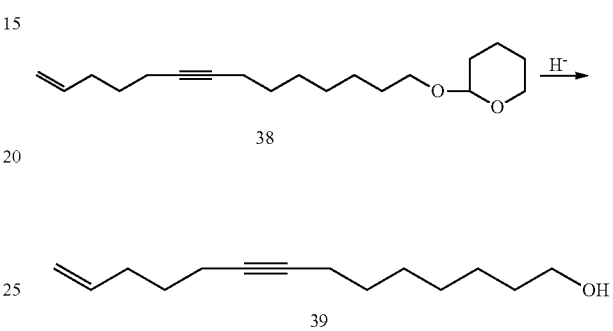

pTSA catalyzed solvolysis of 2-(tetradec-13-en-8-yn-1-yloxy)tetrahydro-2H-pyran (38) (5.8 g, 19.8 mmol) following the procedure described above in the preparation of Analog 1 provided tetradec-13-en-8-yn-1-ol (39) (3.8 g, 85%) as a colorless oil. TLC: 30% EtOAc/hexane, R$_f$=0.55.

$^1$H NMR (CDCl$_3$, 500 MHz) δ 5.81-5.75 (m, 1H), 5.01-4.% (m, 2H), 3.65-3.63 (m, 2H), 2.19-2.12 (m, 4H), 1.66-1.33 (m, 14H). HRMS calcd for C$_{14}$H$_{25}$O [M+1]$^+$ 209.1905, found 209.1909.

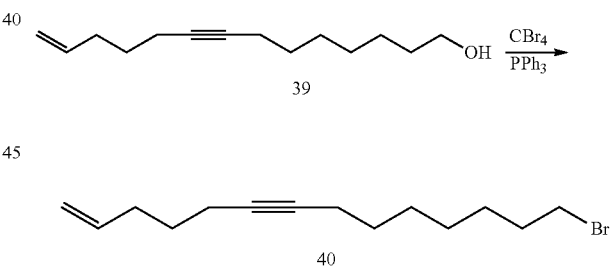

CBr$_4$ (7.8 g, 23.6 mmol) was added slowly to a stirring, 0° C. suspension of triphenylphosphine (5.3 g, 20.1 mmol) and tetradec-13-en-8-yn-1-ol (39) (3.8 g, 18.2 mmol) in CH$_2$Cl$_2$ (20 mL). After 3 h at rt, the reaction was quenched with water (20 mL) and extracted with CH$_2$Cl$_2$ (3×75 mL). The combined organic extracts were dried and concentrated in vacuo. The residue was purified by SiO$_2$ column chromatography using 5% EtOAc/hexanes to afford 14-bromo-tetradec-1-en-6-yne (40) (4.5 g, 92%) as a pale yellow oil. TLC: 10% EtOAc/hexane, R$_f$=0.5.

$^1$H NMR (CDCl$_3$, 500 MHz) δ 5.81-5.75 (m, 1H), 5.09-4.95 (m, 2H), 3.42 (q, J=6.4 Hz, 2H), 2.22-2.18 (m, 6H), 1.81-1.78 (m, 2H), 1.65-1.57 (m, 2H), 1.55-1.38 (m, 8H). HRMS calcd for C$_{14}$H$_{24}$Br [M+1]$^+$ 271.1061, found 271.1069.

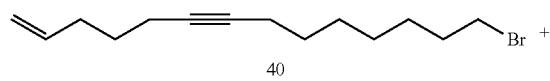

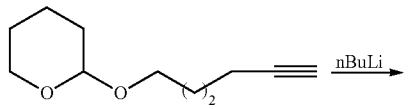

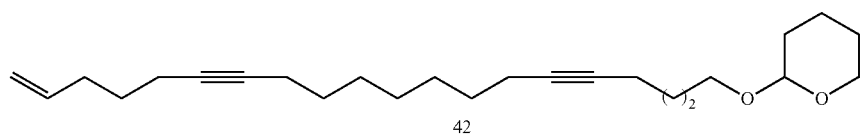

Alkylation of 2-(hex-5-yn-1-yloxy)tetrahydro-2H-pyran (41) (Falck, et al., *J. Med Chem.* 2014, 57, 6965-6972) (3.2 g, 17.5 mmol) with 14-bromotetradec-1-en-6-yne (40) (4.5 g, 17.5 mmol) following the procedure described in the preparation of Analog 1 provided 2-(eicosa-19-en-5,14-diyn-1-yloxy)tetrahydro-2H-pyran (42) (4.5 g, 69%) as a colorless oil that was utilized directly in the next step. TLC: 10% EtOAc/hexane, $R_f$=0.55.

$^1$H NMR (CDCl$_3$, 500 MHz) δ 5.80-5.75 (m, 1H), 5.02-5.00 (m, 2H), 4.55 (t, J=7.5 Hz, 1H), 3.85 (t, J=7.7 Hz, 1H), 3.73-3.71 (m, 1H), 3.53-3.51 (m, 1H), 3.45-3.41 (m, 1H), 2.29-2.11 (m, 10H), 1.81-1.78 (m, 2H), 1.76-1.68 (m, 2H), 1.68-1.45 (m, 12H), 1.38-1.25 (m, 6H).

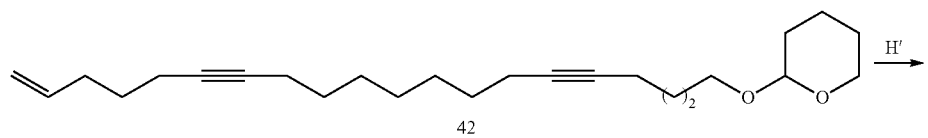

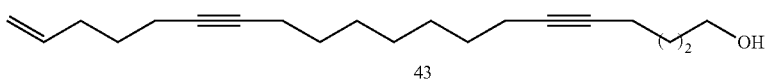

pTSA catalyzed solvolysis of 2-(eicosa-19-en-5,14-diyn-1-yloxy)tetrahydro-2H-pyran (42) (4.4 g, 11.82 mmol) following the procedure described in the preparation of Analog 1 provided eicosa-19-en-5,14-diyn-1-ol (43) (2.5 g, 75%) as a colorless oil. TLC: 20% EtOAc/hexane, $R_f$=0.55.

$^1$H NMR (CDCl$_3$, 500 MHz) δ 5.87-5.75 (m, 1H), 5.04 (d, J=17.1 Hz, 1H), 4.98 (d, J=10.2 Hz, 11H), 3.68 (q, J=5.8 Hz, 2H), 2.24-2.11 (m, 10H), 1.68-1.67 (m, 2H), 1.62-1.52 (m, 4H), 1.50-1.40 (m, 2H), 1.35-1.30 (m, 8H). HRMS calcd for. C$_{20}$H$_{33}$O [M+1]$^+$ 289.2531, found 289.2527.

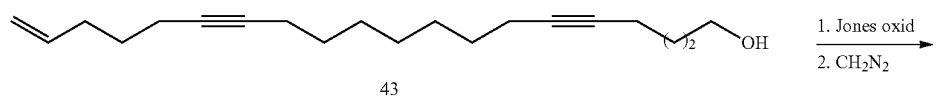

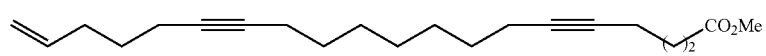

Jones oxidation of eicosa-19-en-5,14-diyn-1-ol (43) (2.0 g, 6.94 mmol) following the procedure described in the preparation of Analog 1 provided eicosa-19-en-5,14-diynoic acid (1.78 g, 85%) as a colorless oil which was used immediately in the next step. TLC: 20% EtOAc/hexanes, $R_f$=0.50.

A saturated ethereal solution of freshly prepared $CH_2N_2$ (10 mL) in $Et_2O$ was added slowly to a stirring, 0° C. suspension of the above crude eicosa-19-en-5,14-diynoic acid (1.78 g, 5.90 mmol) in ether (20 mL). After 30 min, all volatiles were evaporated under reduced pressure and the residue was purified by $SiO_2$ column chromatography to afford methyl eicosa-19-en-5,14-diynoate (44) (1.71 g, 92%) as a colorless oil. TLC: 5% EtOAc/hexanes, $R_f$=0.55.

$^1$H NMR (CDCl$_3$, 500 MHz) δ 5.78-5.70 (m, 1H), 5.05-5.01 (m, 2H), 3.68 (s, 3H), 2.44 (t, J=7.5 Hz, 2H), 2.26-2.09 (m, 10H), 1.83-1.79 (m, 2H), 1.62-1.51 (m, 2H), 1.50-1.24 (m, 10H). HRMS calcd for $C_{21}H_{33}O_2$ [M+1]$^+$ 317.2481, found 317.2485.

mCPBA (0.45 g, 2.1 mmol, 70%) was added in portions to a stirring, 0° C. solution of methyl eicosa-19-en-5,14-diynoate (44) (0.5 g, 1.5 mmol) in $CH_2Cl_2$ (20 mL). After 0.5 h, the reaction mixture was warmed to rt. After 2.5 h, the reaction mixture was diluted with $CH_2Cl_2$ (10 mL) and the organic layer was washed with a saturated aq. solution of $Na_2SO_3$ (20 mL), sat. aq. $NaHCO_3$ (20 mL), water (20 mL), and dried over $Na_2SO_4$. The organic layer was concentrated under reduced pressure and the residue was purified by $SiO_2$ chromatography using 10% EtOAc/hexanes to afford methyl 18-(oxiran-2-yl)octadeca-5,14-diynoate (45) (341 mg, 65%) as an oil. TLC: 10% EtOAc/hexane, $R_f$=0.4.

$^1$H NMR (CDCl$_3$, 500 MHz) δ 3.68 (s, 3H), 2.94-2.85 (m, 1H), 2.77-2.76 (m, 1H), 2.55-2.54 (m, 1H), 2.46 (t, J=7.6 Hz, 2H), 2.27-2.21 (m, 4H), 2.19-2.14 (m, 4H), 1.83-1.80 (m, 2H), 1.72-1.65 (m, 4H), 1.58-1.48 (m, 4H), 1.42-1.25 (m, 6H).

Semi-hydrogenation of methyl 18-(oxiran-2-yl)octadeca-5,14-diynoate (45) (0.2 g, 0.6 mmol) following the procedure described in the preparation of Analog 1 furnished methyl 18-(oxiran-2-yl)octadeca-5(Z),14(Z)-dienoate (46) (1.72 g, 85%) as a colorless oil. TLC: 10% EtOAc/hexane, $R_f$=0.6.

$^1$H NMR (CDCl$_3$, 500 MHz) δ 5.44-5.30 (m, 4H), 3.68 (s, 3H), 2.93-2.91 (m, 1H), 2.76 (dd, J=7.8 Hz, 1H), 2.55-2.51 (m, 1H), 2.33 (t, J=7.6 Hz, 2H), 2.21-2.08 (m, 4H), 2.04-1.98 (m, 4H), 1.71-1.70 (m, 2H), 1.68-1.51 (m, 4H), 1.35-1.26 (m, 10H); $^{13}$C NMR (CDCl$_3$, 101 MHz) δ 174.17, 131.08, 130.53, 128.95, 128.28, 52.29, 51.44, 47.09, 33.41, 31.98, 29.66, 29.63, 29.39, 29.23, 27.19, 27.17, 26.86, 26.48, 25.98, 24.83.

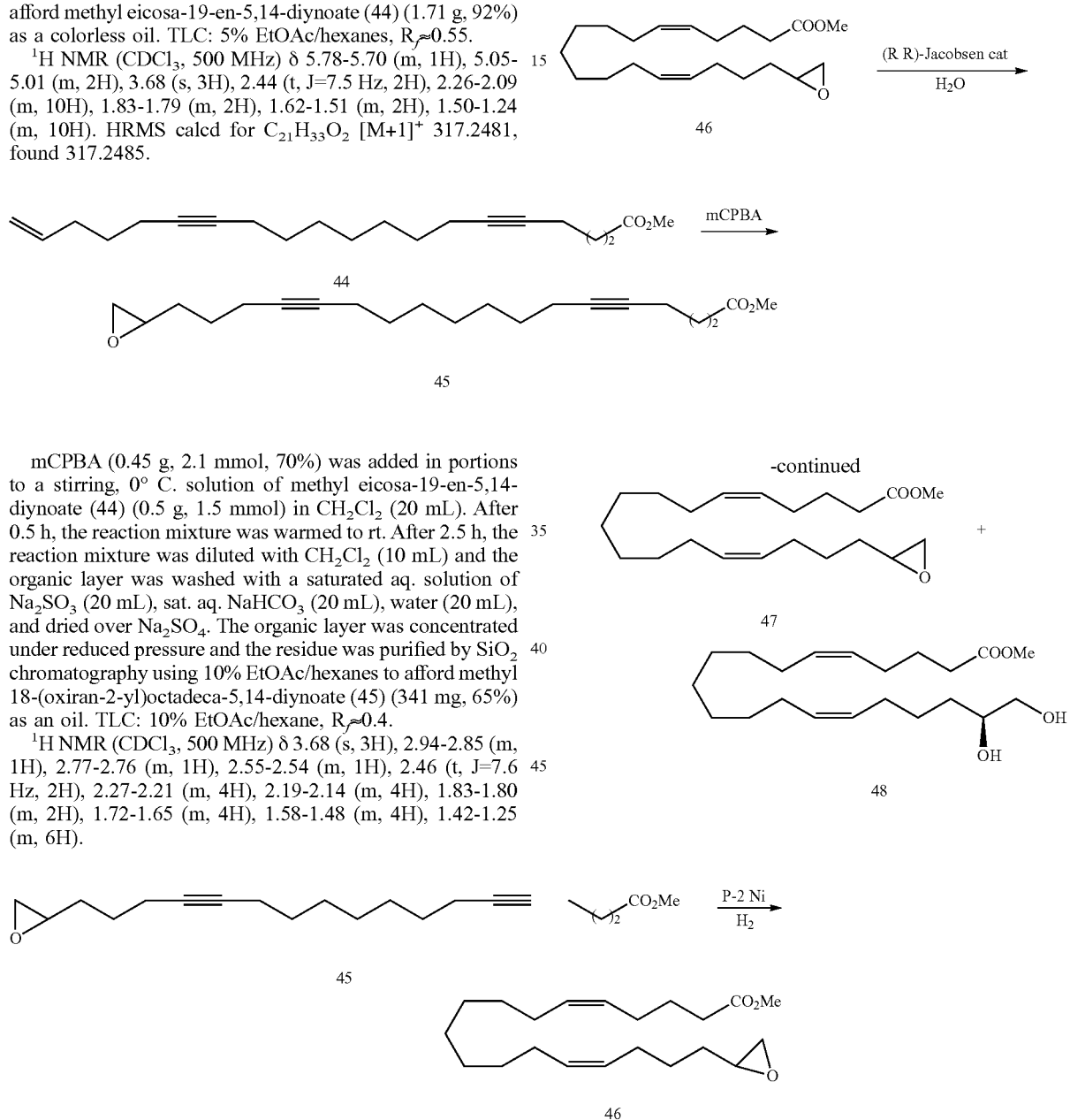

Following literature procedure (Schaus, et al, *J. Am. Chem. Soc.*, 2002, 124, 1307-1315) glacial AcOH (100 μL, 1.6 mmol) was added to a stirring, 0° C. solution of (R,R)-(+)—N,N'-bis(3,5-di-tert-butylsalicylidene)-1,2-cyclohexanediaminocobalt(II) (Jacobsen's catalyst) (2.5 mg, 5 mol %) in dry toluene (3 mL). After 15 min, a solution of methyl 18-(oxiran-2-yl)octadeca-5(Z),14(Z)-dienoate (46) (0.26 g, 0.77 mmol) in THF (2 mL) was added followed by H₂O (7.5 μL, 0.38 mmol) and warmed to rt. After an additional 14 h, all volatiles were removed in vacuo and the residue was purified by SiO₂ column chromatography using 10% EtOAc/hexane as eluant to give methyl 18-((R)-oxiran-2-yl)octadeca-5(Z),14(Z)-dienoate (47) (110 mg, 42%), 94% ee as determined by chiral HPLC (Chiralcel OJ-H). TLC: 10% EtOAc/hexanes, R$_f$≈0.6.

¹H NMR (CDCl₃, 500 MHz) δ 5.47-5.32 (m, 4H), 3.68 (s, 3H), 2.86-2.82 (m, 1H), 2.76 (q, J=3.9 Hz, 1H), 2.55-2.51 (m, 1H), 2.38 (t, J=7.6 Hz, 2H), 2.21-2.08 (m, 4H), 2.04-1.95 (m, 4H), 1.72-1.70 (m, 2H), 1.68-1.49 (m, 4H), 1.32-1.25 (m, 10H); ¹³C NMR (CDCl₃, 101 MHz) δ 174.17, 131.08, 130.53, 128.95, 128.28, 52.29, 51.44, 47.09, 33.41, 31.98, 29.66, 29.63, 29.39, 29.23, 27.19, 27.17, 26.86, 26.48, 25.98, 24.83.

Also isolated was methyl 19(S),20-dihydroxyeicosa-5(Z),14(Z)-dienoate (48) (90 mg, 33%), >99% ee as determined by chiral HPLC (Chiralcel OJ-H). TLC: 50% EtOAc/hexanes, R$_f$≈0.4.

¹H NMR (CDCl₃, 500 MHz) δ 5.45-5.22 (m, 4H), 3.75-3.72 (m, 1H), 3.68 (s, 3H), 3.66-3.65 (m, 11H), 3.48 (t, J=8.2 Hz, 1H), 2.38 (t, J=7.6 Hz, 2H), 2.21-2.08 (m, 8H), 2.04-1.95 (m, 2H), 1.68-1.49 (m, 4H), 1.32-1.25 (m, 101H); ¹³C NMR (CDCl₃, 101 MHz) δ 174.25, 131.07, 130.34, 129.14, 128.24, 72.19, 66.68, 51.44, 51.44, 33.39, 32.61, 29.66, 29.62, 29.39, 29.21, 27.15, 27.08, 26.45, 25.66, 24.81.

128.30, 70.70, 57.08, 51.47, 33.82, 32.43, 29.66, 29.63, 29.39, 29.23, 27.21, 27.17, 26.92, 26.49, 25.50, 24.84.

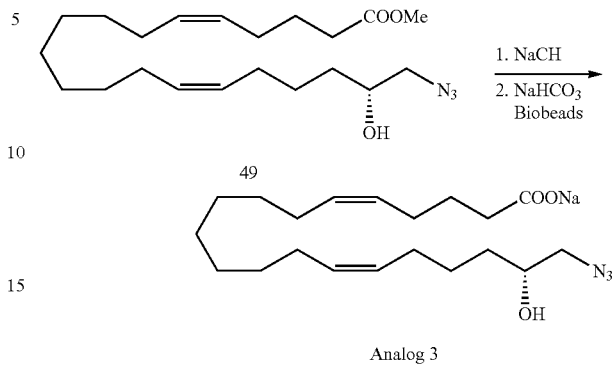

Saponification of methyl 20-azido-19(R)-hydroxyeicosa-5(Z),14(Z)-dienoate (26 mg, 0.07 mmol) and isolation following the procedures described in the preparation of Analog 1 furnished sodium 20-azido-19(R)-hydroxyeicosa-5(Z),14(Z)-dienoate (Analog 3) (15 mg, 55%) as a colorless oil.

¹H NMR (CD₃OD, 500 MHz) δ 5.48-5.31 (m, 4H), 3.73-3.69 (m, 1H), 3.27-3.21 (m, 2H), 2.31 (t, J=7.8 Hz, 2H), 2.18-2.01 (m, 81), 1.72-1.68 (m, 2H), 1.62-1.49 (m, 4H), 1.43-1.32 (m, 10H); ¹³C NMR (CD₃OD, 125 MHz) δ 181.73, 130.11, 129.94, 129.38, 129.22, 70.60, 56.72, 37.67, 33.86, 29.72, 29.67, 29.39, 29.20, 29.18, 29.16, 27.14, 27.02, 27.01, 26.86, 26.78, 25.57.

Analog 4: 20-Azido-19(S)-hydroxyeicosa-5(Z),14(Z)-dienoate

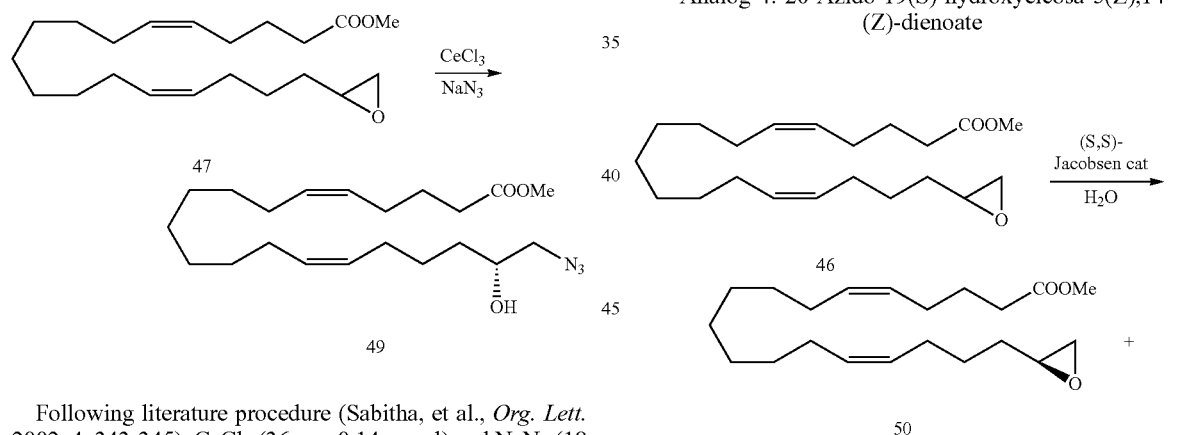

Following literature (Schaus, et al., J. Am. Chem. Soc., 2002, 124, 1307-1315) procedure, glacial AcOH (100 μL, 1.6 mmol) was added to a stirring, 0° C. solution of (S,S)-(+)—N,N'-bis(3,5-di-tert-butylsalicylidene)-1,2-cyclohexanediaminocobalt(II) (Jacobsen's catalyst) (2.5 mg, 5 mol %) in dry toluene (3 mL). After 15 min, a solution of methyl 18-(oxiran-2-yl)octadeca-5(Z),14(Z)-dienoate (46) (0.26 g, 0.77 mmol) in THF (2 mL) followed by H₂O (7.5 μL, 0.38 mmol) were added and warmed to rt. After an Following literature procedure (Sabitha, et al., Org. Lett. 2002, 4, 343-345), CeCl₃ (36 mg, 0.14 mmol) and NaN₃ (18 mg, 0.26 mmol) were added to a solution of methyl 18-((R)-oxiran-2-yl)octadeca-5(Z),14(Z)-dienoate (47) (88 mg, 0.26 mmol) in CH₃CN/H₂O (4 mL, 9:1), then the reaction mixture was heated to 60° C. After 12 h, the reaction was cooled to rt and the CH₃CN was removed under reduced pressure. The remaining reaction mixture was diluted with water (10 mL) and extracted with EtOAc (2×20 mL). The combined organic extracts were dried, concentrated under reduced pressure, and the residue was purified by SiO₂ column chromatography to afford methyl 20-azido-19(R)-hydroxyeicosa-5(Z),14(Z)-dienoate (49) (40 mg, 40%) as an oil. TLC: 20% EtOAc/hexanes, R$_f$≈0.55.

¹H NMR (CDCl₃, 500 MHz) δ 5.49-5.31 (m, 4H), 3.82-3.73 (m, 1H), 3.71 (s, 3H), 3.39 (dd, J=12.4, 3.3 Hz, 11H), 3.26 (dd, J=12.4, 7.4 Hz, 1H), 2.35 (t, J=7.8 Hz, 2H), 2.18-1.95 (m, 8H), 1.68-1.51 (m, 6H), 1.48-1.25 (m, 10H); ¹³C NMR (CDCl₃, 101 MHz) δ 174.22, 131.09, 130.63, additional 14 h, all volatiles were removed in vacuo and the residue was purified by SiO$_2$ column chromatography using 10% EtOAc/hexane as eluant to give a mixture of methyl 18-((S)-oxiran-2-yl)octadeca-5(Z),14(Z)-dienoate (50) (110 mg, 42%), 93% ee as determined by chiral HPLC (Chiralcel OJ-H), and methyl 19(R),20-dihydroxyeicosa-5(Z),14(Z)-dienoate (120 mg, 44%), 93% ee as determined by chiral HPLC (Chiralcel OJ-H). The spectral characteristics of both matched their corresponding enantiomers above.

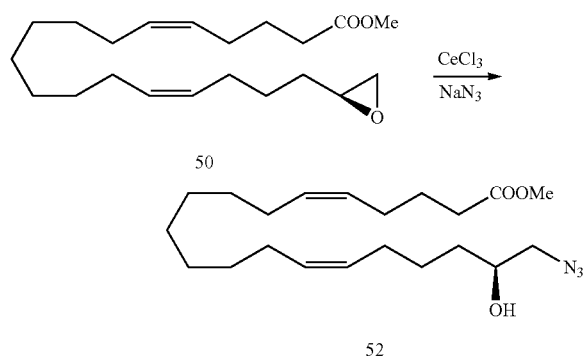

Following literature procedure (Sabitha, et al., Org. Lett. 2002, 4, 343-345), CeCl$_3$ (36 mg, 0.14 mmol) and NaN$_3$ (20 mg, 0.29 mmol) were added to a solution of methyl 18-((S)-oxiran-2-yl)octadeca-5(Z),14(Z)-dienoate (50) (100 mg, 0.29 mmol) in CH$_3$CN/H$_2$O (4 mL, 9:1), then the reaction mixture was heated to 60° C. After 12 h, the reaction was cooled to rt and the CH$_3$CN was removed under reduced pressure. The remaining reaction mixture was diluted with water (10 mL) and extracted with EtOAc (2×20 mL). The combined organic extracts were dried, concentrated under reduced pressure, and the residue was purified by SiO$_2$ column chromatography to afford methyl 20-azido-19(S)-hydroxyeicosa-5(Z),14(Z)-dienoate (52) (45 mg, 40%) as an oil. TLC: 20% EtOAc/hexanes, R$_f$=0.55. The spectral characteristics of 52 matched those of the corresponding enantiomer.

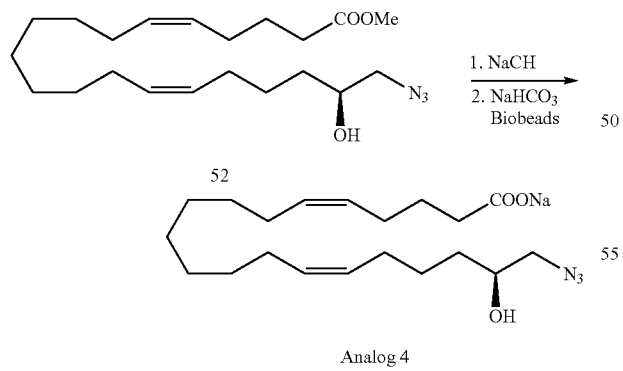

Analog 4

Saponification of methyl 20-azido-19(S)-hydroxyeicosa-5(Z),14(Z)-dienoate (52) (40 mg, 0.10 mmol) and isolation following the procedures described above furnished sodium 20-azido-19(S)-hydroxyeicosa-5(Z),14(Z)-dienoate (Analog 4) (16 mg, 40%) as a colorless oil. The spectral characteristics of Analog 4 matched those of its enantiomer.

Analog 5: Sodium 19(S)-azido-20-hydroxyeicosa-5(Z),14(Z)-dienoate

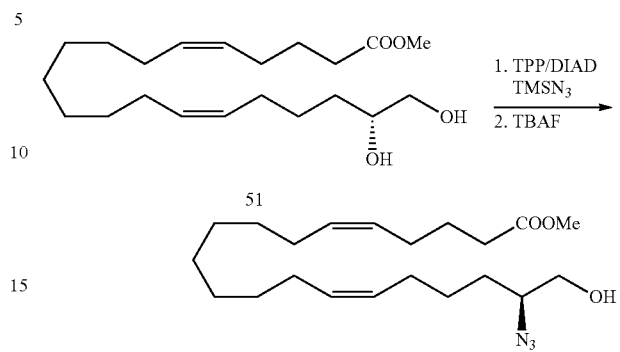

Following literature procedure (He, et al., J. Org. Chem. 1999, 64, 6049-6055), DIAD (0.1 g, 0.45 mmol) was added to a 0° C. solution of methyl 19(R),20-dihydroxyeicosa-5(Z),14(Z)-dienoate (51) (120 mg, 0.3 mmol) and PPh$_3$ (115 mg, 0.4 mmol) in dry toluene (10 mL). After 2 h, TMSN$_3$ (51 µL, 0.4 mmol) was added. Following an additional 14 h at 0° C., all volatiles were removed in vacuo and the residue was dissolved in dry THF (5 mL) and TBAF (0.2 mL of a 1 M soln in THF, 2 mmol) was added. After 1 h, the solvent was removed under reduced pressure and the residue was purified by silica gel chromatography using 20% EtOAc/hexanes to afford methyl 19(S)-azido-20-hydroxyeicosa-5(Z),14(Z)-dienoate (53) (% mg, 75%) as an oil. TLC: 30% EtOAc/hexane, R$_f$=0.5.

$^1$H NMR (CDCl$_3$, 500 MHz) δ 5.47-5.32 (m, 4H), 3.73-3.71 (m, 1H), 3.68 (s, 3H), 3.55 (t, J=7.8 Hz, 11), 3.49-3.46 (m, 11H), 2.34 (t, J=7.8 Hz, 2H), 2.21-2.08 (m, 8H), 2.04-1.95 (m, 2H), 1.72-1.69 (m, 2H), 1.61-1.49 (m, 4H), 1.32-1.22 (m, 8H).

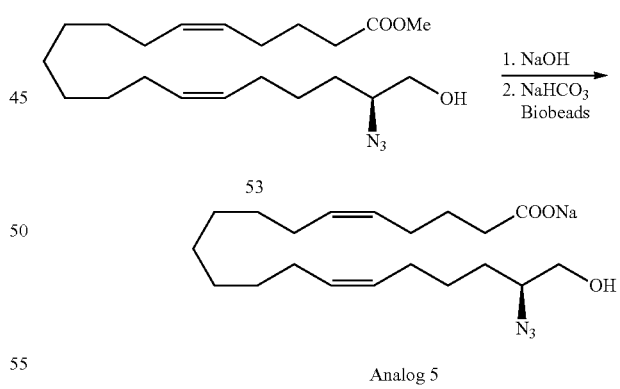

Analog 5

Saponification of methyl 19(S)-azido-20-hydroxyeicosa-5(2),14(Z)-dienoate (3) (80 mg, 0.21 mmol) and isolation following the procedures described in the preparation of Analog 1 furnished sodium 19(S)-azido-20-hydroxyeicosa-5(Z),14(Z)-dienoate (Analog 5) (28 mg, 35%) as a colorless oil.

$^1$H NMR (CDCl$_3$, 500 MHz) δ 5.48-5.29 (m, 4H), 3.72-3.68 (m, 1H), 3.58 (t, J=7.8 Hz, 1H), 3.45-3.38 (m, 1H), 2.22-2.17 (m, 2H), 2.10-2.03 (m, 8H), 1.71-1.64 (m, 2H), 1.52-1.45 (m, 4H), 1.43-1.25 (m, 10H); $^{13}$C NMR (CDCl$_3$,

125 MHz) δ 181.75, 130.43, 129.94, 129.38, 128.97, 64.73, 64.36, 37.77, 30.02, 29.73, 29.65, 29.39, 29.21, 29.17, 27.15, 27.03, 27.00, 26.79, 26.73, 26.16.

Analog 6: Sodium 19(R)-azido-20-hydroxyeicosa-5(Z),14(Z)-dienoate

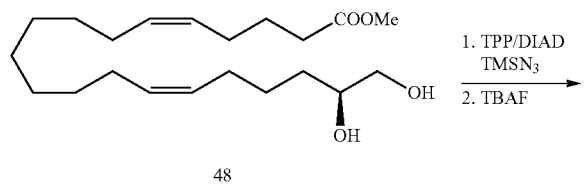

48

1. TPP/DIAD TMSN₃
2. TBAF

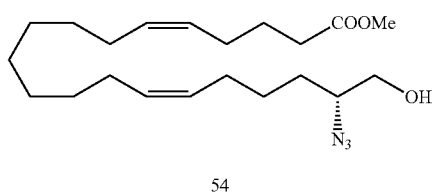

54

Reaction of methyl 19(S),20-dihydroxyeicosa-5(Z),14(Z)-dienoate (48) (62 mg, 0.17 mmol) with DIAD/TMSN₃ and desilylation as described for the preparation of Analog 5 furnished methyl 19(R)-azido-20-hydroxyeicosa-5(Z),14(Z)-dienoate (54) (40 mg, 60%) as an oil whose spectral data matched those of its enantiomer.

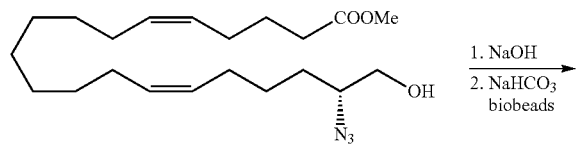

54

1. NaOH
2. NaHCO₃ biobeads

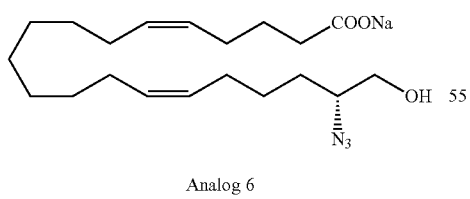

Analog 6

Saponification of methyl 19(R)-azido-20-hydroxyeicosa-5(Z),14(Z)-dienoate (40 mg, 0.10 mmol) and isolation following the procedures described above furnished sodium 19(R)-azido-20-hydroxyeicosa-5(Z),14(Z)-dienoate (Analog 6) (20 mg, 50%) as a colorless oil whose spectral data matched those of its enantiomer.

Analog 7: Sodium (19(S)-hydroxyeicosa-5(Z),14(Z)-dienoyl)glycinate

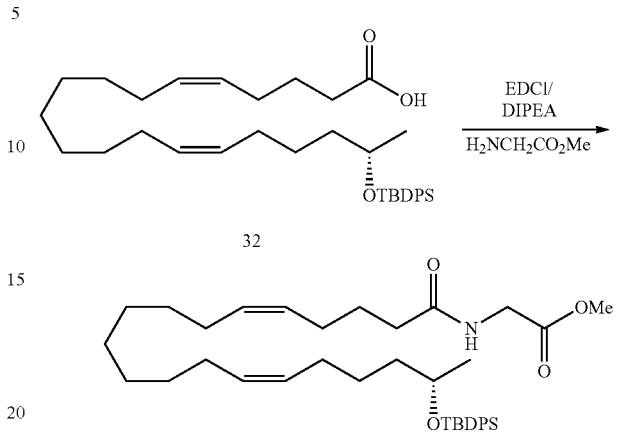

Glycine methyl ester hydrochloride (26 mg, 0.214 mmol) and DMAP (5 mg, 0.01 mmol) were added to a stirring solution of 19(S)-(tert-butyldiphenylsilyloxy)eicosa-5(Z),14(Z)-dienoic acid (32) (100 mg, 0.17 mmol) in anhydrous DMF (20 mL) under an argon atmosphere. After 5 min, 1-ethyl-3-(3-dimethylaminopropyl)carbodiimide hydrochloride (EDCI; 41 mg, 0.214 mmol) was added followed by dry diisopropylethylamine (50 μL, 0.26 mmol). After 12 h, the reaction mixture was diluted with EtOAc (30 mL), washed with water (30 mL), and brine (20 mL). The combined aqueous layers were back-extracted with EtOAc (3×30 mL). The combined organic extracts were dried over Na₂SO₄, concentrated under reduced pressure, and the residue was purified by SiO₂ column chromatography using 30% EtOAc/hexanes as eluent to give methyl (19(S)-(tert-butyldiphenylsilyloxy)eicosa-5(Z),14(Z)-dienoyl)glycinate (55) (87 mg, 78%) as a viscous oil. TLC: 50% EtOAc/hexanes, R_f≈0.45.

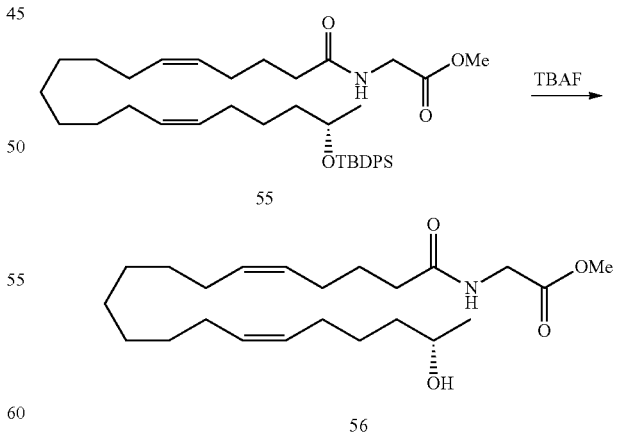

A mixture of methyl (19(S)-(tert-butyldiphenylsilyloxy)eicosa-5(Z),14(Z)-dienoyl)glycinate (55) (95 mg, 0.15 mmol) and tetra-n-butylammonium fluoride (0.30 mL of 1 M soln in THF, 0.3 mmol) in dry THF (10 mL) was stirred at room temperature under an argon atmosphere for 16 h, and then evaporated to dryness in vacuo. The residue was dissolved in EtOAc (50 mL) and washed with water (30 mL), brine (30 mL), dried, and evaporated in vacuo. Purification of the residue via SiO$_2$ column chromatography gave methyl (19(S)-hydroxyeicosa-5(Z),14(Z)-dienoyl) glycinate (56) (36 mg, 62%) as a colorless oil. TLC: 50% EtOAc/hexanes, R$_f$=0.45.

$^1$H NMR (500 MHz, CDCl$_3$) δ 6.04-6.02 (m, 1H), 5.46-5.28 (m, 4H), 4.06 (s, 2H), 3.77 (s, 3H), 3.65-3.63 (m, 1H), 2.25 (t, J=7.7 Hz, 2H), 2.13-1.97 (m, 8H), 1.73-1.71 (m, 2H), 1.59-1.57 (m, 2H), 1.43-1.23 (m, 12H). 1.19 (d, J=6.2 Hz, 3H); $^{13}$C NMR (CDCl$_3$, 101 MHz) δ 173.15, 170.58, 131.08, 130.08, 129.55, 128.40, 68.06, 52.36, 41.15, 39.22, 35.69, 29.73, 29.67, 29.38, 27.23, 27.17, 27.14, 26.58, 25.46, 25.41, 23.46.

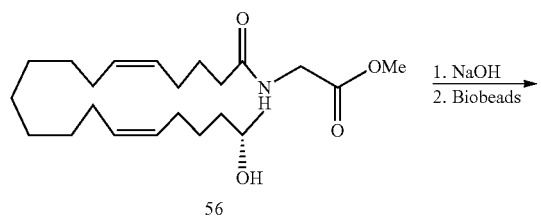

56

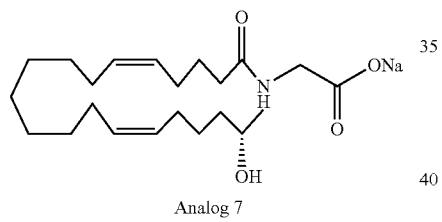

Analog 7

A solution of NaOH (2 mL of a 1 M aq. soln) was added to a 0° C. solution of the above methyl (19(S)-hydroxyeicosa-5(Z),14(Z)-dienoyl)glycinate (56) (30 mg, 0.07 mmol) in THF (25 mL) and deionized H$_2$O (4 mL). After stirring at room temperature overnight, the organic solvent was evaporated under reduced pressure, the resultant aqueous solution was diluted with additional water (5 mL), and BioRad SM-2 Bio-beads (5 g; pre-washed with 0.1 N NH$_4$OH and H$_2$O) were added. After gently stirring for 1 h, the beads were collected on a sintered glass funnel, washed with deionized water (2×10 mL), and then EtOH (3×10 mL). Concentration of the ethanolic washes afforded sodium (19(S)-hydroxyeicosa-5(Z),14(Z)-dienoyl)glycinate (Analog 7) (15 mg, 50%) as a colorless oil. TLC: 80% EtOAc/hexanes, R$_f$=020.

$^1$H NMR (500 MHz, CD$_3$OD) δ 5.41-5.37 (m, 4H), 3.77-3.72 (m, 3H), 2.29-2.24 (m, 2H), 2.11-2.03 (m, 8H), 1.70-1.66 (m, 2H), 1.49-1.17 (m, 14H), 1.14 (d, J=6.2 Hz, 3H); $^{13}$C NMR (101 MHz, CD$_3$OD) δ 174.81, 171.35, 130.26, 129.50, 129.28, 128.46, 67.10, 47.79, 38.70, 35.25, 29.55, 29.43, 29.12, 28.95, 28.90, 26.76, 26.36, 25.51, 25.13, 22.09.

Analog 8: Sodium (19(R)-hydroxyeicosa-5(Z),14 (Z)-dienoyl)glycinate

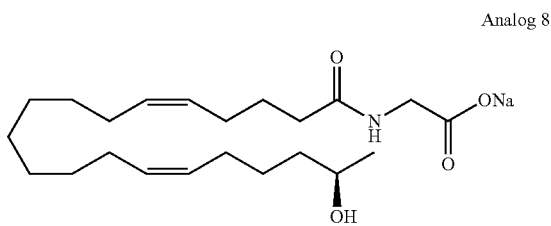

Analog 8

Following the procedures utilized to prepare Analog 7, 19(R)-(tert-butyldiphenylsilyloxy)eicosa-5(Z),14(Z)-dienoic acid was transformed into Analog 8. All yields and spectral data were comparable to their enantiomers.

Analog 9: Disodium (19(S)-hydroxyeicosa-(Z),14 (Z)-dienoyl)-L-aspartate

32

57

L-Aspartic acid dimethyl ester hydrochloride (42 mg, 0.21 mmol) and 1-cyano-2-ethoxy-2-oxoethylidenaminooxy)dimethylamino-morpholino-carbenium hexafluorophosphate (COMU) (79 mg, 0.18 mmol) were added to a stirring solution of 19(S)-(tert-butyldiphenylsilyloxy)eicosa-5(Z),14(Z)-dienoic acid (32) (80 mg, 0.14 mmol) in anhydrous DMF (20 mL) under an argon atmosphere. After 5 min, 1-ethyl-3-(3-dimethylaminopropyl)carbodiimide hydrochloride (EDCI) (35 mg, 0.18 mmol) was added followed by dry diisopropylethylamine (27 μL, 0.21 mmol). After 12 h, the reaction mixture was diluted with EtOAc (30 mL), washed with water (30 mL), and brine (20 mL). The combined aqueous layers were back-extracted with EtOAc (3×30 mL). The combined organic extracts were dried over Na$_2$SO$_4$, concentrated in vacuo, and the residue purified by SiO$_2$ column chromatography using 30% EtOAc/hexanes as eluent to give dimethyl (19(S)-(tert-butyldiphenylsilyloxy) eicosa-5(Z),14(Z)-dienoyl)-L-aspartate (72 mg, 72%) as a viscous oil. TLC: 40% EtOAc/hexanes, R$_f$=0.45.

$^1$H NMR (400 MHz, CDCl$_3$) δ 7.70 (dd, J=1.6, 7.6 Hz, 4H), 7.40-7.38 (m, 6H), 6.48-6.47 (m, 1H), 5.43-5.27 (m, 4H), 4.91-4.87 (m, 1H), 3.86-3.84 (m, 1H), 3.78 (s, 3H), 3.71 (s, 3H), 3.06 (dd, J=4.5, 17.5 Hz, 1H), 2.86 (dd, J=4.5, 17.5 Hz, 1H), 2.25 (t, J=7.5 Hz, 2H), 2.10-1.93 (m, 8H), 1.74-1.65 (m, 2H), 1.49-1.21 (m, 14H), 1.07-1.06 (m, 12H); $^{13}$C NMR (126 MHz, CDCl$_3$) δ 172.74, 171.65, 171.28, 135.87, 134.89, 134.53, 131.08, 130.03, 129.64, 129.44, 129.37, 128.41, 127.46, 127.38, 69.48, 52.80, 52.03, 48.32, 39.00, 36.11, 35.83, 29.77, 29.75, 29.51, 29.33, 29.31, 27.27, 27.23, 27.16, 27.05, 26.60, 25.47, 25.31, 23.25, 19.28. HRMS calcd for C$_{42}$H$_{63}$NNaO$_6$Si [M+Na]$^+$ 728.4322, found 728.4317.

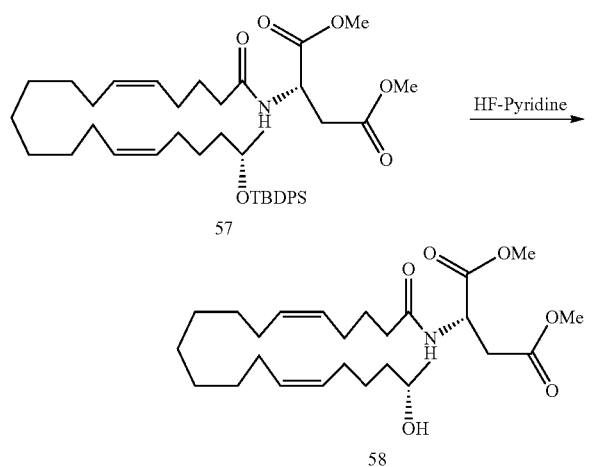

57

58

Hydrogen fluoride-pyridine complex (0.4 mL, 2.7 mmol) was added dropwise over 15 min to a 0° C. solution of dimethyl (19(S)-(tert-butyldiphenylsilyloxy)eicosa-5(Z),14(Z)-dienoyl)-L-aspartate (57) (32 mg, 0.053 mmol) in dry THF (10 mL) in a plastic vial. After stirring at rt for 48 h, the reaction mixture was basified to pH 8 by careful addition of K$_2$CO$_3$ (300 mgs) followed by Et$_3$N (3 mL). The mixture was diluted with THF (10 mL) and stirred for 2 h. Solids were removed by filtration and the solid was washed with Et$_2$O (3×10 mL). The combined filtrate was washed with sat. aq. NaCl (25 mL), dried, and evaporated in vacuo. Purification of the residue via SiO$_2$ column chromatography using 40% EtOAc/hexanes as eluent gave dimethyl (19(S)-hydroxyeicosa-5(Z),14(Z)-dienoyl)-L-aspartate (58) (12 mg, 58%) as a colorless oil. TLC: 50% EtOAc/hexanes, R$_f$=0.45.

$^1$H NMR (400 MHz, CDCl$_3$) δ 6.51-6.50 (m, 1H), 5.44-5.31 (m, 4H), 4.90-4.87 (m, 1H), 3.83-3.80 (m, 11H), 3.77 (s, 31), 3.71 (s, 3H), 3.06 (dd, J=4.5, 17.5 Hz, 11H), 2.86 (dd, J=4.5, 17.5 Hz, 1H), 2.25 (t, J=7.5 Hz, 2H), 2.11-1.97 (m, 8H), 1.74-1.68 (m, 2H), 1.49-1.21 (m, 14H), 1.20 (d, J=6.5 Hz, 3H); $^{13}$C NMR (126 MHz, CDCl$_3$) δ 173.00, 171.95, 171.54, 131.35, 130.59, 129.64, 128.65, 68.30, 53.09, 52.31, 48.54, 39.15, 36.36, 36.13, 29.94, 29.66, 29.52, 29.50, 27.49, 27.46, 27.35, 26.85, 26.13, 25.71, 23.77. HRMS calcd for C$_{26}$H$_{45}$NNaO$_6$ [M+Na]$^+$ 490.3145, found 490.3139.

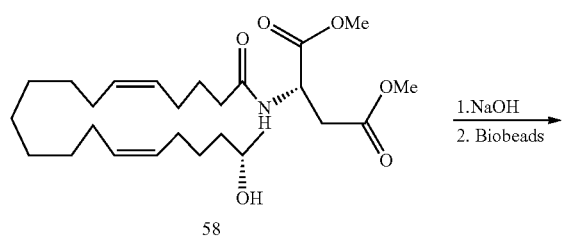

58

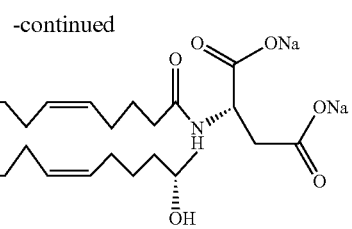

Analog 9

A solution of NaOH (2 mL of a 1 M aqueous soln) was added to a 0° C. solution of dimethyl (19(S)-hydroxyeicosa-5(Z),14(Z)-dienoyl)-L-aspartate (58) (12 mg, 0.025 mmol) in THF (15 mL) and deionized H$_2$O (4 mL). After stirring at room temperature overnight, all THF was removed under reduced pressure and BioRad SM-2 Bio-beads (5 g; prowashed with 0.1 N NH$_4$OH and H$_2$O) were added. After gently stirring for 1 h, the beads were collected on a sintered glass funnel, washed with deionized water (2×10 mL), and then EtOH (3×10 mL). Concentration of the ethanolic washes afforded disodium (19(S)-hydroxyeicosa-5(Z),14(Z)-dienoyl)-L-aspartate (Analog 9) (9 mg, 71%) as a colorless oil. TLC: 80% EtOAc/hexanes, R$_f$=0.2.

$^1$H NMR (400 MHz, CD$_3$OD) δ 5.41-5.35 (m, 4H), 4.96-4.91 (m, 1H), 3.73-3.71 (m, 1M), 2.68-2.67 (m, 2H), 2.25 (t, J=7.5 Hz, 2H), 2.09-2.03 (m, 8H), 1.68-1.66 (m, 2H), 1.49-1.17 (m, 14H), 1.14 (d, J=7.5 Hz, 3H); $^{13}$C NMR (101 MHz, CD$_3$OD) δ 178.72, 173.62, 130.12, 129.62, 129.28, 128.63, 128.38, 67.00, 52.41, 40.60, 38.40, 35.49, 29.51, 29.48, 29.02, 28.97, 26.81, 26.79, 26.60, 25.66, 25.63, 22.23, 19.98. HRMS calcd for C$_{24}$H$_{40}$NNa$_2$O$_6$ [M+1]$^+$ 484.2651, found 484.2646.

Analog 10: Disodium (19(R)-hydroxyeicosa-5(Z),14(Z)-dienoyl)-L-aspartate

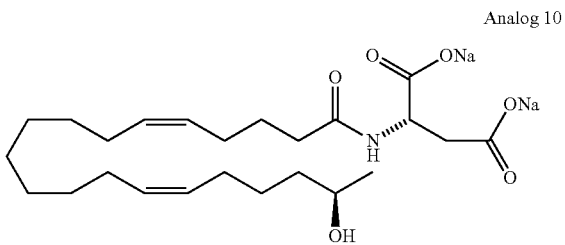

Analog 10

Sequential condensation of 19(R)-(tert-butyldiphenylsilyloxy)eicosa-5(Z),14(Z)-dienoic acid (80 mg, 0.14 mmol) with L-aspartic acid dimethyl ester, desilylation, saponification, and Biobead isolation following the procedures utilized in the preparation of Analog 9 gave disodium (19(R)-hydroxyeicosa-5(Z),14(Z)-dienoyl)-L-aspartate (Analog 10) (62 mg, 62% overall) as a viscous oil. TLC: 50% EtOAc/hexanes, R$_f$=0.45.

$^1$H NMR (500 MHz, CDCl$_3$) δ 7.72-7.65 (m, 4H), 7.46-7.33 (m, 6H), 6.48-6.47 (m, 1H), 5.46-5.23 (m, 4H), 4.88-4.84 (m, 1H), 3.85-3.82 (m, 1H), 3.76 (s, 3H), 3.69 (s, 3H), 3.05 (dd, J=4.3, 17.3 Hz, 11H), 2.86 (dd, J=4.5, 17.5 Hz, 1H), 2.24 (t, J=7.4 Hz, 2H), 2.12-1.88 (m, 8H), 1.71-1.64 (m, 2H), 1.55-1.23 (m, 14H), 1.08-1.03 (m, 12H); $^{13}$C-NMR (126 MHz, CDCl$_3$) δ 172.73, 171.65, 171.28, 135.87, 134.89, 134.53, 131.08, 130.03, 129.64, 129.44, 129.37, 128.41, 127.46, 127.38, 69.48, 52.80, 52.02, 48.32, 39.00, 36.11, 35.84, 29.77, 29.75, 29.51, 29.33, 29.31, 27.28, 27.23, 27.16, 27.05, 26.60, 25.47, 25.31, 23.25, 19.28. HRMS calcd for $C_{24}H_{40}NNa_2O_6[M+1]^+$ 484.2651, found 484.2641.

Analog 11: Sodium 19-hydroxyeicosa-5(Z)-enoate

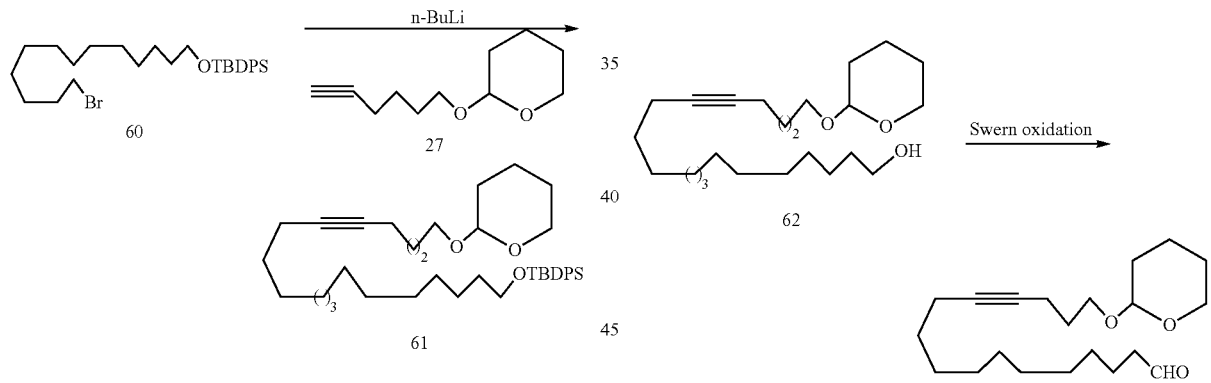

Silylation of 13-bromotridecan-1-ol (Grube, et al., *Eur. J. Org. Chem.* 2006, 1285-1295) (59) (1 g, 3.6 mmol) following the procedure utilized in the preparation of Analog 1 gave (13-bromotridecyloxy)(tert-butyl)diphenylsilane (60) (1.61 g, 87%) as a colorless oil. TLC: 10% EtOAc/hexane, $R_f$=0.55.

$^1$H NMR (CDCl$_3$, 500 MHz) δ 7.69 (dd, J=1.7, 7.8 Hz, 41), 7.54-7.37 (m, 6H), 3.69 (t, J=6.6 Hz, 2H), 3.44 (t, J=7.0 Hz, 2H), 1.98-1.82 (m, 2H), 1.67-1.54 (m, 2H), 1.37-1.32 (m, 2H), 1.29-1.22 (m, 16H), 1.08 (s, 9H); $^{13}$C NMR (CDCl$_3$, 101 MHz) δ 135.59, 134.19, 129.49, 127.58, 64.03, 32.87, 32.61, 29.64, 29.61, 29.58, 29.48, 29.41, 28.22, 26.89, 25.79, 19.25.

Alkylation of 2-(hex-5-yn-1-yloxy)tetrahydro-2H-pyran (Falck, et al. *J. Med Chem.* 2014, 57, 6965-6972) (27) (0.45 g, 2.5 mmol) with (13-bromotridecyloxy)(tert-butyl)diphenylsilane (60) (1.65 g, 3.2 mmol) following the procedure utilized in the preparation of Analog 1 provided tert-butyldiphenyl(19-(tetrahydro-2H-pyran-2-yloxy)nonadec-14-yn-1-yloxy)silane (61) (1.2 g, 78%) as a colorless oil. TLC: 20% EtOAc/hexane, $R_f$=0.45.

$^1$H NMR (CDCl$_3$, 500 MHz) δ 7.68 (dd, J=1.6, 7.6 Hz, 4H), 7.40-7.41 (m, 6H), 4.61-4.58 (m, 1H), 3.89-3.84 (m, 1H), 3.79-3.76 (m, 1H), 3.67 (t, J=6.5 Hz, 2H), 3.54-3.51 (m, 1H), 3.45-3.42 (m, 1H), 2.23-2.20 (m, 2H), 2.18-2.14 (m, 2H), 1.72-1.56 (m, 14H), 1.39-1.27 (m, 18H), 1.04 (s, 9H); $^{13}$C NMR (101 MHz, CDCl$_3$) δ 135.79, 134.39, 129.67, 127.79, 127.77, 127.74, 98.99, 80.77, 80.03, 67.30, 64.23, 62.49, 32.81, 30.97, 29.88, 29.85, 29.80, 29.61, 29.42, 29.39, 29.16, 29.14, 27.09, 26.17, 26.00, 25.72, 19.86, 19.44, 18.99, 18.85. HRMS calcd for $C_{40}H_{62}NaO_3Si$ [M+Na]$^+$ 641.4366, found 641.4360.

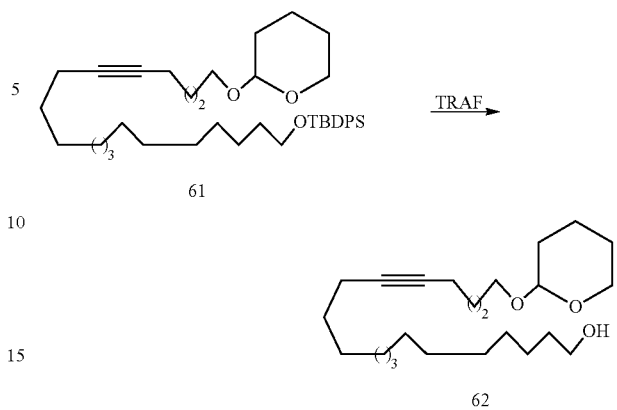

Desilylation of tert-butyldiphenyl(19-(tetrahydro-2H-pyran-2-yloxy)nonadec-14-yn-1-yl)oxysilane (61) (1.2 g, 0.78 mmol) following the procedure described in the preparation of Analog 1 gave 19-(tetrahydro-2H-pyran-2-yl)oxynonadec-14-yn-1-ol (62) (605 mg, 82%) as a colorless oil. TLC: 50% EtOAc/hexane, $R_f$=0.20.

$^1$H NMR (CDCl$_3$, 500 MHz) δ 4.58-4.54 (m, 1H), 3.88-3.84 (m, 1H), 3.77-3.72 (m, 1H), 3.62 (t, J=6.5 Hz, 2H), 3.51-3.48 (m, 1H), 3.42-3.39 (m, 1H), 2.20-2.17 (m, 2H), 2.14-2.11 (m, 2H), 1.58-1.40 (m, 16H), 1.35-1.27 (m, 16H). HRMS calcd for $C_{24}H_{44}NaO_3$ [M+Na]$^+$ 403.3188, found 403.3183.

Swern oxidation of 19-(tetrahydro-2H-pyran-2-yloxy)nonadec-14-yn-1-ol (62) (600 mg, 1.57 mmol) following the procedure utilized in the preparation of Analog 1 provided 19-(tetrahydro-2H-pyran-2-yloxy)nonadec-14-ynal (63) (531 mg, 89%) as a colorless oil which was used immediately in the next step.

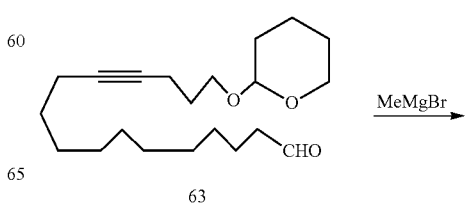

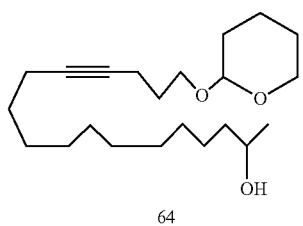

Addition of methylmagnesium bromide to 19-(tetrahydro-2H-pyran-2-yloxy)nonadec-14-ynal (63) (525 mg, 1.38 mmol) following the procedure utilized in the preparation of Analog 12 yielded 20-(tetrahydro-2H-pyran-2-yloxy)eicosa-15-yn-2-ol (64) (405 mg, 74%) as a colorless oil. TLC: 30% EtOAc/hexane, $R_f$=0.30.

$^1$H NMR (CDCl$_3$, 400 MHz) δ 4.58-4.54 (m, 1H), 3.88-3.72 (m, 2H), 3.48-3.39 (m, 3H), 2.20-2.11 (m, 4H), 1.58-1.40 (m, 16H), 1.35-1.27 (m, 19H); 13C NMR (126 MHz, CDCl$_3$) δ 98.79, 80.57, 79.83, 68.20, 67.10, 62.30, 39.39, 30.76, 29.67, 29.65, 29.63, 29.62, 29.60, 29.57, 29.19, 29.16, 28.94, 28.90, 25.95, 25.80, 25.51, 23.51, 19.64, 18.78, 18.64. HRMS calcd for C$_{25}$H$_{46}$NaO$_3$ [M+Na]$^+$ 417.3345, found 417.3339.

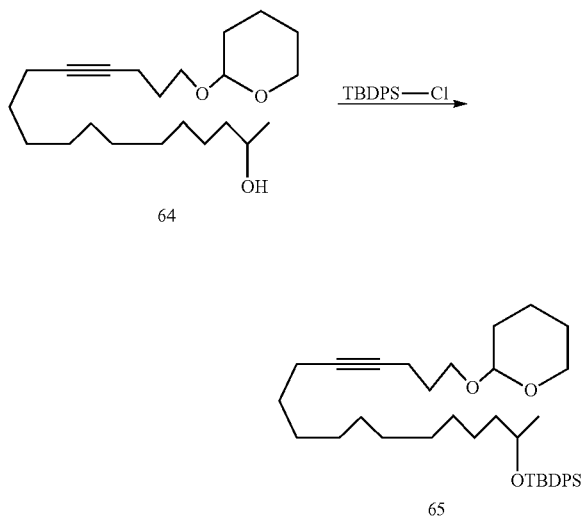

Silylation of 20-(tetrahydro-2H-pyran-2-yloxy)eicosa-15-yn-2-ol (64) (311 mg, 0.79 mmol) following the procedure utilized in the preparation of Analog 1 gave tert-butyldiphenyl((20-(tetrahydro-2H-pyran-2-yloxy)eicosa-15-yn-2-yl)oxy)silane (65) (410 mg, 82%) as a colorless oil. TLC: 30% EtOAc/hexane, $R_f$=0.55.

$^1$H NMR (CDCl$_3$, 400 MHz) δ 7.75-7.68 (m, 4H), 7.40-7.41 (m, 6H), 4.59-4.58 (m, 1H), 3.87-3.77 (m, 3H), 3.76-3.40 (m, 2H), 2.20-2.14 (m, 4H), 1.58-1.40 (m, 6H), 1.35-1.27 (m, 26H), 1.08-1.05 (m, 12H); $^{13}$C NMR (101 MHz, CDCl$_3$) δ 135.87, 135.86, 129.37, 129.31, 127.40, 127.33, 98.77, 80.54, 79.80, 69.61, 67.07, 62.28, 39.44, 30.74, 29.65, 29.59, 29.19, 29.17, 28.92, 28.91, 27.03, 25.93, 25.49, 25.22, 23.22, 19.63, 19.26, 18.77, 18.62. HRMS calcd for C$_{41}$H$_{64}$NaO$_3$Si [M+Na]$^+$ 655.4522, found 655.4517.

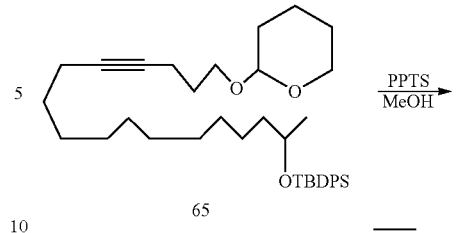

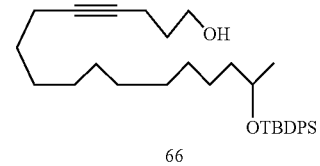

PPTS catalyzed solvolysis of tert-butyldiphenyl(20-(tetrahydro-2H-pyran-2-yloxy)eicosa-15-yn-2-yloxy)silane (65) (311 mg, 0.79 mmol) following the procedure utilized in the preparation of Analog 1 provided 19-(tert-butyldiphenylsilyloxy)eicosa-5-yn-1-ol (66) (410 mg, 82%) as a colorless oil. TLC: 30% EtOAc/hexane, $R_f$=0.44.

$^1$H NMR (CDCl$_3$, 400 MHz) δ 7.70 (dd, J=1.6, 7.6 Hz, 4H), 7.40-7.28 (m, 6H), 3.87-3.84 (m, 1H), 3.71-3.68 (m, 2H), 2.24-2.14 (m, 4H), 1.71-1.67 (m, 2H), 1.61-1.53 (m, 4H), 1.50-1.48 (m, 2H), 1.29-1.21 (m, 18H), 1.09-1.06 (m, 12H); $^{13}$C NMR (126 MHz, CDCl$_3$) δ 136.15, 136.14, 135.23, 134.89, 129.66, 129.60, 127.69, 127.62, 81.02, 79.98, 69.89, 62.76, 45.01, 39.71, 32.13, 29.92, 29.90, 29.87, 29.85, 29.47, 29.43, 29.19, 27.32, 25.63, 25.50, 23.51, 19.54, 19.02, 18.81. HRMS calcd for C$_{36}$H$_{56}$NaO$_2$Si [M+Na]$^+$ 571.3947, found 571.3942.

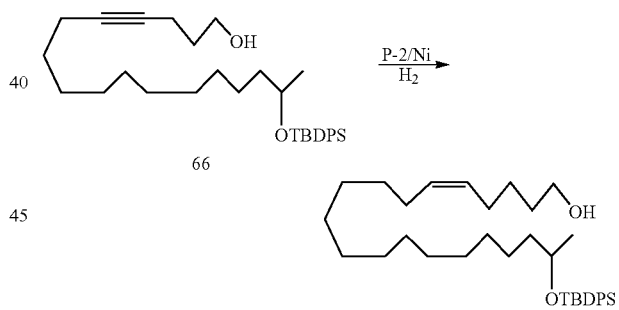

Semi-hydrogenation of 19-(tert-butyldiphenylsilyloxy)eicosa-5-yn-1-ol (66) (100 mg, 0.18 mmol) following the procedure utilized in the preparation of Analog 1 furnished 19-(tert-butyldiphenylsilyloxy)eicosa-5(Z)-en-1-ol (67) (72 g, 72%) as a colorless oil. TLC: 30% EtOAc/hexane, $R_f$=0.45.

$^1$H NMR (CDCl$_3$, 500 MHz) δ 7.73-7.68 (m, 4H), 7.41-7.39 (m, 6H), 5.41-5.25 (m, 2H), 3.89-3.82 (m, 11H), 3.67-3.62 (m, 2H), 1.99-1.93 (m, 4H), 1.71-1.53 (m, 26H), 1.05-1.04 (s, 12H); $^{13}$C NMR (101 MHz, CDCl$_3$) δ 135.79, 134.40, 129.68, 127.79, 127.77, 127.74, 99.00, 80.77, 80.03, 67.30, 64.23, 62.50, 32.82, 30.98, 29.89, 29.86, 29.80, 29.62, 29.43, 29.40, 29.16, 29.14, 27.10, 26.18, 26.01, 25.73, 19.86, 19.45, 19.00, 18.85. HRMS calcd for C$_{36}$H$_{58}$NaO$_2$Si [M+Na]$^+$ 573.4104, found 573.4098.

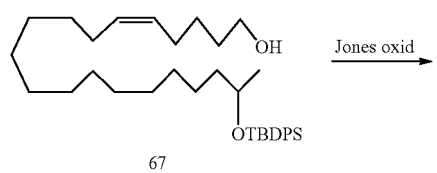

Jones oxidation of 19-(tert-butyldiphenylsilyloxy)eicosa-14(Z)-en-1-ol (67) (100 mg, 0.18 mmol) following the procedure utilized in the preparation of Analog 1 provided 19-(tert-butyldiphenylsilyloxy)eicosa-5(Z)-enoic acid (69 mg, 68%) as a colorless oil. TLC: 50% EtOAc/hexanes, $R_f$=0.55.

$^1$H NMR (CDCl$_3$, 500 MHz) δ 7.76 (dd, J=1.6, 7.6 Hz, 4H), 7.43-7.40 (m, 6H), 5.49-5.44 (m, 2H), 3.91-3.87 (m, 1H), 2.40 (t, J=7.6 Hz, 2H), 2.16-2.06 (m, 4H), 1.77-1.75 (m, 2H), 1.39-1.23 (m, 22H), 1.15-1.10 (s, 12H); $^{13}$C NMR (101 MHz, CDCl$_3$) δ 180.69, 136.16, 135.23, 134.90, 131.64, 129.68, 129.62, 128.39, 127.74, 127.71, 127.68, 127.64, 127.62, 69.90, 39.75, 33.76, 30.01, 29.97, 29.92, 29.90, 29.87, 29.64, 27.55, 27.35, 26.72, 25.53, 24.89, 23.54, 19.55. HRMS calcd for C$_{36}$H$_{58}$NaO$_2$Si [M+Na]$^+$ 587.3896, found 587.3891.

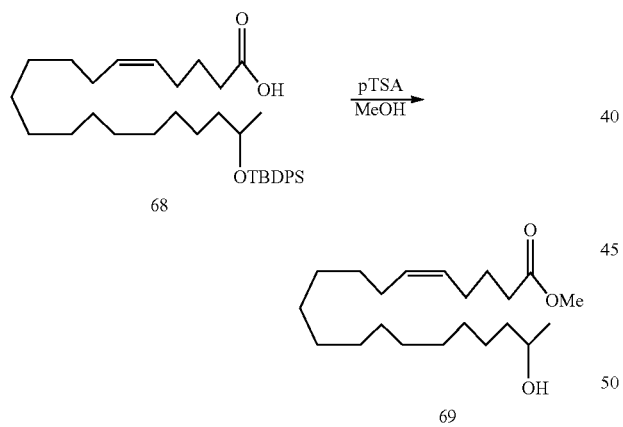

A mixture of p-toluenesulfonic acid (5 mg) and 19-(tert-butyldiphenylsilyloxy)eicosa-5(Z)-enoic acid (68) (85 mg, 0.15 mmol) in MeOH (10 mL) was stirred at 0° C. After 16 h, the reaction was quenched with sat. aq. NaHCO$_3$ (5 mL) and the methanol was removed under reduced pressure. The remaining reaction mixture was diluted with water (50 mL), extracted with EtOAc (2×30 mL), and the combined organic extracts were concentrated in vacuo. The residue was purified by SiO$_2$ column chromatography using 35% EtOAc/hexanes to afford methyl 19-hydroxyeicosa-5(Z)-enoate (69) (33 mg, 65%) as a colorless oil. TLC: 50% EtOAc/hexanes, $R_f$=0.30.

$^1$H NMR (CDCl$_3$, 500 MHz) δ 5.48-5.39 (m, 1H), 5.38-5.29 (m, 1H), 3.87-3.76 (m, 1H), 3.69 (s, 3H), 2.34 (t, J=7.5 Hz, 2H), 2.14-1.98 (m, 4H), 1.72-1.71 (m, 2H), 1.53-1.26 (m, 22H), 1.21 (d, J=6.1 Hz, 3H); $^{13}$C NMR (126 MHz, CDCl$_3$) δ 174.21, 131.20, 128.30, 68.22, 51.49, 39.39, 33.49, 29.71, 29.67, 29.65, 29.62, 29.57, 29.34, 27.24, 26.54, 25.80, 24.90, 23.50.

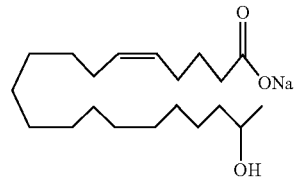

Saponification of methyl 19-hydroxyeicosa-5(Z)-enoate (69) (25 mg, 0.07 mmol) and isolation as described for the preparation of Analog 1 furnished sodium 19-hydroxyeicosa-5(Z)-enoate (Analog 11) (13 mg, 52%) as a colorless oil.

$^1$H NMR (500 MHz, CD$_3$OD) δ 5.40-5.34 (m, 2H), 3.79-3.69 (m, 1H), 2.23-2.18 (m, 2H), 2.14-2.02 (m, 4H), 1.72-1.59 (m, 2H), 1.52-1.30 (m, 22H), 1.16 (d, J=6.2 Hz, 3H); $^{13}$C NMR (101 MHz, CD$_3$OD) δ 174.19, 130.28, 128.45, 67.14, 38.83, 35.26, 29.45, 29.37, 29.34, 29.26, 28.99, 26.78, 26.37, 25.51, 22.10.

Analog 12: Sodium 19-hydroxyeicosa-14(Z)-enoate

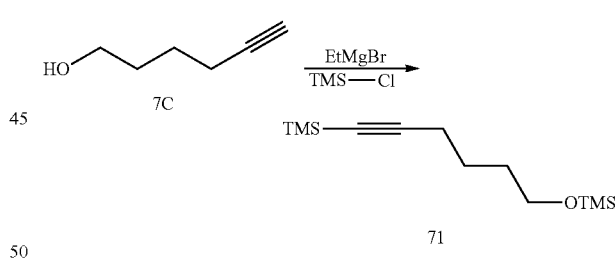

Ethylmagnesium bromide (20.1 mmol, 6.8 mL of a 3 M solution in hexanes) was added dropwise to a stirring, −78° C. solution of commercial hex-5-yn-1-ol (70) (1 g, 10 mmol) in dry THF (25 mL) followed by a solution of TMS-Cl (4.4 g, 40 mmol) in dry THF (10 mL). After 30 min, the reaction mixture was warmed over 3 h to 0° C. The reaction mixture was diluted with Et$_2$O (10 mL), quenched with sat. aq. NH$_4$Cl (25 mL), and extracted with E$_2$O (2×60 mL). The combined ethereal extracts were washed with water (2×100 mL), brine (100 mL), dried over Na$_2$SO$_4$, and concentrated in vacuo to give crude trimethyl(6-(trimethylsilyl)hex-5-yn-1-yloxy)silane (71) (1.7 g, 71%) as a colorless oil whose spectral data were consistent with literature values (Ghomsi, et al., *Tetrahedron Lett.* 2009, 46, 1537-1539). The crude product was used without further purification in the next step.

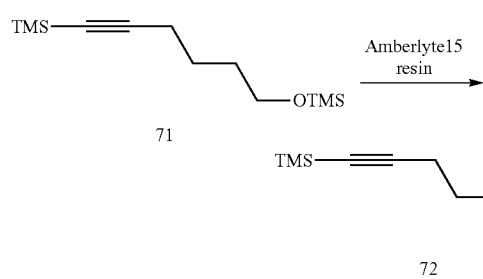

A solution of trimethyl(6-(trimethylsilyl)hex-5-yn-1-yloxy)silane (71) (1.7 g, 7 mmol) in dry Et$_2$O (15 mL) was added to a vigorously stirring suspension of Amberlyte®15 resin (sulphonic acid resin, 250 mg) in dry Et$_2$O (10 mL). After 3 h, the reaction was filtered and the filtrate was concentrated in vacuo. The residue was purified by SiO$_2$ column chromatography using 10% EtOAc/hexanes to afford 6-(trimethylsilyl)hex-5-yn-1-ol (72) (800 mg, 67%) as a colorless oil whose spectral data were consistent with literature values (Ohomsi, et al., *Tetrahedron Lett.* 2009, 46, 1537-1539; Stork, et al., *J. Am. Chem. Soc.* 2005, 127, 16255-16262). TLC: SiO$_2$, EtOAc/hexane (1:4), R$_f$=0.5.

$^1$H NMR (CDCl$_3$, 400 MHz) δ 3.70-3.67 (m, 2H), 2.29-2.17 (m, 2H), 1.70-1.59 (m, 4H), 0.13 (s, 9H).

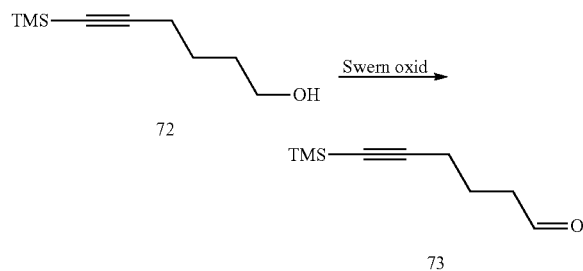

Swern oxidation of 6-(trimethylsilyl)hex-5-yn-1-ol (72) (860 mg, 5 mmol) as utilized in the preparation of Analog 1 provided 6-(trimethylsilyl)hex-5-ynal (73) (Stork, et al., *J. Am. Chem. Soc.* 2005, 127, 16255-16262. (800 mg, 95%) as a colorless oil which was used immediately in the next step. TLC: EtOAc/hexanes (2:8), R$_f$=0.45.

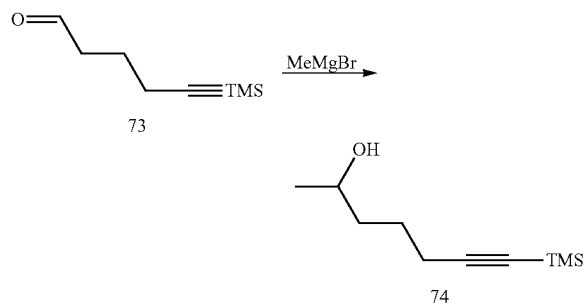

Methylmagnesium bromide (11.9 mmol, 0.39 mL of a 3.0 M solution in ether) was added dropwise to a stirring, −78° C. solution of 6-(trimethylsilyl)hex-5-ynal (73) (800 mg, 4.76 mmol) in dry THF (20 mL). After 30 min, the reaction mixture was warmed over 3 h to 0° C. After dilution with Et$_2$O (10 mL), the reaction mixture was quenched with sat. aq. NH$_4$Cl (15 mL) and extracted with Et$_2$O (2×30 mL). The combined ethereal extracts were washed with water (2×80 mL), brine (80 mL), dried, and then concentrated in vacuo. The residue was purified by SiO$_2$ column chromatography using 10% EtOAc/hexanes to afford 7-(trimethylsilyl)hept-6-yn-2-ol (74) (604 mg, 69%) as a colorless oil. TLC: EtOAc/hexanes (1:4), R$_f$=0.35.

$^1$H NMR (CDCl$_3$, 400 MHz) δ 3.84-3.81 (m, 1H), 2.31-2.18 (m, 2H), 1.71-1.45 (m, 4H), 1.19 (d, J=6.1 Hz, 3H), 0.13 (s, 9H).

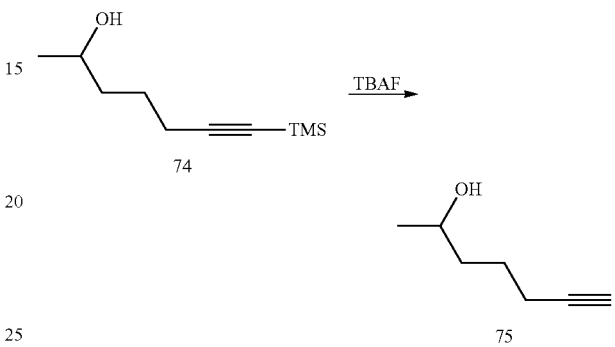

A mixture of 7-(trimethylsilyl)hept-6-yn-2-ol (74) (600 mg, 3.24 mmol) and n-tetrabutylammonium fluoride (3.9 mmol, 3.9 mL of a 1.0 M solution in THF) in anhydrous THF (5 mL) was stirred at 0° C. for 12 h, then evaporated to dryness in vacuo. The residue was dissolved in EtOAc (60 mL), washed with H$_2$O (30 mL), brine (30 mL), dried (Na$_2$SO$_4$), and evaporated in vacuo. Purification of the residue via SiO$_2$ column chromatography using 10% EtOAc/hexanes gave hept-6-yn-2-ol (75) (64 mg, 78%) as a colorless oil whose spectral data were consistent with literature values (Le Drain, et al., *J. Am. Chem. Soc.* 1982, 104, 5473-5483; Peterson, et al., *J. Am. Chem. Soc.* 1969, 91, 4521-4527). The crude product was used immediately in the next step. TLC: EtOAc/hexanes (1:4), R$_f$=0.3.

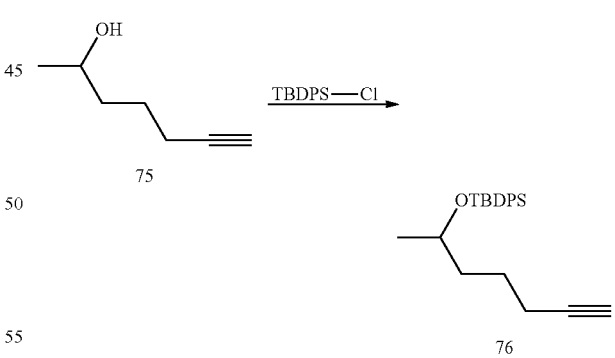

Hept-6-yn-2-ol (75) (284 mg, 2.53 mmol) was silylated as described in the preparation of Analog 1 to give tert-butyl (hept-6-yn-2-yloxy)diphenylsilane (76) (727 mg, 82%) as a colorless oil whose spectral data were consistent with literature values (Moune, et al., *J. Org. Chem.* 1997, 62, 3332-3339). TLC: SiO$_2$, EtOAc/hexane (1:9), R$_f$=0.75.

$^1$H NMR (CDCl$_3$, 500 MHz) δ 7.70 (dd, J=1.6, 7.6 Hz, 4H), 7.41-7.28 (m, 6H), 3.90-3.87 (m, 1H), 2.11-2.10 (m, 2H), 1.94-1.91 (m, 1H), 1.59-1.48 (m, 4H), 1.09-1.07 (m, 12H); $^{13}$C NMR (126 MHz, CDCl$_3$) δ 138.73, 138.71, 135.97, 135.94, 134.77, 134.46, 129.68, 129.58, 127.67, 127.56, 88.83, 69.17, 38.66, 33.02, 27.19, 23.48, 23.34 19.38.

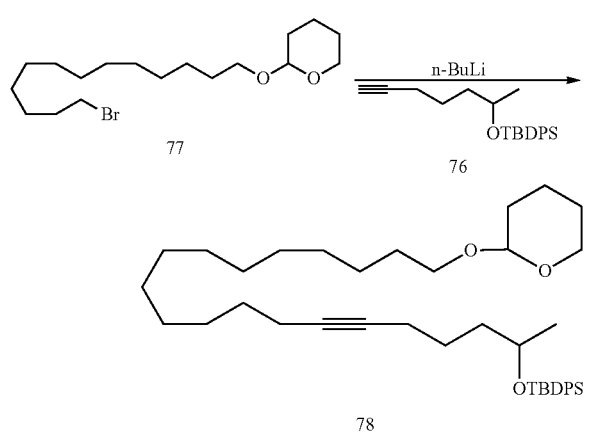

A solution of n-butyllithium (0.34 mL of a 2.5 M solution in hexane, 0.858 mmol) was added dropwise to a stirring, −78° C. solution of tert-butyl(hept-6-yn-2-yloxy)diphenylsilane (76) (250 mg, 0.71 mmol) in anhydrous THF/HMPA (6:1, 16 mL) under an argon atmosphere. After 30 min, the reaction mixture was warmed over 1 h to 0° C., held there for 2 h, then re-cooled to −78° C. To this was added a solution of 2-(13-bromotridecyloxy)tetrahydro-2H-pyran (77) (Grube, et al., *Eur. J. Org. Chem.* 2006, 1285-1295).

(310 mg, 0.857 mmol) in dry THF (5 mL). The reaction temperature was then increased over 3 h to rt. After another 12 h, the reaction was quenched with sat aq. NH$_4$Cl (15 mL) and extracted with EtOAc (2×150 mL). The combined organic extracts were washed with water (2×100 mL), brine (100 mL), dried, and concentrated in vacuo. The residue was purified by SiO$_2$ column chromatography using 10% EtOAc/hexanes to afford tert-butyldiphenyl(20-(tetrahydro-2H-pyran-2-yloxy)eicosa-6-yn-2-yloxy)silane (78) (311 mg, 69%) as a colorless oil. TLC: SiO$_2$, EtOAc/hexane (2:3), R$_f$=0.33.

$^1$H NMR (CDCl$_3$, 500 MHz) δ 7.06 (dd, J=1.6, 7.6 Hz, 4H), 7.39-7.42 (m, 6l), 4.58-4.56 (m, 1H), 3.88-3.83 (m, 2H), 3.73-3.70 (m, 1H), 3.50-3.47 (m, 1H), 3.39-3.35 (m, 1H), 1.99-1.93 (m, 4H), 1.89-1.73 (m, 2H), 1.71-1.67 (m, 10H), 1.69-1.53 (m, 23H), 1.05 (s, 911); $^{13}$C NMR (126 MHz, CDCl$_3$) δ 135.85, 134.87, 134.45, 129.43, 129.36, 127.45, 127.36, 98.83, 80.40, 79.99, 69.18, 67.70, 62.36, 62.34, 38.59, 30.78, 29.75, 29.65, 29.61, 29.61, 29.50, 29.43, 29.19, 29.17, 28.90, 27.02, 26.24, 25.50, 24.86, 23.20, 19.70, 19.27, 18.80, 18.75. HRMS calcd for C$_{29}$H$_{43}$NaO$_2$Si [M+Na]$^+$ 655.4522, found 655.4517.

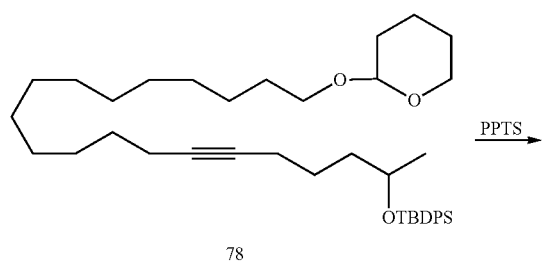

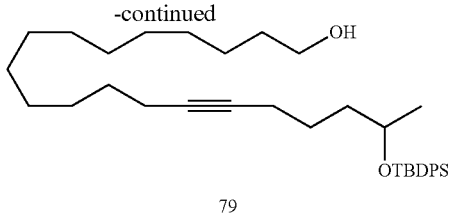

PPTS (5 mg) was added to a stirring, 0° C. solution of tert-butyldiphenyl(20-(tetrahydro-2H-pyran-2-yloxy)eicosa-6-yn-2-yloxy)silane (78) (240 mg, 0.38 mmol) in MeOH (10 mL). After 14 h, the reaction was quenched with sat. aq. NaHCO$_3$ (5 mL), the methanol was removed under reduced pressure, and the remaining material was diluted with water (50 mL). The reaction mixture was extracted with EtOAc (2×50 mL) and the combined organic extracts were concentrated in vacuo. The crude product was purified by SiO$_2$ column chromatography using 25% EtOAc/hexanes to afford 19-(tert-butyldiphenylsilyloxy)eicosa-14-yn-1-ol (79) (166 mg, 80%) as a colorless oil. TLC: 50% EtOAc/hexane, R$_f$=0.45.

$^1$H NMR (CDCl$_3$, 500 MHz) δ 7.06 (dd, J=1.6, 7.6 Hz, 4H), 7.39-7.42 (m, 6H), 3.88-3.87 (m, 1H), 3.66 (t, J=7.5 Hz, 2H), 3.43 (br s, 1H, OH) 1.99-1.93 (m, 4H), 1.71-1.67 (m, 6H), 1.69-1.53 (m, 20H), 1.05-1.04 (m, 12H); $^{13}$C NMR (126 MHz, CDCl$_3$) δ 135.87, 134.88, 134.45, 129.45, 129.38, 127.47, 127.38, 80.42, 80.01, 69.20, 63.12, 38.60, 32.81, 29.65, 29.62, 29.60, 29.57, 29.44, 29.20, 29.17, 28.91, 27.04, 25.74, 24.87, 23.22, 19.29, 18.81, 18.77. HRMS calcd for C$_{36}$H$_{56}$NaO$_2$Si [M+Na]$^+$ 571.3947, found 571.3942.

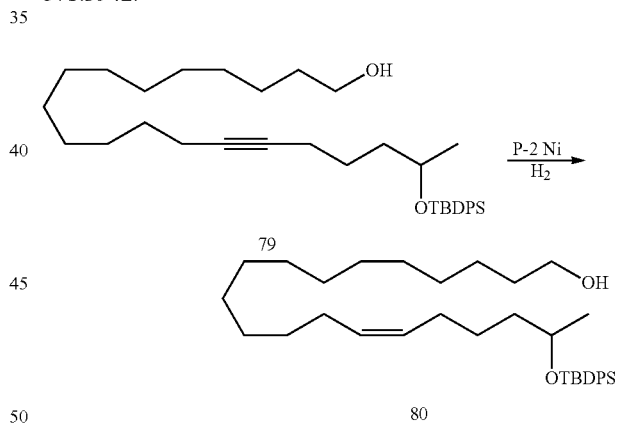

Semi-hydrogenation of 19-(tert-butyldiphenylsilyloxy)eicosa-14-yn-1-ol (79) (320 mg, 0.58 mmol) as described in the preparation of Analog 1 furnished 19-(tert-butyldiphenylsilyloxy)eicosa-14(Z)-en-1-ol (80) (276 g, 86%) as a colorless oil. TLC: 50% EtOAc/hexane, R$_f$=0.46.

$^1$H NMR (CDCl$_3$, 500 MHz) δ 7.06 (dd, J=1.6, 7.6 Hz, 4H), 7.39-7.42 (m, 6H), 5.34-5.25 (m, 2H), 3.85-3.82 (m, 1H), 3.63 (t, J=7.5 Hz, 2H), 3.41 (br s, 1H, OH), 1.99-1.93 (m, 4H), 1.71-1.67 (m, 4H), 1.69-1.53 (m, 22H), 1.05-1.04 (s, 12H); $^{13}$C NMR (126 MHz, CDCl$_3$) δ 136.16, 135.19, 134.83, 130.36, 129.90, 129.72, 129.65, 127.74, 127.66, 69.78, 63.30, 39.30, 33.38, 30.07, 30.02, 30.00, 29.99, 29.98, 29.96, 29.93, 29.91, 29.78, 29.77, 29.65, 27.53, 27.45, 27.35, 26.15, 25.61, 23.53, 19.56. HRMS calcd for C$_{36}$H$_{58}$ClO$_2$Si [M+Cl]$^−$ 585.3895, found 585.3900.

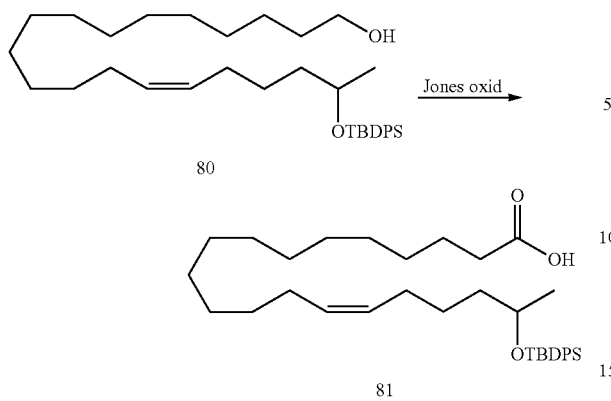

80

81

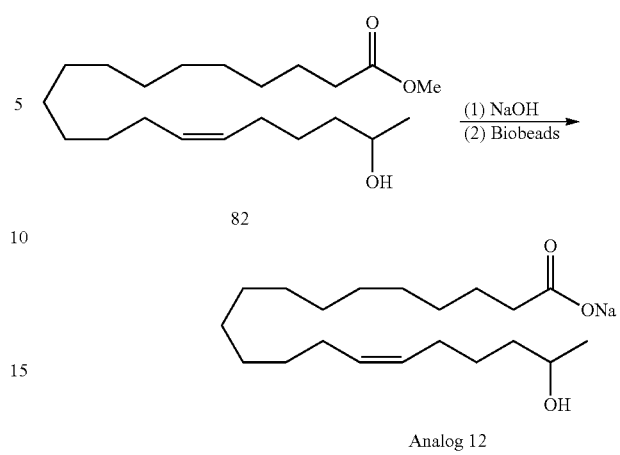

82

Analog 12

Jones oxidation of 19-(tert-butyldiphenylsilyloxy)eicosa-14(Z)-en-1-ol (80) (200 mg, 0.363 mmol) as described in the preparation of Analog 1 provided 19-(tert-butyldiphenylsilyloxy)eicosa-14(Z)-enoic acid (81) (141 g, 69%) as a colorless oil. TLC: 50% EtOAc/hexanes, $R_f$=0.20.

$^1$H NMR (CDCl$_3$, 500 MHz) δ 7.06 (dd, J=1.6, 7.6 Hz, 4H), 7.39-7.42 (m, 6H), 5.37-5.28 (m, 2H), 3.87-3.84 (m, 1H), 2.37 (t, J=7.5 Hz, 2H), 1.99-1.93 (m, 4H), 1.71-1.67 (m, 2H), 1.37-1.28 (m, 22H), 1.08-1.04 (m, 12H); $^{13}$C NMR (101 MHz, CDCl$_3$) δ 180.79, 136.14, 135.17, 134.82, 130.33, 129.88, 129.70, 129.63, 127.75, 127.72, 127.70, 127.67, 127.64, 127.62, 69.76, 39.28, 34.41, 30.05, 29.96, 29.94, 29.90, 29.87, 29.73, 29.62, 29.54, 29.35, 27.54, 27.44, 27.33, 25.60, 24.95, 23.51, 19.54. HRMS calcd for C$_{36}$H$_{56}$O$_3$Si [M−1]$^+$ 563.3921, found 563.3926.

Saponification of methyl 19-hydroxyeicosa-14(Z)-enoate (82) (25 mg, 0.07 mmol) and isolation as described for the preparation of Analog 1 furnished sodium 19-hydroxyeicosa-14(Z)-enoate (Analog 12) (13 mg, 52%) as a colorless oil.

$^1$H NMR (500 MHz, CD$_3$OD) δ 5.40-5.36 (m, 2H), 3.75-3.68 (m, 1H), 2.18 (t, J=7.6 Hz, 2H), 2.14-2.01 (m, 4H), 1.72-1.59 (m, 2H), 1.52-1.27 (m, 22H), 1.17 (d, J=6.2 Hz, 3H); $^{13}$C NMR (CD$_3$OD, 101 MHz) δ 129.63, 129.19, 67.00, 38.34, 37.49, 29.42, 29.40, 29.35, 29.34, 29.32, 29.23, 28.93, 26.73, 26.24, 25.61, 22.11.

Analog 13: Sodium (19-hydroxyeicosa-5(Z)-enoyl)glycinate

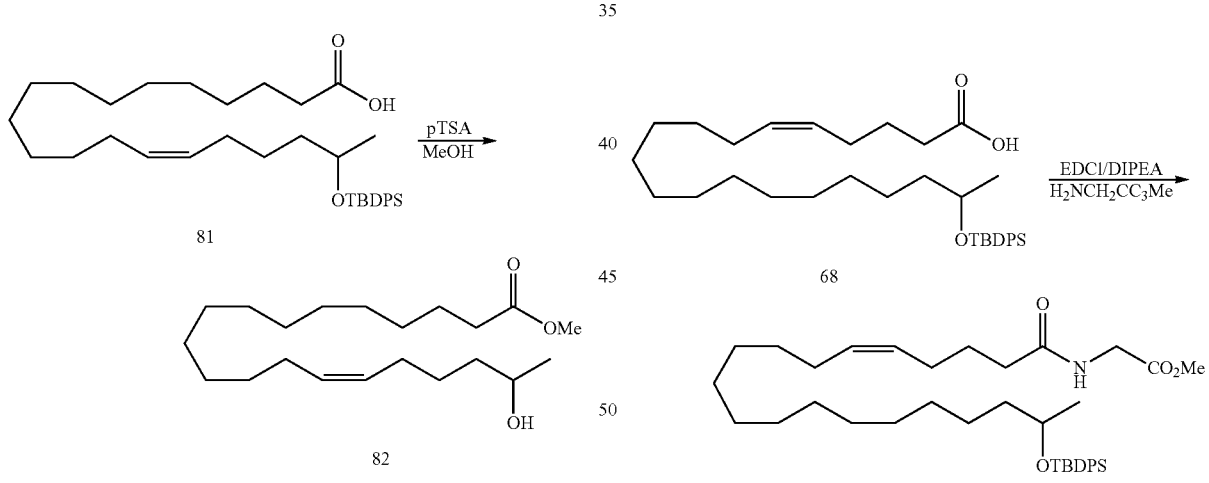

81

82

68

83

19-(tert-Butyldiphenylsilyloxy)eicosa-14(Z)-enoic acid (81) (98 mg, 0.17 mmol) was esterified and de-silylated following the procedure described in the preparation of Analog 11 to give methyl 19-hydroxyeicosa-14(Z)-enoate (82) (37 mg, 64%) as a colorless oil. TLC: 60% EtOAc/hexanes, $R_f$=0.35.

$^1$H NMR (CDCl$_3$, 500 MHz) δ 5.44-5.31 (m, 2H), 3.86-3.76 (m, 1H), 3.68 (s, 3H), 2.32 (t, J=7.5 Hz, 2H), 2.13-1.99 (m, 4H), 1.66-1.62 (m, 2H), 1.54-1.25 (m, 22H), 1.21 (d, J=6.2 Hz, 3H); $^{13}$C NMR (101 MHz, CDCl$_3$) δ 174.35, 130.32, 129.31, 67.99, 51.42, 38.86, 34.08, 29.70, 29.63, 29.59, 29.55, 29.51, 29.41, 29.28, 29.22, 29.11, 27.21, 27.07, 25.84, 24.92, 23.46.

Condensation of 19-(tert-butyldiphenylsilyloxy)eicosa-5(Z)-enoic acid (68) (100 mg, 0.17 mmol) with glycine methyl ester following the procedure utilized in the preparation of Analog 7 gave methyl (19-(tert-butyldiphenylsilyloxy)eicosa-5(Z)-enoyl)glycinate (83) (76 mg, 68%) as a colorless oil. TLC: 50% EtOAc/hexanes, $R_f$=0.40.

$^1$H NMR (CDCl$_3$, 500 MHz) δ 7.71 (dd, J=1.6, 7.6 Hz, 41), 7.71-7.70 (m, 6H), 6.16-6.14 (m, 1H), 5.45-5.43 (m, 11H), 5.36-5.34 (m, 1H), 4.07 (d, J=5.0 Hz, 2H), 3.86-3.85 (m, 1H), 3.77 (s, 3H), 2.38 (t, J=7.5 Hz, 2H), 2.12-2.11 (m, 2H), 2.04-2.03 (m, 2H), 1.76-1.74 (m, 2H), 1.32-1.20 (m, 22H), 1.08-1.07 (s, 12); $^{13}$C NMR (101 MHz, CDCl$_3$) δ

173.38, 170.77, 136.10, 135.19, 134.85, 131.37, 129.62, 129.57, 128.62, 127.68, 127.65, 127.63, 127.58, 127.56, 69.84, 52.55, 41.40, 39.68, 35.92, 29.99, 29.93, 29.90, 29.86, 29.83, 29.61, 27.53, 27.28, 26.83, 25.72, 25.46, 23.48, 19.50. HRMS calcd for $C_{39}H_{61}NNaO_4Si$ [M+Na]$^+$ 658.4268, found 658.4262.

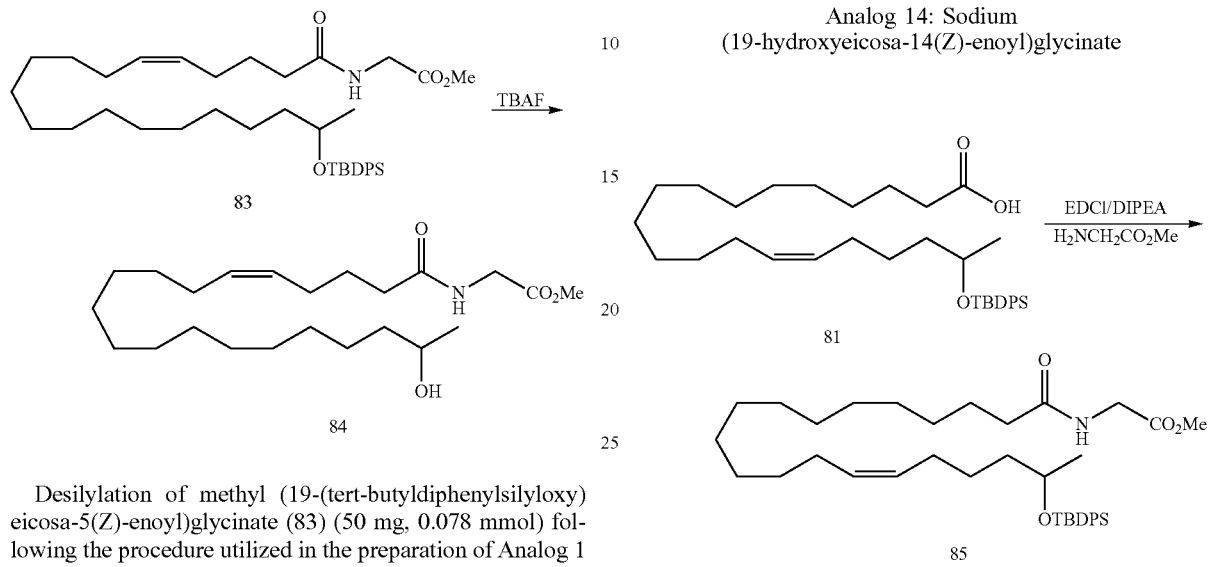

Desilylation of methyl (19-(tert-butyldiphenylsilyloxy) eicosa-5(Z)-enoyl)glycinate (83) (50 mg, 0.078 mmol) following the procedure utilized in the preparation of Analog 1 gave methyl (19-hydroxyeicosa-5(Z)-enoyl)glycinate (84) (17 mg, 55%) as a colorless oil. TLC: 60% EtOAc/hexanes, $R_f$=0.20.

$^1$H NMR (CDCl$_3$, 500 MHz) δ 6.07-6.04 (m, 1H), 5.43-5.32 (m, 2H), 4.06 (d, J=6.5 Hz, 2H), 3.79-3.78 (m, 1H), 3.76 (s, 3H), 2.26 (t, J=7.5 Hz, 2H), 2.12-2.08 (m, 2H), 2.04-1.99 (m, 2H), 1.73-1.71 (m, 3H), 1.43-1.20 (m, 21H), 1.13 (d, J=6.0 Hz, 3H); $^{13}$C NMR (126 MHz, CDCl$_3$) δ 173.51, 170.84, 131.35, 128.63, 68.33, 52.59, 45.00, 41.40, 39.58, 35.92, 29.94, 29.89, 29.86, 29.85, 29.82, 29.77, 29.55, 27.49, 26.83, 26.02, 25.72, 23.68. HRMS calcd for $C_{23}H_{43}NNaO_4$ [M+Na]$^+$ 420.3090, found 420.3084.

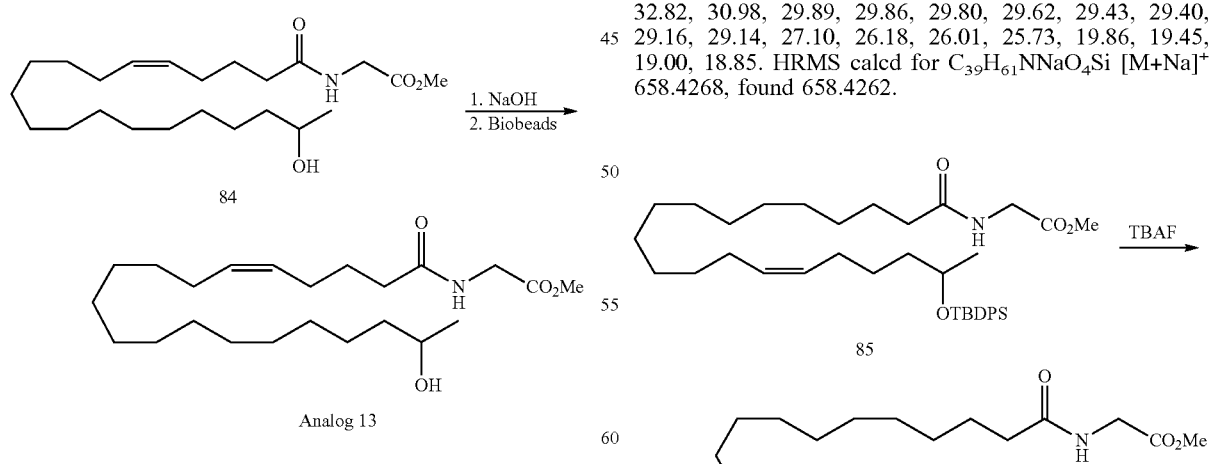

Saponification of methyl (19-hydroxyeicosa-5(Z)-enoyl) glycinate (84) (15 mg, 0.037 mmol) and isolation using SM-2 Biobeads as utilized in the preparation of Analog 7 furnished sodium (19-hydroxyeicosa-5(Z)-enoyl)glycinate (Analog 13) (9 mg, 62%) as a colorless oil. TLC: 80% EtOAc/hexanes, $R_f$=0.20.

$^1$H NMR (CD$_3$OD, 500 MHz) δ 5.41-5.35 (m, 2H), 3.75-3.69 (m, 3H), 2.26 (t, J=8.0 Hz, 2H), 2.11-2.02 (m, 4H), 1.69-1.66 (m, 2H), 1.46-1.29 (m, 22H), 1.14 (d, J=6.0 Hz, 3H); $^{13}$C NMR (101 MHz, CD$_3$OD) δ 175.11, 174.40, 129.64, 129.22, 67.02, 48.22, 48.01, 47.80, 47.58, 47.37, 43.11, 38.37, 35.77, 29.43, 29.35, 29.10, 29.01, 28.94, 26.74, 25.63, 25.47, 22.14. HRMS calcd for $C_{22}H_{41}NNaO_4$ [M+Na+1]$^+$ 406.2933, found 406.2929.

Analog 14: Sodium (19-hydroxyeicosa-14(Z)-enoyl)glycinate

Condensation of 19-(tert-butyldiphenylsilyloxy)eicosa-14(Z)-enoic acid (81) (100 mg, 0.17 mmol) with glycine methyl ester as described in the preparation of Analog 7 gave methyl (19-(tert-butyldiphenylsilyloxy)eicosa-14(Z)-enoyl) glycinate (85) (68 mg, 61%) as a colorless oil. TLC: 80% EtOAc/hexanes, $R_f$=0.55.

$^1$H NMR (CDCl$_3$, 500 MHz) δ 7.71 (dd, J=1.6, 7.6 Hz, 4H), 7.43-7.37 (m, 6H), 6.16-6.14 (m, 1H), 5.37-5.28 (m, 2H), 4.08 (d, J=5 Hz, 2H), 3.88-3.85 (m, 1H), 3.78 (s, 3H), 2.38 (t, J=7.5 Hz, 2H), 1.99-1.93 (m, 4H), 1.71-1.67 (m, 2H), 1.69-1.53 (m, 22H), 1.05-1.04 (m, 12H); $^{13}$C NMR (101 MHz, CDCl$_3$) δ 135.79, 134.40, 129.68, 127.79, 127.77, 127.74, 99.00, 80.77, 80.03, 67.30, 64.23, 62.50, 32.82, 30.98, 29.89, 29.86, 29.80, 29.62, 29.43, 29.40, 29.16, 29.14, 27.10, 26.18, 26.01, 25.73, 19.86, 19.45, 19.00, 18.85. HRMS calcd for $C_{39}H_{61}NNaO_4Si$ [M+Na]$^+$ 658.4268, found 658.4262.

Methyl (19-(tert-butyldiphenylsilyloxy)eicosa-14-enoyl) glycinate (85) (50 mg, 0.078 mmol) was de-silylated as described in the preparation of Analog 7 to give methyl (19-hydroxyeicosa-14(Z)-enoyl)glycinate (86) (20 mg, 64%) as a colorless oil. TLC: 80% EtOAc/hexanes, $R_f$=0.35.

$^1$H NMR (CDCl$_3$, 500 MHz) δ 6.17-6.14 (m, 1H), 5.34-5.28 (m, 2H), 3.99 (d, J=6.5 Hz, 2H), 3.75-3.72 (m, 1H), 3.71 (s, 3H), 2.19 (t, J=7.2 Hz, 2H), 1.99-1.93 (m, 4H), 1.59 (br s, 1H), 1.42-1.38 (m, 2H), 1.30-1.19 (m, 22H), 1.13 (d, J=6.4 Hz, 3H); $^{13}$C NMR (101 MHz, CDCl$_3$) δ 173.65, 170.84, 130.52, 129.57, 68.15, 52.52, 41.34, 39.09, 36.56, 29.90, 29.84, 29.79, 29.77, 29.71, 29.65, 29.53, 29.47, 29.43, 27.41, 27.31, 26.08, 25.77, 23.68. HRMS calcd for C$_{23}$H$_{43}$NNaO$_4$ [M+Na]$^+$ 420.3090, found 420.3084.

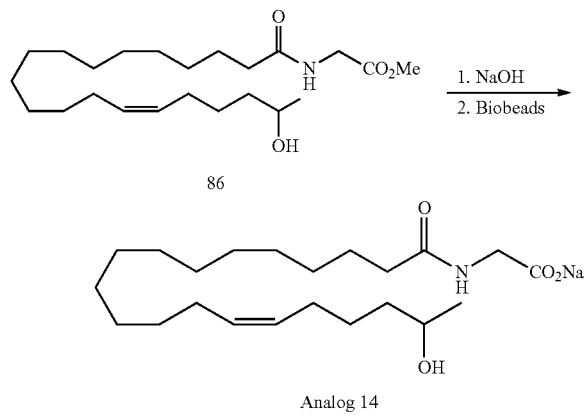

Analog 14

Saponification of methyl (19-hydroxyeicosa-14(Z)-enoyl) glycinate (86) (18 mg, 0.045 mmol) and isolation using SM-2 Biobeads as described in the preparation of Analog 7 furnished sodium (19-hydroxyeicosa-14(Z)-enoyl)glycinate (Analog 14) (10 mg, 54%) as a colorless liquid. TLC: 80% EOAc/hexanes, $R_f$=0.2.

$^1$H NMR (CD$_3$OD, 500 MHz) δ 5.37-5.35 (m, 2H), 3.75-3.69 (m, 3H), 2.24 (t, J=7.2 Hz, 2H), 2.06-2.03 (m, 4H), 1.62-1.55 (m, 2H), 1.44-1.30 (m, 22H), 1.14 (d, J=6.0 Hz, 3H); $^{13}$C NMR (101 MHz, CD$_3$OD) δ 175.11, 174.40, 129.64, 129.22, 67.02, 48.22, 48.01, 47.80, 47.58, 47.37, 43.11, 38.37, 35.77, 29.43, 29.35, 29.10, 29.01, 28.94, 26.74, 25.63, 25.47, 22.14.

HRMS calcd for C$_{22}$H$_{41}$NNaO$_4$[M+Na+1]$^+$ 406.2933, found 406.2928.

Analog 15: Sodium 18-hydroxyeicosa-5(Z),14(Z)-dienoate

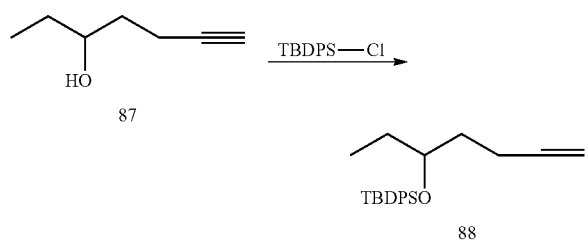

Silylation of hept-6-yn-3-ol (87) (Booth, et al., *Org. Biomol. Chem.* 2007, 5, 1111-1117) (600 mg, 5.35 mmol) following the procedure utilized in the preparation of Analog 1 gave tert-butyl(hept-6-yn-3-yloxy)diphenylsilane (88) (1.48 g, 79%) as a colorless oil. TLC: 10% EtOAc/hexanes, $R_f$=0.85.

$^1$H NMR (500 MHz, CDCl$_3$) δ 7.73-7.66 (m, 4H), 7.47-7.34 (m, 6H), 3.82-3.74 (m, 1H), 2.28-2.16 (m, 2H), 1.87 (t, J=2.6 Hz, 1H), 1.71-1.69 (m, 2H), 1.48-1.46 (m, 2H), 1.07 (s, 9H), 0.76 (t, J=7.4 Hz, 3H); $^{13}$C NMR (101 MHz, CDCl$_3$) δ 136.05, 134.68, 134.34, 129.71, 129.64, 127.68, 127.63, 127.60, 84.53, 73.38, 68.34, 34.65, 29.11, 27.25, 19.58, 14.50, 9.33.

HRMS calcd for C$_{23}$H$_{30}$NaOSi [M+Na]$^+$ 373.1964, found 373.1968.

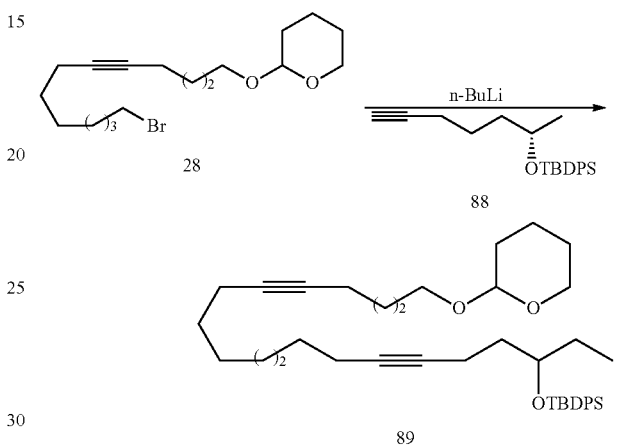

Alkylation of tert-butyl(hept-6-yn-3-yloxy)diphenylsilane (88) (1.32 g, 3.77 mmol) with 2-(13-bromotridec-5-yn-1-yloxy)tetrahydro-2H-pyran (28) (1.66 g, 4.52 mmol) utilizing the procedure described in the preparation pf Analog 1 provided tert-butyldiphenyl(20-(tetrahydro-2H-pyran-2-yloxyeicosa-6,15-diyn-3-yl)oxy)silane (89) (1.44 g, 62%) as a colorless oil that was used directly in the next step. TLC: 20% EtOAc/hexanes, $R_f$=0.65.

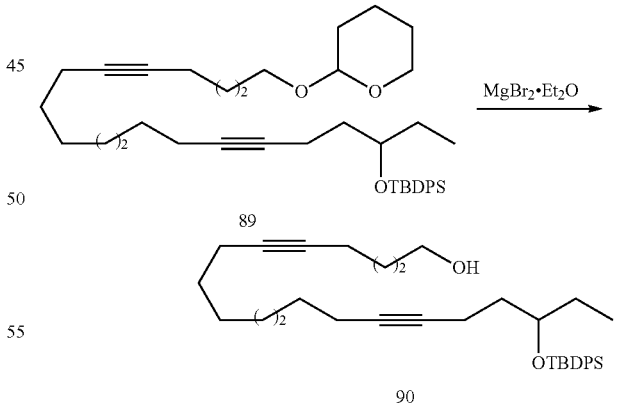

Anhydrous MgBr$_2$·Et$_2$O (1.5 g, 5.71 mmol) was added to a stirring, 0° C. solution of tert-butyldiphenyl((20-(tetrahydro-2H-pyran-2-yloxy)eicosa-6,15-diyn-3-yl)oxy)silane (89) (1.2 g, 1.91 mmol) in dry Et$_2$O (30 mL). After 24 h, the reaction was quenched with sat. aq. NaHCO$_3$ (30 mL) and extracted with EtOAc (3×50 mL). The combined organic extracts were concentrated under reduced pressure and the residue was purified by SiO$_2$ column chromatography to afford 18-(tert-butyldiphenylsilyloxy)eicosa-5,14-diyn-1-ol (90) (644 mg, 62%) as a colorless oil. TLC: 20% EtOAc/hexanes, R$_f$=0.42.

$^1$H NMR (400 MHz, CDCl$_3$) δ 7.71-7.69 (m, 4H), 7.46-7.34 (m, 6H), 3.82-3.74 (m, 1H), 3.68 (q, J=6.3 Hz, 2H), 2.25-2.05 (m, 8H), 1.73-1.54 (m, 6H), 1.53-1.23 (m, 12H), 1.07 (s, 9H), 0.75 (t, J=7.4 Hz, 3H); $^{13}$C NMR (101 MHz, CDCl$_3$) δ 135.90, 135.89, 134.71, 134.37, 129.42, 129.37, 127.44, 127.42, 127.39, 127.35, 80.65, 80.10, 79.96, 79.75, 73.42, 62.52, 35.06, 31.87, 29.07, 29.04, 28.91, 28.76, 28.74, 28.67, 27.06, 25.34, 19.44, 18.73, 18.71, 18.53, 14.73, 9.10. HRMS calcd for C$_{36}$H$_{52}$NaO$_2$Si [M+Na]$^+$ 567.3634, found 567.3635.

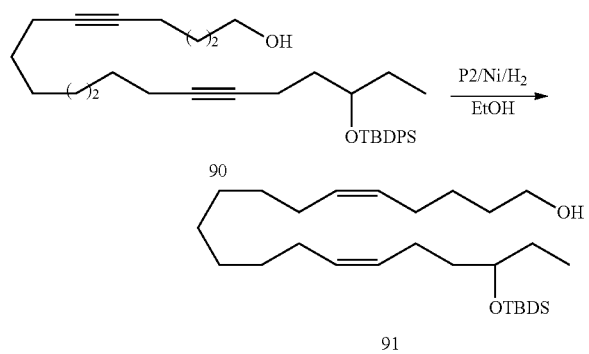

Semi-hydrogenation of 18-(tert-butyldiphenylsilyloxy)eicosa-5,14-diyn-1-ol (90). (350 mg, 0.64 mmol) following the procedure described in the preparation of Analog 1 furnished 18-(tert-butyldiphenylsilyloxy)eicosa-5(Z),14(2)-dien-1-ol (91) (292 g, 83%) as a colorless oil. TLC: 20% EtOAc/hexanes, R$_f$=0.44.

$^1$H NMR (500 MHz, CDCl$_3$) δ 7.76-7.71 (m, 4H), 7.53-7.33 (m, 6H), 5.47-5.13 (m, 4H), 3.71-3.69 (m, 2H), 3.52-3.50 (m, 1H), 2.14-1.89 (m, 8H), 1.57-1.40 (m, 8H), 1.40-1.21 (m, 10H), 1.08 (s, 9H), 0.81 (t, J=7.4 Hz, 3H); $^{13}$C NMR (126 MHz, CDCl$_3$) δ 135.95, 135.94, 134.80, 134.70, 130.40, 129.91, 129.53, 129.41, 129.40, 129.35, 129.34, 127.43, 127.40, 74.12, 62.94, 35.73, 32.40, 29.77, 29.75, 29.50, 29.33, 29.31, 28.89, 27.29, 27.20, 27.11, 26.95, 25.88, 22.93, 19.46, 9.24. HRMS calcd for C$_{36}$H$_{56}$NaO$_2$Si [M+Na]$^+$571.3947, found 571.3948.

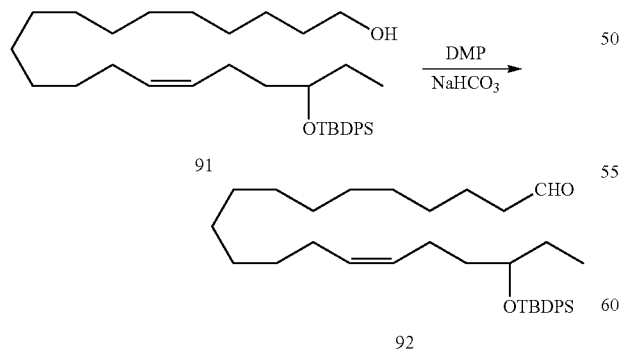

Dess-Martin periodinane (256 mg, 0.60 mmol, 1.2 equiv) and NaHCO$_3$ (51 mg, 0.60 mmol, 1.2 equiv) were added to a stirring, 0° C. solution of 18-tert-butyldiphenylsilyloxy) eicosa-5(Z),14(Z)-dien-1-ol (91) (275 mg, 0.50 mmol) in anhydrous CH$_2$Cl$_2$ (15 mL). After 1 h, the reaction mixture was warmed to rt. Following another 2 h, the reaction mixture was quenched with sat. aq. NaHCO$_3$ (15 mL) and sat. aq. Na$_2$S$_2$O$_3$ (15 mL). After 15 min, the layers were separated and the aqueous layer was extracted with CH$_2$Cl$_2$ (3×15 mL). The organic layer and extracts were combined, dried over Na$_2$SO$_4$, and concentrated in vacuo to afford 18-(tert-butyldiphenylsilyloxy)eicosa-5(Z),14(2)-dienal (92) (243 mg, 89%) as a colorless oil which was used immediately in the next step. TLC: 20% EtOAc/hexanes, R$_f$=0.65.

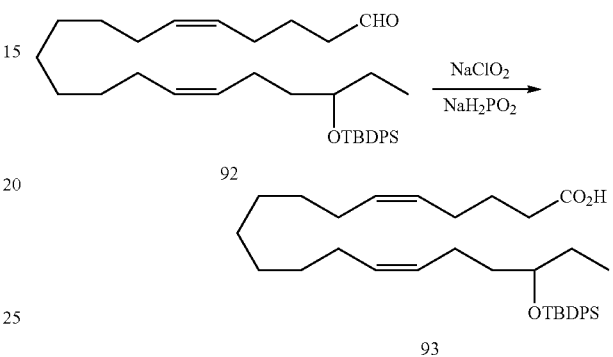

NaH$_2$PO$_4$ (64 mg, 0.46 mmol) and NaClO$_2$ (42 mg, 0.46 mmol) were added to a solution of 18-(tert-butyldiphenylsilyloxy)eicosa-5(Z),14(Z)-dienal (92) (210 mg, 0.38 mmol) and 2,3-dimethylbut-2-ene (0.50 mmol) in t-BuOH/EtOH/H$_2$O (1/1/0.5, 5 mL). After 18 h, the reaction mixture was diluted with EtOAc (50 mL), extracted with EtOAc (2×30 mL), and the combined organic extracts were concentrated in vacuo. The residue was purified by SiO$_2$ column chromatography to afford 18-(tert-butyldiphenylsilyloxy)eicosa-5(Z),14(Z)-dienoic acid (93) (134 mg, 62%) as a colorless oil. TLC: 50% EtOAc/hexanes, R$_f$=0.30.

$^1$H NMR (500 MHz, CDCl$_3$) 7.79-7.70 (m, 4H), 7.51-7.37 (m, 6H), 5.53-5.44 (m, 1H), 5.43-5.20 (m, 3H), 3.77-3.76 (m, 11H), 2.42 (t, J=7.5 Hz, 2H), 2.20-1.93 (m, 8H), 1.81-1.71 (m, 2H), 1.53-1.50 (m, 4H), 1.43-1.31 (m, 10H), 1.13 (s, 9H), 0.85 (t, J=7.4, 3); $^{13}$C NMR (126 MHz, CDCl$_3$) δ 180.27, 135.98, 135.97, 134.81, 134.71, 131.37, 129.93, 129.54, 129.44, 129.43, 128.19, 127.46, 127.43, 74.14, 35.76, 33.51, 29.78, 29.75, 29.52, 29.35, 29.33, 28.93, 27.31, 27.22, 27.15, 26.49, 24.66, 22.97, 19.48, 9.27. HRMS calcd for C$_{36}$H$_{54}$NaO$_3$Si [M+Na]$^+$ 585.3740, found 585.3750.

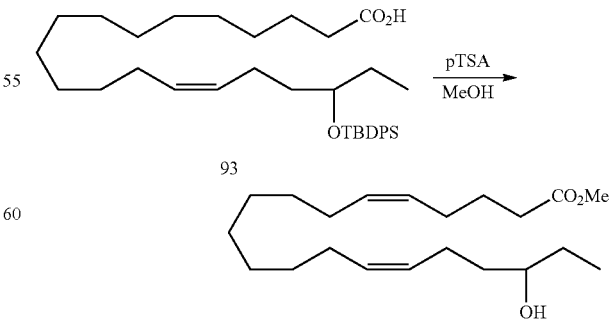

18-(tert-butyldiphenylsilyloxy)eicosa-5(Z),14(Z)-dienoic acid (93) (98 mg, 0.17 mmol) was esterified and do-silylated following the procedure described in the preparation of Analog 11 to give methyl 18-hydroxyeicosa-5(Z),14(Z)-dienoate (94) (37 mg, 64%) as a colorless oil. TLC: 60% EtOAc/hexanes, $R_f$=0.35.

$^1$H NMR (500 MHz, CDCl$_3$) δ 5.48-5.28 (m, 4H), 3.68 (s, 3H), 3.57-3.56 (m, 1H), 2.33 (t, J=7.5 Hz, 2H), 2.07-2.06 (m, 8H), 1.76-1.65 (m, 2H), 1.62-1.40 (m, 4H), 1.40-1.25 (m, 10H), 0.96 (t, J=7.4 Hz, 3H); $^{13}$C NMR (126 MHz, CDCl$_3$) δ 174.17, 131.13, 130.56, 129.23, 128.33, 72.99, 51.46, 36.80, 33.46, 30.17, 29.70, 29.67, 29.42, 29.26, 27.21, 26.53, 24.89, 23.60, 9.89. HRMS calcd for C$_{21}$H$_{38}$NaO$_3$ [M+Na]$^+$ 361.2719, found 361.2709.

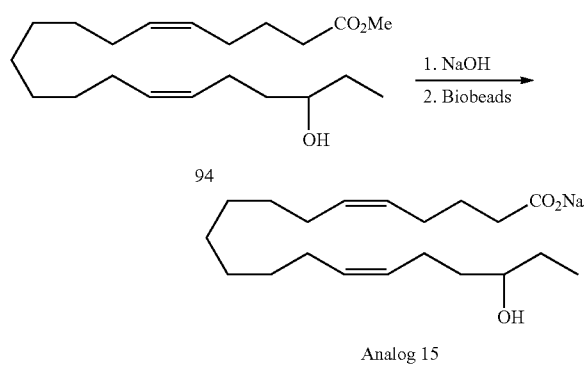

Saponification of methyl 18-hydroxyeicosa-5(Z),14(Z)-dienoate (94) (11 mg, 0.032 mmol) and isolation following the procedures described in the preparation of Analog 1 furnished sodium 18-hydroxyeicosa-5(2),14(Z)-dienoate (Analog 15) (9 mg, 82%) as a colorless oil. TLC: 60% EtOAc/hexanes, $R_f$=0.1.

$^1$H NMR (400 MHz, CD$_3$OD) δ 5.44-5.29 (m, 4H), 3.46-3.42 (m, 1H), 2.24-2.16 (m, 2H), 2.07-1.98 (m, 8H), 1.70-1.57 (m, 2H), 1.55-1.26 (m, 14H), 0.93 (t, J=7.4 Hz, 3H); $^{13}$C NMR (101 MHz, CD$_3$OD) δ 129.77, 129.65, 129.07, 129.03, 71.99, 36.57, 29.60, 29.48, 29.45, 29.16, 28.97, 28.94, 26.81, 26.78, 26.72, 26.33, 23.16, 8.97.

Analog 16: Sodium (18-hydroxyeicosa-5(Z),14(Z)-dienoyl)glycinate

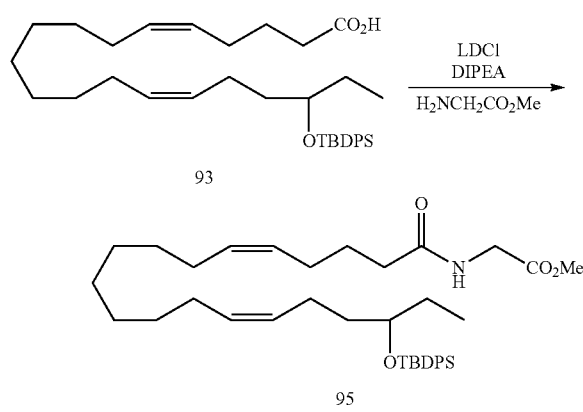

Condensation of 18-(tert-butyldiphenylsilyloxy)eicosa-5 (Z),14(Z)-dienoic acid (93) (130 mg, 0.23 mmol) with glycine methyl ester as described in the preparation of Analog 7 gave methyl (18-(tert-butyldiphenylsilyloxy)eicosa-5(Z),14(Z)-dienoyl)glycinate (95) (76 mg, 68%) as a colorless oil. TLC: 50% EtOAc/hexanes, $R_f$=0.45.

$^1$H NMR (400 MHz, CDCl$_3$) δ 7.74-7.67 (m, 4H), 7.47-7.35 (m, 6H), 5.94 (s, 1H), 5.48-5.39 (m, 11H), 5.39-5.25 (m, 2H), 5.25-5.16 (m, 1H), 4.08 (dd, J=5.1, 1.8 Hz, 2H), 3.79 (s, 3H), 3.75-3.67 (m, 1H), 2.31-2.23 (m, 2H), 2.16-1.88 (m, 8H), 1.79-1.68 (m, 2H), 1.56-1.41 (m, 4H), 1.38-1.26 (m, 10H), 1.08 (s, 9H), 0.81 (t, J=7.5 Hz, 3H); 13C NMR (101 MHz, CDCl$_3$) δ 173.12, 170.54, 135.91, 135.90, 134.74, 134.65, 131.10, 129.86, 129.48, 129.39, 129.37, 128.41, 127.40, 127.37, 127.34, 74.06, 52.34, 41.17, 35.69, 29.73, 29.48, 29.32, 29.28, 28.86, 27.28, 27.16, 27.08, 26.60, 25.48, 22.90, 19.43, 9.21. HRMS calcd for C$_{39}$H$_{59}$NNaO$_4$Si [M+Na]$^+$ 656.4111, found 656.4116.

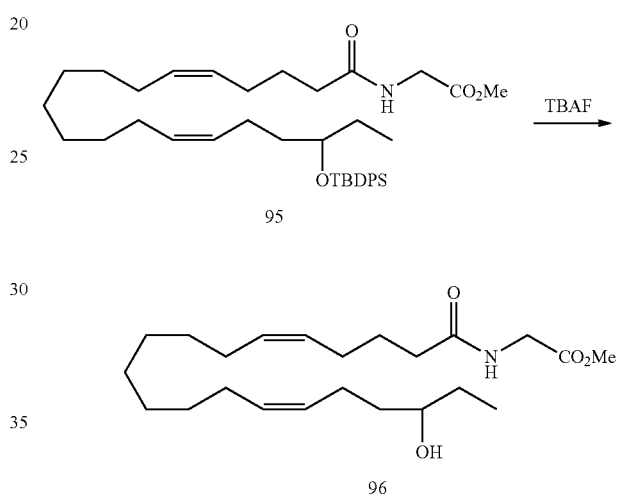

Methyl 18-(tert-butyldiphenylsilyloxy)eicosa-5(Z),14(Z)-dienoyl)glycinate (95) (30 mg, 0.047 mmol) was de-silylated as described in the preparation of Analog 7 to give methyl 18-hydroxyeicosa-5(Z),14(Z)-dienoyl)glycinate (96) (11 mg, 58%) as a colorless oil. TLC: 50% EtOAc/hexanes, $R_f$=3.

$^1$H NMR (CDCl$_3$, 400 MHz) δ 5.95-5.92 (m, 1H), 5.44-5.26 (m, 4H), 4.05 (d, J=5.1 Hz, 2H), 3.76 (s, 3H), 3.57-3.54 (m, 1H), 2.33-2.26 (m, 2H), 2.21-1.93 (m, 8H), 1.77-1.65 (m, 2H), 1.57-1.48 (m, 8H), 1.31-1.21 (m, 6H), 0.94 (t, J=7.4 Hz, 3H); $^{13}$C NMR (101 MHz, CDCl$_3$) δ 173.08, 170.56, 135.89, 131.10, 130.56, 129.21, 128.40, 127.38, 127.34, 73.01, 52.37, 41.17, 36.77, 35.72, 30.16, 29.66, 29.36, 29.22, 27.21, 27.18, 27.06, 26.59, 25.45, 23.59, 9.89. HRMS calcd for C$_{23}$H$_{41}$NNaO$_4$ [M+Na]$^+$ 418.2933, found 418.2932.

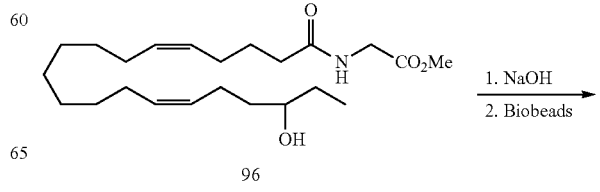

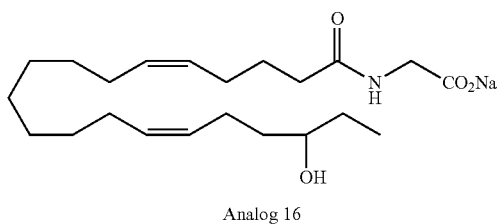

Analog 16

Saponification of methyl (18-hydroxyeicosa-5(Z),14(Z)-dienoyl)glycinate (96) (11 mg. 0.027 mmol) and isolation as described in the preparation of Analog 7 furnished sodium (18-hydroxyeicosa-5(414(Z)-dienoyl)glycinate (Analog 16) (9 mg, 84%) as a colorless oil. TLC: 80% EtOAc/hexanes, R$_f$=0.10.

$^1$H NMR (CDCl$_3$, 400 MHz) δ 5.41-5.36 (m, 4H), 3.74-3.71 (m, 2H), 3.47-3.44 (m, 1H), 2.25 (t, J=7.7 Hz, 2H), 2.07-2.02 (m, 8H), 1.72-1.58 (m, 2H), 1.55-1.26 (m, 14H), 0.93 (t, J=7.4 Hz, 3H); $^{13}$C NMR (101 MHz, CDCl$_3$) δ 174.20, 171.21, 130.25, 129.65, 129.05, 128.45, 72.00, 36.56, 35.32, 29.59, 29.43, 29.12, 28.95, 28.92, 26.76, 26.70, 26.36, 25.52, 23.14, 8.95.

Analog 17: Sodium 2-(19-hydroxy-19-methyle-icosa-5(Z),14(Z)-dienamido)acetate

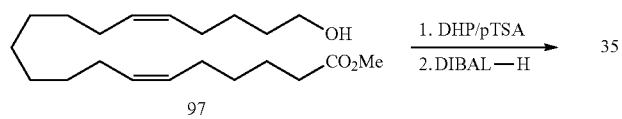

97

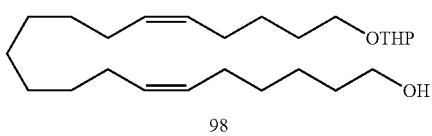

98

Dihydropyran (0.27 g, 3.25 mmol) and pTSA (0.056 g, 0.29 mmol) were added to a stirring 0° C. solution of methyl 20-hydroxyeicosa-6(Z),15(Z)-dienoate (WO 99/43310) (methyl 20-HEDE, 1.0 g, 2.95 mmol) In anhydrous dichloromethane (25 mL) under an argon atmosphere. After 1 h, the reaction was quenched with water (5 mL), diluted with CH$_2$Cl$_2$ (50 mL), washed with water (2×100 mL), brine (100 mL), dried over Na$_2$SO$_4$, and concentrated under reduced pressure. The residue was purified by SiO$_2$ column chromatography using 5-25% EtOAc/hexanes as eluent to give methyl 20-((tetrahydro-2H-pyran-2-yl)oxy)eicosa-6(Z),15(Z)-dienoate (1.18 g, 95%) whose spectral data were consistent with literature values. The crude product was used for the next step without any further purification.

DIBAL-H (0.79 g, 5.58 mmol, 1 M soln in THF) was added to a −78° C. solution of the above THP-ester (1.18 g, 2.79 mmol) in anhydrous CH$_2$Cl$_2$ (50 mL) under an argon atmosphere. After 1 h, the reaction was quenched with sat aq. Na$_2$SO$_4$ (5 mL), diluted with CH$_2$Cl$_2$ (100 mL), washed with water (2×100 mL), brine (100 mL) dried over Na$_2$SO$_4$, and concentrated under reduced pressure. The residue was purified by SiO$_2$ column chromatography to give 20-(tetrahydro-2H-pyran-2-yloxy)eicosa-6(Z),15(2)-dien-1-ol (98) (0.94 g, 85%) as a colorless oil. TLC: 50% EtOAc/hexanes, R$_f$=0.25.

$^1$H NMR (CDCl$_3$, 500 MHz) δ 5.34-5.33 (m, 4H), 4.56 (t, 1H, J=4.0 Hz), 3.90-3.80 (m, 1H), 3.85-3.72 (m, 1H), 3.75-3.63 (m, 2H), 3.51-3.45 (m, 1H), 1.40-3.35 (m, 1H), 2.12-1.92 (m, 8H), 1.95-1.20 (m, 26H).

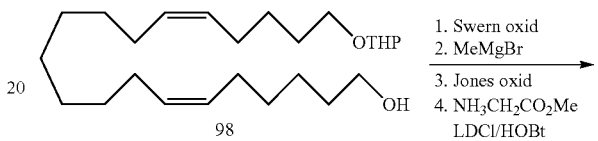

98

1. Swern oxid
2. MeMgBr
3. Jones oxid
4. NH$_3$CH$_2$CO$_2$Me LDCl/HOBt

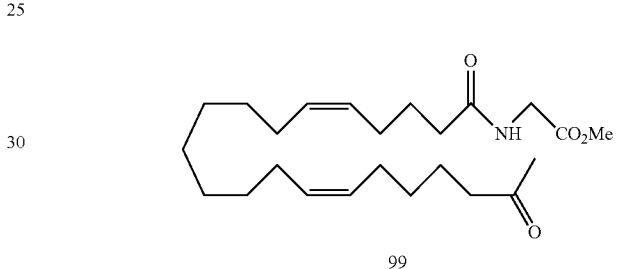

99

Without chromatographic purification of intermediates, 20-(tetrahydro-2H-pyran-2-yloxy)eicosa-6(Z),15(Z)-dien-1-ol (98) (0.93 g, 2.37 mmol) was sequentially subjected to (i) Swern oxidation (91% crude), (ii) McMgBr addition (81% crude), and (ii) Jones oxidation (75% crude) following the procedures described above to give 20-oxohenicosa-5(Z),14(Z)-dienoic acid (75% crude).

EDCI (0.38 g, 2.00 mmol), HOBt (0.16 g, 1.20 mmol), DIPEA (0.26 g, 2.00 mmol), and glycine methyl ester hydrochloride (0.19 g, 1.5 mmol) were added sequentially to a stirring, rt solution of the foregoing crude keto-acid (0.34 g, 0.99 mmol) in anhydrous THF (15 mL) under an argon atmosphere. After 12 b, the reaction mixture was diluted with EtOAc (50 mL), washed with water (2×50 mL), brine (50 mL), dried over Na$_2$SO$_4$, and concentrated under reduced pressure. The residue was purified by SiO$_2$ column chromatography to give methyl 2-(20-oxoheneicosa-5(Z),14(2)-dienamido)acetate (99)(0.38 g, 91%) as a colorless semisolid. TLC: 75% EtOAc/hexanes, R$_f$=0.25.

$^1$H NMR (CDCl$_3$, 500 MHz) δ 5.97 (br s, 1H, NH), 5.37-5.31 (m, 4H), 4.04 (d, 1H, J=5.15 Hz), 3.74 (s, 3H), 2.41 (t, 2H, J=6.85 Hz), 2.23 (t, 2H, J=7.45 Hz), 2.12 (s, 3H), 2.10-1.97 (m, 6H), 1.70-1.57 (m, 4H), 1.35-1.20 (m, 12H); $^{13}$C NMR (101 MHz, CDCl$_3$) δ 173.62, 173.5.6, 170.53, 170.50, 131.04, 130.35, 129.05, 128.36, 52.31, 41.15, 36.14, 35.60, 29.62, 29.32, 29.24, 29.19, 29.17, 27.18, 27.14, 26.85, 26.55, 25.47, 25.19.

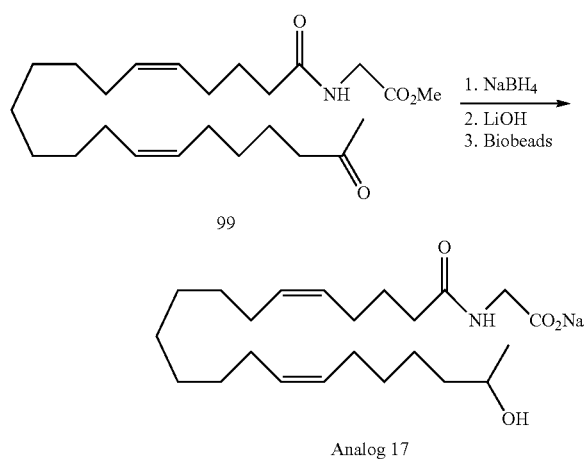

Analog 17

NaBH₄ (0.064 g, 1.71 mmol) was added to a stirring, 0° C. solution of methyl 2-(20-oxoheneicosa-5(Z),14(Z)-dienamido)acetate (99) (0.35 g, 0.85 mmol) in anhydrous MeOH (10 mL). After 30 min, the reaction mixture was quenched with sat. aq. NH₄Cl (10 mL) and extracted with EtOAc (3×10 mL). The combined extracts were washed with water (2×50 mL), brine (50 mL), dried over Na₂SO₄, and concentrated under reduced pressure to give the corresponding alcohol (0.33 g, 95% crude).

¹H NMR (CDCl₃, 500 MHz) δ 6.09-6.07 (m, 1H, NH), 5.46-5.28 (m, 4H), 4.06 (d, J=5.2 Hz, 2H), 3.81-3.79 (m, 1H), 3.77 (s, 3H), 2.29-2.21 (m, 2H), 2.14-1.95 (m, 8H), 1.77-1.58 (m, 2H), 1.52-1.24 (m, 16H), 1.19 (d, J=6.2 Hz, 3H); ¹³C NMR (CDCl₃, 101 MHz) δ 173.15, 170.58, 131.08, 130.08, 129.55, 128.40, 68.06, 52.36, 41.15, 39.22, 35.69, 29.73, 29.67, 29.38, 29.25, 27.23, 27.17, 27.14, 26.58, 25.46, 25.41, 23.46.

An aq. solution of LiOH (3.71 mL of a 1 M soln, 4 equiv) was added to a 0° C. solution of the crude alcohol (0.33 g, 0.81 mmol) in THF/H₂O (4:1, 10 mL). After stirring at rt for 12 h, the reaction mixture was diluted with EtOAc (50 mL), acidified to pH 4 with 1N HCl, washed with water (2×50 mL), brine (50 mL), dried over Na₂SO₄, and concentrated under reduced pressure. The residue was purified by SiO₂ column chromatography using a gradient (0-75%) of EtOAc/hexanes as eluent to give 2-(20-hydroxyheneicos-5(Z),14(Z)-dienamido)acetic acid (0.30 g, 97%) as a colorless semi-solid. TLC: 75% EtOAc/hexanes, R$_f$=0.10.

¹H NMR (CDCl₃, 500 MHz) δ 6.34-6.32 (m, 1H, NH), 5.33-5.30 (m, 4H), 4.02 (d, 2H, J=5.15 Hz), 3.82-3.81 (m, 1H), 2.25 (t, 2H, J=7.45 Hz), 2.05-1.95 (m, 8H), 1.71-1.66 (m, 2H), 1.50-1.20 (m, 10H), 1.19-1.17 (m, 6H); ¹³C NMR (CDCl₃, 75 MHz) δ 174.25, 172.21, 131.32, 130.25, 129.64, 128.40, 68.59, 39.04, 35.75, 29.75, 29.43, 29.33, 29.29, 29.20, 27.30, 27.24, 27.20, 25.40, 23.28.

The above 2-(19-hydroxy-19-methyleicosa-5(Z),14(Z)-dienamido)acetic acid was basified and isolated as describe for the preparation of Analog 7 using NaOH and SM-2 Biobeads to give sodium 2-(19-hydroxy-19-methyleicosa-5 (Z),14(Z)-dienamido)acetate (Analog 17).

¹H NMR (500 MHz, CD₃OD) δ 5.41-5.34 (m, 4H), 3.75-3.70 (m, 3H), 2.34-2.23 (m, 2H), 2.15-1.97 (m, 8H), 1.69-1.66 (m, 2H), 1.44-1.17 (m, 16H), 1.16 (d, J=6.2 Hz, 3H); ¹³C NMR (101 MHz, CD₃OD) δ 174.81, 171.35, 13026, 129.50, 129.28, 128.46, 67.10, 47.79, 38.70, 35.25, 29.55, 29.43, 29.12, 28.95, 28.90, 26.76, 26.72, 26.36, 25.51, 25.13, 22.09.

Analog 18: Sodium 2-(19-hydroxy-19-methyle-icosa-5(Z),14(Z)-dienamido)acetate

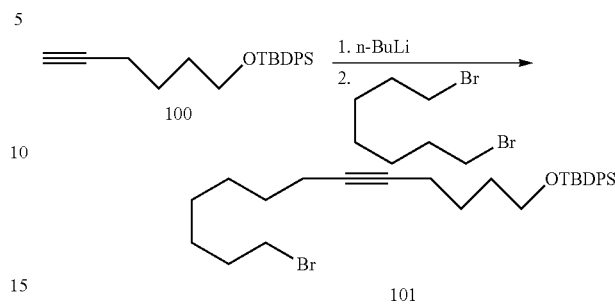

A solution of n-BuLi (0.95 g, 14.85 mmol, 1.5 M soln in THF) was added dropwise to a stirring, −78° C. solution of commercial tert-butyl(hex-5-yn-1-yloxy)diphenylsilane (5 g, 14.85 mmol) in anhydrous THF (50 mL) under an argon atmosphere. After 45 min, the reaction mixture was slowly cannulated into a −78° C. solution of commercial 1,7-dibromoheptane (11.49 g, 44.55 mmol) in anhydrous THF/HMPA (4:1, 50 mL). After stirring for 1 h, the reaction mixture was warmed to room temperature. Following another 18 h, the reaction was quenched with sat. aq. NH₄Cl (50 mL), diluted with ether (200 mL), washed with water (2×100 mL), and brine (100 mL). The combined organic extracts were dried over Na₂SO₄ and concentrated under reduced pressure. The residue was purified by SiO₂ column chromatography using a gradient from 0-5% EtOAc/hexanes as eluent to afford (13-bromotridec-5-yn-1-yloxy) (tert-butyldiphenyl)silane* (101) (WO 99/43310; Baldwin, et al., *Org. Lett.*, 2001, 3, 1145-1148) (6.47 g, 85%) as a colorless oil. TLC: 5% EtOAc/hexanes, R$_f$=0.80.

¹H NMR (CDCl₃, 500 MHz) δ 7.67 (d, 4H, J=6.3 Hz), 7.45-7.32 (m, 6H), 3.69 (t, J=12.55 Hz, 2H), 2.39 (t, J=13.75 Hz, 2H), 2.18-2.13 (m, 4H), 1.86-1.82 (m, 2H), 1.70-1.20 (m, 12H), 1.06 (s, 9H); ¹³C NMR (CDCl₃, 75 MHz) δ 135.7, 134.1, 129.6, 127.7, 80.3, 80.2, 63.6, 34.0, 32.8, 31.8, 29.1, 28.7, 28.4, 28.2, 26.9, 25.6, 19.3, 18.8, 18.6.

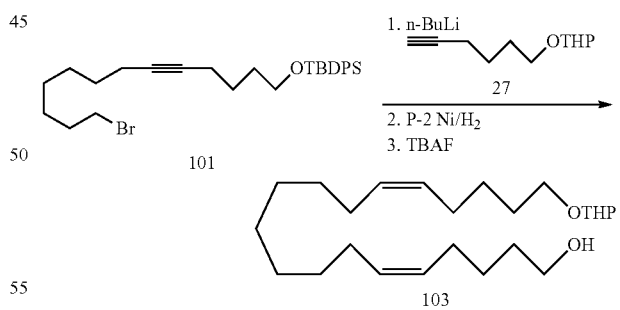

A solution of n-BuLi (0.81 g, 12.56 mmol, 1.5 M soln in THF) was added dropwise to a stirring, −78° C. solution of 2-(hex-5-yn-1-yloxy)tetrahydro-2H-pyran (27) (2.29 g, 12.59 mmol) in anhydrous THF (50 mL). After 45 min, a solution of (13-bromotridec-5-yn-1-yloxy)(tert-butyldiphenyl)silane (101) (6.47 g, 12.60 mmol) in anhydrous THF/HMPA (4:1, 50 mL) was added slowly. After 1 h, the reaction mixture was warmed to room temperature. Following another 12 h, the reaction was quenched with sat. aq. NH₄Cl and extracted with ether (3×60 mL). The combined ethereal extracts were washed with water (2×100 mL), brine (100 mL), dried over Na₂SO₄, and concentrated under reduced pressure. The crude residue was purified via SiO₂ column chromatography using a gradient from 0-5% EtOAc/hexanes as eluent to afford tert-butyldiphenyl((19-(tetrahydro-2H-pyran-2-yloxy)nonadeca-5,14-diyn-1-yl)oxy)silane (102) (6.74 g, 87%) as a colorless oil which was sufficiently pure to be used directly in the next step. TLC: 10% EtOAc/hexanes, $R_f$=0.45.

$^1$H NMR (CDCl₃, 500 MHz) δ 7.68 (dd, J=1.6, 7.6 Hz, 4H), 7.40-7.38 (m, 6H), 4.55-4.53 (m, 11H) 3.83 (t, J=7.5 Hz, 1H), 3.75-3.73 (m, 1H), 3.71 (t, J=7.5 Hz, 1H), 3.68-3.65 (m, 1H), 3.45 (t, J=7.0 Hz, 2H), 2.25-2.18 (m, 8H), 1.78-1.72 (m, 2H), 1.67-1.66 (m, 4H), 1.65-1.25 (m, 18H), 1.05 (s, 9H).

NaBH₄ (0.29 g, 7.67 mmol) was added in portions to a vigorously stirring, room temperature solution of Ni(OAc)₂·4H₂O (2.18 g, 8.76 mmol) in absolute ethanol (60 mL) under hydrogen (1 atm). After 15 min, freshly distilled ethylenediamine (1.97 g, 32.87 mmol) was added to the black suspension, followed after a further 15 min by a solution of tert-butyldiphenyl((19-(tetrahydro-2H-pyran-2-yloxy)nonadeca-5,14-diyn-1-yl)oxy)silane (102) (6.74 g, 10.95 mmol) in absolute EtOH (10 mL). After 1 h, the reaction mixture was diluted with Et₂O (100 mL) and pass through a small bed of silica gel. The bed was rinsed with another portion of ether and the combined ethereal filtrates were concentrated under reduced pressure to give a colorless oil (6.44 g, 95%). Without further analysis, the crude product was dissolved in THF (50 mL) and TBAF (8.16 g, 31.21 mmol) was added in portions. After 12 h, the solvent was removed in vacuo and the residue was purified by SiO₂ column chromatography to give 19-(tetrahydro-2H-pyran-2-yloxy)nonadeca-5(Z),14(Z)-dien-1-ol (103) (3.38 g, 81% over 2 steps) as a colorless oil. TLC: 50% EtOAc/hexanes, $R_f$=0.25.

$^1$H NMR (CDCl₃, 500 MHz) δ 5.34-5.33 (m, 4H), 4.56 (t, 1H, J=4.0 Hz), 3.90-3.85 (m, 1H), 3.83-3.72 (m, 1H), 3.71-3.61 (m, 2H), 3.51-3.45 (m, 1H), 3.40-3.35 (m, 1H), 2.12-1.92 (m, 8H), 1.58-1.20 (in, 24H).

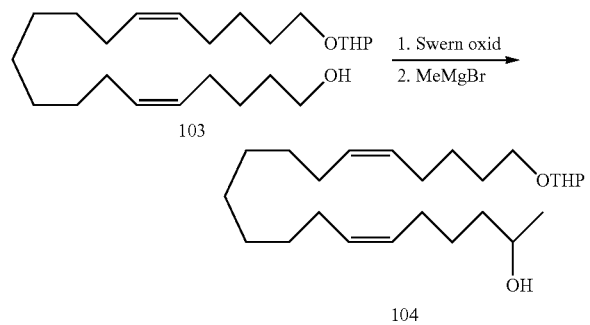

Swern oxidation of 19-(tetrahydro-2H-pyran-2-yloxy)nonadeca-5(Z),14(Z)-dien-1-ol (103) (1.96 g, 4.97 mmol) using the procedure utilized in the preparation of Analog 1 provided 19-(tetrahydro-2H-pyran-2-yloxy)nonadeca-5(Z),14(Z)-dienal (1.85 g, 98%) as a colorless oil which was used immediately in the next step.

The above crude aldehyde (1.85 g, 4.89 mmol) was dissolve in anhydrous Et₂O (25 mL), cooled to 0° C., and a solution of eMgBr (0.69 g, 5.86 mmol, 3 M in Et₂O) was added dropwise. After 1 h at rt, the reaction was quenched using sat. sq. NH₄Cl, diluted with Et₂O (100 mL), washed with water (2×100 mL), then brine (100 mL), dried over Na₂SO₄, and concentrated under reduced pressure to give 20-(tetrahydro-2H-pyran-2-yloxy)eicosa-6(Z),15(Z)-dien-2-ol (104) (1.93 g, 85%) that was sufficiently pure to be used directly in the next step. TLC: 50% EtOAc/hexanes, $R_f$=0.35.

$^1$H NMR (CDCl₃, 400 MHz) δ 5.40-5.29 (m, 4H), 4.58-4.53 (m, 1H), 3.89-3.69 (m, 3H), 3.51-3.45 (m, 1H), 3.38-3.34 (m, 1H), 2.07-1.95 (m, 8H), 1.86-1.76 (m, 1H), 1.73-1.65 (m, 1H), 1.63-1.22 (m, 16H), 1.17 (t, J=6.0 Hz, 3H); $^{13}$C NMR (CDCl₃, 100 MHz) δ 1302, 130.1, 129.4, 129.3, 98.7, 67.9, 69.4, 62.1, 38.8, 30.7, 29.7, 29.6, 29.4, 29.3, 29.2, 27.1, 27.1, 27.0, 26.9, 26.3, 25.4, 23.4, 19.5.

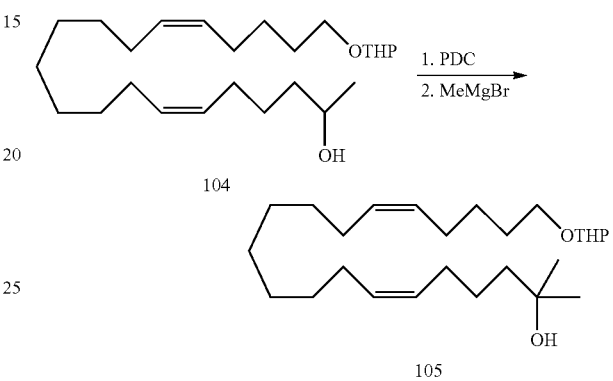

PDC (7.14 g, 19.00 mmol) was added in portions to a stirring solution of 20-(tetrahydro-2H-pyran-2-yloxy)eicosa-6(Z),15(Z)-dien-2-ol (104) (1.5 g, 3.80 mmol) in anhydrous CH₂Cl₂ (50 mL). After 2 h, the reaction mixture was pass through a small bed of silica gel/diatomaceous earth (60:40, w/w) and the bed was rinsed with another portion of CH₂Cl₂ (20 mL). The combined filtrates were concentrated under reduced pressure to give a colorless oil which was dissolved in anhydrous Et₂O (50 mL) and cooled to 0° C. A solution of McMgBr (1.75 g, 22.40 mmol, 3 M in Et₂O) was added dropwise. After stirring at rt for 1 h, the reaction was quenched using sat. aq. NH₄Cl (12 mL) and extracted using Et₂O (3×30 mL). The combined ethereal extracts were washed with water (2×100 mL), brine (100 mL) dried over Na₂SO₄, and concentrated under reduced pressure to afford crude 2-methyl-20-(tetrahydro-2H-pyran-2-yloxy)eicosa-6(Z),15(Z)-dien-2-ol (105) (1.328 g) that was used directly in the next step. TLC: 50% EtOAc/hexanes, $R_f$=0.40.

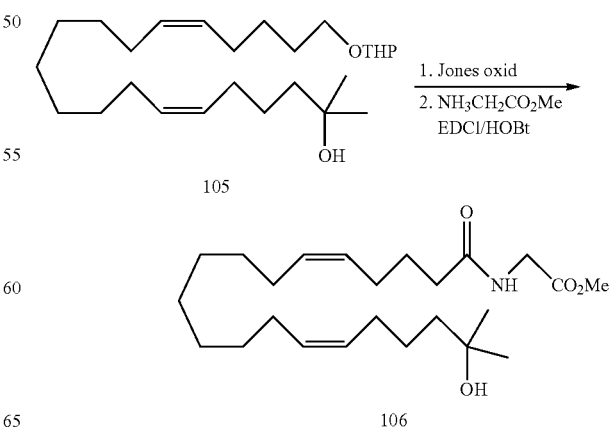

A freshly prepared solution of Jones reagent (1 mL of a 10 M soln) was added dropwise to a stirring, 0° C. solution of the above crude 2-methyl-20-(tetrahydro-2H-pyran-2-yloxy)eicosa-6(Z),15(Z)-dien-2-ol (105) (0.5 g, 1.22 mmol) in acetone (15 mL). After 2 h, the reaction mixture was quenched by the slow addition of isopropyl alcohol (1 mL). The precipitated green mass was removed via filtration and the filter cake was washed with acetone (10 mL). The combined filtrates were concentrated under reduced pressure to give a gummy solid that was dissolved in EtOAc (30 mL), washed with brine, dried over anhydrous $Na_2SO_4$, and concentrated in vacuo to give 19-hydroxy-19-methyleicosa-5(Z),14(Z)-dienoic acid (0.34 g) as a colorless oil. This product was used for next step without any further purification.

EDCI (0.38 g, 2.00 mmol), HOBt (0.16 g, 1.20 mmol), DIPEA (0.26 g, 2.00 mmol), and glycine methyl ester hydrochloride (0.19 g, 1.5 mmol) were added successively to a rt solution of crude 19-hydroxy-19-methyleicosa-5(Z),14(Z)-dienoic acid (0.34 g, 0.99 mmol) in anhydrous THF (30 mL). After 12 h, the reaction mixture was diluted with EtOAc (30 mL), washed with water (2×30 mL), brine (30 mL), dried over $Na_2SO_4$, and concentrated under reduced pressure. The residue was purified by $SiO_2$ column chromatography to give methyl 2-(19-hydroxy-19-methyleicosa-5(Z),14(Z)-dienamido)acetate (106) (0.38 g, 93%) as a colorless semi-solid. TLC: 75% EtOAc/hexanes, $R_f$=0.25.

$^1$H NMR (CDCl$_3$, 500 MHz) δ 6.13 (br s, 1H, NH), 5.41-5.20 (m, 4H), 4.05 (d, 2H, J=5.15 Hz), 3.72 (s, 3H), 2.21 (t, 2H, J=7.45 Hz), 2.05-1.95 (m, 8H), 1.70-1.64 (m, 2H), 1.52-1.36 (m, 4H), 1.34-1.20 (m, 10H), 1.17 (s, 6H); $^{13}$C NMR (CDCl$_3$, 75 MHz) δ 173.26, 170.68, 131.36, 130.54, 129.54, 128.51, 70.98, 52.41, 43.60, 41.23, 35.75, 29.75, 29.74, 29.47, 29.45, 29.28, 29.26, 27.65, 27.27, 26.67, 25.55, 24.57.

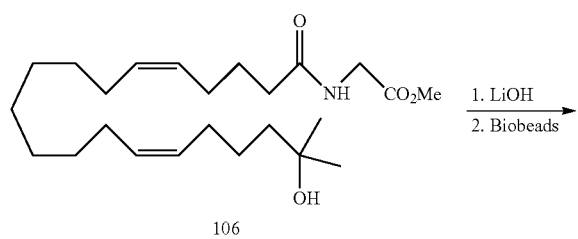

106

1. LiOH
2. Biobeads

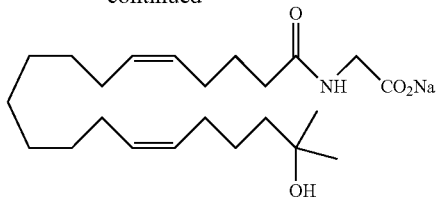

Analog 18

A solution of LiOH (3.71 mL of a 1 M aq. soln, 4 equiv) was added to a stirring 0° C. solution of methyl 2-(19-hydroxy-19-methyleicosa-5(Z),14(Z)-dienamido)acetate (106) (0.38 g, 0.93 mmol) in THF/H$_2$O (4:1, 10 mL). After stirring at rt for 12 h, the reaction mixture was diluted with EtOAc (50 mL), acidified to pH 4 with 1 N aq. HCl, washed with water (2×50 mL), brine (50 mL), dried over $Na_2SO_4$, and concentrated under reduced pressure. The crude residue was purified by $SiO_2$ column chromatography to give 2-(19-hydroxy-19-methyleicosa-5(Z),14(Z)-dienamido)acetic acid (0.34 g, 95%) as a colorless semi-solid. TLC: 75% EtOAc/hexanes, $R_f$=0.10.

$^1$H NMR (CDCl$_3$, 500 MHz) δ 6.57-6.30 (br s, 1H, NH), 5.41-5.20 (m, 4H), 4.02 (d, 2H, J=5.2 Hz), 2.25 (t, 2H, J=7.5 Hz), 2.05-1.95 (m, 8H), 1.70-1.64 (m, 2H), 1.52-1.36 (m, 4H), 1.34-1.20 (m, 10H), 1.17 (s, 6H); $^{13}$C NMR (CDCl$_3$, 75 MHz) δ 174.2, 172.3, 131.3, 130.4, 129.5, 128.4, 71.9, 49.4, 41.5, 35.7, 29.7, 29.4, 29.3, 29.3, 29.0, 27.3, 27.2, 24.5.

The above 2-(19-hydroxy-19-methyleicosa-5(Z),14(Z)-dienamido)acetic acid was basified and isolated as describe in the preparation of Analog 7 using NaOH and SM-2 Biobeads to give sodium 2-(19-hydroxy-19-methyleicosa-5(Z),1,4(Z)-dienamido)acetate (Analog 18).

$^1$H NMR (500 MHz, CD$_3$OD) δ 5.43-5.29 (m, 4H), 3.73 (s, 2H), 2.24 (dd, J=8.4, 6.9 Hz, 2H), 2.08-2.01 (m, 8H), 1.72-1.60 (m, 2H), 1.51-1.26 (m, 14H), 1.16 (s, 6H); $^{13}$C NMR (101 MHz, CD$_3$OD) δ 175.12, 174.16, 130.25, 129.62, 129.27, 128.46, 69.92, 43.13, 43.02, 35.26, 29.42, 29.12, 28.95, 28.91, 27.76, 27.28, 26.76, 26.74, 26.37, 25.51, 24.19.

Analog 19: Sodium 19-hydroxynonadeca-5(Z),14(Z)-dienoate

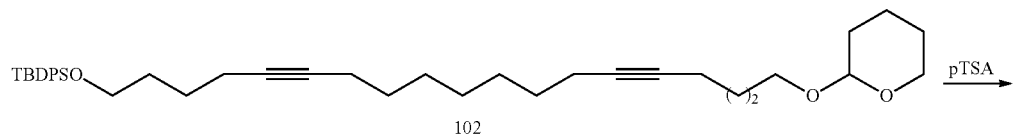

102 pTSA

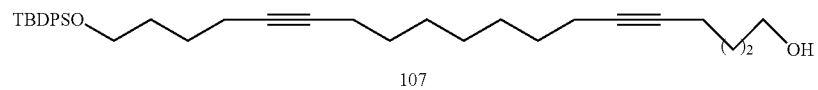

107

Solvolysis of tert-butyldiphenyl(19-((tetrahydro-2H-pyran-2-yloxy)nonadeca-5,14-diyn-1-yl)oxy)silane (102) (10 g, 16.2 mmol) using pTSA following the procedure described in the preparation of Analog 1 provided 19-(tert-butyldiphenylsilyloxy)nonadeca-5,14-diyn-1-ol (107) (6.4 g, 75%) as a colorless oil. TLC: 30% EtOAc/hexane, $R_f \approx 0.55$.

$^1$H NMR (CDCl$_3$, 500 MHz) δ 7.70 (dd, J=1.6, 7.6 Hz, 4H), 7.40-7.36 (m, 6H), 3.75-3.73 (m, 4H), 2.19-2.17 (m, 8H), 1.76-1.75 (m, 2H), 1.65-1.63 (m, 4H), 1.55-1.45 (m, 6H), 1.32-1.30 (m, 4H), 1.28-1.24 (m, 2H), 1.05 (s, 9H).

methyl 19-(tert-butyldiphenylsilyloxy)nonadeca-5(Z),14(Z)-dienoate (109) (2.35 g, 92%) as a colorless oil. TLC: 10% EtOAc/hexanes, $R_f \approx 0.55$.

$^1$H NMR (CDCl$_3$, 500 MHz) δ 7.72 (d, J=7 Hz, 4H), 7.42-7.38 (m, 6H), 5.45-5.29 (m, 4H), 3.62-3.60 (m, 5H), 2.33 (t, J=7.5 Hz, 2H), 2.18-1.95 (m, 8H), 1.72-1.70 (m, 2H), 1.66-1.62 (m, 2H), 1.38-1.36 (m, 2H), 1.35-1.23 (m, 10H), 1.05 (s, 9H); $^{13}$C NMR (101 MHz, CDCl$_3$) δ 174.12, 135.54, 134.13, 131.13, 129.93, 129.69, 129.44, 128.29, 127.53, 63.92, 51.44, 33.44, 32.47, 29.75, 29.67, 29.44, 27.21, 27.18, 26.85, 26.51, 25.45, 24.87, 19.20.

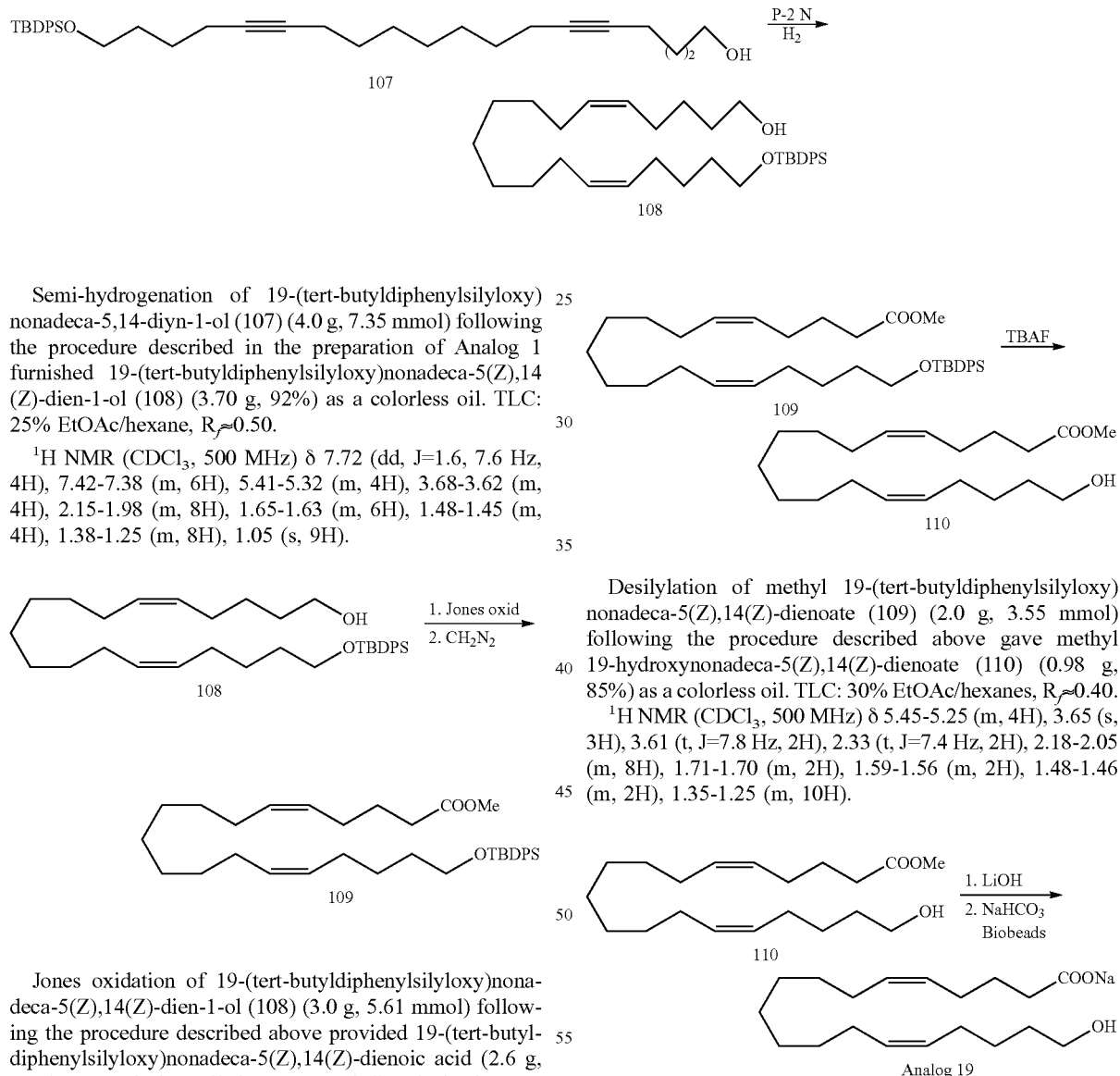

Semi-hydrogenation of 19-(tert-butyldiphenylsilyloxy)nonadeca-5,14-diyn-1-ol (107) (4.0 g, 7.35 mmol) following the procedure described in the preparation of Analog 1 furnished 19-(tert-butyldiphenylsilyloxy)nonadeca-5(Z),14(Z)-dien-1-ol (108) (3.70 g, 92%) as a colorless oil. TLC: 25% EtOAc/hexane, $R_f \approx 0.50$.

$^1$H NMR (CDCl$_3$, 500 MHz) δ 7.72 (dd, J=1.6, 7.6 Hz, 4H), 7.42-7.38 (m, 6H), 5.41-5.32 (m, 4H), 3.68-3.62 (m, 4H), 2.15-1.98 (m, 8H), 1.65-1.63 (m, 6H), 1.48-1.45 (m, 4H), 1.38-1.25 (m, 8H), 1.05 (s, 9H).

Jones oxidation of 19-(tert-butyldiphenylsilyloxy)nonadeca-5(Z),14(Z)-dien-1-ol (108) (3.0 g, 5.61 mmol) following the procedure described above provided 19-(tert-butyldiphenylsilyloxy)nonadeca-5(Z),14(Z)-dienoic acid (2.6 g, 85%) as a colorless oil that was used directly in the next reaction. TLC: 30% EtOAc/hexanes, $R_f \approx 0.45$.

$^1$H NMR (CDCl$_3$, 500 MHz) δ 7.72 (d, J=7 Hz, 4H), 7.42-7.38 (m, 6H), 5.45-5.29 (m, 4H), 3.68 (t, J=8.0 Hz, 2H), 2.33 (t, J=7.5 Hz, 2H), 2.18-1.95 (m, 8H), 1.72-1.70 (m, 2H), 1.66-1.62 (m, 2H), 1.38-1.36 (m, 2H), 1.35-1.23 (m, 10H), 1.05 (s, 9H).

Esterification of 19-(tert-butyldiphenylsilyloxy)nonadeca-5(Z),14(Z)-dienoic acid (2.5 g., 4.5 mmol) with diazomethane following the procedure described above provided Desilylation of methyl 19-(tert-butyldiphenylsilyloxy)nonadeca-5(Z),14(Z)-dienoate (109) (2.0 g, 3.55 mmol) following the procedure described above gave methyl 19-hydroxynonadeca-5(Z),14(Z)-dienoate (110) (0.98 g, 85%) as a colorless oil. TLC: 30% EtOAc/hexanes, $R_f \approx 0.40$.

$^1$H NMR (CDCl$_3$, 500 MHz) δ 5.45-5.25 (m, 4H), 3.65 (s, 3H), 3.61 (t, J=7.8 Hz, 2H), 2.33 (t, J=7.4 Hz, 2H), 2.18-2.05 (m, 8H), 1.71-1.70 (m, 2H), 1.59-1.56 (m, 2H), 1.48-1.46 (m, 2H), 1.35-1.25 (m, 10H).

Saponification of methyl 19-hydroxynonadeca-5(Z),14(Z)-dienoate (110) (1 g, 3.04 mmol) and isolation following the procedures described above furnished sodium 19-hydroxynonadeca-5(Z),14(Z)-dienoate (Analog 19) (850 mg, 80%) as a colorless oil.

$^1$H NMR (CDCl$_3$, 500 MHz) δ 5.45-5.25 (m, 4H), 3.61 (t, J=7.8 Hz, 2H), 2.33 (t, J=7.4 Hz, 2H), 2.18-2.05 (m, 8H), 1.71-1.68 (m, 2H), 1.59-1.53 (m, 2H), 1.48-1.44 (m, 2H), 1.35-1.28 (m, 10H).

Analog 20: Sodium (19-hydroxynouadeca-5(Z),14(Z)-dienoyl)glycinate

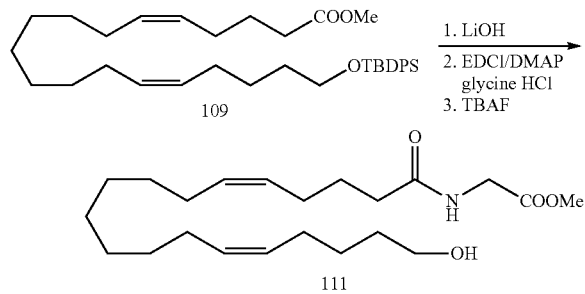

Saponification of methyl 19-(tert-butyldiphenylsilyloxy)nonadeca-5(Z),14(Z)-dienoate (109) following the procedure above provided 19-(tert-butyldiphenylsilyloxy)nonadeca-5(Z),14(Z)-dienoic acid that was used in the next step without further purification. TLC: 30% EtOAc/hexanes, $R_f$≈0.25.

$^1$H NMR (400 MHz, CDCl$_3$) δ 7.68-7.64 (m, 4H), 7.45-7.30 (m, 6I), 5.47-5.21 (m, 4H), 3.64 (td, J=6.5, 0.8 Hz, 2H), 2.34 (t, J=7.5 Hz, 2H), 2.13-1.90 (m, 8H), 1.68 (app pentet, J=5.3 Hz, 2H), 1.55 (app pentet, J=5.2 Hz, 2H), 1.45-1.22 (m, 12H), 1.03 (s, 9H); $^{13}$C NMR (101 MHz, CDCl$_3$) δ 179.47, 135.54, 134.12, 131.31, 129.93, 129.69, 129.44, 128.09, 127.53, 63.93, 33.29, 32.46, 29.74, 29.66, 29.48, 29.43, 27.22, 26.85, 26.41, 25.44, 24.58, 19.20.

Condensation of 19-(tert-butyldiphenylsilyloxy)nonadeca-5(Z),14(Z)-dienoic acid (1.0 g, 1.77 mmol) with glycine methyl ester following the procedure described above gave methyl 19-(tert-butyldiphenylsilyl)oxy)nonadeca-5(Z),14(Z)-dienoyl)glycinate (0.91 g, 83%) as a colorless oil. TLC: 40% EtOAc/hexanes, $R_f$≈0.50.

$^1$H NMR (CDCl$_3$, 500 MHz) δ 7.70 (d, J=7.0 Hz, 4H), 7.42-7.39 (m, 6H), 5.91 (br s, 1H), 5.45-5.31 (m, 4H), 4.18 (d, J=8.0 Hz, 2H), 3.75 (s, 3H), 3.64 (t, J=7.3 Hz, 2H), 2.25 (t, J=8.0 Hz, 2H), 2.16-1.97 (m, 8H), 1.69-1.67 (m, 2H), 1.61-1.56 (m, 2H), 1.38-1.26 (m, 12H), 1.05 (s, 9H); $^{13}$C NMR (101 MHz, CDCl$_3$) δ 173.06, 170.53, 135.53, 134.12, 131.11, 129.92, 129.69, 129.45, 128.37, 127.54, 63.92, 52.33, 41.16, 35.69, 32.47, 29.76, 29.70, 29.48, 29.45, 29.29, 29.28, 27.21, 27.18, 26.85, 26.58, 25.45, 19.20.

Desilylation of 19-(tert-butyldiphenylsilyloxy)nonadeca-5(Z),14(Z)-dienoyl)glycinate (2.2 g, 3.55 mmol) following the procedure described above gave methyl 19-hydroxynonadeca-5(Z),14(Z)-dienoyl)glycinate (111) (1.1 g, 86%) as a colorless oil. TLC: 60% EtOAc/hexanes, $R_f$≈0.45.

$^1$H NMR (CDCl$_3$, 500 MHz) δ 5.99 (br s, 1H), 5.44-5.25 (m, 4H), 4.04 (d, J=7.5 Hz, 2H), 3.75 (s, 3H), 3.65 (t, J=7.0 Hz, 2H), 2.25 (t, J=8 Hz, 2H), 2.16-1.97 (m, 8H), 1.69-1.67 (m, 2H), 1.61-1.56 (m, 4H), 1.38-1.25 (m, 10H); $^{13}$C NMR (101 MHz, CDCl$_3$) δ 173.10, 170.57, 131.12, 130.12, 129.55, 128.40, 62.97, 52.37, 41.18, 35.72, 32.69, 29.68, 29.52, 29.37, 29.26, 27.24, 27.16, 27.13, 26.59, 25.46, 25.38.

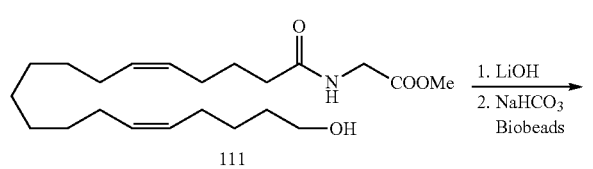

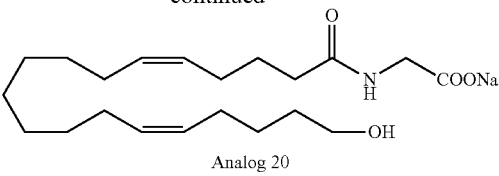

Saponification of methyl (19-hydroxynonadeca-5(Z),14(Z)-dienoyl)glycinate (111) (1.2 g, 3.15 mmol) and isolation following the procedures described above furnished sodium (19-hydroxynonadeca-5(Z),14(Z)-dienoyl)glycinate (Analog 20) (1.1 g, 90%) as a colorless oil. TLC: 80% EtOAc/hexanes, $R_f$≈0.20.

$^1$H NMR (CD$_3$OD, 500 MHz) δ 5.42-5.38 (m, 4H), 3.76 (s, 2H), 3.55 (t, J=6.5 Hz, 2H), 2.28 (t, J=7.5 Hz, 2H), 2.15-2.01 (m, 8H), 1.66-1.67 ((m, 2H), 1.52-1.48 (m, 2H), 1.38-1.25 (m, 12H); $^{13}$C NMR (101 MHz, CD$_3$OD) δ 175.17, 174.17, 130.26, 129.52, 129.28, 128.48, 61.54, 43.16, 35.27, 32.18, 29.44, 29.34, 29.13, 28.97, 26.79, 26.77, 26.73, 26.39, 25.52, 25.19.

Analog 21: 19-(1H-Tetrazol-5-yl)nonadeca-6(Z),15(Z)-dien-2-ol

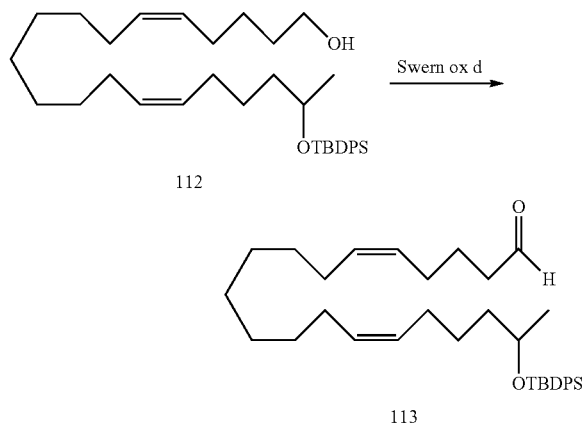

Swern oxidation of 19-(tert-butyldiphenylsilyloxy)eicosa-5(Z),14(Z)-dien-1-ol* (112) (200 mg, 0.36 mmol) following the procedure described above provided 19-(tert-butyldiphenylsilyloxy)eicosa-5(Z),14(Z)-dienal (113) (190 mg, 95%) as a colorless oil which was used immediately in the next step.

*Prepared as described above for the synthesis of 19(S)-(tert-butyldiphenylsilyloxy)eicosa-5(Z),14(Z)-dien-1-ol using

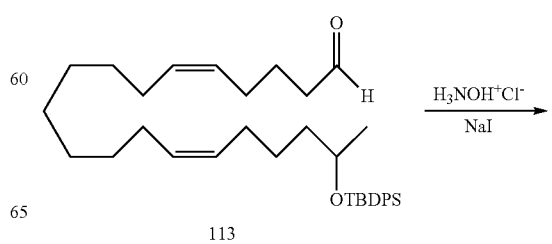

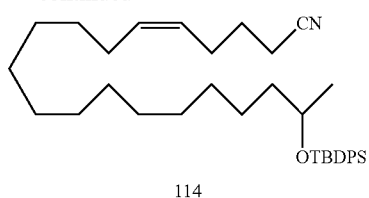

114

Following literature procedure, (Ballini, et al., Syndett 2003, 1841-1843) hydroxylamine hydrochloride (31.4 mg, 0.452 mmol) and NaI (24 mg, 0.173 mmol) were added to a stirring solution of 19-(tert-butyldiphenylsilyloxy)eicosa-5(Z),14(Z)-dienal (113) (190 mg, 0.347 mmol) in dry $CH_3CN$ (20 mL) under an argon atmosphere. After heating under reflux for 2 h, the reaction mixture was cooled, evaporated to half volume under reduced pressure, diluted with water (5 mL), and extracted with EtOAc (3×20 mL). The aqueous layer was back-extracted with EtOAc (2×20 mL). The combined organic extracts were washed with water (30 mL), brine (20 mL), dried over $Na_2SO_4$, and concentrated in vacuo. The residue was purified by $SiO_2$ column chromatography using 5% EtOAc/hexanes as eluent to give 19-(tert-butyldiphenylsilyloxy)eicosa-5(Z),14(Z)-dienenitrile (114) (104 mg, 55%) as a colorless oil. TLC: 10% EtOAc/hexanes, $R_f$≈0.7.

$^1$H NMR (CDCl$_3$, 400 MHz) δ 7.69-7.64 (m, 4H), 7.43-7.32 (m, 6H), 5.52-5.42 (m, 1H), 5.37-5.21 (m, 3H), 3.88-3.78 (m, 1H), 2.32 (t, J=7.2 Hz, 2H), 2.22-2.14 (m, 2H), 2.06-1.86 (m, 6H), 1.75-1.65 (m, 2H), 1.51-1.20 (m, 14H), 1.03 (d, J=6.0 Hz, 3H), 1.03 (s, 9H); $^{13}$C NMR (101 MHz, CDCl$_3$) δ 135.85, 135.54, 134.90, 134.55, 132.54, 129.99, 129.64, 129.45, 129.39, 129.32, 127.54, 127.42, 127.39, 127.34, 126.62, 119.68, 69.47, 39.00, 29.72, 29.63, 29.44, 29.26, 27.28, 27.19, 27.15, 27.02, 25.95, 25.36, 25.28, 23.20, 19.25, 16.43.

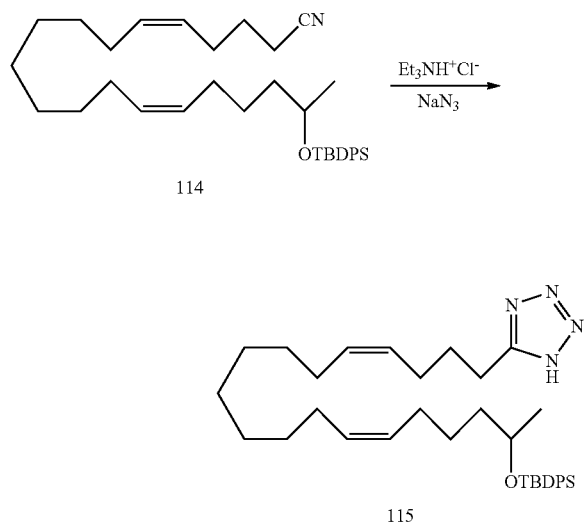

under an argon atmosphere. After stirring under reflux for 48 h in a sealed tube, the reaction mixture was cooled to room temperature and acidified with con. HCl (4 mL). Following an additional 5 min at it, the reaction mixture was extracted with EtOAc (3×20 mL). The combined organic extracts were washed with water (10 mL), brine (10 mL), dried over $Na_2SO_4$, concentrated in vacuo, and the residue purified by preparative $SiO_2$ thin layer chromatography (PTLC) using 5% MeOH/$CH_2Cl_2$ as eluent to give 5-(18-(tert-butyldiphenylsilyloxy)nonadeca-4(Z),13(Z)-dien-1-yl)-1H-tetrazole (115) (44 mg, 41%) as a colorless oil. TLC: 5% MeOH/$CH_2Cl_2$, $R_f$≈0.4.

$^1$H NMR (CDCl$_3$, 400 MHz) δ 7.69-7.63 (m, 4H), 7.42-7.31 (m, 6H), 0.5.45-5.37 (m, 1H), 5.35-5.20 (m, 3H), 3.87-3.77 (m, 1H), 3.04 (t, J=7.6 Hz, 2H), 2.18-2.10 (m, 2H), 2.00-1.85 (m, 8H), 1.52-1.14 (m, 14H), 1.05-1.01 (m, 12H); $^{17}$C NMR (101 MHz, CDCl$_3$) δ 135.84, 134.85, 134.50, 131.74, 130.00, 129.62, 129.41, 129.35, 127.52, 127.43, 127.35, 69.55, 38.98, 29.72, 29.63, 29.45, 29.26, 27.53, 27.28, 27.18, 27.13, 27.02, 26.45, 25.29, 23.19, 22.96, 19.24.

Desilylation of 5-(18-(tert-butyldiphenylsilyloxy)nonadeca-4(Z),13(Z)-dien-1-yl)-1H-tetrazole (115) (40 mg, 0.068 mmol) following the procedure described above gave 19-(1H-tetrazol-5-yl)nonadeca-6(Z),15(Z)-dien-2-ol (Analog 21) (17 mg, 55%) as a colorless oil. TLC: 10% MeOH/$CH_2Cl_2$, $R_f$≈0.30.

$^1$H NMR (CDCl$_3$, 400 MHz) δ 6.51 (br s, 1H), 5.43-5.25 (m, 4H), 3.93-3.83 (m, 1H), 2.98 (t, J=7.8 Hz, 2H), 2.15-1.91 (m, 10H), 1.60-1.16 (m, 17H); $^{13}$C NMR (CDCl$_3$, 100 MHz) δ 131.60, 130.47, 129.21, 127.70, 68.69, 38.66, 29.41, 29.03, 29.02, 28.92, 27.57, 27.09, 26.98, 26.46, 25.79, 23.29, 23.03.

Synthesis of Photoactivated Cross-Linker (PCL)

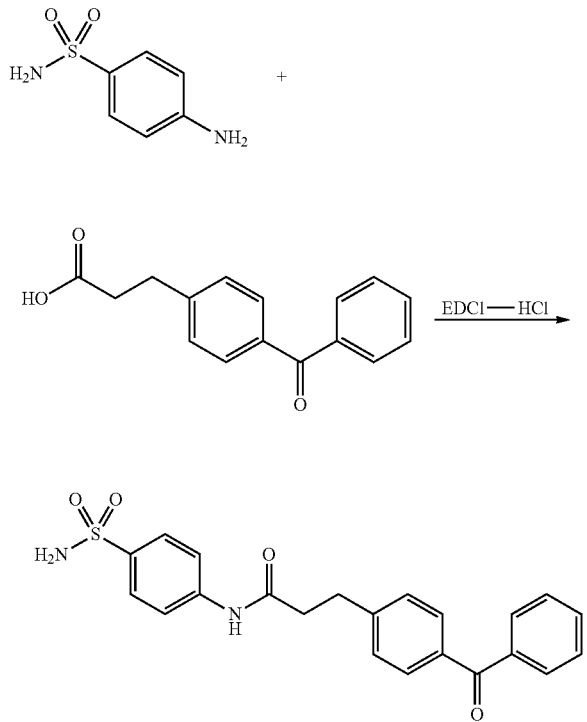

Solid 1-(3-dimethylaminopropyl)-3-ethylcarbodiimide hydrochloride (EDCI·HCl) (255 mg, 1.33 mmol) was added in portions to a stirring, rt solution 3-(4-benzoylphenyl) propanoic acid (Jose, et al. *J. Med Chem.* 2012, 55, 824-836 (200 mg, 0.786 mmol), commercial p-sulfanilamide (135 mg, 0.786 mmol), and hydroxybenzotriazole (HOBT) (116 mg, 0.865 mmol) in anhydrous DMF (5 mL). After 18 h, the reaction mixture was diluted with water (20 mL). The resultant precipitate was collected by filtration, washed with water (30 mL) and dried in vacuo at 30° C. to give 3-(4-benzoylphenyl)-N-(4-sulfamoylphenyl)propanamide (224 mg, 70%) as a white powder. TLC: 80% EtOAc/hexanes, $R_f$=0.5.

$^1$H NMR (400 MHz, DMSO) δ 10.29 (s, 1H), 7.82-7.64 (m, 9H), 7.57 (d, J=8.0, 2H), 7.45 (d, J=8.0, 2H), 7.24 (s, 2H), 3.03 (t, J=7.6, 2H), 2.75 (d, J=7.6, 2H).

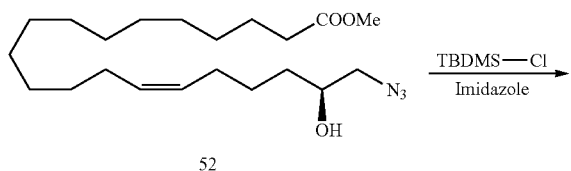

Imidazole (59 mg, 0.86 mmol), TBDMS-Cl (52 mg, 0.34 mmol), and DMAP (5 mg) were added to a stirring, 0° C. solution of methyl 20-azido-19(S)-hydroxyeicosa-5(Z),14 (Z)-dienoate (52) (110 mg, 0.28 mmol) in dry $CH_2Cl_2$ (15 mL). After stirring at room temperature for 48 h, the reaction mixture was quenched with water (5 mL) and extracted with $CH_2Cl_2$ (3×6 mL). The combined organic extracts were washed with brine (10 mL), dried over $Na_2SO_4$, and concentrated under reduced pressure. The residue was purified by $SiO_2$ column chromatography using hexanes/EtOAc (94:6) to give methyl 20-azido-19(S)-(tert-butyldimethylsilyloxy)eicosa-5(Z),14(Z)-dienoate (134 mg, 94%) as a colorless oil. TLC: 20% EtOAc/hexane, $R_f$=0.6.

$^1$H NMR (CDCl$_3$, 400 MHz) δ 5.45-5.24 (m, 4H), 3.76-3.65 (m, 1H), 3.65 (s, 3H), 3.23 (dd, J=12.4, 4.1 Hz, 1H), 3.12 (dd, J=12.5, 5.9 Hz, 1H), 2.30 (t, J=7.5 Hz, 2H), 2.11-1.92 (m, 8H), 1.74-1.63 (m, 2H), 1.58-1.43 (m, 2H), 1.43-1.22 (m, 1H), 0.89 (s, 91H), 0.09 (s, 3H), 0.07 (s, 3H); $^{13}$C NMR (CDCl$_3$, 101 MHz) δ 174.07, 131.09, 130.50, 129.05, 128.31, 71.69, 56.62, 51.42, 34.65, 33.42, 29.70, 29.67, 29.43, 29.26, 27.25, 27.19, 27.15, 26.51, 25.77, 25.21, 24.86, 17.99, −4.64, −4.67.

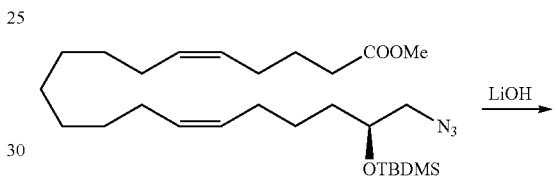

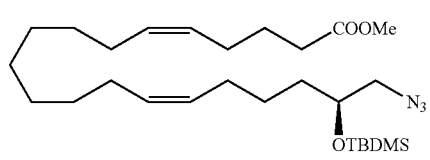

A solution of LiOH (0.8 mL of 1 M aq. soln, 0.78 mmol) and methyl 20-azido-19(S)(tert-butyldimethylsilyloxy)eicosa-5(Z),14(Z)-dienoate (130 mg, 0.26 mmol) in THF (4 mL) and deionized $H_2O$ (1 mL) was stirred at rt for 16 h, then the organic solvent was evaporated under reduced pressure. The resultant aqueous solution was acidified to pH 4.5 with 1N HCl (2 mL) at 0° C. and extracted with EtOAc (3×10 mL). The organic extracts were washed with brine (10 mL), dried over $Na_2SO_4$, and concentrated under reduced pressure. The residue was purified by $SiO_2$ column chromatography eluting with a gradient of 0-5% IPA/hexanes to afford 20-azido-19(S)-(tert-butyldimethylsilyloxy)eicosa-5 (Z),14(Z)-dienoic acid (114 mg, 90%) as a colorless oil. TLC: 60% EtOAc/hexane, $R_f$=0.5.

$^1$H NMR (CDCl$_3$, 400 MHz) δ 5.47-5.25 (m, 4H), 3.79-3.10 (m, 1H), 3.24 (dd, J=12.4, 4.1 Hz, 1H), 3.13 (dd, J=12.5, 5.9 Hz, 1H), 2.35 (t, J=7.5 Hz, 2H), 2.14-1.93 (m, 8H), 1.70 (p, J=7.5 Hz, 2H), 1.59-1.44 (m, 2H), 1.44-1.23 (m, 12H), 0.90 (s, 9H), 0.10 (s, 3H), 0.08 (s, 3H); $^{13}$C NMR (CDCl$_3$, 101 MHz) δ 180.18, 131.30, 130.52, 129.06, 128.12, 71.71, 56.62, 34.65, 33.43, 29.71, 29.67, 29.43, 29.27, 29.26, 27.26, 27.22, 27.16, 26.42, 25.79, 25.22, 24.58, 18.01, −4.63, −4.66.

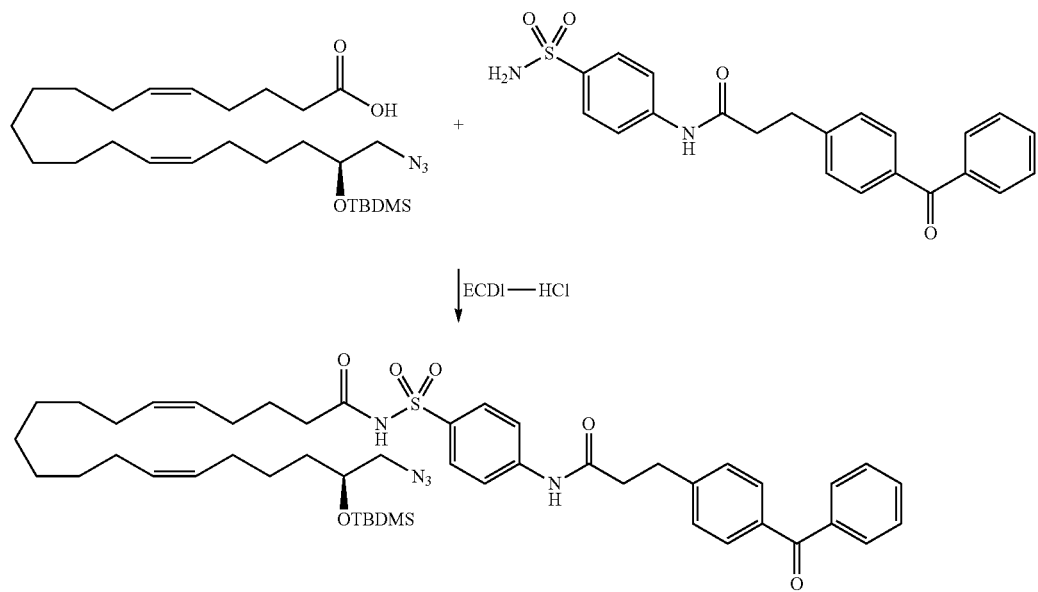

A mixture of 3-(4-benzoylphenyl)-N-(4-sulfamoylphenyl)propanamide (26 mg, 0.06 mmol), EDCI·HCl (7 mg, 0.045 mmol), and DMAP (6 mg, 0.045 mmol) was subjected to high vacuum for 30 min at rt. The mixture was then dissolved in dry DMF (1 mL) and a solution of 20-azido-19(S)-(tert-butyldimethylsilyloxy)eicosa-5(Z),14(Z)-dienoic acid (20 mg, 0.04 mmol) in anhydrous DMF (1 mL) was added. After 12 h, the mixture was charged with water (10 mL) and extracted with EtOAc (3×30 mL). The organic layer was washed with water (5×2 mL), brine (10 mL), dried over $Na_2SO_4$, and concentrated under reduced pressure. The residue was purified by $SiO_2$ column chromatography eluting with a gradient of 50-70% EtOAc/hexanes to afford 20-azido-N-((4-(3-(4-benzoylphenyl)propanamido)phenyl)sulfonyl)-19(S)-(tert-butyldimethylsilyloxy)eicosa-5(Z),14(Z)-dienamide (25 mg, 70%) as a waxy solid. TLC: 60% EtOAc/hexanes, $R_f$=0.45.

$^1$H NMR (500 MHz, CDCl$_3$) δ 8.03-7.99 (m, 2H), 7.96 (s, 1H), 7.82-7.74 (m, 4H), 7.71-7.64 (m, 2H), 7.64-7.57 (m, 1H), 7.52-7.47 (m, 2H), 7.44 (s, 1H), 7.39-7.33 (m, 2H), 5.44-5.28 (m, 3H), 5.23-5.21 (m, 1H), 3.79-3.67 (m, 11H), 3.26 (dd, J=12.4, 4.1 Hz, 11H), 3.20-3.10 (m, 3H), 2.78 (t, J=7.5 Hz, 2H), 2.23 (t, J=7.5 Hz, 2H), 2.05-1.95 (m, 8H), 1.65-1.63 (m, 2H), 1.55-1.20 (m, 2H), 1.36-1.25 (m, 12H), 0.91 (s, 9H), 0.11 (s, 3H), 0.09 (s, 3H).

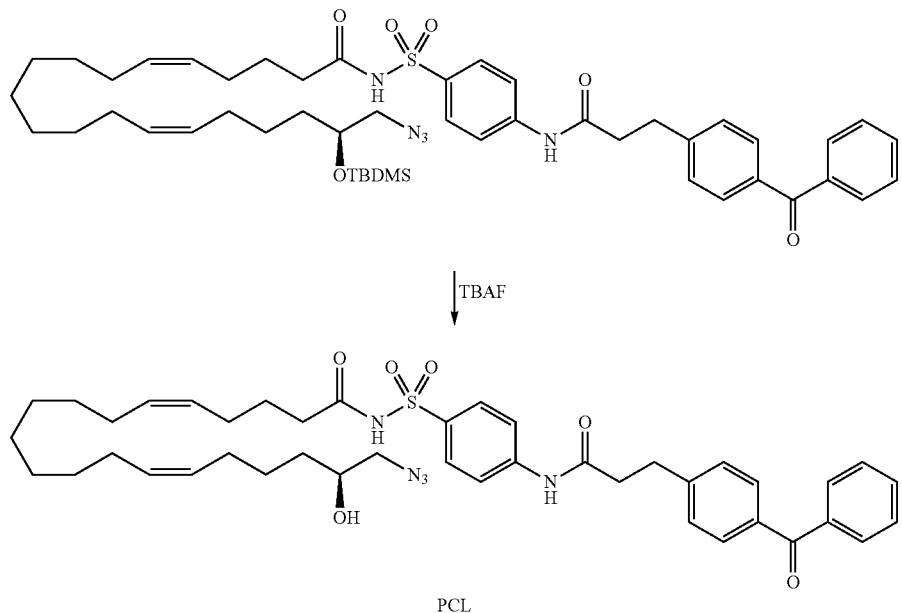 [SMILES: CC(C)(C)[Si](C)(C)O[C@@H](CCC/C=C\CCCCCCC/C=C\CCCC(=O)NS(=O)(=O)c1ccc(NC(=O)CCc2ccc(C(=O)c3ccccc3)cc2)cc1)CN=[N+]=[N-] ; "TBAF" ; [N-]=[N+]=NC[C@@H](O)CCC/C=C\CCCCCCC/C=C\CCCC(=O)NS(=O)(=O)c1ccc(NC(=O)CCc2ccc(C(=O)c3ccccc3)cc2)cc1]

PCL n-Tetrabutylammonium fluoride (TBAF) (27 μL of a 1 M soln in THF, 0.027 mmol) was added to a stirring, 0° C. solution of 20-azido-N-((4-(3-(4-benzoylphenyl)propanamido)phenyl)sulfonyl)-19(S)-(tert-butyldimethylsilyloxy) eicosa-5(Z),14(Z)-dienamide (20 mg, 0.022 mmol) in dry THF (1.0 mL). After stirring at rt for 24 h, the reaction mixture was quenched with sat. aq. NH$_4$Cl (5 mL) and extracted with EtOAc (3×6 mL). The organic extracts were washed with water (1.0 mL), brine (1.0 mL) and dried over Na$_2$SO$_4$, concentrated under reduced pressure and purified by PTLC eluting with 5% MeOH/CH$_2$Cl$_2$ to give 20-azido-N-((4-(3-(4-benzoylphenyl)propanamido)phenyl)sulfonyl)-19(S)-hydroxyeicosa-5(Z),14(Z)-dienamide (PLC) (15 mg, 86%) as a white waxy solid. TLC: 5% MeOH/CH$_2$Cl$_2$, R$_f$=0.45.

$^1$H NMR (400 MHz, CDCl$_3$) δ 8.35 (s, 1H), 7.85 (d, J=8.9 Hz, 2H), 7.75 (dd, J=8.3, 1.4 Hz, 2H), 7.70 (d, J=8.2 Hz, 2H), 7.63-7.53 (m, 3H), 7.49-7.42 (m, 2H), 7.31 (d, J=8.2 Hz, 2H), 5.46-5.05 (m, 4H), 3.78-3.68 (m, 11H), 3.35 (dd, J=12.4, 3.4 Hz, 1H), 3.23 (dd, J=12.5, 7.3 Hz, 1H), 3.11 (t, J=7.7 Hz, 2H), 2.77 (t, J=7.7 Hz, 2H), 2.23 (t, J=7.6 Hz, 2H), 2.06-1.86 (m, 8H), 1.62-1.54 (m, 2H), 1.48-1.41 (m, 2H), 1.31-1.18 (m, 12H).

$^{13}$C NMR (101 MHz, CDCl$_3$) δ 197.10, 171.19, 170.92, 145.73, 143.12, 137.38, 135.73, 132.86, 132.67, 131.58, 130.71, 130.56, 130.07, 129.54, 128.91, 128.40, 128.36, 127.76, 119.13, 70.83, 57.03, 38.63, 35.64, 33.81, 31.06, 29.58, 29.54, 29.27, 29.15, 29.13, 27.15, 26.91, 26.17, 25.52, 24.19.

19(R)-Fluoroeicosa-5(Z),14(Z)-dienoic acid

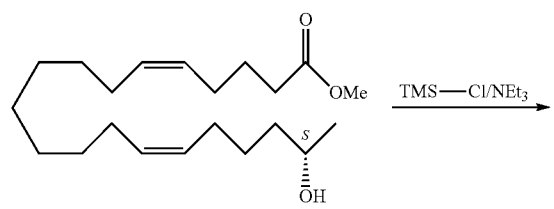

Methyl 19(S)-hydroxyeicosa-5(Z),14(Z)-dienoate (60 mg, 0.177 mmol) was silylated with TMS-Cl following literature procedure (Bartoszewicz, et al., *Synlett*, 2008, 37-40) to give methyl 19(S)-(trimethylsilyloxy)eicosa-5(Z), 14(Z)-dienoate (58 mg, 80%) as a labile colorless oil which was used immediately in the next step. TLC: SiO$_2$, EtOAc/hexane (1:9), R$_f$=0.75.

$^1$H NMR (CDCl$_3$, 500 MHz) δ 5.46-5.27 (m, 4H), 3.85-3.71 (m, 1H), 3.67 (s, 3H), 2.32 (t, J=7.5 Hz, 2H), 2.12-1.93 (m, 8H), 1.74-1.64 (m, 2H), 1.52-1.24 (m, 14H), 1.20 (d, J=6.2 Hz, 2H), 1.14 (d, J=6.1 Hz, 3H), 0.12 (s, 9H).

Following literature procedure (Yasushi, et al., *Tetrahedron* 1995, 51, 8771-8782; Bin Omar, et al., ARKIVOC2003, 7, 190-199), diethylaminosulfur trifluoride (DAST) (45 mg, 0.282 mmol) was added to a stirring, -78° C. solution of methyl 19(S)-(trimethylsilyloxy)eicosa-5(Z), 14(Z)-dienoate (58 mg, 0.141 mmol) in CH$_2$Cl$_2$ (5 mL). After 2 h, the reaction mixture was warmed over 1 h to -30° C., then quenched via slow cannulation into a stirring solution of sat aq. NaHCO$_3$ (5 mL). The reaction mixture was extracted with CH$_2$Cl$_2$ (2×50 mL) and the combined organic extracts were concentrated in vacuo. The residue was purified by SiO$_2$ column chromatography using 5% EtOAc/hexanes to afford methyl 19(R)-fluoroeicosa-5(Z), 14(Z)-dienoate (25 mg, 52%) as a colorless oil. TLC: 5% EtOAc/hexane, R$_f$=0.45.

$^1$H NMR (CDCl$_3$, 400 MHz) δ 5.46-5.33 (m, 4H), 4.72-4.65 (m, 0.5H), 4.60-4.52 (m, 0.5H), 3.68 (s, 3H), 2.34-2.23 (m, 2H), 2.12-1.92 (m, 8H), 1.73-1.59 (m, 2H), 1.34-1.31 (m, 2H), 1.29-1.21 (m, 15H); $^{13}$C NMR (101 MHz, CDCl$_3$) δ 174.10, 131.09, 130.47, 129.08, 128.29, 90.86 (d, J$_{C,F}$=164.2 Hz), 51.42, 36.42 (d, J$_{C,F}$=20.7 Hz), 33.42, 29.67, 29.64, 29.40, 29.24, 27.19, 27.18, 26.86, 26.49, 25.12 (d, J$_{C,F}$=4.9 Hz), 24.85, 20.97 (d, J$_{C,F}$=22.9 Hz); $^{19}$F NMR (470 MHz, CDCl$_3$) δ0 -172.30--172.51 (m). HRMS calcd for C$_{21}$H$_{37}$FNaO$_2$ [M+Na]$^+$ 363.2675, found 363.2673. [α]$^{20}_D$-4.1° (c 2.3, CHCl$_3$).

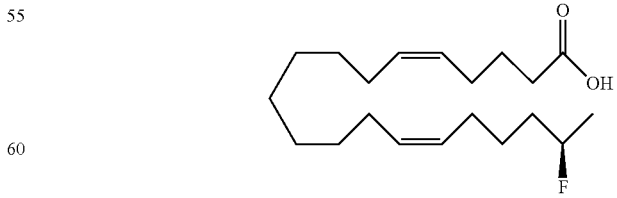

Saponification of methyl 19(R)-fluoroeicosa-5(Z),14(Z)-dienoate (25 mg, 0.073 mmol) as described above furnished 19(R)-fluoroeicosa-5(Z),14(Z)-dienoic acid (20 mg, 84%) as a colorless liquid. TLC: 80% EtOAc/hexanes, R$_f$=0.2.

¹H NMR (CDCl₃, 400 MHz) δ 5.46-5.24 (m, 4H), 4.72-4.65 (m, 0.5H), 4.61-4.53 (m, 0.5H), 2.34 (t, J=7.5 Hz, 2H), 2.13-1.92 (m, 8H), 1.73-1.59 (m, 2H), 1.34-1.31 (m, 2H), 1.29-1.21 (m, 15H); ¹³C NMR (101 MHz, CDCl₃) δ 179.76, 131.29, 130.49, 129.09, 128.11, 128.09, 90.91 (d, $J_{C,F}$=164.2 Hz), 36.43 (d, $J_{C,F}$=20.6 Hz), 33.35, 29.67, 29.64, 29.60, 29.52, 29.46, 29.40, 29.28, 29.24, 27.20, 26.87, 26.40, 25.12 (d, $J_{C,F}$=4.9 Hz), 24.57, 20.98 (d, $J_{C,F}$=22.8 Hz); ¹⁹F NMR (376 MHz, CDCl₃) δ −172.26−−172.44 (m). HRMS calcd for C₂₀H₃₅FNaO₂ [M+Na]⁺ 349.2519, found 349.2511. [α]²⁰_D −3.34° (c 1.3, CHCl₃).

20-Fluoroeicosa-5(Z),14(Z)-dienoic acid

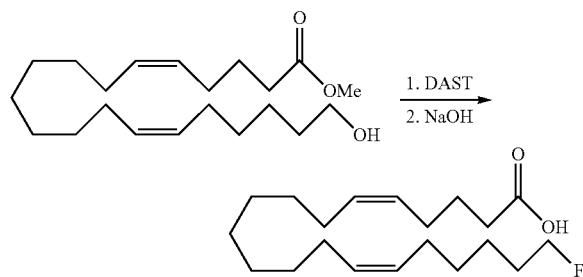

Sequential fluorination of methyl 20-hydroxyeicosa-5(Z),14(Z)-dienoate (Yu, et al., *Bioorg. Med Chem.* 2003, 11, 2803-2821) (500 mg, 1.47 mmol) with DAST and saponification as described above gave 20-fluoroeicosa-5(Z),14(Z)-dienoic acid (43 mg, 72%) as a colorless oil. TLC: 50% EtOAc/hexanes, R_f=0.35.

¹H NMR (CDCl₃, 400 MHz) δ 5.47-5.26 (m, 4H), 4.43 (dt, $J_{HF}$=47.4 Hz, $J_{HH}$=6.2 Hz, 2H), 2.36 (t, J=7.5 Hz, 2H), 2.10-2.00 (m, 8H), 1.78-1.61 (m, 4H), 1.48-1.23 (m, 14H); ¹³C NMR (101 MHz, CDCl₃) δ 179.97, 131.30, 130.25, 129.34, 128.12, 84.14 (d, $J_{C,F}$=164.1 Hz), 33.42, 30.31 (d, $J_{C,F}$=19.3 Hz), 29.71, 29.66, 29.63, 29.55, 29.42, 29.35, 29.32, 29.26, 27.22, 27.21, 27.03, 26.42, 24.79 (d, $J_{C,F}$=5.5 Hz), 24.59.

(20-Fluoroeicosa-5(Z),14(Z)-dienoyl)glycine

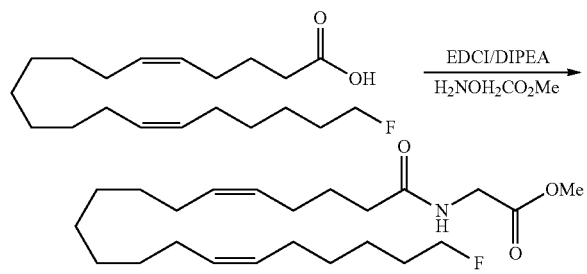

Condensation of 20-fluoroeicosa-5(Z),14(Z)-dienoic acid (50 mg, 0.15 mmol) with glycine methyl ester as described above gave methyl (20-fluoroeicosa-5(Z),14(Z)-dienoyl)glycinate (43 mg, 72%) as a colorless oil. TLC: 50% EtOAc/hexanes, R_f=0.35.

¹H NMR (CDCl₃, 400 MHz) δ 5.91 (s, 1H), 5.44-5.24 (m, 4H), 4.42 (dt, $J_{H,F}$=47.4 Hz, $J_{H,H}$=6.2 Hz, 2H), 4.03 (d, J=5.1 Hz, 2H), 3.75 (s, 3H), 2.27-2.18 (m, 2H), 2.14-1.93 (m, 8H), 1.77-1.60 (m, 4H), 1.46-1.21 (m, 14H).

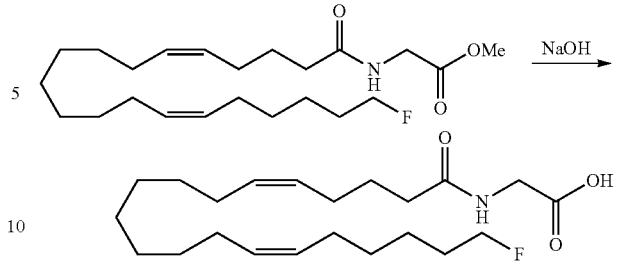

Saponification of methyl (20-fluoroeicosa-5(Z),14(Z)-dienoyl)glycinate (40 mg, 0.10 mmol) as described above furnished (20-fluoroeicosa-5(Z),14(Z)-dienoyl)glycine (27 mg, 70%) as a colorless oil. TLC: 80% EtOAc/hexanes, R_f=0.2.

¹H NMR (CDCl₃, 400 MHz) δ 6.21-6.13 (m, 1H), 5.47-5.25 (m, 4H), 4.44 (dt, $J_{H,F}$=47.3 Hz, $J_{H,H}$=6.2 Hz, 2H), 4.06 (d, J=5.1 Hz, 2H), 2.27 (t, J=7.7 Hz, 2H), 2.09-1.98 (m, 8H), 1.72-1.69 (m, 4H), 1.40-1.22 (m, 14H); ¹³C NMR (101 MHz, CDCl₃) δ 174.22, 131.25, 130.24, 129.36, 128.20, 84.19 (d, $J_{C,F}$=163.9 Hz), 35.60, 30.31 (d, $J_{C,F}$=19.4 Hz), 29.71, 29.68, 29.44, 29.31, 29.28, 29.26, 27.26, 27.20, 27.03, 26.52, 25.40, 24.78 (d, $J_{C,F}$=5.5 Hz).

2,5,8,11,14,17-Hexaoxanonadecan-19-yl 20-fluoroeicosa-5(Z),14(Z)-dienoate

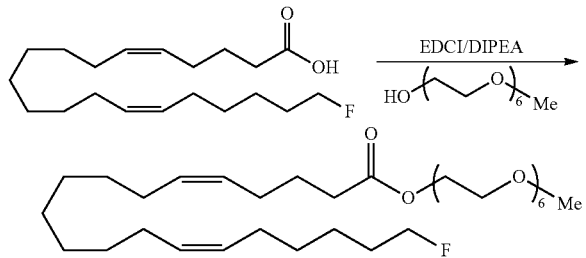

Esterification of 20-fluoroeicosa-5(Z),14(Z)-dienoic acid (100 mg, 0.30 mmol) as described above with 2,5,8,11,14,17-hexaoxanonadecan-19-ol (PEG₆-methyl ether) gave 2,5,8,11,14,17-hexaoxanonadecan-19-yl 20-fluoroeicosa-5(Z),14(Z)-dienoate (114 mg, 62%) as a colorless oil. TLC: 50% EtOAc/hexanes, R_f=0.35.

¹H NMR (CDCl₃, 400 MHz) δ 5.44-5.25 (m, 4H), 4.43 (dt, $J_{H,H}$=47.4, $J_{H,H}$=6.2 Hz, 2H), 4.25-4.18 (m, 2H), 3.72-3.60 (m, 20H), 3.57-3.50 (m, 2H), 3.37 (s, 3H), 2.33 (t, J=7.6 Hz, 2H), 2.11-1.94 (m, 8H), 1.69-1.54 (m, 4H), 1.46-1.22 (m, 15H); ¹³C NMR (101 MHz, CDCl₃) δ 173.64, 131.07, 130.23, 129.34, 128.33, 84.13 (d, $J_{C,F}$=164.1 Hz), 71.91, 70.60, 70.59, 70.56, 70.54, 70.50, 69.17, 63.37, 59.02, 33.60, 30.30 (d, $J_{C,F}$=19.4 Hz), 29.71, 29.68, 29.44, 29.31, 29.27, 29.26, 27.21, 27.03, 26.52, 24.85, 24.78 (d, $J_{C,F}$=5.5 Hz); ¹⁹F NMR (376 MHz, CDCl₃) δ −192.38−−192.84 (m).

A person of skill in the art may use the disclosure of 20-HETE analogs herein to synthesize these or other compositions with 20-HETE antagonist activity using methods which are known to a person of skill in the art.

Exemplary 20-HETE analogs according to the present invention am shown in Tables 1 and 2, above.

Example 2

Vasoactivity of 20-HETE Antagonists

The compounds shown in Tables 1 and 2 were evaluated for their ability to modulate the activity of 20-HETE. Table 1 depicts the structures of several 20-HETE analogs studied and their classification based on their effects on vasoactivity. The bioassay used to evaluate vasoactivity is based on the ability of 20-HETE to enhance the responsiveness of arteries to the constrictor activity of phenylephrine (PE). Any analog that increased the $EC_{50}$ to PE was classified as a 20-HETE antagonist, while any analog that decreased the $EC_{50}$ to PE was classified as a 20-HETE agonist. The fold increase or decrease of the $EC_{50}$ to PE for each compound is shown in Table A. Based on their activities, all analogs were classified as either 20-HETE agonists or 20-HETE antagonists.

Figure 2:
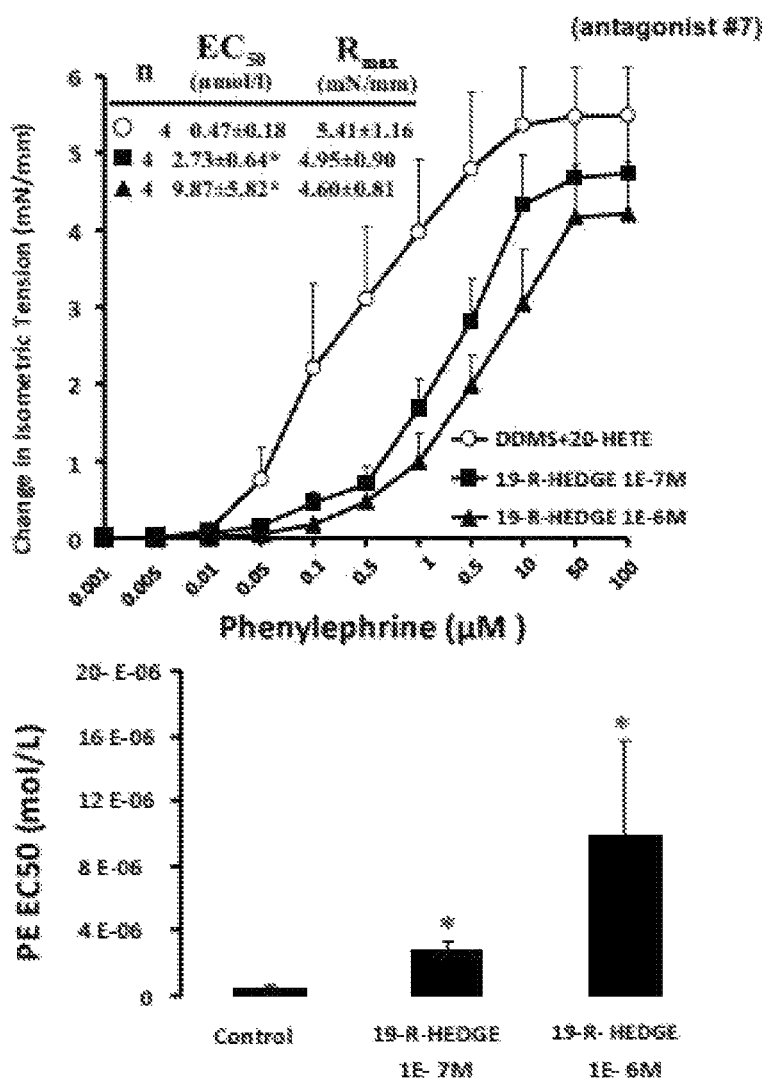
FIG. 2 shows bioassay data demonstrating the vasoactivity of compound 7 shown in Table 1.

Exemplary data from bioassays used to assess vasoactivity of selected compounds listed in Table 1 and Table 2 is shown in FIGS. 1-2.

Example 3

20-HETE Antagonist Act to Prevent Hypertension and Vascular Remodeling

The role of 20-HETE antagonists in lowering blood pressure, preventing and reversing vascular and renal damage associated with hypertension, modulating hyperglycemia, and modulating insulin resistance in obesity, was evaluated.

Figure 3:
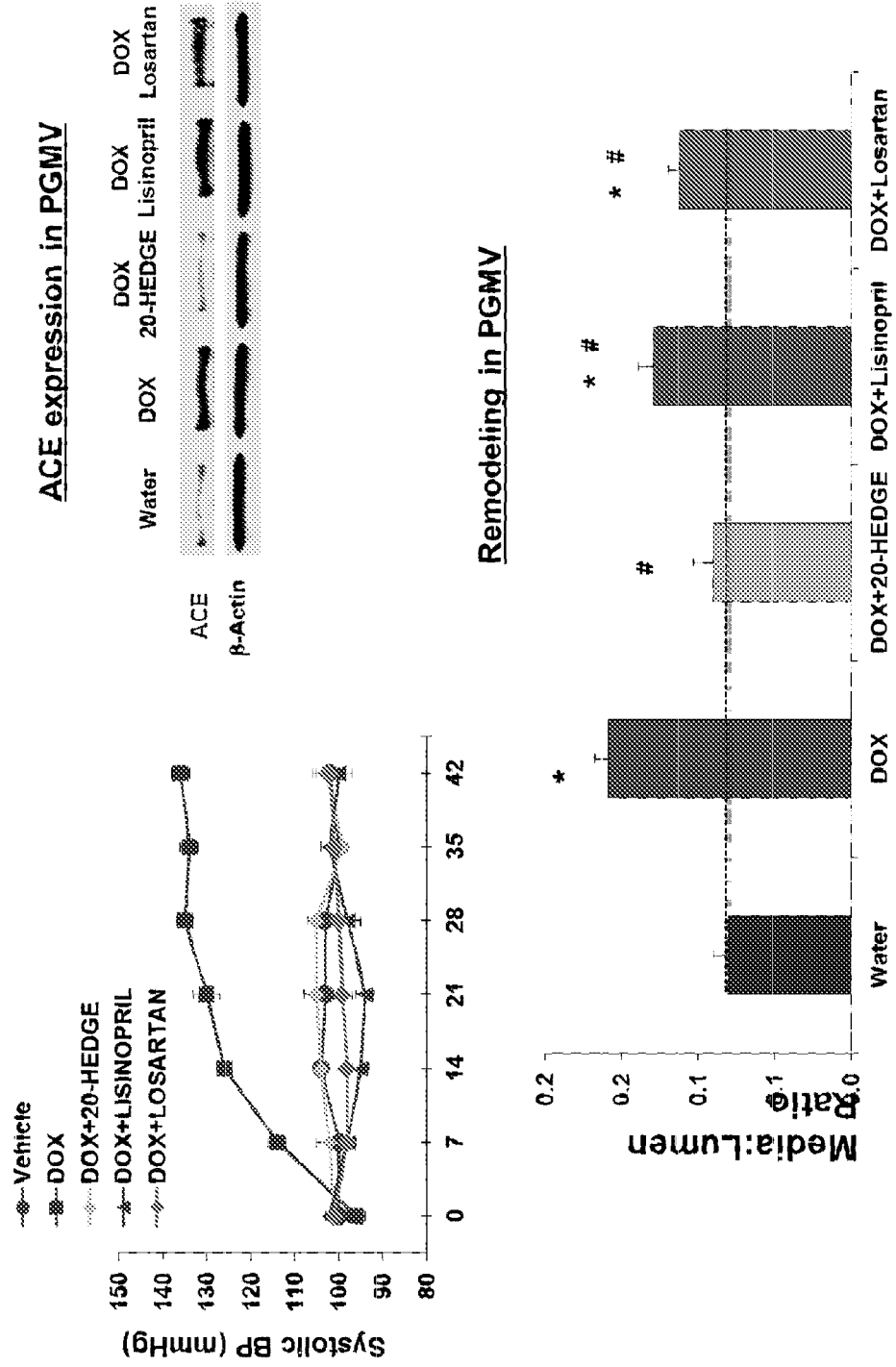
FIG. 3 demonstrates that the 20-HETE antagonist 2-(20-hydroxyeicosa-6(Z),15(Z)-dienamido)acetic acid [aka N-(20-hydroxyeicos-6(Z),15(Z)-dienoyl)glycine](20-6,15-HEDGE) decreases systolic blood pressure as effectively as the angiotensin-converting enzyme (ACE) inhibitors lisinopril and losartan at several time points when used in combination with doxazosin (DOX) in mouse models of hypertension.

FIG. 3 demonstrates that the 20-HETE antagonist 20-HEDGE decreases systolic blood pressure as effectively as the ACE inhibitors lisinopril and losartan at several time points when used in combination with DOX in mouse models of hypertension. As also shown in FIG. 3, 20-HEDGE decreases ACE expression in preglomerular microvessels (PGMV) compared with lisinopril and losartan, as well as decreasing vascular remodeling.

Systolic blood pressure measurements were taken using the CODA tail-cuff system (Kent Scientific), which utilizes volume pressure recording sensor technology. Mice were acclimated to the machine for one week prior to day 0 and blood pressure was monitored throughout the length of the experiment. Values within ±10% of their mean blood pressure measurements were obtained. At the end of the experiment, mice were anesthetized with ketamine (70 mg/kg) and xylazine (70 mg/kg) and laporotomy was performed. Preglomerular arteries were microdissected and collected for western blot analysis, lipid extraction and functional studies. Measurements of Media Thickness, Media to Lumen Ratio, and Medial Cross-Sectional Area (CSA) Segments of renal interlobar arteries were dissected and mounted on a pressurized myograph and equilibrated for 1 h in oxygenated krebs buffer at 37° C. The operator was blinded to treatments except for the blood pressure range of the animal. Lumen diameters from normotensive animals were determined at 100 mmHg and hypertensive animals at 140 mmHg. Measurements of outer diameter (OD) and inner diameter (ID) under passive conditions were used to calculate media thickness [(OD−ID)/2], media to lumen ratio (OD−ID)/ID], and medial cross-sectional area [$CSA = (\pi/4) \times (OD^2 - ID^2)$] 20-SOLA Administration: The water-soluble 20-HETE antagonist 20-SOLA [2,5,8,11,14,17-hexaoxanonadecan-19-yl 20-hydroxyicosa-6(Z),15(Z)-dienoate] was administered 10 mg/kg per day in drinking water. Expression of ACE. Renal preglomerular microvessels were collected and lysed with 1×RIPA (Radio-Immunoprecipitation Assay) buffer (Sigma, St Louis, Mo.) containing protease and phosphatase inhibitor cocktails (Roche Applied Sciences, New York, N.Y.). Protein concentrations were determined using the Bradford protein assay (Eppendorf BioPhotometer). Protein samples (20 µg) were loaded onto a 4-20% Mini-PROTEAN TGX precast gel (Bio-Rad, Hercules, Calif.) with respective loaded EZ-Run Prestained Rec Protein Ladder (Fisher BioReagents, Waltham, Mass.) markers. SDS-polyacrylamide gels were transferred to Tran-Blot Turbo Mini PVDF membranes (Bio-Rad, Hercules, Calif.) followed by blocking buffer (Li-Cor, Lincoln, Nebr.) and subsequent incubation with primary and secondary antibodies. Antibodies included: ACE (N-20) (SC-12184, Santa Cruz, Biotechnology, Dallas, Tex.) goat polyclonal IgG (1:200, Santa Cruz Biotechnology), anti-β-Actin mouse monoclonal IgG (Sigma, St Louis, Mo.), donkey anti-goat IRDye 800CW (1:1000, Li-Cor, Lincoln, Nebr.), and goat anti-mouse IRDye 800CW (1:10000, Li-Cor, Lincoln, Nebr.). Membrane fluorescence-based immunodetection was conducted using the Li-Cor Odyssey Infrared Imaging System (Li-Cor, Lincoln, Nebr.) and respective band density was quantified using the Odyssey Application Software Version 3.0.21.

Figure 4:
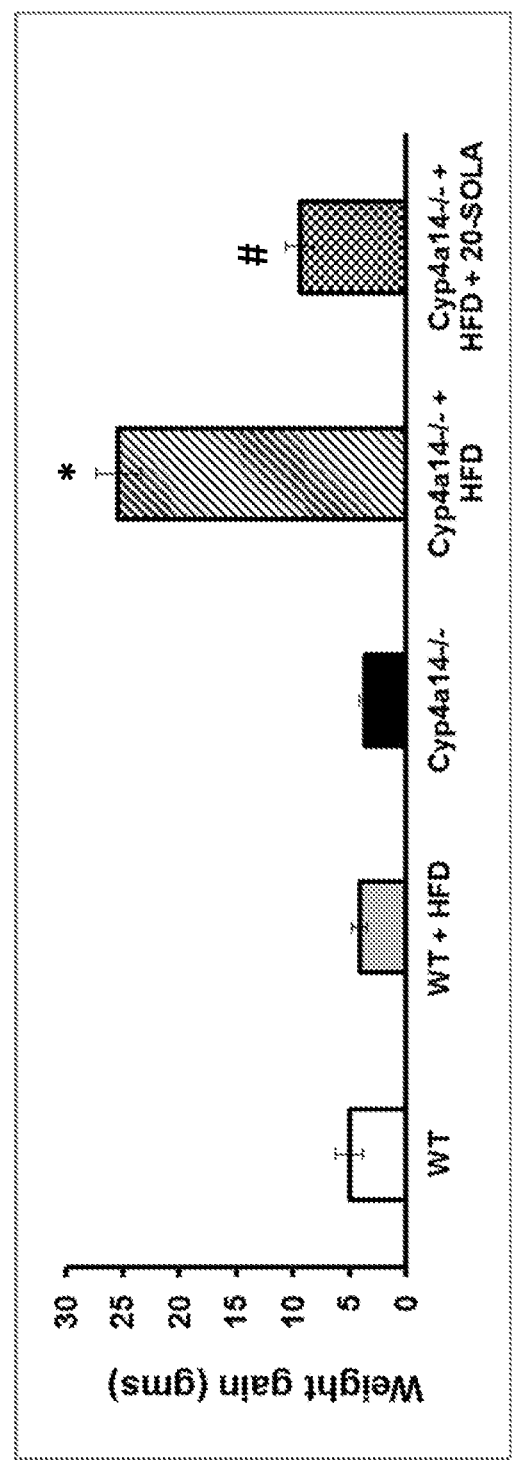
FIG. 4 that the 20-HETE antagonist 2,5,8,11,14,17-hexaoxanonadecan-19-yl 20-hydroxyeicosa-6(Z),15(Z)-dienoate (20-6,15-SOLA) attenuates high-fat diet-induced obesity in Cyp4a14−/− mice overexpressing 20-HETE.
Figure 5:
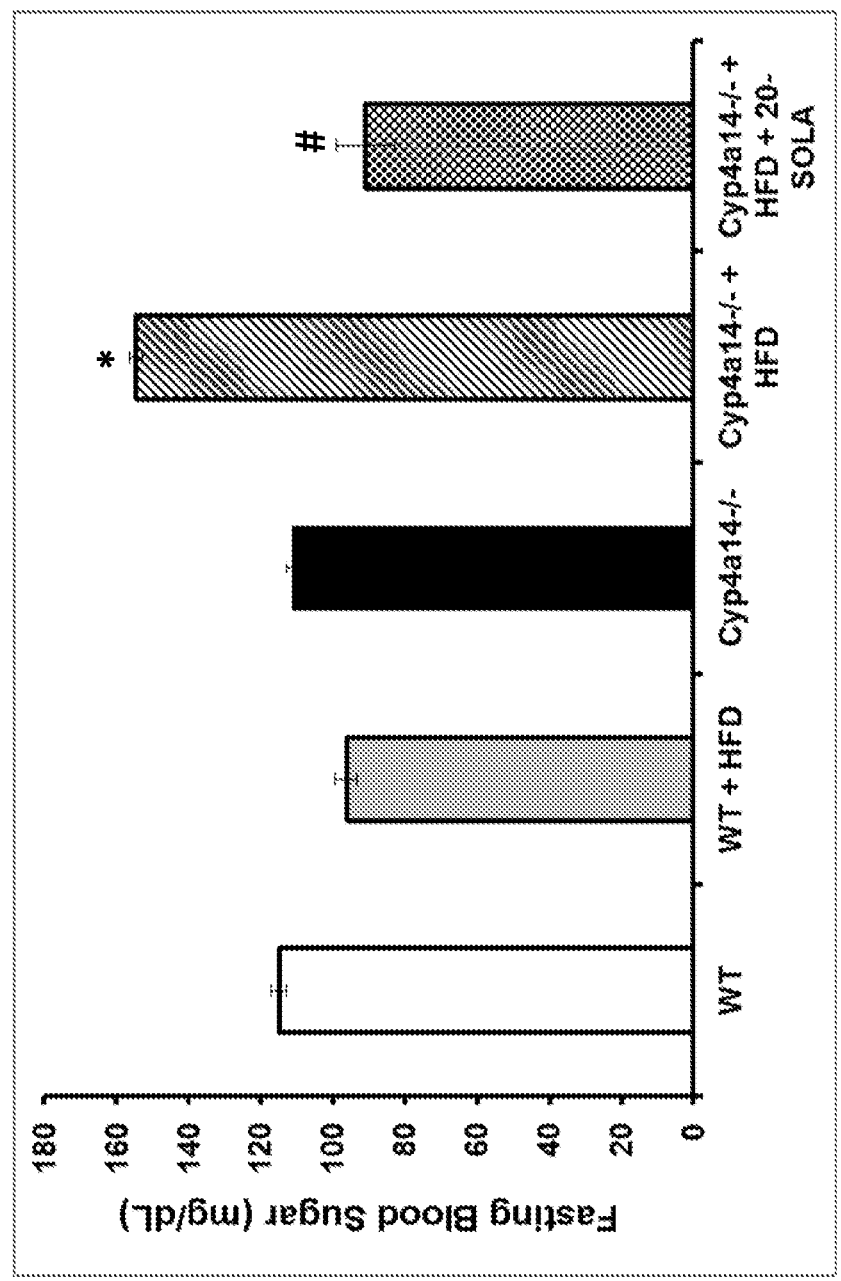
FIG. 5 demonstrates that high-fat diet-induced hyperglycemia is normalized by 20-6,15-SOLA in Cyp4a14−/− mice.
Figure 6:
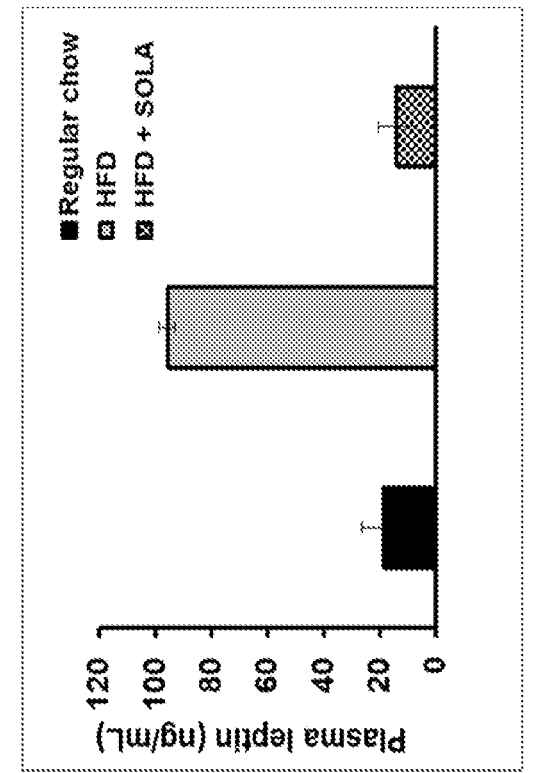
FIG. 6 demonstrates that 20-6,15-SOLA alleviates hyperinsulinemia and hyperleptinemia in Cyp4a14−/− mice on a high-fat diet.
Figure 6:
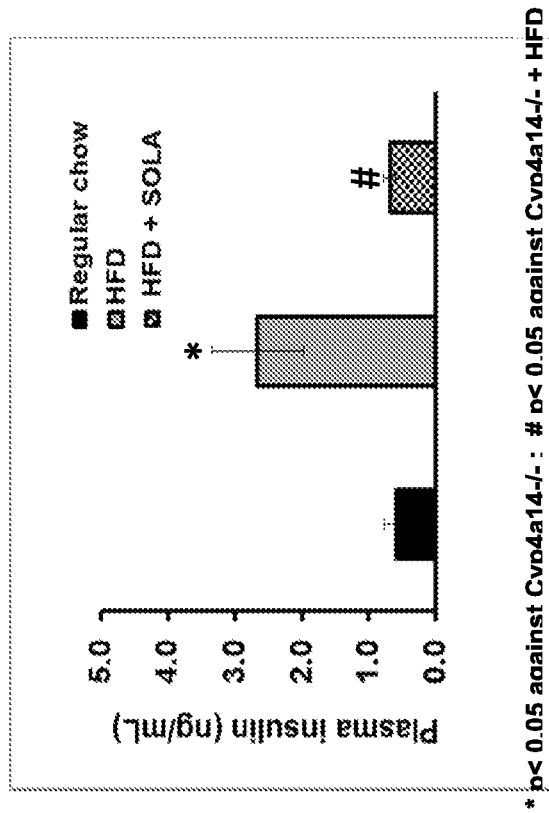

FIG. 4 demonstrates that the 20-HETE antagonist 20-6,15-SOLA attenuates high-fat diet-induced obesity in Cyp4a14−/− mice overexpressing 20-HETE. FIG. 5 shows that high-fat diet-induced hyperglycemia is normalized by 20-6,15-SOLA in Cyp4a14−/− mice. IG. 6 shows that 20-6,15-SOLA alleviates hyperinsulinemia and hyperleptinemia in Cyp4a14−/− mice on a high-fat diet. Together, these results demonstrate that 20-HETE antagonists, as provided by the present invention, act to prevent obesity-associated hyperglycemia and insulin resistance.

Figure 7:
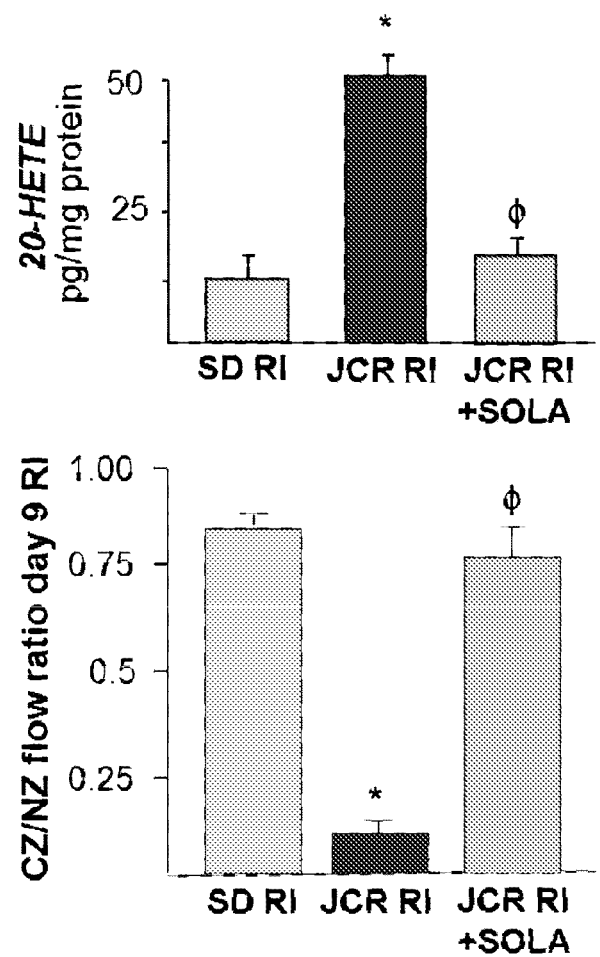
FIG. 7 demonstrates that blockade of 20-HETE using 20-6,15-SOLA attenuates impaired coronary collateral growth (CCG) in rat models of metabolic syndrome (JCR rats) compared with normal rats (SD rats).

FIG. 7 shows that blockade of 20-HETE using 20-6,15-SOLA attenuates impaired coronary collateral growth (CCG) in rat models of metabolic syndrome (JCR rats) compared with normal rats (SD rats).

Example 4

Identification of GPR75-20-HETE Pairing

In order to identify the receptor through which the 20-HETE analogs of the invention mediate vasoactivity, crosslinking analogs, click chemistry, proteomics, and cell signaling assays were conducted.

Figure 8:
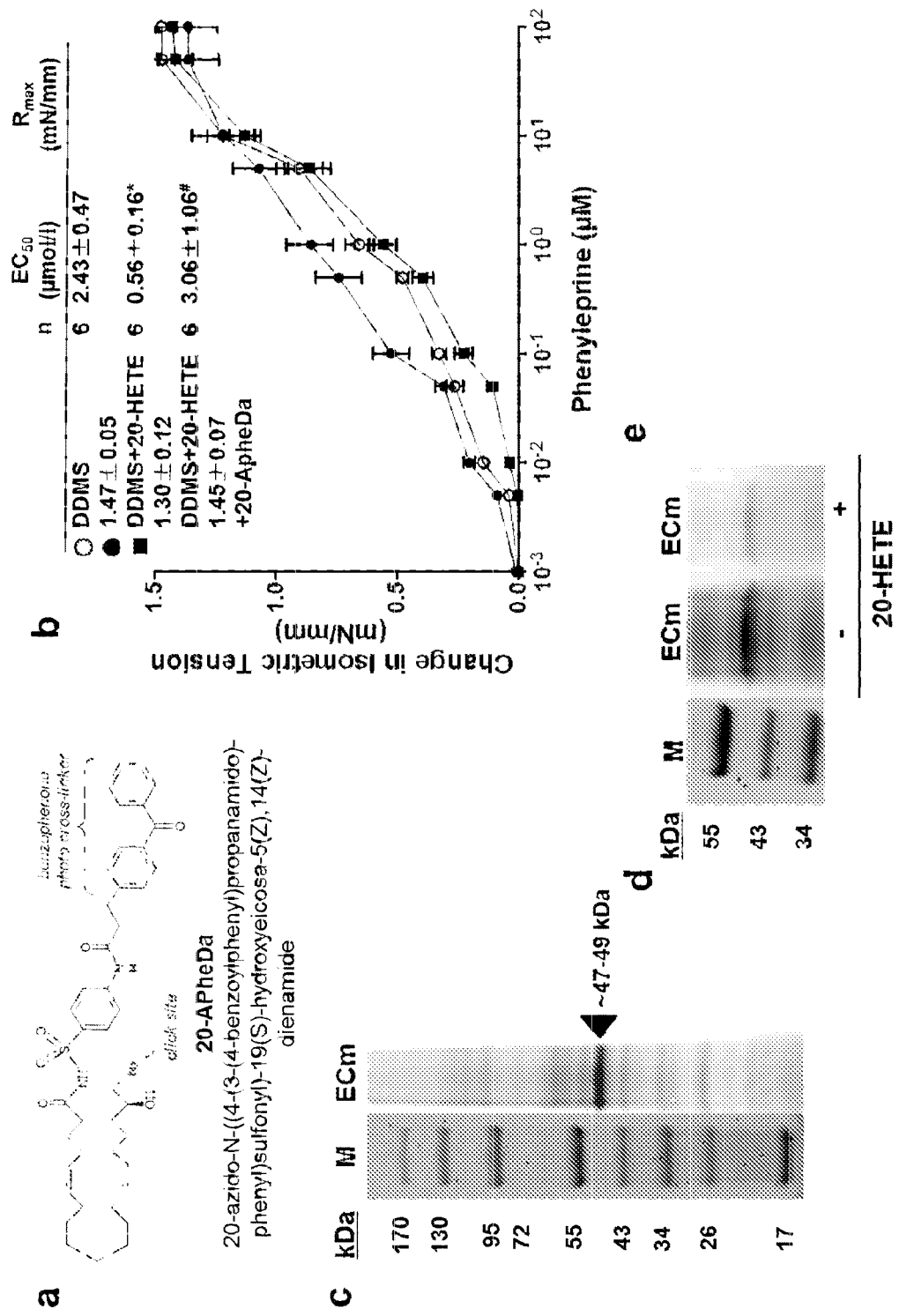
FIG. 8 demonstrates a crosslinking study of 20-HETE binding using a 20-HETE analog, 20-azido-N-((4-(3-(4-benzoylphenyl)propanamido)-phenyl)sulfonyl)-19(S)-hydroxyeicosa-5(Z),14(Z)-dienamide (20-APheDa), containing a photoreactive crosslinker.
Figure 9:
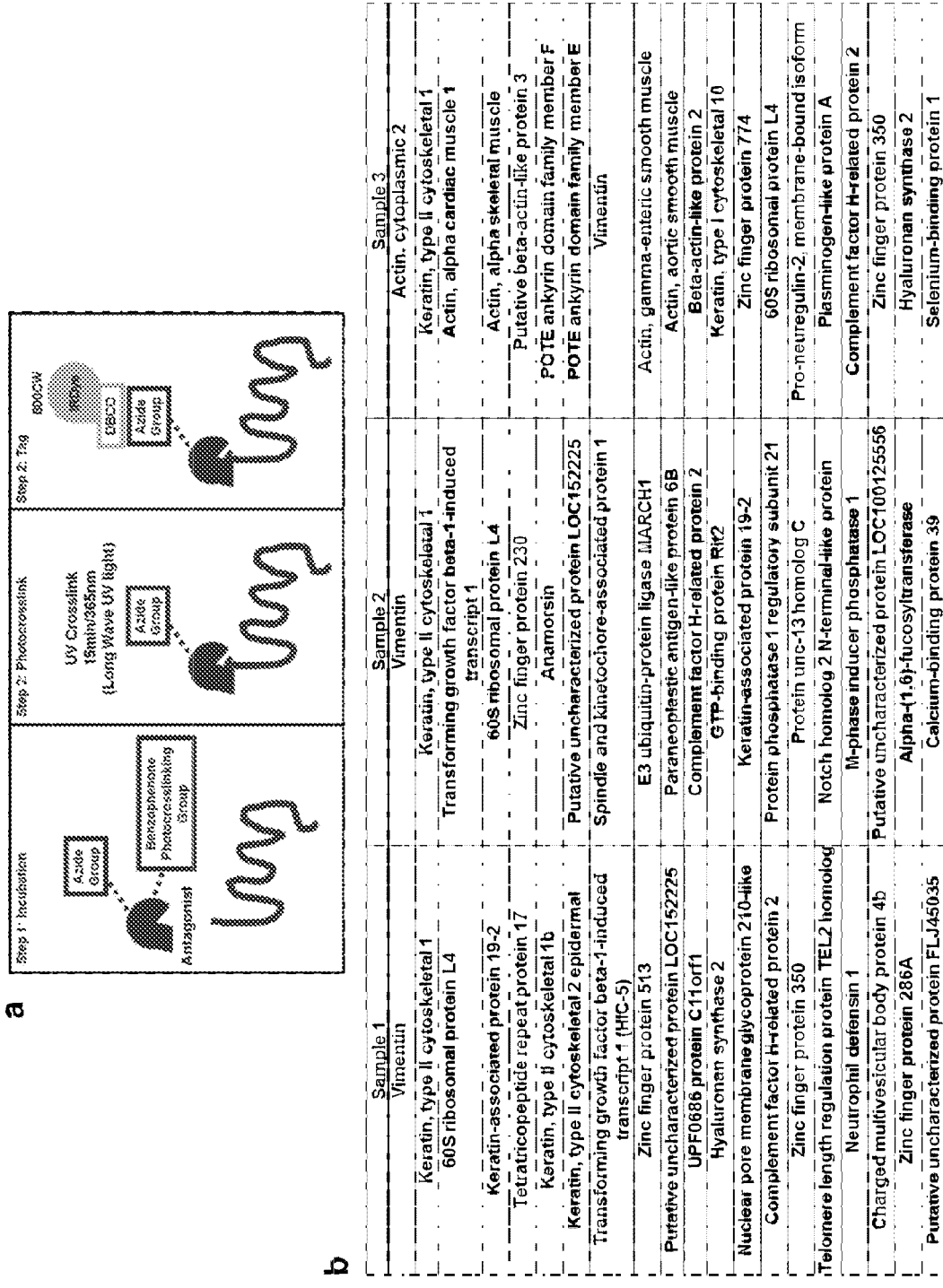
FIG. 9 demonstrates an assay and analysis of 20-ApheDa-protein complexes of the crosslinking study of FIG. 8.

An analog of 20-HETE, 20-azido-N-((4-(3-(4-benzoylphenyl)propanamido)-phenyl)sulfonyl)-19(S)-hydroxyeicosa-5(Z),14(Z)-dienamide (20-APheDa; FIG. 8*a*) was synthesized, that contained benzophenone, a photoreactive crosslinker for protein binding, and an azide, for selective binding to a click-chemistry dibenzocyclooctyne (DBCO) 800CW Infrared Dye (FIG. 9*a*). This analog functions as a 20-METE antagonist as demonstrated by its ability to block 20-HETE-mediated sensitization of PE vasoconstriction by decreasing (4-fold) the $EC_{50}$ to PE (FIG. 8*b*). When incubated with membrane fractions of human endothelial cells (EC) followed by 15 min of UV (365 nm) crosslinking and 1 h incubation with the click reagent (DBCO-IRdye 800CW, LiCor), an intense band of approximately 47-49 kDa was detected (FIG. 8*c*). The formation of this band was competed with by excess amounts of 20-HETE, but not 12-HETE (FIG. 8*d-e*).

Figure 10:
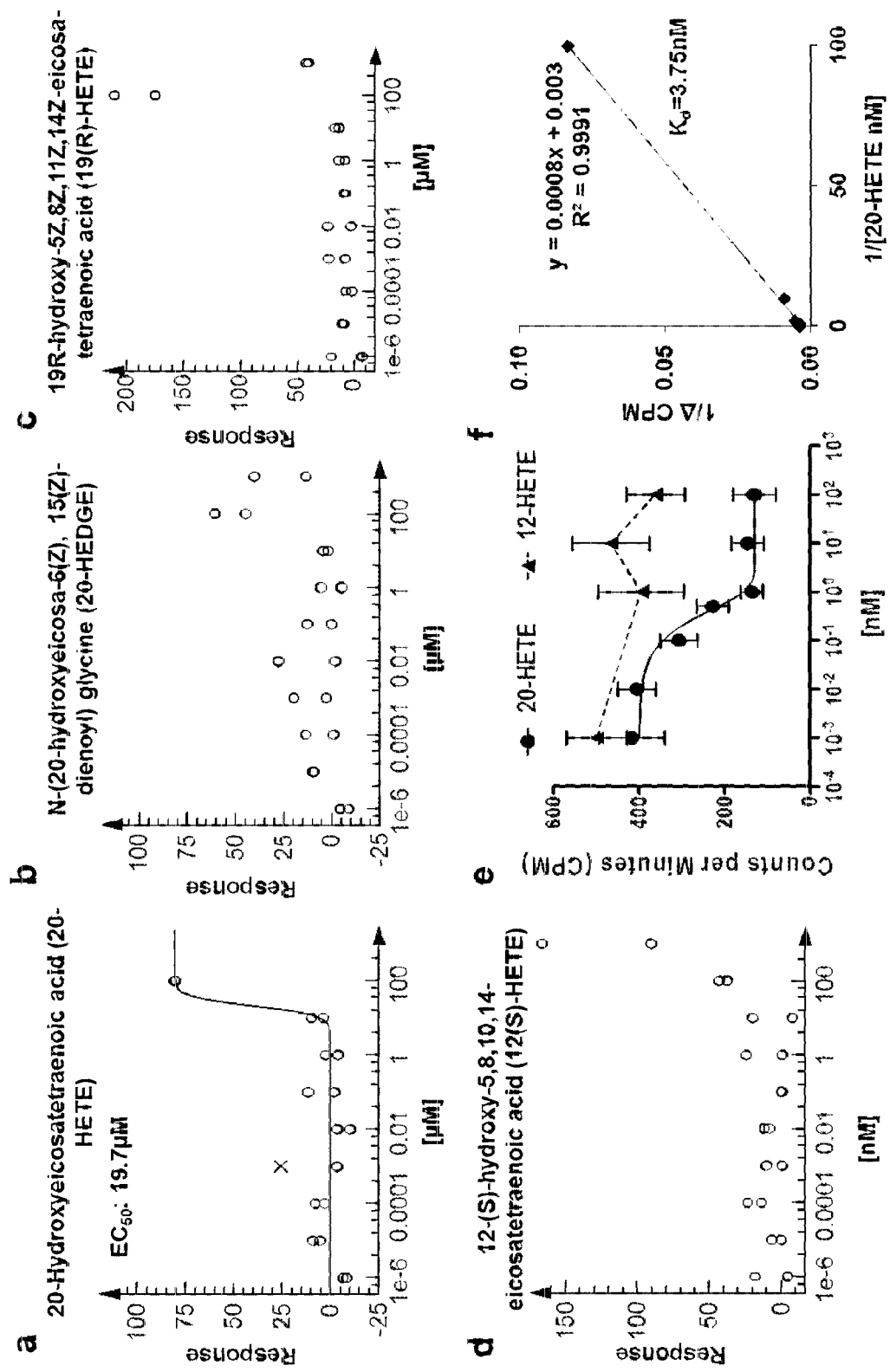
FIG. 10 demonstrates GPR75 activation, as measured by β-arrestin recruitment, by 20-HETE, but not 12(S)-hydroxyeicosa-5(Z),8(Z),10(E),14(Z)-tetraenoic acid [12(S)-HETE], 20-6,15-HEDGE, or 19(R)-HETE.

In-gel 20-APheDa-protein complexes were extracted and protein sequenced by Applied Biomics. Analysis of sequenced profiles identified several proteins and domains including transforming growth factor beta-1-induced transcript 1 (TGFB1I1/HIC-5), POTE ankyrin domain family members, Zinc finger proteins, and GTP-binding proteins (FIG. 9b). These findings suggested the presence of GIT1, a G protein-coupled receptor (GPCR)-kinase interacting protein-1 scaffold protein with ADP-ribosylating factor GTPase activity and a GPCR. The use of search engines such as http://www.genecards.org/ to find GIT1-interacting proteins revealed an association with the orphan receptor GPR75, a $G_{q\alpha}$ protein-coupled receptor.

β-arrestin represents a robust and widely used screening technology for GPCR-ligand pairing. GPCR-mediated β-arrestin recruitment is also recognized as a distinct intracellular signaling pathway, and ligand-receptor interactions may show a bias toward β-arrestin over classical GPCR signaling pathways. In this assay, 20-HETE, but not 12(S)-HETE, the 20-HETE antagonist 20-6,15-HEDGE, nor 19(R)-HETE, activated GPR75, i.e., increased β-arrestin recruitment (FIG. 10a-d). While the estimated $EC_{50}$ for 20-HETE activation of GPR75 expressed in CHO cells by the β-arrestin GPCR assay was 19.7 μmol/l, analysis of displacement assays in membrane fractions from EC using [$^3H_8$] 20-METE demonstrated a $K_d$ of 3.75 nmol/l (FIG. 10e-1). This concentration better represents 20-HETE's biological activity wherein maximal changes in NO bioavailability and ACE expression have been seen in the range of 5-10 nmol/l. These results show that 20-HETE binds to EC membranes and that it pairs with GPR75 and activates it by recruiting β-arrestin to the c-terminal of the GPCR.

Example 5

Figure 11:
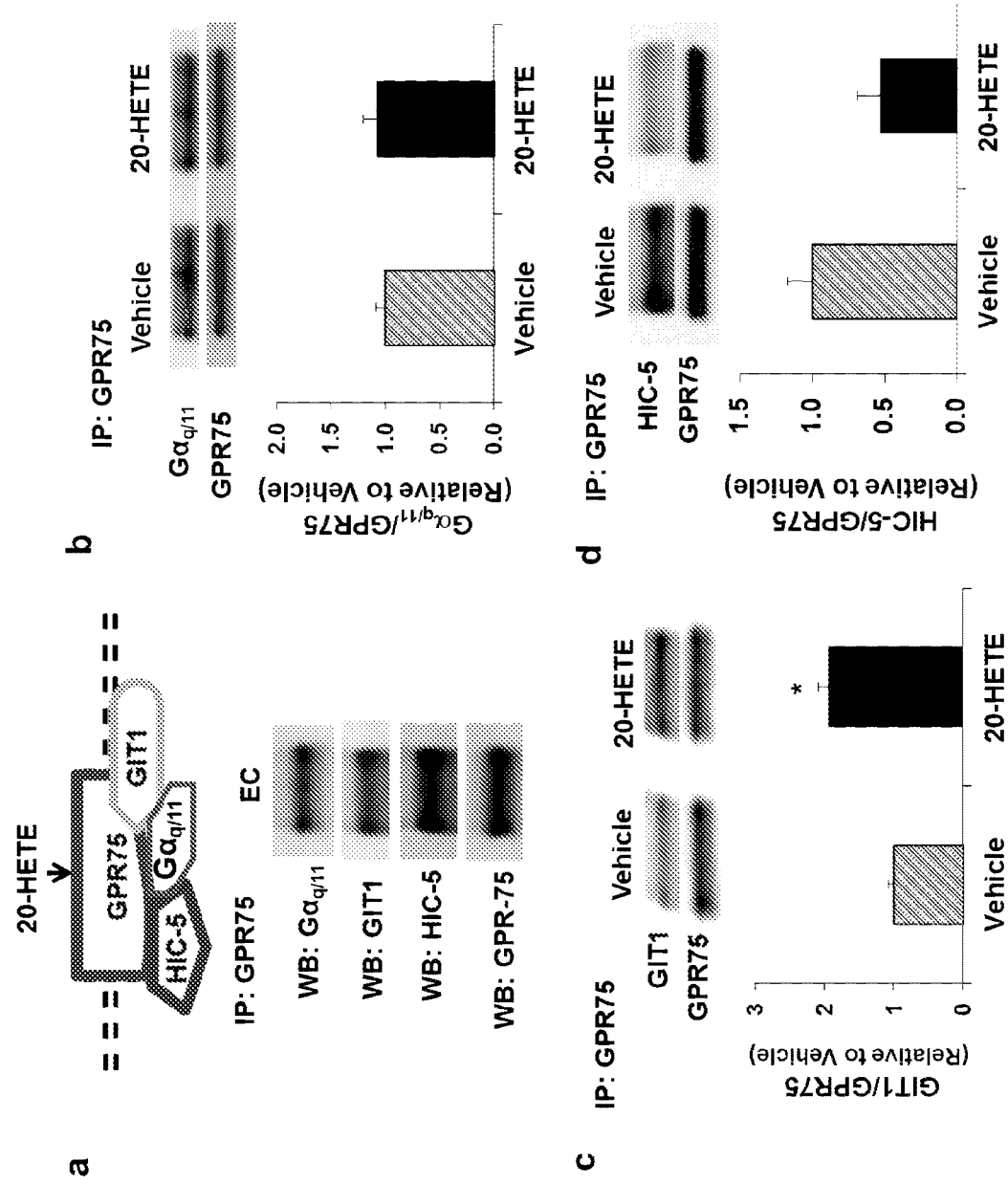
FIG. 11 demonstrates immunoprecipitation assays showing that 20-METE alters the association of GPR75 with $G\alpha_{q/11}$, GIT1 and HIC-5 in human microvascular endothelial cells (HMVEC).

20-HETE Alters the Association of GPR75 with $G\alpha_{q/11}$, GIT1 and HIC-5 HMVEC Immunoprecipitation of GPR75 in EC further indicated its association with $G\alpha_{q/11}$, GIT1 and HIC-5 (FIG. 11a). Incubation of EC with 20-HETE at 10 nM for 5 min increased GPR75-GIT1 association by 2-fold and GPR75-HIC-5 dissociation by 60% (FIGS. 11c and d). No change in GPR75-$G_{\alpha q/11}$ association was detected in EC (FIG. 11b). The inability of 20-HETE to dissociate $G_{\alpha q/11}$ from GPR75 suggests a dominant G-protein-independent biased 20-HETE-signaling mechanism in EC.

Example 6

Figure 12:
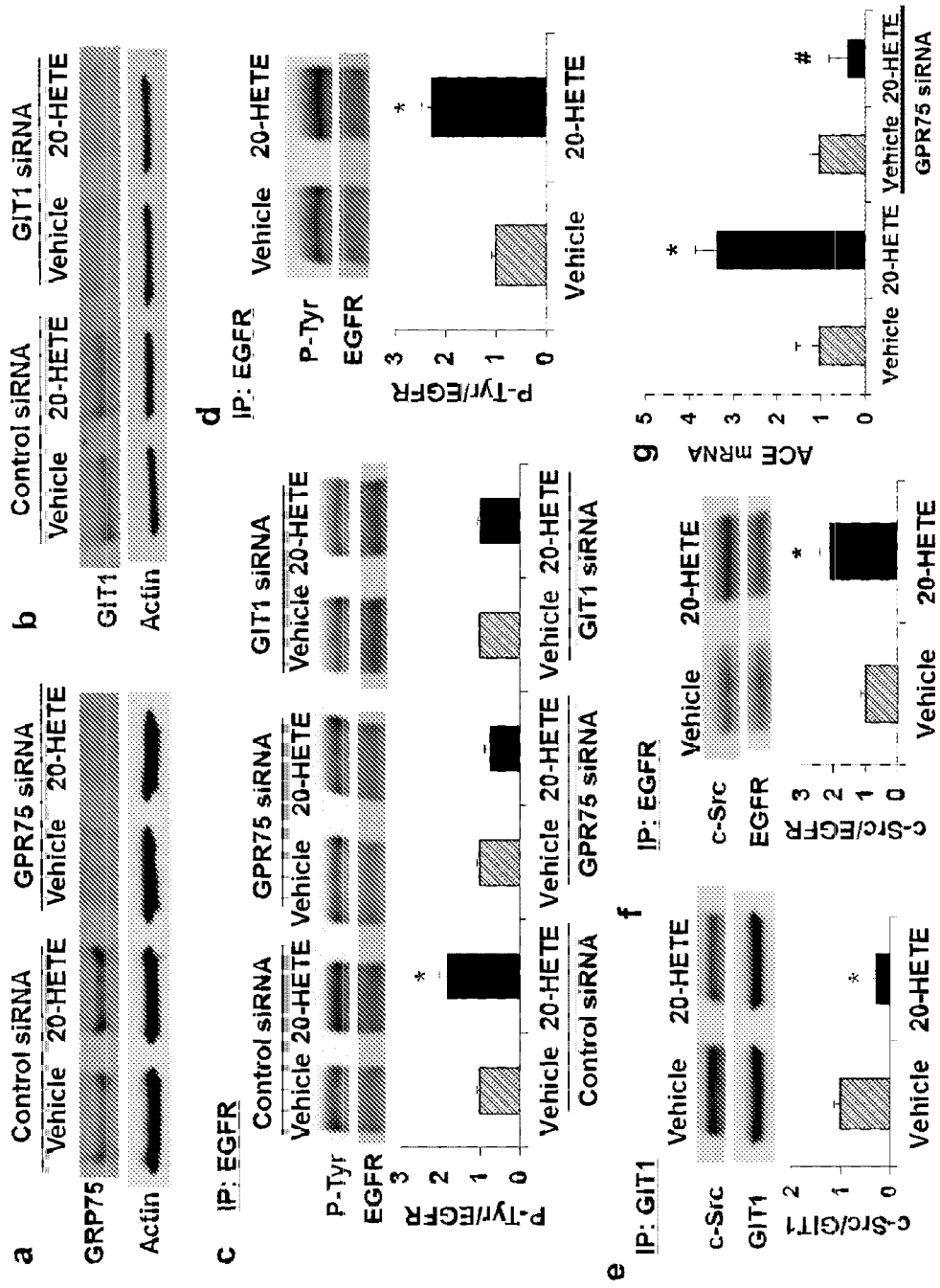
FIG. 12 demonstrates that GPR75 and GIT1 are required for 20-HETE-mediated epidermal growth factor receptor (EGFR) phosphorylation and downstream signaling.

GPR75 and GIT1 are Required for 20-HETE-Mediated EGFR Phosphorylation and Downstream Signaling The phosphorylation of EGFR was identified as the first step in 20-HETE-mediated activation of a MAPK-IKKβ-NFκB signaling pathway that leads to eNOS uncoupling, ACE induction and inflammatory cytokine production in EC. To investigate the role of GPR75 and GIT1 in the 20-HETE-mediated phosphorylation of EGFR, small interfering RNAs (siRNA) against GPR75 and GIT1 were used. Transfection of EC with siRNA against GPR75 and GIT1 showed a maximal knockdown of 85 and 70%, respectively (FIG. 12a-b). 20-HETE increased tyrosine phosphorylation of EGFR in EC transduced with control siRNA by 1.99±0.16-fold (FIG. 12c). 20-HETE-stimulated EGFR tyrosine phosphorylation was completely prevented in EC transduced with either GPR75 or GIT1 siRNA (FIG. 12c). In addition, within the same time frame in which 20-HETE stimulated a 2-3 fold increase in EGFR phosphorylation (FIG. 12d), it also decreased the association of c-Src with GIT1 (FIG. 12e) and increased association of c-Src with EGFR (FIG. 12f), suggesting that 20-HETE binding to GPR75 activates a c-SRC-mediated EGFR phosphorylation via GIT1.

Example 7

20-HETE-Mediated Induction of ACE mRNA Requires GPR75

Figure 13:
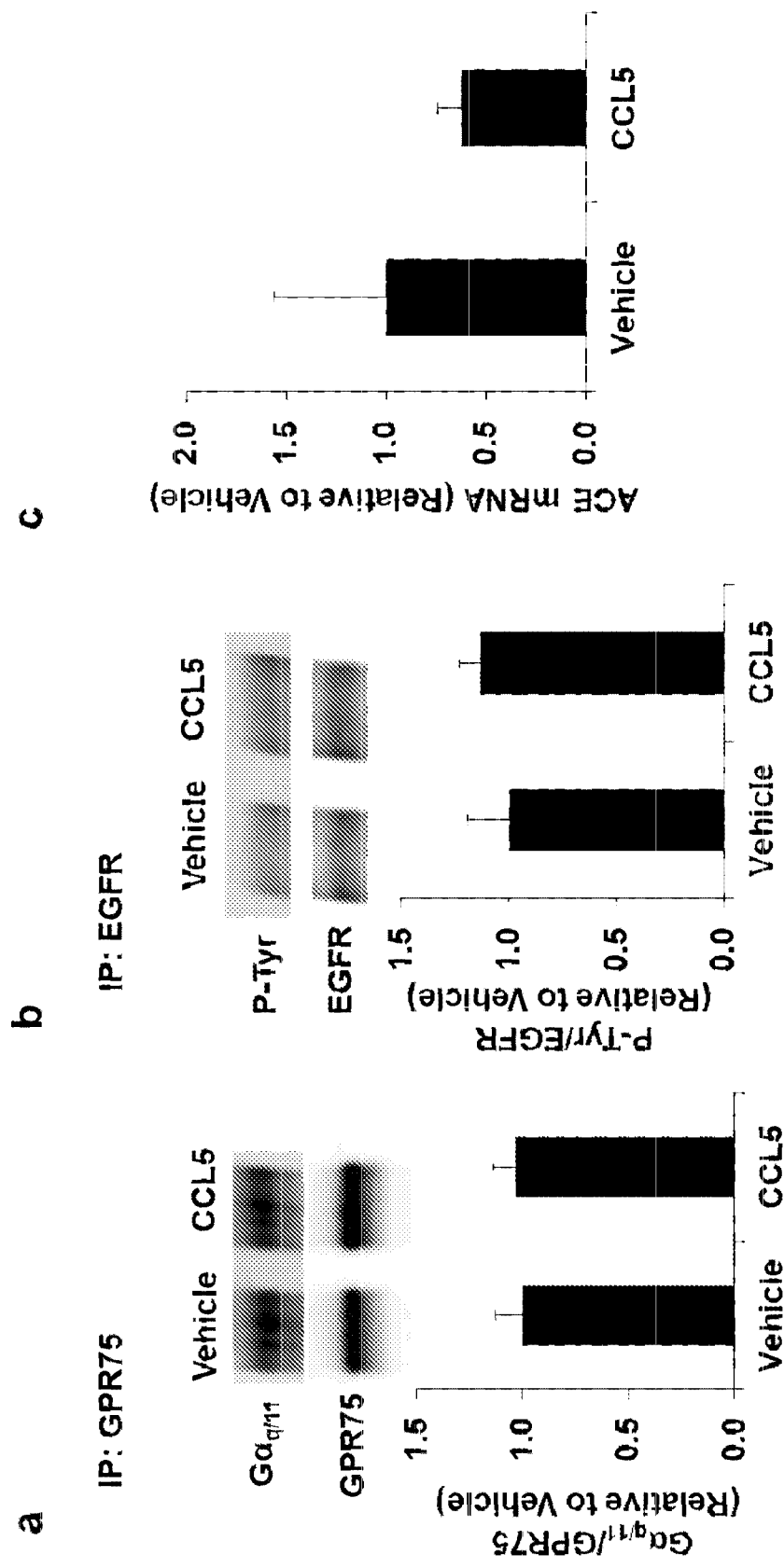
FIG. 13 demonstrates that CCL5, a proposed GPR75 ligand, did not induce ACE transcription nor did it increase EGFR tyrosine phosphorylation or $G\alpha_{q/11}$-GPR75 association in endothelial cells (EC).

One of the most prominent effects of 20-HETE in the vascular endothelium is induction of ACE transcription. The present disclosure shows that suppression of GPR75 in hEC by GPR75-specific siRNAs negated the 20-HETE-induced increase in ACE mRNA (FIG. 12g) indicating that GPR75-20-HETE pairing is a necessary step for 20-HETE-mediated induction of ACE. Importantly, CCL5, a proposed GPR75 ligand, did not induce ACE transcription nor did it increase EGFR tyrosine phosphorylation or $G\alpha_{q/11}$-GPR75 association in EC (FIG. 13).

Example 8

Figure 14:
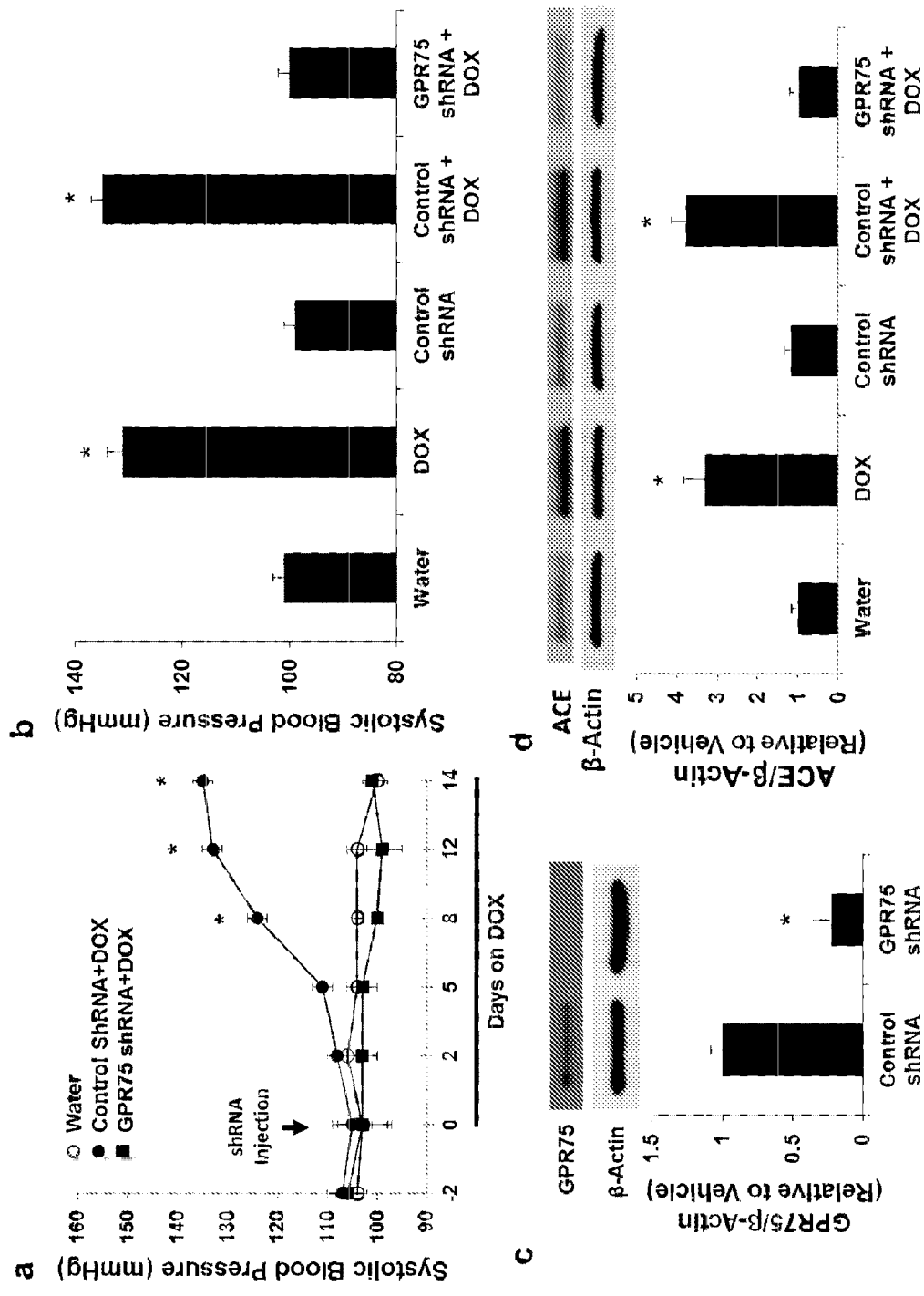
FIG. 14 demonstrates that GPR75 knockdown using GPR75-targeted shRNA prevents 20-HETE-dependent hypertension, vascular dysfunction and remodeling.
Figure 15:
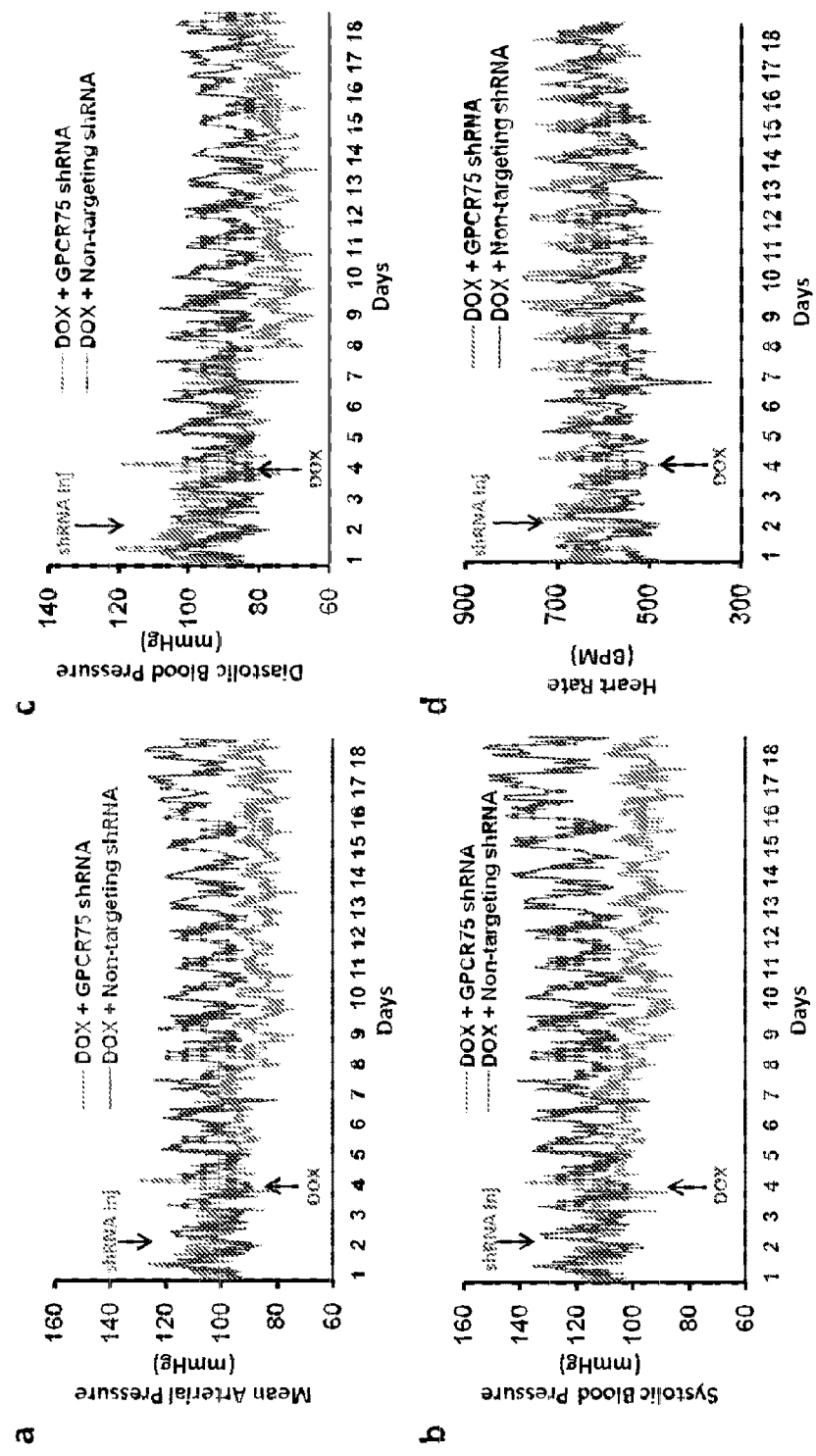
FIG. 15 demonstrates mean arterial pressure, diastolic blood pressure, systolic blood pressure, and heart rate in mice receiving GPR75-targeted shRNA lentiviral particles.
Figure 16:
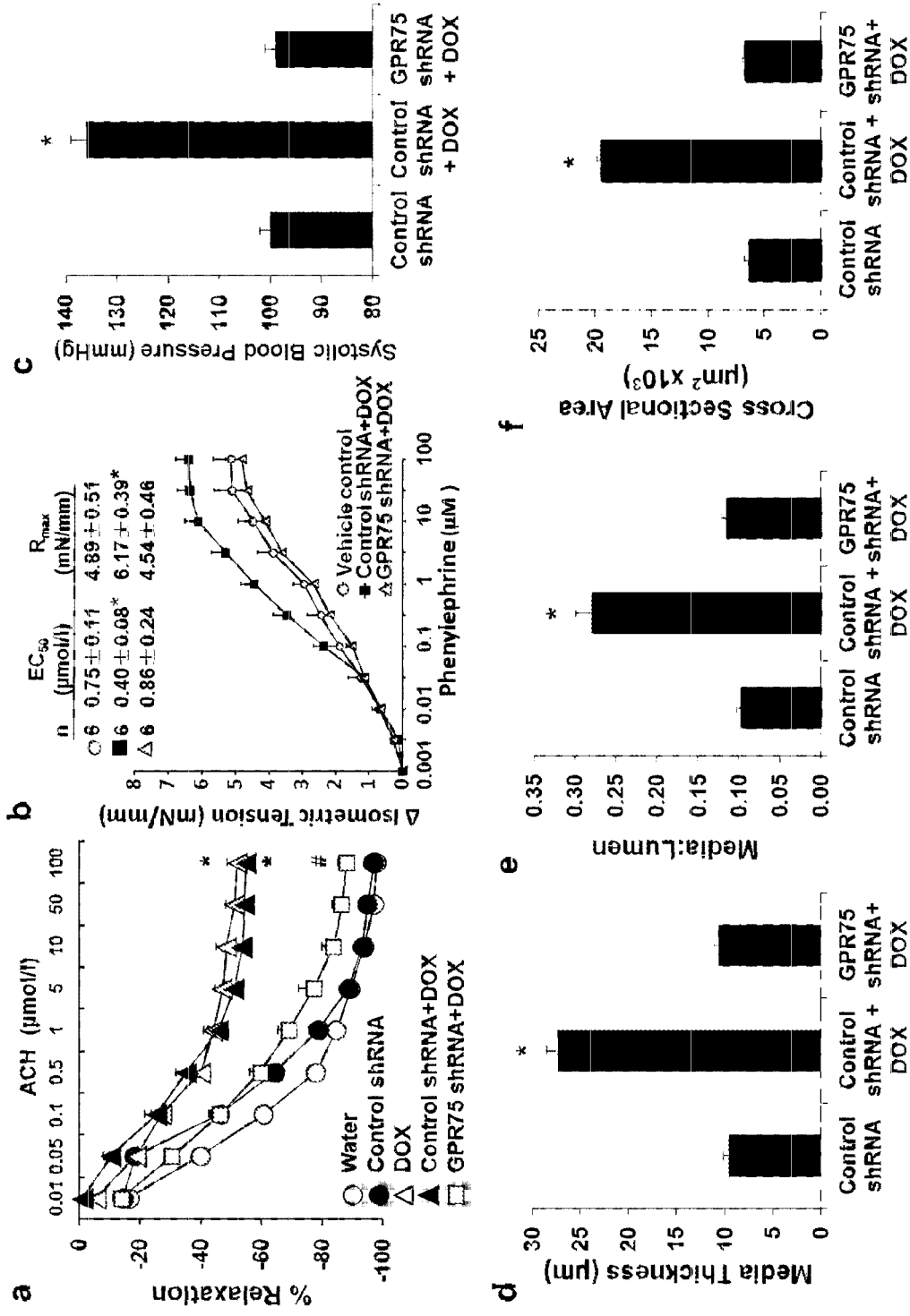
FIG. 16 demonstrates that knockdown of GPR75 interferes with the ability of DOX to impair relaxations to acetylcholine and increase contractions to phenylephrine (PE).

GPR75 Knockdown Prevent 20-HETE-Dependent Hypertension, Vascular Dysfunction and Remodeling Conditional Cyp4a12tg mice display vascular dysfunction and hypertension, both of which are prevented and reversed by either inhibiting the biosynthesis or blocking the actions of 20-HETE. This model was used to assess whether GPR75 is necessary for the pro-hypertensive actions of 20-HETE. Mice were given a bolus injection of either control or GPR75-targeted shRNA lentiviral particles into the retroorbital sinus followed by administration of DOX in the drinking water to induce Cyp4a12-20-HETE synthase. Administration of DOX to Cyp4a12tg mice that received a bolus of control shRNA lentiviral particles or its vehicle resulted in a rapid and marked increase in systolic blood pressure (135±2 and 131±3 mmHg, respectively) (FIG. 14a-b). In contrast, DOX administration to Cyp4a12tg mice that received a bolus of GPR75-targeted shRNA failed to increase blood pressure (FIG. 14a-b; FIG. 15). Western blot analysis of renal preglomerular microvessels from mice receiving GPR75-targeted shRNA lentiviral particles confirmed an 80% knockdown of GPR75 levels (FIG. 16). Similar reduction in GPR75 expression was seen in other tissues. Elevated vascular ACE has been characterized as a hallmark of the DOX-induced 20-HETE-dependent hypertension in Cyp4a12tg mice. In line with previous studies, vascular ACE expression was significantly elevated in DOX− as well as in DOX+non-targeted/control shRNA-treated Cyp4a12tg mice (3.29±0.52- and 3.78±0.35-fold increase, respectively). In contrast, vascular ACE expression was not induced in DOX-treated Cyp4a12tg mice that received GPR75-targeted shRNA lentiviral particles (FIG. 14d), further substantiating the notion that the GPR75-20-HETE pairing is vital to 20-HETE-mediated induction of ACE.

20-HETE-dependent endothelial dysfunction and enhanced sensitivity to constrictor stimuli are characteristics of the hypertensive phenotype of DOX-treated Cyp4a12tg mice. It is shown in the present disclosure that knockdown of GPR75 interferes with the ability of DOX to impair relaxations to acetylcholine and increase contractions to PE. The vascular relaxation in response to acetylcholine was markedly reduced in arteries from DOX-treated (55%±3%) as compared to arteries from water-treated Cyp4a12tg mice (99±2%). Administration of GPR75-targeted, but not control, shRNA lentiviral particles prevented DOX-induced impairment in the relaxing response to acetylcholine (88%±3% relaxation) (FIG. 16a). Likewise, administration of GPR75-targeted shRNA prevented the DOX-induced increases in contractions to PE. Treatment with DOX increased sensitivity to PE as evidenced by a reduction in $EC_{50}$ and an increase in $R_{max}$ when compared to water-treated Cyp4a12tg mice (FIG. 16b). However, the $EC_{50}$ to PE in arteries from DOX-treated mice that received GPR75-targeted shRNA was unchanged and was not different from the $EC_{50}$ in arteries from control mice (FIG. 16b).

Remodeling of the renal microvasculature is a striking pathology associated with chronic hypertension. Prolonged exposure of the vasculature to high levels of 20-HETE as in the Cyp4a12tg mice receiving DOX for more than 30 days leads to remodeling of microvessels in a 20-HETE-dependent manner. Importantly, Cyp4a12tg mice receiving control shRNA+DOX for 35 days display hypertension along with increases in media thickness, media to lumen ratio and cross sectional area (FIG. 16c-f). In contrast, microvascular remodeling did not occur in arteries from DOX-treated Cyp4a12tg mice that received GPR75-targeted shRNA (FIG. 16d-e). Taken together, these data demonstrate that activation of GPR75 is a necessary step in 20-HETE-mediated hypertension, endothelial dysfunction, vascular smooth muscle contractions, and microvascular remodeling.

Figure 17:
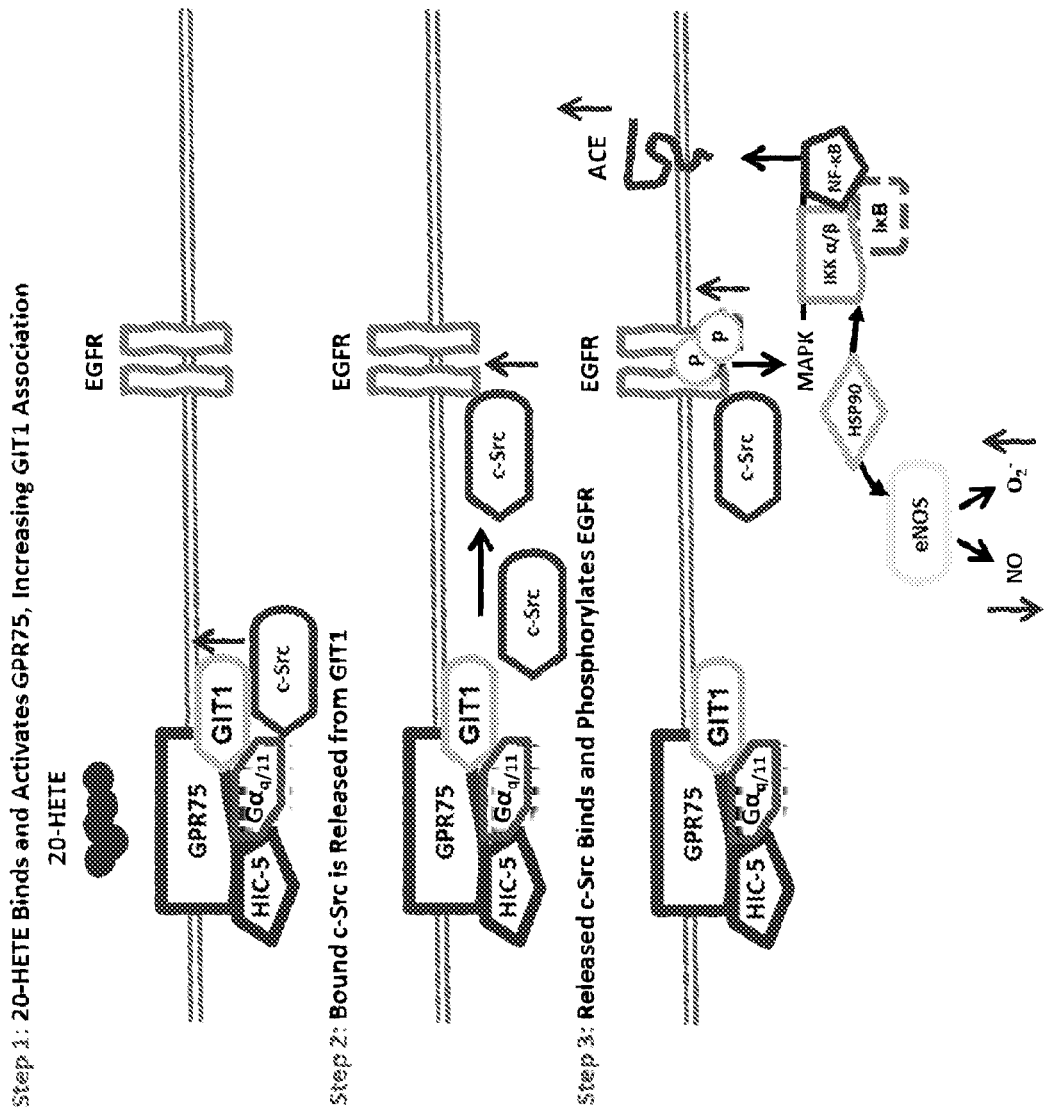
FIG. 17 demonstrates a proposed model for 20-HETE-GPR75-mediated signaling in endothelial cells.

FIG. 17 shows a proposed model for 20-HETE-GPR75-mediated signaling in endothelial cells. 20-HETE-GPR75 binding stimulates recruitment of β-arrestin and increased association with GIT1 that facilitates c-Src-mediated EGFR transactivation. The 20-HETE-GPR75-mediated activation of EGFR results in the stimulation of downstream cascades that regulate vascular ACE expression and decreases in NO bioavailability. Increases in vascular ACE result in increases in blood pressure that are dependent on the activation of GPR75 by 20-HETE.

Example 9

Treatment of Diabetic Nephropathy Using 20-HETE Analogs

Figure 18:
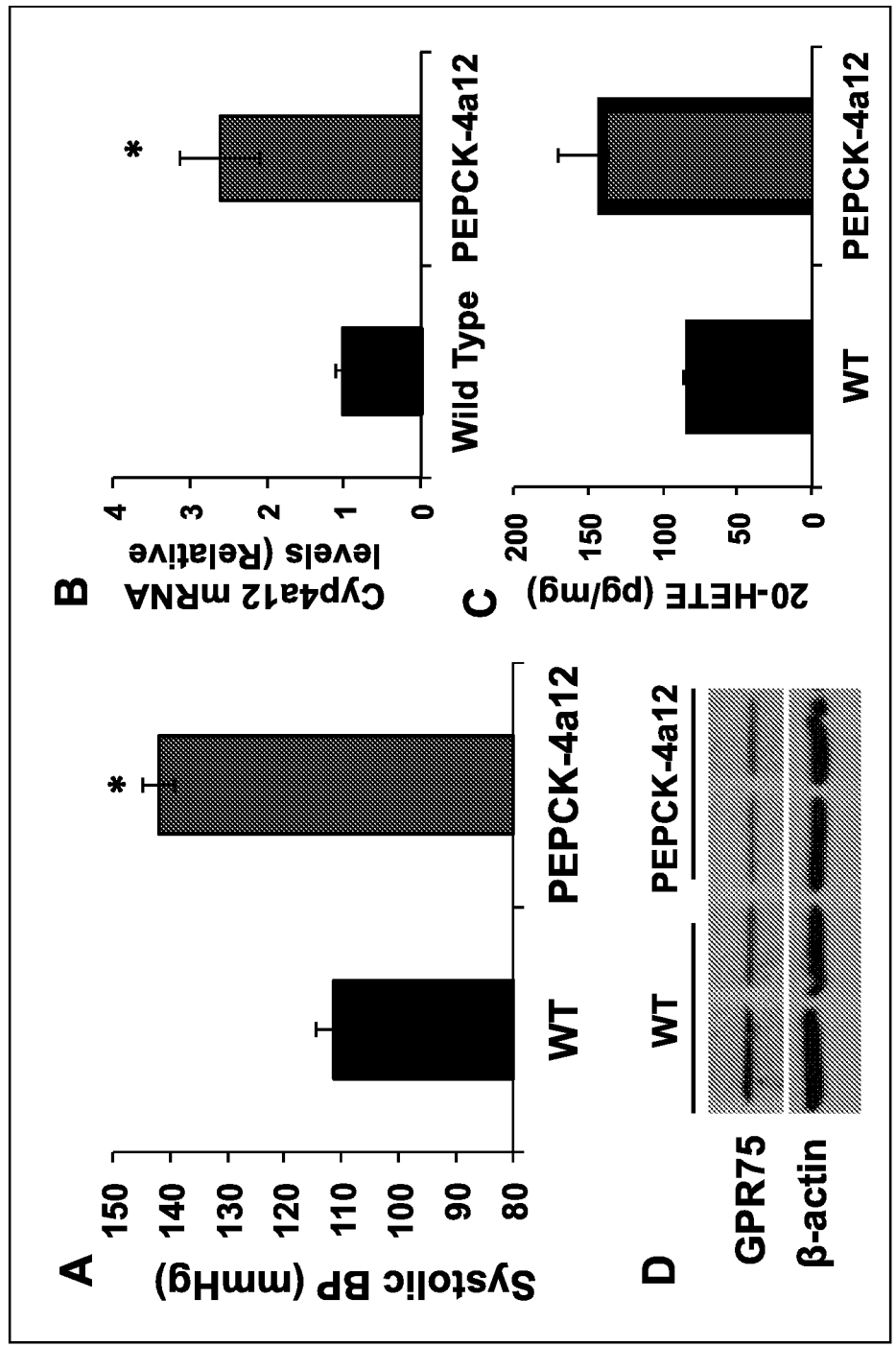
Figure 19:
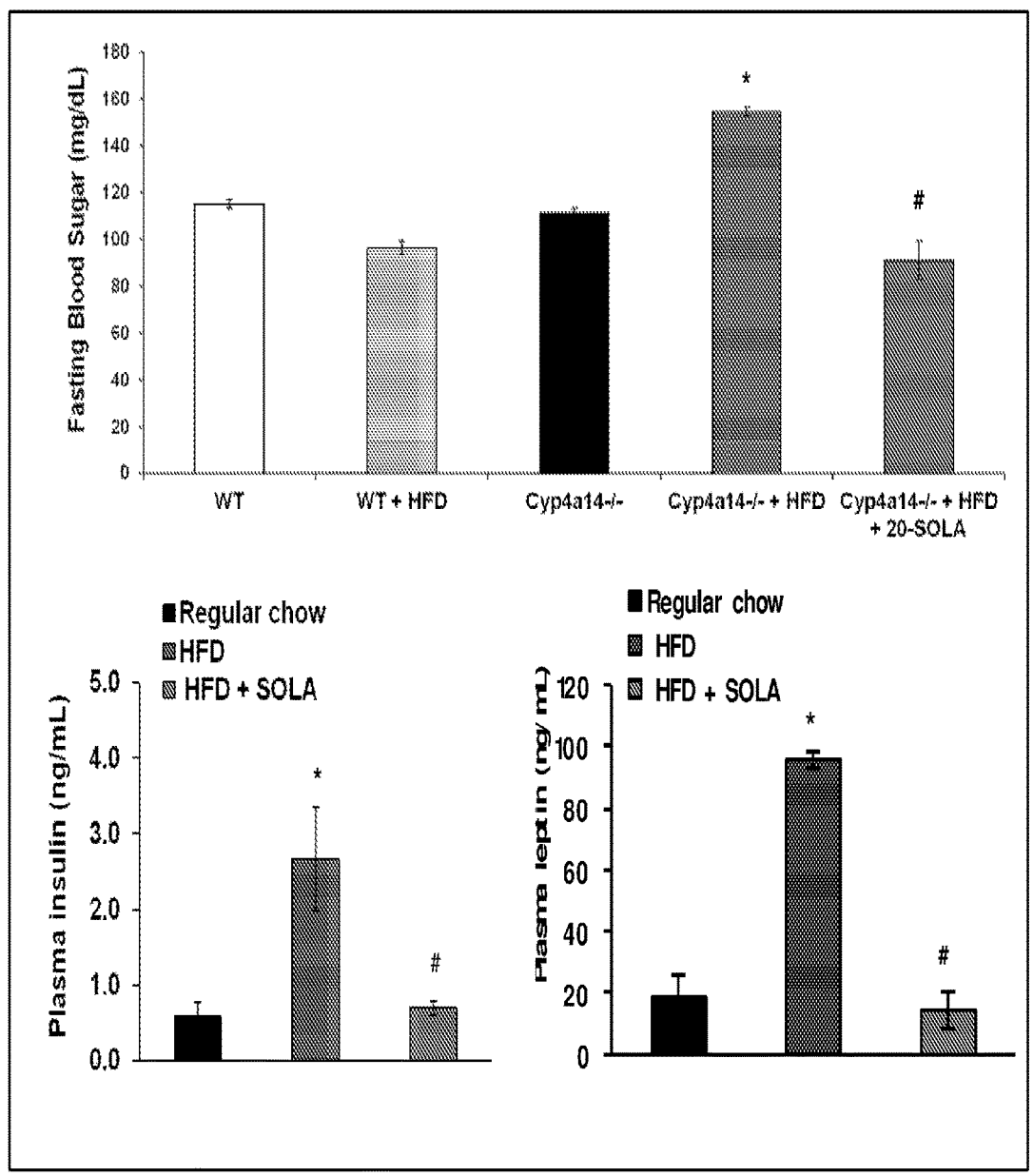
FIG. 19 shows that administration of a 20-HETE antagonist to obese mice ameliorate hyperglycemia and hyperinsulinemia.

Diabetic nephropathy (DN), a major complication of diabetes, is characterized by hypertrophy, extracellular matrix accumulation, fibrosis and proteinuria leading to loss of renal function. Hypertrophy is a major factor inducing proximal tubular epithelial cells injury. The inventors have shown that 20-HETE cause vascular hypertrophy and have documented high levels of 20-HETE in the proximal tubules as well as expression of its receptor GPR75. Moreover, increased production of 20-HETE in the proximal tubules leads to hypertension, a major risk factor for chronic kidney disease (FIG. 18). Several studies have also documented a role for 20-HETE in the development of kidney injury and nephropathy in animal models. Several clinical studies have shown elevated levels of 20-HETE in patient with chronic and polycystic kidney diseases that manifest characteristics similar to that seen in the diabetic kidney. The use of the 20-HETE antagonists of the present invention to block 20-HETE actions or 20-HETE-GPR75 pairing is useful in the treatment of nephropathy as the result of diabetes or other kidney injury. Administration of a 20-HETE antagonist to obese mice ameliorates hyperglycemia and hyperinsulinemia (FIG. 19), demonstrating that such treatment is useful in preventing or treating diabetic nephropathy.

Example 10

Treatment of Diabetic Retinopathy Using 20-HETE Analogs

Diabetic retinopathy is classified as a microvascular, disease, and is characterized by microaneurysms, hemorrhages, pericyte loss, increased microvascular permeability, exudates, capillary basement membrane thickening, capillary occlusion, shunts, venous beading, edema, and neovascularization. 20-HETE is a lipid mediator of the microcirculation including the cerebral microcirculation. A recent study showed that inhibition of 20-HETE synthesis attenuated retinal hemodynamic changes induced by diabetes. The inventors have previously reported that 20-HETE is angiogenic and as such can contribute to neovascularization of the retina. In addition, GPR75, the 20-HETE receptor, is highly expressed in retinal microvessels. The 20-HETE antagonists of the present invention are useful in treating diabetic retinopathy based on blockage of 20-HETE-mediated endothelial activation (inflammation, proliferation, angiogenesis) as well as thrombosis.

Example 11

Identification of 20-HETE Analogs by Screening Compounds for GPR75 Binding

Identification of 20-HETE analogs is based on the ability of 20-HETE to increase the association of GIT1 with GPR75 in endothelial cells. An antagonist prevents 20-HETE-mediated increase in GPR75-GIT1 association. The protocol is consists of GPR75 immunoprecipitation followed by immunoblotting with GIT1 antibodies. The nucleotide sequence of GPR75 is provided as SEQ ID NO: 1, and the amino acid sequence of GPR75 is provided as SEQ ID NO: 2.

Immunoprecipitation. Human microvessel endothelial cells (HMVECs) were cultured on 6-well plates to 80-90% confluence and starved in serum-free media for 12 h. Cells were treated with 20-HETE (10 nmol/L) or its vehicle (PBS) for 5 min. In some experiment, cells were incubated with CCL5. Cells were lysed with 1×RIPA (Radio-Immunoprecipitation Assay) buffer (Sigma, St Louis, Mo.) containing protease and phosphatase inhibitor cocktails (Roche Diagnostics, Indianapolis, Ind.). Protein concentrations were determined using the Bradford protein assay (Eppendorf BioPhotometer). Immunoprecipitation was conducted using the Dynabeads Protein G Immunoprecipitation Kit (Life Technologies, Grand Island, N.Y.). Dynabeads were incubated with primary antibodies against human EGFR antibody (AHR5062, Invitrogen, Camarillo, Calif.), GPR75 (sc-164538, Santa Cruz, Biotechnology, Dallas, Tex.), and GIT1 (sc-9657, Santa Cruz, Biotechnology, Dallas, Tex.), for one hour prior to washing and incubation with 5 μg of HMVEC or EA.hy926 cell lysate overnight. Samples were then washed and eluted per manufacturer's protocol and loaded onto a 4-20% Mini-PROTEAN TGX precast gel (Bio-Rad, Hercules, Calif.) and transferred using the Trans-Blot® Turbo™ transfer system to a PVDF membrane. Immunoblotting for respective associated proteins was conducted using phosphorylated tyrosine antibody (SC-7020, Santa Cruz, Biotechnology, Dallas, Tex.), EGFR antibody (AHR5062, Invitrogen, Camarillo, Calif.), GPR75 (sc-164538, Santa Cruz, Biotechnology, Dallas, Tex.), GIT1 (sc-9657, Santa Cruz, Biotechnology, Dallas, Tex.), G alpha q/11 (sc-392, Santa Cruz, Biotechnology, Dallas, Tex.), c-SRC (sc-19, Santa Cruz, Biotechnology, Dallas, Tex.).

Membrane fluorescence-based immunodetection was conducted using the appropriate LI-COR secondary IRDye antibody and LI-COR Odyssey Infrared Imaging System (LI-COR, Lincoln, Nebr.). Respective band density was quantified using the Odyssey Application Software Version 3.0.21.

Western Blot Analysis. Samples were lysed with 1×RIPA (Radio-Immunoprecipitation Assay) buffer (Sigma, St. Louis, Mo.) containing protease and phosphatase inhibitor cocktails (Roche Diagnostics, Indianapolis, Ind.). Protein concentrations were determined using the Bradford protein assay (Eppendorf BioPhotometer): Samples (20 μg) were run on a 4-20% Mini-PROTEAN TGX precast gel (Bio-Rad, Hercules, Calif.) and transferred using the Trans-Blot® Turbo™ transfer system to a PVDF membrane. Primary antibodies included: ACE (sc-12184, Santa Cruz, Biotechnology, Dallas, Tex.), 1-Actin monoclonal IgG (Sigma, St Louis, Mo.). Membrane fluorescence-based immunodetection was conducted using the appropriate LI-COR secondary IRDye antibody and LI-COR Odyssey Infrared Imaging System (LI-COR, Lincoln, Nebr.). Respective band density was quantified using the Odyssey Application Software Version 3.0.21.

The invention claimed is:

1. A compound of formula I or II:

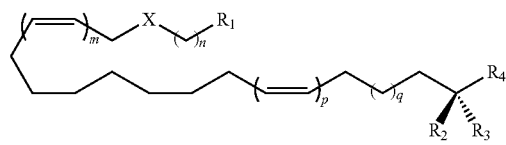

(I)

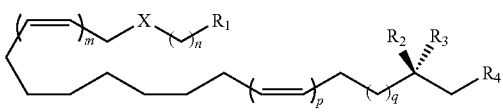

(II)

wherein:

a) R is OH, $C_1$-$C_3$, F, or H and $R_3$ is OH, $C_1$-$C_3$, F, or H; $R_2$ is OH and $R_3$ is $C_1$-$C_3$, F, or H; or $R_3$ is OH and $R_2$ is $C_1$-$C_3$, F, or H;

b) $R_4$ is $C_1$-$C_3$, H, F, or —$CH_2N_3$ (azide);

c) either n is 1 and m is 1 or n is 3 and m is 0;
either q is 1 and p is 1 or q is 3 and p is 0;
either m is 0 and p is 1, m is 1 and p is 0, or m is 1 and p is 1; and
either X is O or C and n is 1, or X is C and n is 3; and d) $R_1$ is $CO_2R_5$, wherein $R_5$ is H or a pharmaceutically acceptable salt; $R_1$ is $NR_8R_9$; or $R_1$ is $C(O)R_6$, wherein $R_6$ is $OR_7$; $R_6$ is $NR_8R_9$; $R_6$ is a D-/L-/D,L-α-amino acid (MW<250); $R_6$ is —$NHS(O)_2R_{10}$; $R_6$ is polyethylene glycol (MW<350); $R_6$ is glycerol; $R_6$ is glyceride mono- or diester (MW<800); or $R_6$ is a carboxylate isostere or mimetic selected from the group consisting of:

—$P(O)(OH)_2$ or salts thereof
—$S(O)_2OH$ or salts thereof

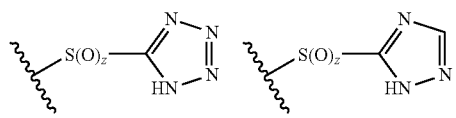

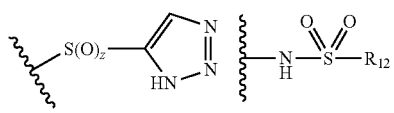

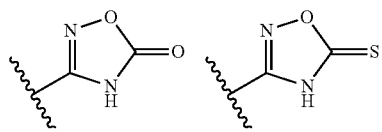

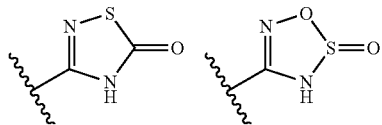

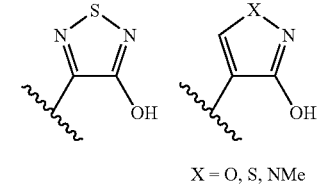

X = O, S, NMe

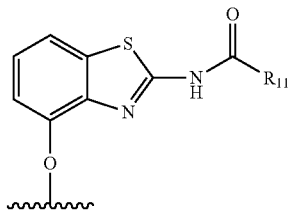

$R_{11} = C_1$—$C_4$

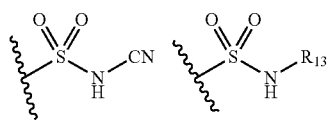

$R_{13}$ = lower alkyl

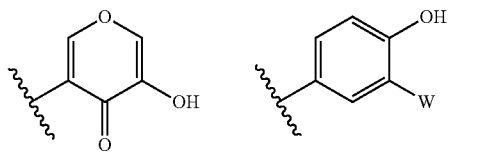

W = Cl, $CF_3$, $CO_2R_{14}$ ($R_{14}$ = lower alkyl), $NHC(O)R_{15}$ ($R_{15}$ = lower alkyl, $CF_3$, Ph), H

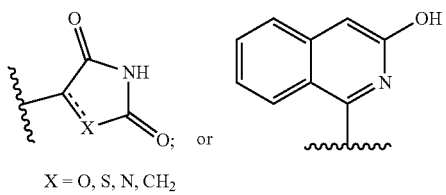

X = O, S, N, $CH_2$ wherein ii) a lower alkyl is a $C_1$-$C_6$ alkyl or cycloalkyl; ii) $R_7$ is a $C_1$-$C_6$ alkyl or cycloalkyl, or a benzyl; iii) $R_8$ is H, a $C_1$-$C_6$ alkyl or cycloalkyl, or a benzyl; $R_9$ is H, a $C_1$-$C_6$ alkyl or cycloalkyl, or a benzyl; or $R_8$ and $R_9$ together constitute a 3-7 membered ring with the nitrogen;

and iv) $R_{10}$ is a phenyl, a $C_1$-$C_5$ alkyl or cycloalkyl, or $CF_3$.

2. The compound of claim 1, having the formula of Formula I:

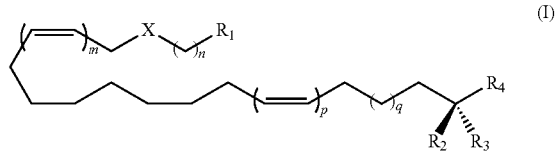

(I)

3. The compound of claim 1, having the formula of Formula II:

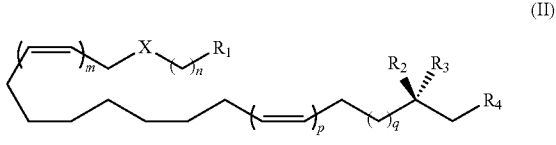

(II)

4. The compound of claim 2, wherein:
a) $R_1$ =$C(O)R_6$;
b) $R_6$=a glycine sodium salt;
b m=1;
c) n=1;
d) p=1;
e) q=1;
f) $R_2$ =OH and $R_3$ =H; or $R_2$=H and $R_3$ =OH; and
g) $R_4$=$CH_3$.

5. The compound of claim 1, having the formula:

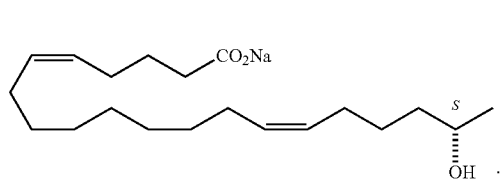
(1-1)

6. The compound of claim 1, having the formula:

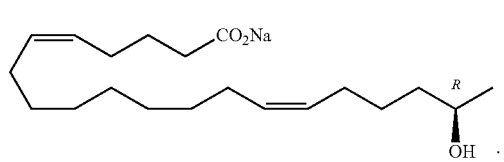
(1-2)

7. The compound of claim 1, having the formula:

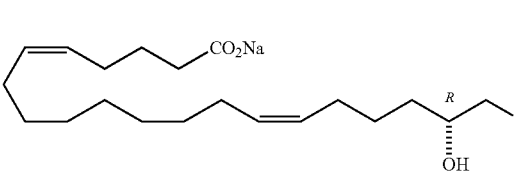
(1-3)

8. The compound of claim 1, having the formula:

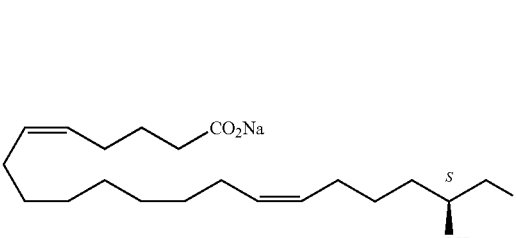
(1-4)

9. The compound of claim 1, having the formula:

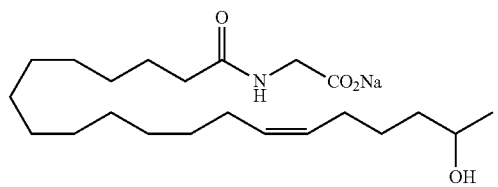
(1-7a)

10. The compound of claim 1, having the formula:

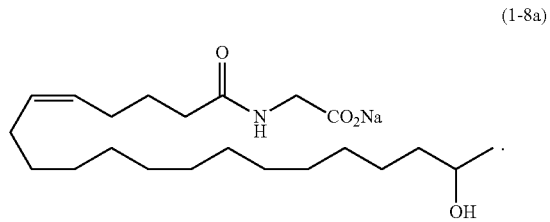
(1-8a)

11. The compound of claim 1, having the formula:

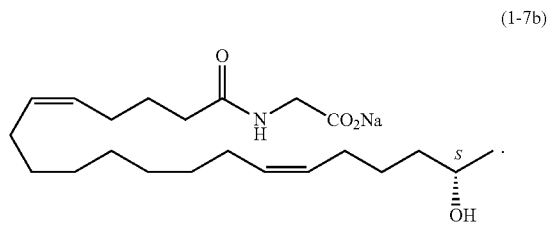
(1-7b)

12. The compound of claim 1, having the formula:

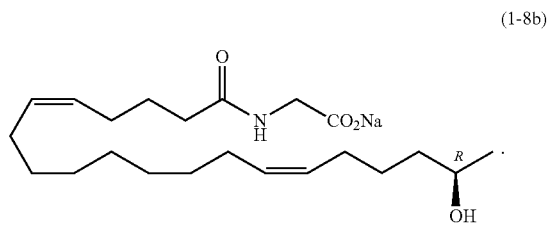
(1-8b)

13. The compound of claim 1, having the formula:

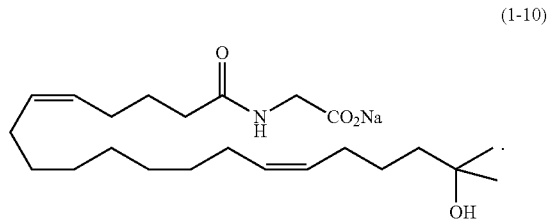
(1-10)

14. The compound of claim 1, having the formula:

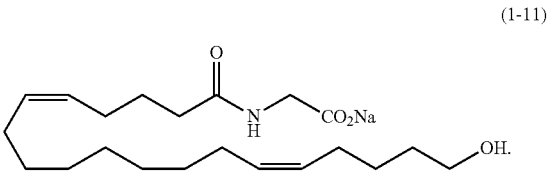
(1-11)

15. The compound of claim 1, having the formula:

(1-12)

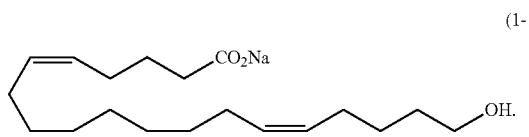

16. The compound of claim 1, having the formula:

(1-13)

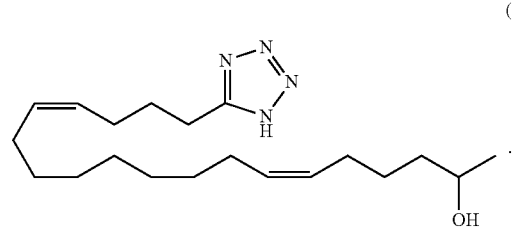

17. The compound of claim 1, having the formula:

(1-14)

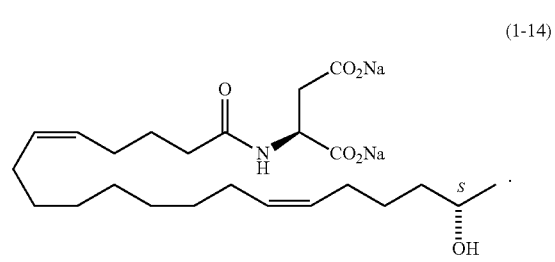

18. The compound of claim 1, having the formula:

(1-15)

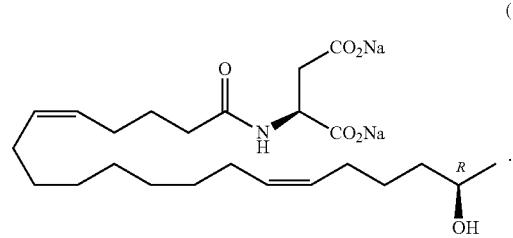

19. The compound of claim 1, having the formula:

(1-16)

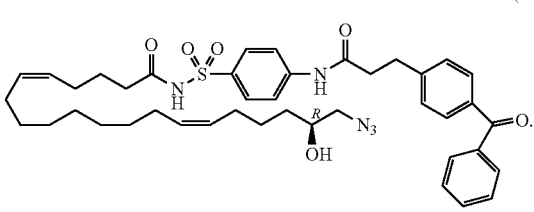

Photo-crosslinker

20. The compound of claim 1, having the formula:

(1-17)

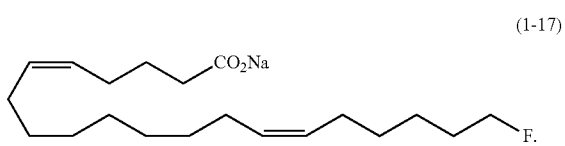

21. The compound of claim 1, having the formula:

(2-2)

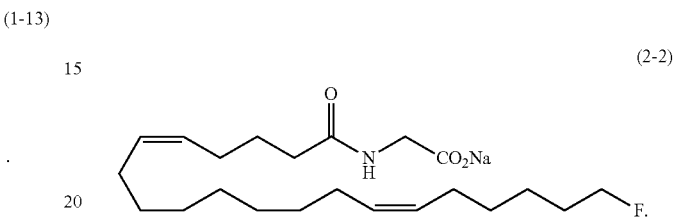

22. The compound of claim 1, having the formula:

(2-5)

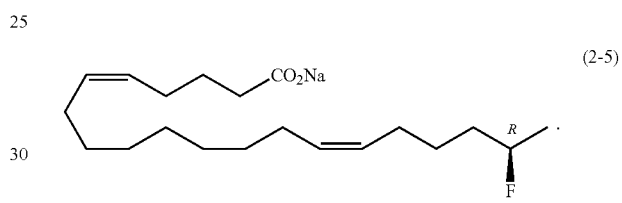

23. The compound of claim 1, having the formula:

(2-6)

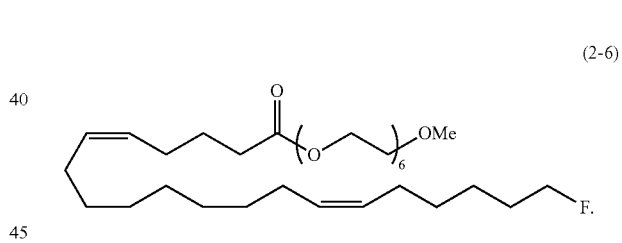

24. A pharmaceutical composition comprising a compound of claim 1 and a pharmaceutically acceptable carrier, buffer or diluent.

25. A method of treating cardiovascular disease, renal disease, diabetic retinopathy, stroke, obesity, metabolic syndrome, cancer, or tumor growth in a subject comprising administering to said subject a therapeutically sufficient amount of a compound as shown in claim 1.

26. The method of claim 25, wherein administering comprises local, regional, systemic, or continual administration.

27. The method of claim 25, further comprising providing to said subject a second therapy.

28. The method of claim 25, wherein said subject is a human.

* * * * *

UNITED STATES PATENT AND TRADEMARK OFFICE
CERTIFICATE OF CORRECTION

PATENT NO. : 11,690,825 B2
APPLICATION NO. : 16/083404
DATED : July 4, 2023
INVENTOR(S) : John R. Falck, Michal L. Schwartzman and Victor Garcia It is certified that error appears in the above-identified patent and that said Letters Patent is hereby corrected as shown below:

In the Claims

Column 110, Claim 1, Line 64 delete "R is OH, C1-C3, F, or H and R3 is OH, C1-C3, F, or H;" and insert --R2 is OH, C1-C3, F, or H and R3 is OH, C1-C3, F, or H;--

Signed and Sealed this
Eleventh Day of June, 2024

Katherine Kelly Vidal
*Director of the United States Patent and Trademark Office*

SEQUENCE LISTING

<160> NUMBER OF SEQ ID NOS: 2

<210> SEQ ID NO 1
<211> LENGTH: 7121
<212> TYPE: DNA
<213> ORGANISM: Homo sapiens

<400> SEQUENCE: 1

```
aggcccgggt gtccggcgga gggggcggtg ccctcggcgt ctccgtgact gcgcctctgc      60
gcccgcgtct tgccgcggct cccgggatgc gcggaggcgg tggcgatggc gatgatgcct     120
ctagtcctgc atcatccaga gcggcaggcg gagctggggt ccggactgcg agatggagga     180
ggggcggcgc tgcggccacc cggcaggtga gaggccgcgg gccctggag gaggacaacc      240 ccacgatgcc ggagacggct cccggaggct ggcgggatag cgaggagcgc ggctgcgctg     300
ggccaggccc ggctccgcgt acctgtcttc ctggtgcggc ctgcagggta gccttctcgc     360
ccgtccctgc cggttcccag gctctgctcg gccgtggaac ccccccacc cacccaccca     420 ccgcccctac cctggctgag ccctcctaac ccaccacccc tctgcggcat tcttttgcaa     480
gcttacctgg cccggcctag gccctcctta ccgtcacctc acccttctcc gggaagcccc     540
tacccaccgc cagcccctca cggggggtc gaccttccct gcccgcagtt tcccactctg      600
tcctcaggct gggggctccc tggcctcttc atccctccca tcaaatgact caggtcttcc     660
catcccatta gctgctccgg gttcaatgta gttctactgg atagaaagag caagggcttt     720
gaaatcagat aatgaccttg gggaagttat ctaacctccc tgaggttttc ctgatcgata     780
gaaatacaat gggaatcaca ataatacaga accttgctct ctgtgaggat taggctttga     840
aaatgctaac ctaagacatt ttggggcgcg cggggaatgg ggttggaaga attcaggtcg     900
tgagttgatt tatgaaagcc cctatagcat gttttaatgt tcactaaaaa tttaaaacag     960
cacactagat atatcagagg ctgttcacat atcttaatga aaaatcattg ccactcaaat    1020
tatacaataa attttcatcc atattctttg cttgctagtt acttcaggat gtctcatttg    1080
taagaatatg catgtgaatt cattcttact gcagctaata tgcatgctta agactggtgt    1140
tccagcttaa aatctttctg attttgtgac tttaatcaca tcttctataa cctattctcc    1200
gtcccagaga tgaagagtag cttgtatgtt tgcattgcaa ataacatggg taatctttat    1260
tgaatattta tgagtagcaa agcagtatta atttattccc cttccaaaac cacttttatt    1320
ttctgccgtc atcatgtcat tccaaattat ggtcacagcc tccttttct taaagtctca    1380 ggagttacta ctaagacctg agtttacttt ccctccattt tcttgatttc tgttatacta    1440 aagttttttct gcaaaccttt tcgtcttttc tgtcctctgc ttttttctccc ttttctcttc    1500 ccagcccatg attccttttt ttctaattat ctcaatagga gtgattatg attactttat     1560 atgtgaacta cagttagata catagaagaa tgtgtgtgtg tgtgtgtgtg tgtgtgtgtg    1620
```

```
tgtgtgtgtg tctatctgta tctacataga tgtagatata gctatatagg tgtatcagaa    1680
tttcggattc cagaaagttt cagtggggaa gggattgcaa tacctattca taggattatt    1740
gtgagaatga aataaagctt gataatttat gtaaagcctc tagaataggt gcctggtgtg    1800
taataaccac ttaatacttc tgacctgggg atgcctccca aaaaggtttt tttgttgttc    1860
gggttagcat ggtggtgaag agtgtggaag agcaactgct tagattcaaa tccatgttcc    1920
accactttag ataacctctc tttgacttgg tttcctcatc tgcaaaatgg agatgttata    1980
tcaagtattt cagggttgtt atgaggactc aataagctaa tagtgtggaa cattgagaaa    2040
agtacctggc acatcataag cacttgataa aattaatata ctaataatga tgctgataat    2100
tatactgcca ttgttatttc ctgacctgga attcttattt tttttaattt actgaaggct    2160
gggtacagtg gctcacacct gtaatctcag cactttggga ggccaaagca ggcagattgc    2220
ttgagcccag aagttggaga ccagtgaggg caacatagtg agactccatc tctattaaaa    2280
atatatatat tgaaaaattt aaaatttgtt gaaaaaatgt aactgtacaa aacgtgaaag    2340
ttgcctctcc tctaccccaa atcacctttt ttcctcctgc ctcctattct tgactaatgt    2400
tagtgcttca tcatctcatt tttctcctaa tcccttttc caaatatctc ttagcctgag    2460
gtcttcataa cttccatcat cccgcttcat tattacctag ttacttttca tttgtcttag    2520
catcctaatt ccagactcct cattcttcta atttccccag gccaaattcc tgcatccctc    2580
ttcacccctc ttcatctctc tacctccaaa gaggaaaccc ttggagataa gggggttaga    2640
gacaccagta tcacctccct gctcttcctg cctcctcaaa ttgttttctc ttctacttcc    2700
cttttcataa attagctgta atactcctgt tagcaacttt taaaaacagt aaaaaattgt    2760
cttcctcggc cgggcgcggt ggctcacgcc tgtaatccca gcactttggg aggccgaggc    2820
gggtggatca tgaggtcagg agatcgagac catcctggct aacaaggtga aaccccgtct    2880
ctactaaaaa tacaaaaaaa aaattagccg ggcacggtgg cgggcgcctg tagtcccagc    2940
tactcgggag gctgaggcag gagaatggcg tgaacccggg aagcggagct tgcagtgagc    3000
cgagattgcg ccactgcagt ccgcagtccc gcctgggcga cagagcgaga ctccgtctca    3060
aaaaaaaaaa aaaaaaaaaa aaaaaaattg tctttctcat tatataggta tcaaaagtgt    3120
tcagaaacaa atatacagcc tttaagtgga aatagagcta tctggtacta ttttttaaaaa    3180 attctaacca tcaagaaaca aaagttcagg attttcttct cttatggaac ttttatttga    3240
aaggaaagta tagaaaagtt ggtctcactt tccagtggac aaattcacca tatcgtcctg    3300
atctgtacca tatgaatgtt aagaatatag attaagttat ctttttcctt gattaaggac    3360
accagtcaat tatatggatt tcccaggact ggtatatgtc tgatagtcac tggcatggct    3420
gtatctgttg ttaaatgtgg agagacttct gtattgggta gtccatagct gctaattgga    3480
gccccaggta atccctgact gacctggttc attccgctgt accccttga tctggcaact    3540 aaagggttaa cagctggagg cttctgggat ccagcttgag ctggtggtta agtacactga    3600
acatcagccc tggacctctg cagtgccact tattgttcct aaaattctag attaaggcaa    3660
accctttttg gttgtcaaga acatagtgct gtctccaagg aacagcttag tcggtcccac    3720
cagaagcatc tgttgggagc aggttgggca ccaacccttg caggactttg ggatttggga    3780
caatgtagat ttgtgtgagt gcacattaag tctcattgca aaatagaaaa aaaaagtta    3840 ggaaaaagga gcaagaagtt attcttttaa agtagagact gccttactca tcgtagcacc    3900
tagcacctgg cgtaatgctg gcatatggta tgcacataat taatataaat tgagcgaacg    3960
```

```
aatgcaggaa tgggtgcatg cctcctgctt caccatcagg atattcttgt tgggataatg      4020
gtaactcaca tttatatagc agtttagact ttacaatgtg gtgctttgca ccttgtaaat      4080
ttctaatata attccaacat ccttggttac ttccagtttt ccgtctcaca tgtagtccta      4140
cacaaggttt ttttccaaag gagaatatgt agttaattgg ccaagaaatt gcaagctggg      4200
ggaaaaatta taaatactgg gaaataaagg attcttcata gggaacgaaa cagggtttgt      4260
taatgattta tgggaattat gtgaagggcc acattatgca tcaacaatac cctccagcct      4320
atatttcaag cacatgcagt ttttgccgc agtgcttctg ctgcaaagac ctaccccac       4380 ttctcttagc ctgtctgtcc ccactccata cccccgacct ttcatccagc tggcctgtgc      4440
ttgctaaagc tccctttatc ctttcccagc tccctttcca tgttggagta ggttcccccc      4500
ttccatgctc tcatagcacc ctgcaacctt attaggctgt aattattaca tagttagatt      4560
gatctccaac tagattgtca tctctttggt ggagagatta cgttcttgtg tatcttcagt      4620
gcctgacaca gaagtgtttc taaaagtaac atctgcacac ccctcaaaca gaatcacaag      4680
gggcgaggcc aagaaatctg ctctccaagt gataacttaa acttttttaac atgctcttca     4740 ggtgacactt aaacttgttt gaaaacctct gtgtcataaa actaaatatt agctggatga      4800
atgtatttgt atcttttctct gtgttggcct ttgtgaggag aaatgctgtc tatgcaccaa    4860
atcagagctg aaaaattcta gtgttttgtt aaaaaaaaa aagagagaga gagagctggg      4920
tttggtggtg catgcctgta gtcccagcta cttgggaagc taagccagga ggactgcttg     4980
agcacaggag ttcaagtcca gcctgggcaa catggtaaga ccccattgct aataaatgaa     5040 taaattttc tctcaaggtg agagatacta gtactaatac tactactaat aatgagatca     5100
ctgtatgaat tccttctgt ttctacatta atcccttct gtttctgggt gtgcattttt        5160
gtgtgtaggc ttatctgtct tgggcctctt ttgtcacata ttgctcatct gtgagctgag      5220
gccctgactc actgagtatt tttggggagc agaagaagga gacatttctc tccgaaaatg      5280
aactcaacag gccaccttca ggatgccccc aatgccacct cgctccatgt gcctcactca     5340
caggaaggaa acagcacctc tctccaggag ggtcttcagg atctcatcca cacagccacc     5400
ttggtgacct gtacttttct actggcggtc atcttctgcc tgggttccta tggcaacttc     5460
attgtcttct tgtccttctt cgatccagcc ttcaggaaat tcagaaccaa cttttgatttc    5520 atgatcctga acctgtcctt ctgtgacctc ttcatttgtg gagtgacagc ccccatgttc     5580
acctttgtgt tattcttcag ctcagccagt agtatcccgg atgctttctg cttcactttc     5640
catctcacca gttcaggctt catcatcatg tctctgaaga cagtggcagt gatcgccctg     5700
caccggctcc ggatggtgtt ggggaaacag cctaatcgca cggcctcctt tccctgcacc     5760
gtactcctca ccctgcttct ctgggccacc agtttcaccc ttgccacctt ggctaccttg     5820
aaaaccagca agtcccacct ctgtcttccc atgtccagtc tgattgctgg aaaagggaaa     5880
gccattttgt ctctctatgt ggtcgacttc accttctgtg ttgctgtggt ctctgtctct     5940
tacatcatga ttgctcagac cctgcggaag aacgctcaag tcagaaagtg ccccctgta     6000 atcacagtcg atgcttccag accacagcct ttcatgggg tccctgtgca gggaggtgga     6060
gatcccatcc agtgtgccat gccggctctg tataggaacc agaattacaa caaactgcag     6120
cacgttcaga cccgtggata taccaagagt cccaaccaac tggtcacccc tgcagcaagc     6180
cgactccagc tcgtatcagc catcaacctc tccactgcca aggattccaa agccgtggtc     6240
acctgtgtga tcattgtgct gtcagtcctg gtgtgctgtc ttccactggg gatttccttg     6300
gtacaggtgg ttctctccag caatgggagc ttcattcttt accagtttga attgtttgga     6360
```

-continued

```
tttactctta tatttttcaa gtcaggatta aacccttta tatattctcg gaacagtgca    6420
gggctgagaa ggaaagtgct ctggtgcctc caatacatag gcctgggttt tttctgctgc    6480
aaacaaaaga ctcgacttcg agccatggga aagggaacc tcgaagtcaa cagaaacaaa    6540
tcctcccatc atgaaacaaa ctctgcctac atgttatctc caaagccaca gaagaaattt    6600
gtggaccagg cttgtggccc aagtcattca aagaaagta tggtgagtcc caagatctct    6660
gctggacatc aacactgtgg tcagagcagc tcgaccccca tcaacactcg gattgaacct    6720
tactacagca tctataacag cagcccttcc caggaggaga gcagcccatg taacttacag    6780
ccagtaaact cttttggatt tgccaattca tatattgcca tgcattatca caccactaat    6840
gacttagtgc aggaatatga cagcacttca gccaagcaga ttccagtccc ctccgtttaa    6900
agtcatggag ctataggat cttatgtaaa cagttttgt ttctgatagt aatggactt     6960
attctaactt gagatcagtg gcggatcaaa acctacaaga ttcaactgaa aagttggcag    7020
ttatggtttt ctttcatctg atgtgtcagt atctgttgat ttgctttgta gtttgttgac    7080
atcttaagat ttgatgtgaa agttttagat tttttaccct g                       7121
```

<210> SEQ ID NO 2
<211> LENGTH: 540
<212> TYPE: PRT
<213> ORGANISM: Homo sapiens

<400> SEQUENCE: 2

```
Met Asn Ser Thr Gly His Leu Gln Asp Ala Pro Asn Ala Thr Ser Leu
1               5                   10                  15

His Val Pro His Ser Gln Glu Gly Asn Ser Thr Ser Leu Gln Glu Gly
            20                  25                  30

Leu Gln Asp Leu Ile His Thr Ala Thr Leu Val Thr Cys Thr Phe Leu
        35                  40                  45

Leu Ala Val Ile Phe Cys Leu Gly Ser Tyr Gly Asn Phe Ile Val Phe
    50                  55                  60

Leu Ser Phe Phe Asp Pro Ala Phe Arg Lys Phe Arg Thr Asn Phe Asp
65                  70                  75                  80

Phe Met Ile Leu Asn Leu Ser Phe Cys Asp Leu Phe Ile Cys Gly Val
                85                  90                  95

Thr Ala Pro Met Phe Thr Phe Val Leu Phe Ser Ser Ala Ser Ser
                100                 105                 110

Ile Pro Asp Ala Phe Cys Phe Thr Phe His Leu Thr Ser Ser Gly Phe
        115                 120                 125

Ile Ile Met Ser Leu Lys Thr Val Ala Val Ile Ala Leu His Arg Leu
    130                 135                 140

Arg Met Val Leu Gly Lys Gln Pro Asn Arg Thr Ala Ser Phe Pro Cys
145                 150                 155                 160

Thr Val Leu Leu Thr Leu Leu Trp Ala Thr Ser Phe Thr Leu Ala
                165                 170                 175

Thr Leu Ala Thr Leu Lys Thr Ser Lys Ser His Leu Cys Leu Pro Met
            180                 185                 190

Ser Ser Leu Ile Ala Gly Lys Gly Lys Ala Ile Leu Ser Leu Tyr Val
        195                 200                 205

Val Asp Phe Thr Phe Cys Val Ala Val Val Ser Val Ser Tyr Ile Met
    210                 215                 220

Ile Ala Gln Thr Leu Arg Lys Asn Ala Gln Val Arg Lys Cys Pro Pro
225                 230                 235                 240
```

```
Val Ile Thr Val Asp Ala Ser Arg Pro Gln Pro Phe Met Gly Val Pro
                245                 250                 255

Val Gln Gly Gly Gly Asp Pro Ile Gln Cys Ala Met Pro Ala Leu Tyr
                260                 265                 270

Arg Asn Gln Asn Tyr Asn Lys Leu Gln His Val Gln Thr Arg Gly Tyr
                275                 280                 285

Thr Lys Ser Pro Asn Gln Leu Val Thr Pro Ala Ala Ser Arg Leu Gln
                290                 295                 300

Leu Val Ser Ala Ile Asn Leu Ser Thr Ala Lys Asp Ser Lys Ala Val
305                 310                 315                 320

Val Thr Cys Val Ile Ile Val Leu Ser Val Leu Cys Cys Leu Pro
                325                 330                 335

Leu Gly Ile Ser Leu Val Gln Val Val Leu Ser Ser Asn Gly Ser Phe
                340                 345                 350

Ile Leu Tyr Gln Phe Glu Leu Phe Gly Phe Thr Leu Ile Phe Phe Lys
                355                 360                 365

Ser Gly Leu Asn Pro Phe Ile Tyr Ser Arg Asn Ser Ala Gly Leu Arg
370                 375                 380

Arg Lys Val Leu Trp Cys Leu Gln Tyr Ile Gly Leu Gly Phe Phe Cys
385                 390                 395                 400

Cys Lys Gln Lys Thr Arg Leu Arg Ala Met Gly Lys Gly Asn Leu Glu
                405                 410                 415

Val Asn Arg Asn Lys Ser Ser His His Glu Thr Asn Ser Ala Tyr Met
                420                 425                 430

Leu Ser Pro Lys Pro Gln Lys Lys Phe Val Asp Gln Ala Cys Gly Pro
                435                 440                 445

Ser His Ser Lys Glu Ser Met Val Ser Pro Lys Ile Ser Ala Gly His
                450                 455                 460

Gln His Cys Gly Gln Ser Ser Thr Pro Ile Asn Thr Arg Ile Glu
465                 470                 475                 480

Pro Tyr Tyr Ser Ile Tyr Asn Ser Ser Pro Ser Gln Glu Glu Ser Ser
                485                 490                 495

Pro Cys Asn Leu Gln Pro Val Asn Ser Phe Gly Phe Ala Asn Ser Tyr
                500                 505                 510

Ile Ala Met His Tyr His Thr Thr Asn Asp Leu Val Gln Glu Tyr Asp
                515                 520                 525

Ser Thr Ser Ala Lys Gln Ile Pro Val Pro Ser Val
                530                 535                 540
```